US009701989B2

(12) United States Patent
Zhu et al.

(10) Patent No.: US 9,701,989 B2
(45) **Date of Patent: *Jul. 11, 2017**

(54) RECOMBINANT MICROBIAL CELLS THAT PRODUCE AT LEAST 28% EICOSAPENTAENOIC ACID AS DRY CELL WEIGHT

(71) Applicant: E I DU PONT DE NEMOURS AND COMPANY, Wilmington, DE (US)

(72) Inventors: Quinn Qun Zhu, West Chester, PA (US); Seung-Pyo Hong, Hockessin, DE (US); Pamela L Sharpe, Wilmington, DE (US); Narendra S Yadav, Wilmington, DE (US); Xiaochun Fan, Wilmington, DE (US); Michael Dauner, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/132,022

(22) Filed: Dec. 18, 2013

(65) Prior Publication Data

US 2014/0186906 A1 Jul. 3, 2014

Related U.S. Application Data

(60) Provisional application No. 61/740,502, filed on Dec. 21, 2012.

(51) Int. Cl.

| | |
|---|---|
| ***C12P 7/64*** | (2006.01) |
| ***C12N 1/16*** | (2006.01) |
| ***C12N 9/10*** | (2006.01) |

(52) U.S. Cl.

CPC .............. *C12P 7/6427* (2013.01); *C12N 1/16* (2013.01); *C12N 9/1029* (2013.01);

(Continued)

(58) Field of Classification Search

None

See application file for complete search history.

(56) References Cited

U.S. PATENT DOCUMENTS

| | | | |
|---|---|---|---|
| 7,238,482 | B2 | 7/2007 | Picataggio et al. |
| 7,267,976 | B2 | 9/2007 | Yadav et al. |

(Continued)

FOREIGN PATENT DOCUMENTS

| | | |
|---|---|---|
| CA | 2517253 | 9/2004 |
| WO | 2004076617 | 9/2004 |

OTHER PUBLICATIONS

Chen et al., The Yeast Acylglycerol Acyltransferase LCA1 is a Key Component of Lands Cycle for Phosphatidylcholine Turnover, FEBS Letters (2007), vol. 581, pp. 5511-5516.

(Continued)

*Primary Examiner* — Robert Mondesi
*Assistant Examiner* — Richard Ekstrom

(57) ABSTRACT

Recombinant microbial cells are disclosed herein that produce an oil comprising at least 28 percent eicosapentaenoic acid (EPA) measured as a weight percent of dry cell weight. These cells may comprise a polynucleotide sequence encoding an active acyl-CoA:lysophosphatidylcholine acyltransferase (LPCAT) comprising at least one amino acid mutation in a membrane-bound O-acyltransferase motif. In addition, the cells may comprise a down-regulation of an endogenous polynucleotide sequence encoding Sou2 sorbitol utilization protein, and/or one or more polynucleotides encoding phospholipid:diacylglycerol acyltransferase (PDAT), delta-12 desaturase, a dihomo-gamma-linolenic acid (DGLA) synthase multizyme, delta-8 desaturase, malonyl-CoA synthetase (MCS), or acyl-CoA:lysophosphatidic acid acyltransferase (LPAAT). Also disclosed are methods of using (Continued)

Figure 1:
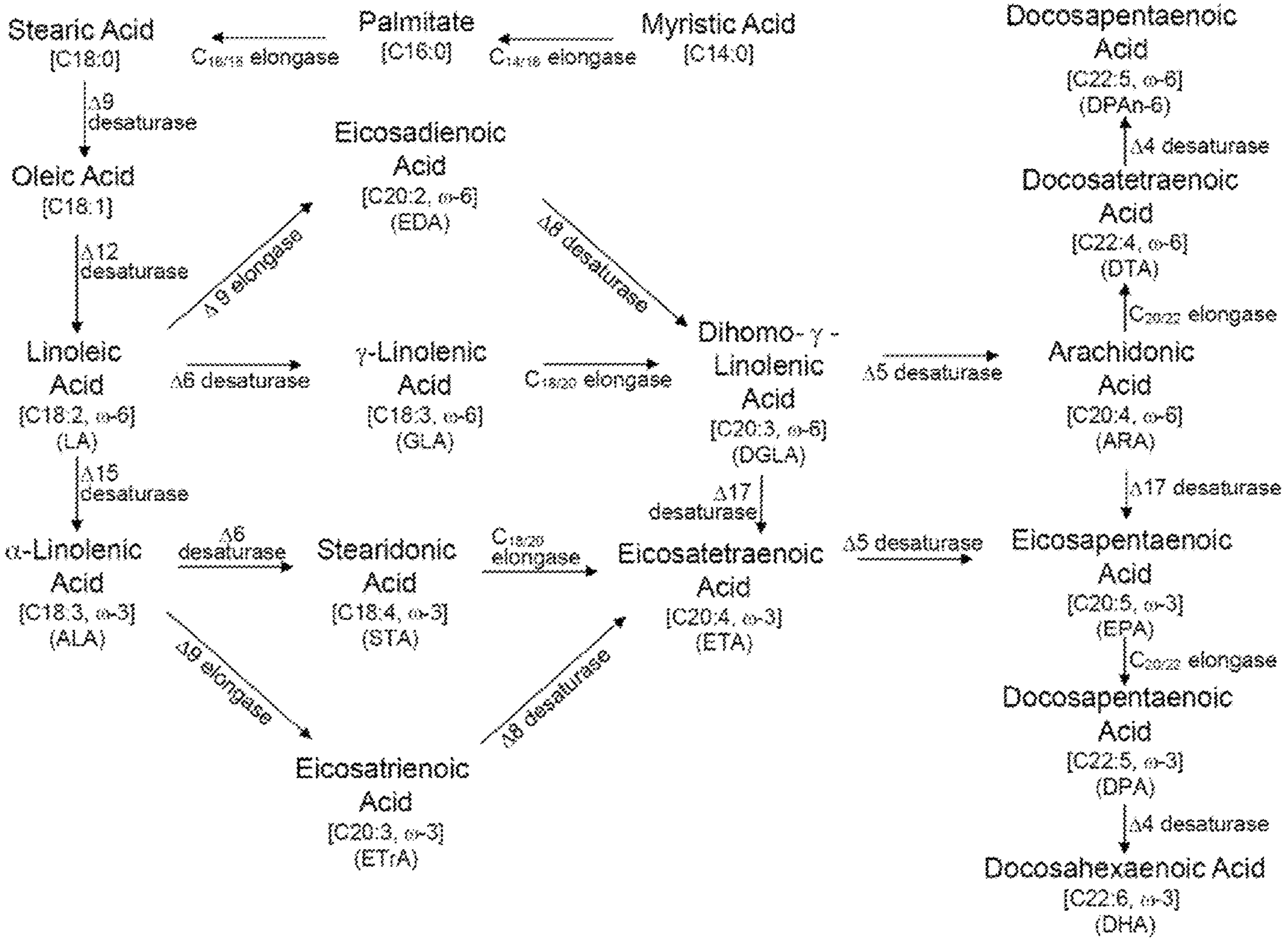

the recombinant microbial cells to produce oil containing omega-3 polyunsaturated fatty acids such as EPA.

11 Claims, 11 Drawing Sheets

(52) U.S. Cl.
CPC ........... *C12P 7/6463* (2013.01); *C12P 7/6472* (2013.01); *C12Y 203/01023* (2013.01); *Y02P 20/52* (2015.11)

(56) References Cited

U.S. PATENT DOCUMENTS

| | | | | |
|---|---|---|---|---|
| 7,732,155 | B2 | 6/2010 | Zou et al. | |
| 7,932,077 | B2 | 4/2011 | Damude et al. | |
| 9,005,940 | B2 * | 4/2015 | Zhu | C12P 7/6427 435/134 |
| 9,347,075 | B2 * | 5/2016 | Bostick | C12P 7/6427 |
| 9,416,382 | B2 * | 8/2016 | Bostick | C12P 7/6427 |
| 2006/0094090 | A1 * | 5/2006 | Damude et al. | 435/134 |
| 2006/0168687 | A1 * | 7/2006 | Renz et al. | 800/281 |
| 2006/0174376 | A1 * | 8/2006 | Renz et al. | 800/281 |
| 2008/0145867 | A1 | 6/2008 | Zou et al. | |
| 2009/0093543 | A1 | 4/2009 | Xue et al. | |
| 2009/0094707 | A1 * | 4/2009 | Cirpus et al. | 800/13 |
| 2010/0068789 | A1 | 3/2010 | Xue et al. | |
| 2010/0317072 | A1 | 12/2010 | Hong et al. | |
| 2010/0317882 | A1 | 12/2010 | Yadav et al. | |
| 2011/0059496 | A1 | 3/2011 | Zhu | |
| 2011/0162104 | A1 * | 6/2011 | Damude et al. | 800/281 |
| 2012/0052537 | A1 | 3/2012 | Hong et al. | |
| 2012/0060242 | A1 * | 3/2012 | Senger et al. | 800/298 |
| 2012/0115231 | A1 * | 5/2012 | Ochiai | 435/440 |
| 2012/0252079 | A1 | 10/2012 | Zhu et al. | |
| 2012/0252093 | A1 | 10/2012 | Zhu | |
| 2013/0089910 | A1 | 4/2013 | Zhu | |
| 2013/0089911 | A1 | 4/2013 | Zhu et al. | |
| 2013/0097733 | A1 * | 4/2013 | Senger et al. | 800/298 |
| 2013/0338388 | A1 * | 12/2013 | Petrie et al. | 554/224 |

OTHER PUBLICATIONS

Benghezal et al., SLC1 and SLC4 Encode Partially Redundant Acyl-Coenzyme A 1-Acylglycerol-3-Phosphate O-Acyltransferases of Budding Yeast, J. Biol. Chemistry (2007), vol. 282, No. 42, pp. 30845-30855.

Dahlqvist et al., Phospholipid: Diacylglycerol Acyltransferase: An Enzyme That Catalyzes the Acyl-CoA-Independent Formation of Triacylglycerol in Yeast and Plants, PNAS (2000) vol. 97, No. 12, pp. 6487-6492.

Hishikawa et al., Discovery of a Lysophospholipid Acyltransferase Family Essential for Membrane Assymetry and Diversity, PNAS (2008), vol. 105, No. 8, pp. 2830-2835.

Jami et al., The Penicillium Chrysogenum Extracellular Proteome, Conversion From a Food-Rotting Strain to a Versatile Cell Factory for White Biotechnology, Molecular & Cellular Proteomics (2010), vol. 9, pp. 2729-2744.

Janbon et al., Monosomy of a Specific Chromosome Determins L-Sorbose Utilization: A Novel Regulatory Mechanism in Candida Albicans, PNAS (1998), vol. 95, pp. 5150-5155.

Lee et al., Caenorhabditis Elegans MBOA-7, A Member of the MBOAT Family, Is Required for Selective Incorporation of Polyunsaturated Fatty Acids Into Phosphatidylinositol, Molecular Biology of the Cell (2008), vol. 19, pp. 1174-1184.

Oelkers et al., A Lecithin Cholesterol Acyltransferase-Like Gene Mediates Diacylglycerol Esterification in Yeast, J. Biol. Chemistry (2000), vol. 275, No. 21, pp. 15609-15612.

Riekhof et al., Identification and Characterization of the Major Lysophosphatidylethanolamine Acyltransferase in *Saccharomyces cerevisiae*, J. Biol. Chemistry (2007), vol. 282, No. 39, pp. 28344-28352.

Shindou et al., Identification of Membrane O-Acyltransferase Family Motifs, Biochemical and Biophysical Research Communications (2009), vol. 383, pp. 320-325.

Stahl et al., A Family of Eukaryotic Lysophospholipid Acyltransferases With Broad Specificity, FEBS Letters (2008), vol. 582, pp. 305-309.

Tamaki et al., LPT1 Encodes a Membrane-Bound O-Acyltransferase Involved in the Acylation of Lysophospholipids in the Yeast *Saccharomyces cerevisiae* (2007), vol. 282, No. 47, pp. 34288-34298.

* cited by examiner

A)
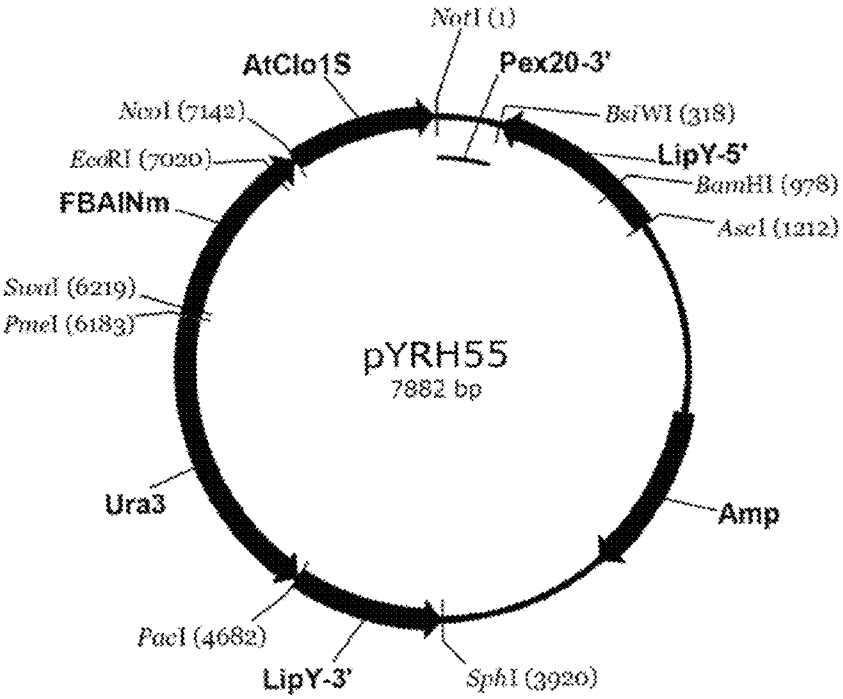
B)
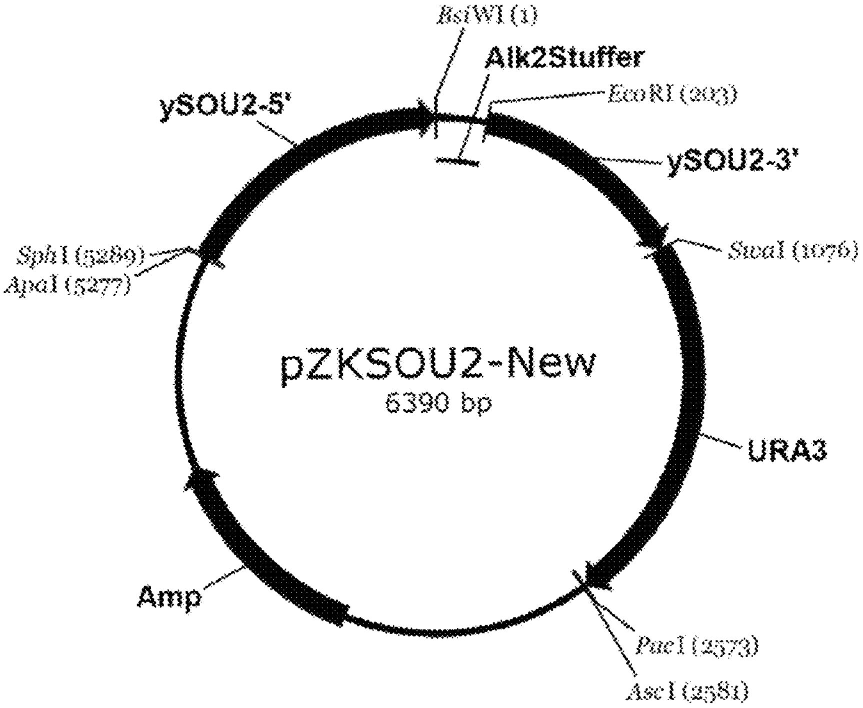
Figure 4

TGACGAGGGGTGTTTGGGCGCTGGAAGCGTAATTTTCGTCTTGAATGGGCCGTCGAGACTTGGGGTTCGACCCCGACTAAATGGCGC
ACCGCTAGATTCTCTTTTGGCGACTTTCTCGGGATTCTAGTCACCCCCGCAATGTTCCAGCTTACGGTTTGAGACAGTACACGACTG
GCTAGGCGAGTTGTTGAAGTCGTAGCGTAGAGTGGGAGGCATGACGTCACGGGACAGCTGCGTGCACCACGCGAGCAGGTCAATTGA
CCTCATTTGAGTGGTGTGGCTTGGCGTTCTAGCGGTGGCGGCGTTGTCGAGCTCCCTCTACTTGTAGTGAGATTATGTCGACGAGCG
GGGGGGACTTCCATTGTGCTTGCCACTGCTAGTGCAGTACAACTGAAAGCTAAACCGCAATCAATCCCAAACTGCATGTCCGCCTTA
ACTCTGATATGTTATCAAGAGAGTGGTGTGGTGAGGTGAGGTGAGGTGACGTGGACAAGTTGATGGGGAGTTGGGGCATTGACAAAA
GGGAAATTGCAGGGGGATTCCGCCGGCTATATATATCTTATGTCTGCTCAATTCCCAGACGGCTCCACACAAAACCAAGATACCACA
CCATCATGGTCACACCGGGTACATAACTCCCATCCATCTCATCCCACTTGCATGGCGACCGGAGAGAGAAAGCCCGGGGAGAGCACG
TCGGCGCGGTCCCCAGGGCGACAACCAAAACAAAATCACCGAGTGACTCCGAAAGCCGCGTTCCAACAC▶CCCCCCAAAATCCCCCC
CTCAAACACGTCAGCCACCTGTCCCCCGAAAATTAACTTCACTGACATGGCGCAGCTATTAAGGCTAAAGTGAATGCATGGCTCATC
TTTGTTTGCTGGTTGCTACTGTGACTGAGGTAAAAACCCTCGCTCCCAAGTCTATATATACCTGGGTGTGCTCCCTCGAACAGACC
CGTCACAGTAAAACTACTACCTCCATACACAGCACCACCTCAATCATGTCTGGACCTTCCACCCTCGCCACGGGACTGCACCCTCTC
CCCACAGAGACCCCAAAGTTCCCCACCAACATCATGGACCGATTCTCCCTCAAGGGTAAGGTTGCCTCCGTCACCGGCTCCTCGTCA
GGTATCGGCTACTGCGTGGCCGAGGCCTACGCCCAGGCCGGTGCCGACGTGGCCATCTGGTACAACTCCCACCCCGCCGACGCAAAG
GCTGAGCACCTCGCTAAGACCTACGGCGTCAAGGCCAAGGCCTACAAGTGCCCTGTCACCGACGCCGCCGC◀CGTGGAGTCCACCAT
CCAGCAGATCGAGAAGGACTTTGGCACCATTGACATCTTCGTCGCCAACGCTGGTGTCCCCTGGACCGCCGGCCCCATGATCGACGT
GCCCGACAACAAGGAGTGGGACAAGGTCATCAACCTGGATCTCAACGGTGCCTACTACTGCGCCAAGTACGCCGGCCAGATCTTCAA
GAAGAAGGGCAAGGGATCCTTCATCTTCACCGCCTCCATGTCCGGCCACATTGTCAACATCCCCCAGATGCAGGCCTGCTACAACGC
CGCCAAGGCCGCTCTGCTGCACCTGTCTCGATCGCTGGCCGTCGAGTGGGCCGGCTTTGCCCGATGCAACACAGTCTCCCCTGGCTA
CATGGCCACCGAGATCTCCGACTTTGTCCCCAAGGAGACCAAGGAGAAGTGGTGGCAGCTCATTCCCATGGGCCGAGAGGGAGACCC
CTCCGAGCTCTACCTACCTCTACCTTGCCTCTGATGCTGCCACCTACACCACTGGTGCCGACATTATCGTCGATGGTGGCTACTGCG
CTCCTTAGAGGATGTATATAGATAATGATTGTTTATGATTAGACATTGATTGAGTGTAGTTGGACATTAGCAGTCAGATAGGCAACG
AAGATCATCCAAGTCTGAATACATACCCATACAAATCATACAAGTAAATGATGGAATTACTCATATAAGTATGTACTTACTTGTACC
GAATTGCCAATGAATGTCAATCAGAACGCAGTATGTACAAGTACTCGCACAATATCATAAGGCACTCGAATGT (SEQ ID NO:8)

Figure 5

A)
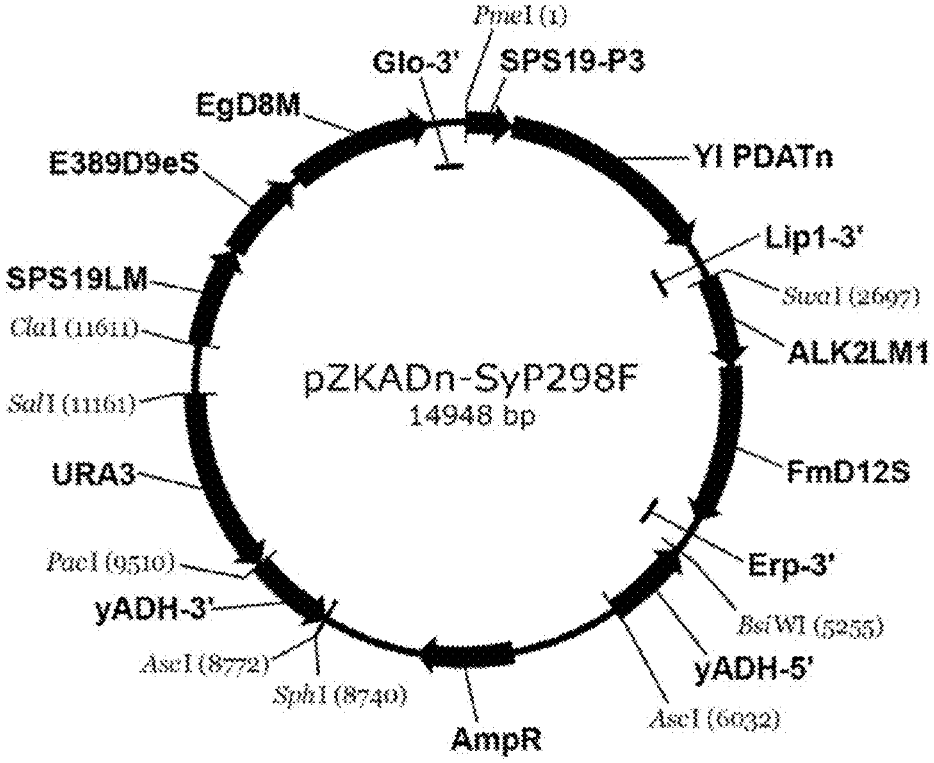
B)
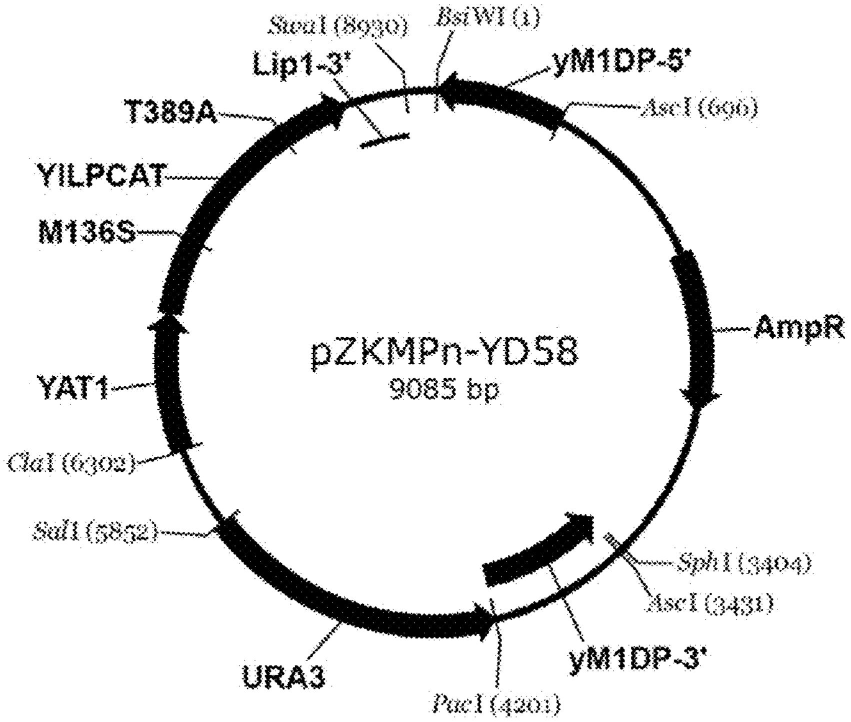
Figure 7

A)
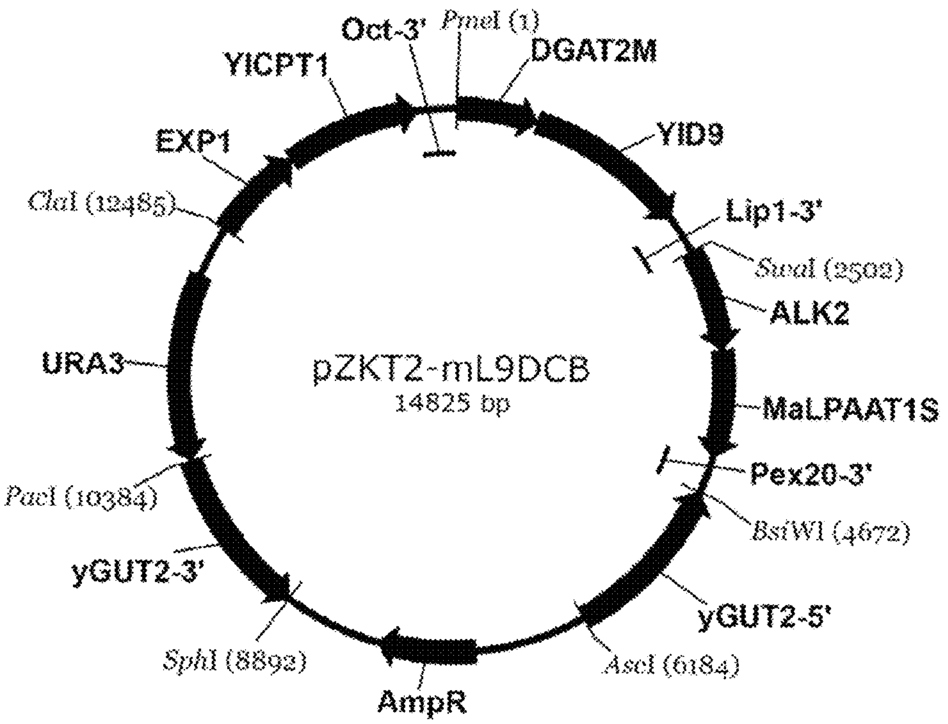
B)
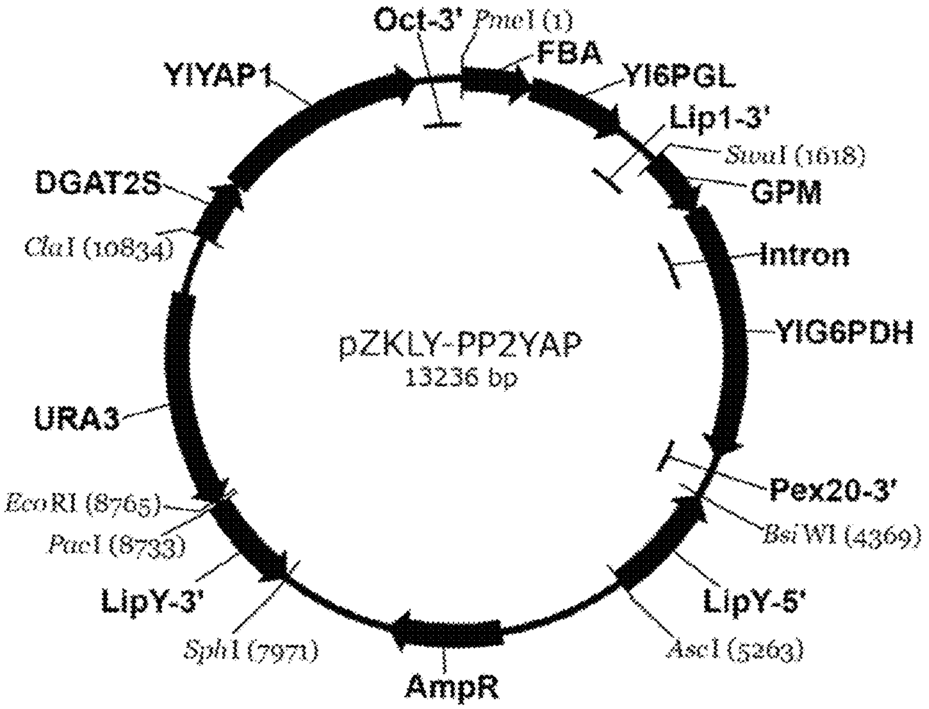
Figure 9

SEQUENCE LISTING

<160> NUMBER OF SEQ ID NOS: 84

<210> SEQ ID NO 1
<211> LENGTH: 7880
<212> TYPE: DNA
<213> ORGANISM: Artificial sequence
<220> FEATURE:
<223> OTHER INFORMATION: Construct pYRH55 for expressing AtClo1S

<400> SEQUENCE: 1
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120

```
ggatatttat gtttgacact tgagaatgta cgatacaagc actgtccaag tacaatacta    180
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgttgattga ggtggagcca gatgggctat tgtttcatat    360
atagactggc agccacctct ttggcccagc atgtttgtat acctggaagg gaaaactaaa    420
gaagctggct agtttagttt gattattata gtagatgtcc taatcactag agattagaat    480
gtcttggcga tgattagtcg tcgtcccctg tatcatgtct agaccaactg tgtcatgaag    540
ttggtgctgg tgttttacct gtgtactaca agtaggtgtc ctagatctag tgtacagagc    600
cgtttagacc catgtggact tcaccattaa cgatggaaaa tgttcattat atgacagtat    660
attacaatgg acttgctcca tttcttcctt gcatcacatg ttctccacct ccatagttga    720
tcaacacatc atagtagcta aggctgctgc tctcccacta cagtccacca caagttaagt    780
agcaccgtca gtacagctaa aagtacacgt ctagtacgtt tcataactag tcaagtagcc    840
cctattacag atatcagcac tatcacgcac gagtttttct ctgtgctatc taatcaactt    900
gccaagtatt cggagaagat acactttctt ggcatcaggt atacgaggga gcctatcaga    960
tgaaaaaggg tatattggat ccattcatat ccacctacac gttgtcataa tctcctcatt   1020
cacgtgattc atttcgtgac actagtttct cactttcccc cccgcaccta tagtcaactt   1080
ggcggacacg ctacttgtag ctgacgttga tttatagacc caatcaaagc gggttatcgg   1140
tcaggtagca cttatcattc atcgttcata ctacgatgag caatctcggg catgtccgga   1200
aaagtgtcgg gcgcgccagc tgcattaatg aatcggccaa cgcgcgggga gaggcggttt   1260
gcgtattggg cgctcttccg cttcctcgct cactgactcg ctgcgctcgg tcgttcggct   1320
gcggcgagcg gtatcagctc actcaaaggc ggtaatacgg ttatccacag aatcagggga   1380
taacgcagga aagaacatgt gagcaaaagg ccagcaaaag gccaggaacc gtaaaaaggc   1440
cgcgttgctg gcgtttttcc ataggctccg cccccctgac gagcatcaca aaaatcgacg   1500
ctcaagtcag aggtggcgaa acccgacagg actataaaga taccaggcgt ttccccctgg   1560
aagctccctc gtgcgctctc ctgttccgac cctgccgctt accggatacc tgtccgcctt   1620
tctcccttcg ggaagcgtgg cgctttctca tagctcacgc tgtaggtatc tcagttcggt   1680
gtaggtcgtt cgctccaagc tgggctgtgt gcacgaaccc cccgttcagc ccgaccgctg   1740
cgccttatcc ggtaactatc gtcttgagtc caacccggta agacacgact tatcgccact   1800
ggcagcagcc actggtaaca ggattagcag agcgaggtat gtaggcggtg ctacagagtt   1860
cttgaagtgg tggcctaact acggctacac tagaagaaca gtatttggta tctgcgctct   1920
gctgaagcca gttaccttcg gaaaaagagt tggtagctct tgatccggca aacaaaccac   1980
cgctggtagc ggtggttttt ttgtttgcaa gcagcagatt acgcgcagaa aaaaaggatc   2040
tcaagaagat cctttgatct tttctacggg gtctgacgct cagtggaacg aaaactcacg   2100
ttaagggatt ttggtcatga gattatcaaa aaggatcttc acctagatcc ttttaaatta   2160
aaaatgaagt tttaaatcaa tctaaagtat atatgagtaa acttggtctg acagttacca   2220
atgcttaatc agtgaggcac ctatctcagc gatctgtcta tttcgttcat ccatagttgc   2280
ctgactcccc gtcgtgtaga taactacgat acgggagggc ttaccatctg gccccagtgc   2340
tgcaatgata ccgcgagacc cacgctcacc ggctccagat ttatcagcaa taaaccagcc   2400
agccggaagg gccgagcgca gaagtggtcc tgcaacttta tccgcctcca tccagtctat   2460
taattgttgc cgggaagcta gagtaagtag ttcgccagtt aatagtttgc gcaacgttgt   2520
```

-continued

```
tgccattgct acaggcatcg tggtgtcacg ctcgtcgttt ggtatggctt cattcagctc   2580
cggttcccaa cgatcaaggc gagttacatg atcccccatg ttgtgcaaaa aagcggttag   2640
ctccttcggt cctccgatcg ttgtcagaag taagttggcc gcagtgttat cactcatggt   2700
tatggcagca ctgcataatt ctcttactgt catgccatcc gtaagatgct tttctgtgac   2760
tggtgagtac tcaaccaagt cattctgaga atagtgtatg cggcgaccga gttgctcttg   2820
cccggcgtca atacgggata ataccgcgcc acatagcaga actttaaaag tgctcatcat   2880
tggaaaacgt tcttcggggc gaaaactctc aaggatctta ccgctgttga gatccagttc   2940
gatgtaaccc actcgtgcac ccaactgatc ttcagcatct tttactttca ccagcgtttc   3000
tgggtgagca aaaacaggaa ggcaaaatgc cgcaaaaaag ggaataaggg cgacacggaa   3060
atgttgaata ctcatactct tcctttttca atattattga agcatttatc agggttattg   3120
tctcatgagc ggatacatat ttgaatgtat ttagaaaaat aaacaaatag gggttccgcg   3180
cacatttccc cgaaaagtgc cacctgatgc ggtgtgaaat accgcacaga tgcgtaagga   3240
gaaaataccg catcaggaaa ttgtaagcgt taatattttg ttaaaattcg cgttaaattt   3300
ttgttaaatc agctcatttt ttaaccaata ggccgaaatc ggcaaaatcc cttataaatc   3360
aaaagaatag accgagatag ggttgagtgt tgttccagtt tggaacaaga gtccactatt   3420
aaagaacgtg gactccaacg tcaaagggcg aaaaaccgtc tatcagggcg atggcccact   3480
acgtgaacca tcaccctaat caagtttttt ggggtcgagg tgccgtaaag cactaaatcg   3540
gaaccctaaa gggagccccc gatttagagc ttgacgggga aagccggcga acgtggcgag   3600
aaaggaaggg aagaaagcga aaggagcggg cgctagggcg ctggcaagtg tagcggtcac   3660
gctgcgcgta accaccacac ccgccgcgct taatgcgccg ctacagggcg cgtccattcg   3720
ccattcaggc tgcgcaactg ttgggaaggg cgatcggtgc gggcctcttc gctattacgc   3780
cagctggcga aaggggggatg tgctgcaagg cgattaagtt gggtaacgcc agggttttcc   3840
cagtcacgac gttgtaaaac gacggccagt gaattgtaat acgactcact atagggcgaa   3900
ttgggcccga cgtcgcatgc attccgacag cagcgactgg gcaccatgat caagcgaaac   3960
accttccccc agctgccctg gcaaaccatc aagaacccta ctttcatcaa gtgcaagaac   4020
ggttctactc ttctcacctc cggtgtctac ggctggtgcc gaaagcctaa ctacaccgct   4080
gatttcatca tgtgcctcac ctgggctctc atgtgcggtg ttgcttctcc cctgccttac   4140
ttctacccgg tcttcttctt cctggtgctc atccaccgag cttaccgaga ctttgagcga   4200
ctggagcgaa agtacggtga ggactaccag gagttcaagc gacaggtccc ttggatcttc   4260
atcccttatg ttttctaaac gataagctta gtgagcgaat ggtgaggtta cttaattgag   4320
tggccagcct atgggattgt ataacagaca gtcaatatat tactgaaaag actgaacagc   4380
cagacggagt gaggttgtga gtgaatcgta gagggcggct attacagcaa gtctactcta   4440
cagtgtacta acacagcaga gaacaaatac aggtgtgcat tcggctatct gagaattagt   4500
tggagagctc gagaccctcg gcgataaact gctcctcggt tttgtgtcca tacttgtacg   4560
gaccattgta atggggcaag tcgttgagtt ctcgtcgtcc gacgttcaga gcacagaaac   4620
caatgtaatc aatgtagcag agatggttct gcaaaagatt gatttgtgcg agcaggttaa   4680
ttaagtcata cacaagtcag ctttcttcga gcctcatata agtataagta gttcaacgta   4740
ttagcactgt acccagcatc tccgtatcga gaaacacaac aacatgcccc attggacaga   4800
tcatgcggat acacaggttg tgcagtatca tacatactcg atcagacagg tcgtctgacc   4860
```

-continued

```
atcatacaag ctgaacaagc gctccatact tgcacgctct ctatatacac agttaaatta   4920
catatccata gtctaacctc taacagttaa tcttctggta agcctcccag ccagccttct   4980
ggtatcgctt ggcctcctca ataggatctc ggttctggcc gtacagacct cggccgacaa   5040
ttatgatatc cgttccggta gacatgacat cctcaacagt tcggtactgc tgtccgagag   5100
cgtctccctt gtcgtcaaga cccaccccgg gggtcagaat aagccagtcc tcagagtcgc   5160
ccttaggtcg gttctgggca atgaagccaa ccacaaactc ggggtcggat cgggcaagct   5220
caatggtctg cttggagtac tcgccagtgg ccagagagcc cttgcaagac agctcggcca   5280
gcatgagcag acctctggcc agcttctcgt tgggagaggg gactaggaac tccttgtact   5340
gggagttctc gtagtcagag acgtcctcct tcttctgttc agagacagtt tcctcggcac   5400
cagctcgcag gccagcaatg attccggttc cgggtacacc gtgggcgttg gtgatatcgg   5460
accactcggc gattcggtga caccggtact ggtgcttgac agtgttgcca atatctgcga   5520
actttctgtc ctcgaacagg aagaaaccgt gcttaagagc aagttccttg agggggagca   5580
cagtgccggc gtaggtgaag tcgtcaatga tgtcgatatg ggttttgatc atgcacacat   5640
aaggtccgac cttatcggca agctcaatga gctccttggt ggtggtaaca tccagagaag   5700
cacacaggtt ggtttttcttg gctgccacga gcttgagcac tcgagcggca aaggcggact   5760
tgtggacgtt agctcgagct tcgtaggagg gcattttggt ggtgaagagg agactgaaat   5820
aaatttagtc tgcagaactt tttatcggaa ccttatctgg ggcagtgaag tatatgttat   5880
ggtaatagtt acgagttagt tgaacttata gatagactgg actatacggc tatcggtcca   5940
aattagaaag aacgtcaatg gctctctggg cgtcgccttt gccgacaaaa atgtgatcat   6000
gatgaaagcc agcaatgacg ttgcagctga tattgttgtc ggccaaccgc gccgaaaacg   6060
cagctgtcag acccacagcc tccaacgaag aatgtatcgt caaagtgatc caagcacact   6120
catagttgga gtcgtactcc aaaggcggca atgacgagtc agacagatac tcgtcgacgt   6180
ttaaacagtg tacgcagatc tactatagag gaacatttaa attgccccgg agaagacggc   6240
caggccgcct agatgacaaa ttcaacaact cacagctgac tttctgccat tgccactagg   6300
ggggggcctt tttatatggc caagccaagc tctccacgtc ggttgggctg cacccaacaa   6360
taaatgggta gggttgcacc aacaaaggga tgggatgggg ggtagaagat acgaggataa   6420
cggggctcaa tggcacaaat aagaacgaat actgccatta agactcgtga tccagcgact   6480
gacaccattg catcatctaa gggcctcaaa actacctcgg aactgctgcg ctgatctgga   6540
caccacagag gttccgagca ctttaggttg caccaaatgt cccaccaggt gcaggcagaa   6600
aacgctggaa cagcgtgtac agtttgtctt aacaaaaagt gagggcgctg aggtcgagca   6660
gggtggtgtg acttgttata gcctttagag ctgcgaaagc gcgtatggat ttggctcatc   6720
aggccagatt gagggtctgt ggacacatgt catgttagtg tacttcaatc gccccctgga   6780
tatagccccg acaataggcc gtggcctcat ttttttgcct tccgcacatt tccattgctc   6840
gatacccaca ccttgcttct cctgcacttg ccaaccttaa tactggttta cattgaccaa   6900
catcttacaa gcgggggggct tgtctagggt atatataaac agtggctctc ccaatcggtt   6960
gccagtctct tttttccttt ctttccccac agattcgaaa tctaaactac acatcacaga   7020
attccgagcc gtgagtatcc acgacaagat cagtgtcgag acgacgcgtt ttgtgtaatg   7080
acacaatccg aaagtcgcta gcaacacaca ctctctacac aaactaaccc agctctggta   7140
ccatgggctc caagaccgag atgatggagc gagacgctat ggccaccgtc gctccttacg   7200
cacccgttac ctaccaccga agagcccgag tcgacctgga cgatcgactt cccaaacctt   7260
```

```
acatgcctcg agccctgcag gctcctgacc gagagcatcc ctacggaact cctggtcaca   7320

agaactacgg cctctccgtg ctgcagcagc atgtctcttt ctttgacatt gatgacaacg   7380

gaatcattta cccctgggag acctactccg gtctgcggat gctcggcttc aacatcattg   7440

gatctctgat cattgccgct gtcatcaacc ttacactcag ctacgccacc ctgcctggtt   7500

ggcttccctc tcccttcttt cccatctaca ttcacaacat tcataagtcc aagcacggct   7560

ccgacagcaa gacttacgac aatgaaggac gattcatgcc cgtcaacctc gagctgatct   7620

tctcgaagta cgccaagacc ctgcccgaca agctctcctt gggagagctg tgggagatga   7680

ccgaaggcaa ccgagatgct tgggacatct ttggatggat tgccggcaag atcgagtggg   7740

gtctgctcta cctgctcgct cgagacgagg aaggcttctt gtccaaggag gccattcgaa   7800

gatgctttga cggttctctg ttcgagtact gtgccaagat ctatgctggt atcagcgagg   7860

ataagaccgc atactattaa                                               7880
```

<210> SEQ ID NO 2
<211> LENGTH: 738
<212> TYPE: DNA
<213> ORGANISM: Artificial sequence
<220> FEATURE:
<223> OTHER INFORMATION: A. thaliana caleosin-1 codon-omptimized for expression in Y. lipolytica

<400> SEQUENCE: 2

```
atgggctcca agaccgagat gatggagcga gacgctatgg ccaccgtcgc tccttacgca     60

cccgttacct accaccgaag agcccgagtc gacctggacg atcgacttcc caaaccttac    120

atgcctcgag ccctgcaggc tcctgaccga gagcatccct acggaactcc tggtcacaag    180

aactacggcc tctccgtgct gcagcagcat gtctctttct ttgacattga tgacaacgga    240

atcatttacc cctgggagac ctactccggt ctgcggatgc tcggcttcaa catcattgga    300

tctctgatca ttgccgctgt catcaacctt acactcagct acgccaccct gcctggttgg    360

cttccctctc ccttctttcc catctacatt cacaacattc ataagtccaa gcacggctcc    420

gacagcaaga cttacgacaa tgaaggacga ttcatgcccg tcaacctcga gctgatcttc    480

tcgaagtacg ccaagaccct gcccgacaag ctctccttgg gagagctgtg ggagatgacc    540

gaaggcaacc gagatgcttg ggacatcttt ggatggattg ccggcaagat cgagtggggt    600

ctgctctacc tgctcgctcg agacgaggaa ggcttcttgt ccaaggaggc cattcgaaga    660

tgctttgacg gttctctgtt cgagtactgt gccaagatct atgctggtat cagcgaggat    720

aagaccgcat actattaa                                                  738
```

<210> SEQ ID NO 3
<211> LENGTH: 245
<212> TYPE: PRT
<213> ORGANISM: Arabidopsis thaliana

<400> SEQUENCE: 3

```
Met Gly Ser Lys Thr Glu Met Met Glu Arg Asp Ala Met Ala Thr Val
1               5                   10                  15

Ala Pro Tyr Ala Pro Val Thr Tyr His Arg Arg Ala Arg Val Asp Leu
            20                  25                  30

Asp Asp Arg Leu Pro Lys Pro Tyr Met Pro Arg Ala Leu Gln Ala Pro
        35                  40                  45

Asp Arg Glu His Pro Tyr Gly Thr Pro Gly His Lys Asn Tyr Gly Leu
    50                  55                  60
```

```
Ser Val Leu Gln Gln His Val Ser Phe Phe Asp Ile Asp Asp Asn Gly
65                  70                  75                  80

Ile Ile Tyr Pro Trp Glu Thr Tyr Ser Gly Leu Arg Met Leu Gly Phe
                85                  90                  95

Asn Ile Ile Gly Ser Leu Ile Ile Ala Ala Val Ile Asn Leu Thr Leu
            100                 105                 110

Ser Tyr Ala Thr Leu Pro Gly Trp Leu Pro Ser Pro Phe Phe Pro Ile
        115                 120                 125

Tyr Ile His Asn Ile His Lys Ser Lys His Gly Ser Asp Ser Lys Thr
    130                 135                 140

Tyr Asp Asn Glu Gly Arg Phe Met Pro Val Asn Leu Glu Leu Ile Phe
145                 150                 155                 160

Ser Lys Tyr Ala Lys Thr Leu Pro Asp Lys Leu Ser Leu Gly Glu Leu
                165                 170                 175

Trp Glu Met Thr Glu Gly Asn Arg Asp Ala Trp Asp Ile Phe Gly Trp
            180                 185                 190

Ile Ala Gly Lys Ile Glu Trp Gly Leu Leu Tyr Leu Leu Ala Arg Asp
        195                 200                 205

Glu Glu Gly Phe Leu Ser Lys Glu Ala Ile Arg Arg Cys Phe Asp Gly
    210                 215                 220

Ser Leu Phe Glu Tyr Cys Ala Lys Ile Tyr Ala Gly Ile Ser Glu Asp
225                 230                 235                 240

Lys Thr Ala Tyr Tyr
                245
```

<210> SEQ ID NO 4
<211> LENGTH: 6390
<212> TYPE: DNA
<213> ORGANISM: Artificial sequence
<220> FEATURE:
<223> OTHER INFORMATION: Construct pZKSOU2-New for down-regulating endogenous Y. lipolytica SOU2 expression

<400> SEQUENCE: 4

```
gtacgggcgg atgttgactc aattgaagct agatcaacag gactttatta ttcagctcca      60

aaaaatcctc acattacata aatttctctc cccccgtaac ctggatgtgc tccaaatcag     120

cttctctcgg ggacagagat gtatcacctc ggagaatatc tgtccgattt gaatgatatc     180

aactgtaatg gacttaaccg ggaattcgtg gagtccacca tccagcagat cgagaaggac     240

tttggcacca ttgacatctt cgtcgccaac gctggtgtcc cctggaccgc cggccccatg     300

atcgacgtgc ccgacaacaa ggagtgggac aaggtcatca acctggatct caacggtgcc     360

tactactgcg ccaagtacgc cggccagatc ttcaagaaga agggcaaggg atccttcatc     420

ttcaccgcct ccatgtccgg ccacattgtc aacatccccc agatgcaggc ctgctacaac     480

gccgccaagg ccgctctgct gcacctgtct cgatcgctgg ccgtcgagtg ggccggcttt     540

gcccgatgca acacagtctc ccctggctac atggccaccg agatctccga ctttgtcccc     600

aaggagacca aggagaagtg gtggcagctc attcccatgg gccgagaggg agacccctcc     660

gagctctacc tacctctacc ttgcctctga tgctgccacc tacaccactg gtgccgacat     720

tatcgtcgat ggtggctact gcgctcctta gaggatgtat atagataatg attgtttatg     780

attagacatt gattgagtgt agttggacat tagcagtcag ataggcaacg aagatcatcc     840

aagtctgaat acatacccat acaaatcata caagtaaatg atggaattac tcatataagt     900

atgtacttac ttgtaccgaa ttgccaatga atgtcaatca gaacgcagta tgtacaagta     960
```

-continued

```
ctcgcacaat atcataaggc actcgaatgt tcaagaagtc atcattttgg tgattcgggg   1020
aaatacttga cacctttgtt gatgcaactt gactccataa gtaggaaacc catttaaatg   1080
agtatctgtc tgactcgtca ttgccgcctt tggagtacga ctccaactat gagtgtgctt   1140
ggatcacttt gacgatacat tcttcgttgg aggctgtggg tctgacagct gcgttttcgg   1200
cgcggttggc cgacaacaat atcagctgca acgtcattgc tggctttcat catgatcaca   1260
tttttgtcgg caaaggcgac gcccagagag ccattgacgt tctttctaat ttggaccgat   1320
agccgtatag tccagtctat ctataagttc aactaactcg taactattac cataacatat   1380
acttcactgc cccagataag gttccgataa aaagttctgc agactaaatt tatttcagtc   1440
tcctcttcac caccaaaatg ccctcctacg aagctcgagc taacgtccac aagtccgcct   1500
ttgccgctcg agtgctcaag ctcgtggcag ccaagaaaac caacctgtgt gcttctctgg   1560
atgttaccac caccaaggag ctcattgagc ttgccgataa ggtcggacct tatgtgtgca   1620
tgatcaaaac ccatatcgac atcattgacg acttcaccta cgccggcact gtgctccccc   1680
tcaaggaact tgctcttaag cacggtttct tcctgttcga ggacagaaag ttcgcagata   1740
ttggcaacac tgtcaagcac cagtaccggt gtcaccgaat cgccgagtgg tccgatatca   1800
ccaacgccca cggtgtaccc ggaaccggaa tcattgctgg cctgcgagct ggtgccgagg   1860
aaactgtctc tgaacagaag aaggaggacg tctctgacta cgagaactcc cagtacaagg   1920
agttcctagt cccctctccc aacgagaagc tggccagagg tctgctcatg ctggccgagc   1980
tgtcttgcaa gggctctctg gccactggcg agtactccaa gcagaccatt gagcttgccc   2040
gatccgaccc cgagtttgtg gttggcttca ttgcccagaa ccgacctaag ggcgactctg   2100
aggactggct tattctgacc cccggggtgg gtcttgacga caagggagac gctctcggac   2160
agcagtaccg aactgttgag gatgtcatgt ctaccggaac ggatatcata attgtcggcc   2220
gaggtctgta cggccagaac cgagatccta ttgaggaggc caagcgatac cagaaggctg   2280
gctgggaggc ttaccagaag attaactgtt agaggttaga ctatggatat gtaatttaac   2340
tgtgtatata gagagcgtgc aagtatggag cgcttgttca gcttgtatga tggtcagacg   2400
acctgtctga tcgagtatgt atgatactgc acaacctgtg tatccgcatg atctgtccaa   2460
tggggcatgt tgttgtgttt ctcgatacgg agatgctggg tacagtgcta atacgttgaa   2520
ctacttatac ttatatgagg ctcgaagaaa gctgacttgt gtatgactta attaacgcgg   2580
cgcgccagct gcattaatga atcggccaac gcgcggggag aggcggtttg cgtattgggc   2640
gctcttccgc ttcctcgctc actgactcgc tgcgctcggt cgttcggctg cggcgagcgg   2700
tatcagctca ctcaaaggcg gtaatacggt tatccacaga atcaggggat aacgcaggaa   2760
agaacatgtg agcaaaaggc cagcaaaagg ccaggaaccg taaaaaggcc gcgttgctgg   2820
cgtttttcca taggctccgc ccccctgacg agcatcacaa aaatcgacgc tcaagtcaga   2880
ggtggcgaaa cccgacagga ctataaagat accaggcgtt tccccctgga agctccctcg   2940
tgcgctctcc tgttccgacc ctgccgctta ccggatacct gtccgccttt ctcccttcgg   3000
gaagcgtggc gctttctcat agctcacgct gtaggtatct cagttcggtg taggtcgttc   3060
gctccaagct gggctgtgtg cacgaacccc ccgttcagcc cgaccgctgc gccttatccg   3120
gtaactatcg tcttgagtcc aacccggtaa gacacgactt atcgccactg gcagcagcca   3180
ctggtaacag gattagcaga gcgaggtatg taggcggtgc tacagagttc ttgaagtggt   3240
ggcctaacta cggctacact agaagaacag tatttggtat ctgcgctctg ctgaagccag   3300
```

-continued

```
ttaccttcgg aaaaagagtt ggtagctctt gatccggcaa acaaaccacc gctggtagcg   3360
gtggtttttt tgtttgcaag cagcagatta cgcgcagaaa aaaggatctc aagaagatc    3420
ctttgatctt ttctacgggg tctgacgctc agtggaacga aaactcacgt taagggattt   3480
tggtcatgag attatcaaaa aggatcttca cctagatcct tttaaattaa aaatgaagtt   3540
ttaaatcaat ctaaagtata tatgagtaaa cttggtctga cagttaccaa tgcttaatca   3600
gtgaggcacc tatctcagcg atctgtctat ttcgttcatc catagttgcc tgactccccg   3660
tcgtgtagat aactacgata cgggagggct taccatctgg ccccagtgct gcaatgatac   3720
cgcgagaccc acgctcaccg gctccagatt tatcagcaat aaaccagcca gccggaaggg   3780
ccgagcgcag aagtggtcct gcaactttat ccgcctccat ccagtctatt aattgttgcc   3840
gggaagctag agtaagtagt tcgccagtta atagtttgcg caacgttgtt gccattgcta   3900
caggcatcgt ggtgtcacgc tcgtcgtttg gtatggcttc attcagctcc ggttcccaac   3960
gatcaaggcg agttacatga tcccccatgt tgtgcaaaaa agcggttagc tccttcggtc   4020
ctccgatcgt tgtcagaagt aagttggccg cagtgttatc actcatggtt atggcagcac   4080
tgcataattc tcttactgtc atgccatccg taagatgctt ttctgtgact ggtgagtact   4140
caaccaagtc attctgagaa tagtgtatgc ggcgaccgag ttgctcttgc ccggcgtcaa   4200
tacgggataa taccgcgcca catagcagaa ctttaaaagt gctcatcatt ggaaaacgtt   4260
cttcggggcg aaaactctca aggatcttac cgctgttgag atccagttcg atgtaaccca   4320
ctcgtgcacc caactgatct tcagcatctt ttactttcac cagcgtttct gggtgagcaa   4380
aaacaggaag gcaaaatgcc gcaaaaaagg gaataagggc gacacggaaa tgttgaatac   4440
tcatactctt cctttttcaa tattattgaa gcatttatca gggttattgt ctcatgagcg   4500
gatacatatt tgaatgtatt tagaaaaata aacaaatagg ggttccgcgc acatttcccc   4560
gaaaagtgcc acctgatgcg gtgtgaaata ccgcacagat gcgtaaggag aaaataccgc   4620
atcaggaaat tgtaagcgtt aatattttgt taaaattcgc gttaaatttt tgttaaatca   4680
gctcattttt taaccaatag gccgaaatcg gcaaaatccc ttataaatca aaagaataga   4740
ccgagatagg gttgagtgtt gttccagttt ggaacaagag tccactatta aagaacgtgg   4800
actccaacgt caaagggcga aaaaccgtct atcagggcga tggcccacta cgtgaaccat   4860
caccctaatc aagttttttg gggtcgaggt gccgtaaagc actaaatcgg aaccctaaag   4920
ggagcccccg atttagagct tgacggggaa agccggcgaa cgtggcgaga aaggaaggga   4980
agaaagcgaa aggagcgggc gctagggcgc tggcaagtgt agcggtcacg ctgcgcgtaa   5040
ccaccacacc cgccgcgctt aatgcgccgc tacagggcgc gtccattcgc cattcaggct   5100
gcgcaactgt tgggaagggc gatcggtgcg ggcctcttcg ctattacgcc agctggcgaa   5160
agggggatgt gctgcaaggc gattaagttg ggtaacgcca gggttttccc agtcacgacg   5220
ttgtaaaacg acggccagtg aattgtaata cgactcacta tagggcgaat tgggcccgac   5280
gtcgcatgct cctctgtgac ccgagtgttg ctggacgttc gatgttcgat gctcggcaca   5340
tgccggttcg aacaggaatt atagcgttca tctggagttg gacgcaagca aaaaagcaaa   5400
tgagggagtt atgggagggt tccgagaagt gaaaaatcgg tcaatgggtt agtttgaagt   5460
ctcgttttgt tcgtgttggc gagacaagaa gaatggtata attttcgcac caaaaagaga   5520
ccgtttatcg tggattatgg gggtgtgatg tggggggagg ggggagatgc cccatctctg   5580
gcaaccctat ttgacgatag ttgctggagg cttgacagga cttggtgacg aggggtgttt   5640
gggcgctgga agcgtaattt tcgtcttgaa tgggccgtcg agacttgggg ttcgaccccg   5700
```

actaaatggc gcaccgctag attctctttt ggcgactttc tcgggattct agtcaccccc 5760
gcaatgttcc agcttacggt ttgagacagt acacgactgg ctaggcgagt tgttgaagtc 5820
gtagcgtaga gtgggaggca tgacgtcacg ggacagctgc gtgcaccacg cgagcaggtc 5880
aattgacctc atttgagtgg tgtggcttgg cgttctagcg gtggcggcgt tgtcgagctc 5940
cctctacttg tagtgagatt atgtcgacga gcgggggga cttccattgt gcttgccact 6000
gctagtgcag tacaactgaa agctaaaccg caatcaatcc caaactgcat gtccgcctta 6060
actctgatat gttatcaaga gagtggtgtg gtgaggtgag gtgaggtgac gtggacaagt 6120
tgatggggag ttggggcatt gacaaaaggg aaattgcagg gggattccgc cggctatata 6180
tatcttatgt ctgctcaatt cccagacggc tccacacaaa accaagatac cacaccatca 6240
tggtcacacc gggtacataa ctcccatcca tctcatccca cttgcatggc gaccggagag 6300
agaaagcccg gggagagcac gtcggcgcgg tccccagggc gacaaccaaa acaaaatcac 6360
cgagtgactc cgaaagccgc gttccaacac 6390

<210> SEQ ID NO 5
<211> LENGTH: 14948
<212> TYPE: DNA
<213> ORGANISM: Artificial sequence
<220> FEATURE:
<223> OTHER INFORMATION: Construct pZKADn-SyP298F for expressing YlPDAT, FmD12S, and E389D9eS/EgD8M

<400> SEQUENCE: 5
aaactttttt cacccccagg ctgttattcc ggggaataag gctggtcatg atggggttgg 60
aaagtctaaa tttttgtggg acaaagaaag caggtatcgt gccactaaga aaatagactt 120
ttaggcaccc cagatttttg gaaaccttaa taggagacta cttccgtttc ctaattagga 180
cttccgcgac cccagacaaa gcggcttgga gtaggcctcg tgtccggcct agggcagaaa 240
cagctccgga actcgattga gaagccgtac tctggaaagt ctagaggaag ttccaaggtc 300
gagtctcttc gatataaaag gacgccatcg aagctctgta gttcgatatc aaatactgac 360
aacagtttcc aaacacacaa acacacacac acacacacac acacatacaa ccatggccac 420
acaacctgtg aatcggaagg cgactgtcga gcgggtcgag ccagcagtgg aggtggctga 480
ctccgagtcc gaggccaaga ccgacgtcca cgttcaccac catcatcacc accacaagcg 540
aaaatccgtc aagggcaaga ttctcaactt cttcacccga agtcgacgta tcaccttcgt 600
cctcggcgcc gtggtcggtg tgatagccgc gggatactac gctgcgccac cggagctcag 660
cattgatatc gacgctcttc tcggcgactt gccctcgttc gactttgacg ctctatctct 720
cgacaacttg tcgatggaca gtgtgtcgga ctttgtacaa gacatgaaat cgcggtttcc 780
gaccaagatt ctgcaggagg cggccaagat cgagaagcac cagaaaagcg aacagaaggc 840 tgccccttttt gctgtgggca aggctatgaa gagcgaggga ctcaacgcca agtacccggt 900
ggtgctggtg cccggcgtca tctccacggg actggagagc tggtccctgg agggaaccga 960
ggagtgtccc accgagtcgc acttcagaaa gcgaatgtgg ggctcctggt acatgatccg 1020
agtcatgctg ctggacaagt actgctggct gcagaacctg atgctggaca cagagaccgg 1080
tctagaccct ccccatttca agctgcgagc cgcccaggga tttgcctccg ccgacttctt 1140
tatggcaggc tactggctgt ggaacaagct gctcgagaac ctggctgtta ttggatacga 1200
tacggataca atgtctgctg cggcctacga ctggagactg tcctaccctg atttggagca 1260
ccgagacgga tacttctcca agctcaaagc ttcaatcgaa gagactaagc gtatgacagg 1320

-continued

```
tgagaagaca gttctgacgg gccattcgat gggctcccag gtcatcttct acttcatgaa   1380
gtgggctgag gccgagggat atggaggagg aggtcccaac tgggtcaatg accatattga   1440
atcctttgtc gacatttccg gctccatgct gggtactccc aagaccctgg ttgctcttct   1500
gtctggagaa atgaaggata ccgtgcagct gaacgcgatg gctgtgtatg gactggagca   1560
gttcttctct cgacgagagc gagccgatct gctgcgaaca tggggaggaa ttgcttccat   1620
gattcccaag ggtggtaagg ctatctgggg tgatcattct ggagcccctg atgacgagcc   1680
cggccagaat gtcacctttg gcaacttcat caagttcaag gagtccttga ccgagtactc   1740
tgctaagaac ctcactatgg atgaaaccgt tgacttcctg tattctcagt ctcccgagtg   1800
gtttgtgaac cgaaccgagg gtgcttactc ctttggaatt gccaagactc gaaagcaggt   1860
tgagcagaat gagaagcgac cttctacctg gagcaaccct ctggaagctg ctctccccaa   1920
tgcccccgat ctcaagatct actgcttcta tggagtcggt aaggataccg agcgagccta   1980
ctactaccag gatgagccca atcccgagca gaccaacttg aacgtcagta tcgctggaaa   2040
cgaccctgat ggtgtgctta tgggtcaggg cgatggaacc gtctcccttg tgacccatac   2100
catgtgtcac cgatggaagg acgagaactc caagttcaac cctggtaacg cccaggtcaa   2160
ggttgtggag atgttgcacc agcctgatcg acttgatatt cgaggcggtg ctcagactgc   2220
cgagcatgtg gacattctgg ggcgttctga gttgaacgag atggttctga aggtggctag   2280
tggaaaggga aatgagattg aagagagagt catctccaac attgatgagt gggtgtggaa   2340
gattgatctc ggcagcaatt aggcggccgc atgagaagat aaatatataa atacattgag   2400
atattaaatg cgctagatta gagagcctca tactgctcgg agagaagcca agacgagtac   2460
tcaaagggga ttacaccatc catatccaca gacacaagct ggggaaaggt tctatataca   2520
ctttccggaa taccgtagtt tccgatgtta tcaatggggg cagccaggat ttcaggcact   2580
tcggtgtctc ggggtgaaat ggcgttcttg gcctccatca agtcgtacca tgtcttcatt   2640
tgcctgtcaa agtaaaacag aagcagatga agaatgaact tgaagtgaag gaatttaaat   2700
cacatggaac ctttgctatt tcggggataa ccccctttgc cattgcacga tggacgtggc   2760
aaaagaaaga tcgccctgcg ggatacttta tcatgtggtc acatgctgtg attagaaata   2820
aagaaaaagg tgctttttttg gcgctgtgat taacatctcg tctgccgtgc tctactagtc   2880
gcaatagcaa aaactcgctt aatagtgtgc atagtgcggg gtagcaggat actgaactac   2940
agtacgattt gcttgctact gcttgtagca attaccttta ctgtagggac cacacctcct   3000
ggtttcaatg tctttcctcg cctcgacaaa gcaaaactgt cacccaatca caccttgttc   3060
atattcatta gtgcatccgt taaccttgac atgacacttc tcatactagt gatagggctg   3120
tagttgagac aagttgattc acacggatac atacaaagcc tcagagagca aatgttatat   3180
actcagggac cgaccaatca aaaaaacaca ctcctaataa ccaccatttc catctacgcg   3240
tactcactct gtcagctgcc ccacattgcc caatgcacaa tgcacaatga tgtgtgcaaa   3300
caacgcaatc aaaagtctat ggatgctgac caaactctga tcaccaagtt gcgaacatga   3360
aaaagaagac ctgtgtatat ataagtaagg gggagagccc taactagatc tttcgaaaac   3420
cccccgacct tcaccttcca caaccatgat catcttatac gttttggccg ttgcggtctc   3480
cttcctcatc ttcaagagag tcacctacac catggcctcc acctcggctc tgcccaagca   3540
gaaccctgcc ctccgacgaa ccgtcacttc caccactgtg accgactcgg agtctgctgc   3600
cgtctctccc tccgattctc ccagacactc ggcctcctct acatcgctgt cttccatgtc   3660
```

-continued

```
cgaggtggac attgccaagc ccaagtccga gtacggtgtc atgctggata cctacggcaa   3720
ccagttcgaa gttcccgact tcaccatcaa ggacatctac aacgctattc ccaagcactg   3780
cttcaagcga tctgctctca agggatacgg ctacattctt cgagacattg tcctcctgac   3840
taccactttc agcatctggt acaactttgt gacacccgag tacattccct ccactcctgc   3900
tcgagccggt ctgtgggctg tgtacaccgt tcttcaggga ctcttcggta ctggactgtg   3960
ggtcattgcc cacgagtgtg gacatggtgc tttctccgat tcccgaatca tcaacgacat   4020
tactggctgg gtgcttcact cttccctgct tgttccctac ttcagctggc aaatctccca   4080
ccggaagcat cacaaggcca ctggaaacat ggagcgagac atggtcttcg ttcctcgaac   4140
ccgagagcag caagctactc gactcggcaa gatgacccac gaactcgccc atcttaccga   4200
ggaaactcct gctttcaccc tgctcatgct tgtgcttcag caactggtcg gttggcccaa   4260
ctatctcatt accaacgtta ctggacacaa ctaccatgag cggcagcgag agggtcgagg   4320
caagggaaag cacaacggtc ttggcggtgg agttaaccat ttcgatcccc gatctcctct   4380
gtacgagaac agcgacgcca agctcatcgt gctctccgac attggcattg gtcttatggc   4440
caccgctctg tactttctcg ttcagaagtt cggattctac aacatggcca tctggtactt   4500
cgttccctac ttgtgggtta accactggct cgtcgccatt acctttctgc agcacacaga   4560
tcctactctt ccccactaca ccaacgacga gtggaacttt gtgcgaggtg ccgctgcaac   4620
catcgaccga gagatgggct tcattggacg tcatctgctc cacggcatta tcgagactca   4680
cgtcctgcat cactacgtct cttccattcc cttctacaat gcggacgaag ctaccgaggc   4740
catcaaacct atcatgggca agcactatcg agctgatgtc caggacggtc ctcgaggatt   4800
cattcgagcc atgtaccgat ctgcacgaat gtgccagtgg gttgaaccct ccgctggtgc   4860
cgagggagct ggcaagggtg tcctgttctt tcgaaaccga aacaatgtgg gcactcctcc   4920
cgctgtcatc aagcccgttg cctaagcggc cgcaaataga ttaaggaaga tgttattgtt   4980
gagagtgggt agactagaga tacgccttgg atacgtcacg tgatgcgagg caatgagaca   5040
gacagatttt cgtgtacccg cacgttagta gacgtaggaa acgtcgacga atatgacagt   5100
gtgatccatt ctatacaacg accttgtttt cagactacag tacagtacag taatcaacag   5160
tttcattatc tattcactgt cgaaactcta agctcgcgat agctgcaagt tagtttataa   5220
aaaatggagt ttcaaatttc aagacactct acacgtacga acgcacggta tcggagcatc   5280
ggatacccca cattgagcca acctactttg tagtgtacat actgtagaga agagggacgc   5340
ttcgacatga ttggccgatg tgggcatgta gaaacacgat atatggtgct tactaatgga   5400
cacttgcaca accatttctc ttctagggta acctcgacag tgacagccgt tttttctgcg   5460
ctagcgtgtc gtcgtatttt tggtttcgac atgttaagat ttgtggggca atcgagcgac   5520
attaaggtgc atcggatcat cggcccaagg gagagtcact ggagtctcgt agggtggagg   5580
aaaagagcaa tttgggacga tttggggcga tttgaagacg gattggggca ggtgtttgtc   5640
acgtgactgt ggtattacta ttactaatcg tcattgttcg aaagtcctgt caattgtatc   5700
actttggtgg gtctaccaaa acactggtca aatctacgcc acatgaaaat ataaagtttc   5760
acattagcca cattgagggg tacccttagt tggaatctac aaggagggat gcagtgaaaa   5820
atgttccttt gatccttcag agatgaaaat gccattgacc aatcacagcg ggtttaaaga   5880
gtggcgaaaa gagccccttt tttgcaccgg ttggcccagc agccacgtga ctggcccctt   5940
ccccatccca ctcaactgtt gaggaggtgg gatgccaaga tgcaccgtca atgtacttcc   6000
gtgtatcctt ctgcaattga tccgagatag gcgcgccagc tgcattaatg aatcggccaa   6060
```

cgcgcgggga gaggcggttt gcgtattggg cgctcttccg cttcctcgct cactgactcg 6120
ctgcgctcgg tcgttcggct gcggcgagcg gtatcagctc actcaaaggc ggtaatacgg 6180
ttatccacag aatcagggga taacgcagga aagaacatgt gagcaaaagg ccagcaaaag 6240
gccaggaacc gtaaaaaggc cgcgttgctg gcgtttttcc ataggctccg cccccctgac 6300
gagcatcaca aaaatcgacg ctcaagtcag aggtggcgaa acccgacagg actataaaga 6360
taccaggcgt ttccccctgg aagctccctc gtgcgctctc ctgttccgac cctgccgctt 6420
accggatacc tgtccgcctt tctcccttcg ggaagcgtgg cgctttctca tagctcacgc 6480
tgtaggtatc tcagttcggt gtaggtcgtt cgctccaagc tgggctgtgt gcacgaaccc 6540
cccgttcagc ccgaccgctg cgccttatcc ggtaactatc gtcttgagtc caacccggta 6600
agacacgact tatcgccact ggcagcagcc actggtaaca ggattagcag agcgaggtat 6660
gtaggcggtg ctacagagtt cttgaagtgg tggcctaact acggctacac tagaagaaca 6720
gtatttggta tctgcgctct gctgaagcca gttaccttcg gaaaaagagt tggtagctct 6780
tgatccggca aacaaaccac cgctggtagc ggtggttttt ttgtttgcaa gcagcagatt 6840
acgcgcagaa aaaaaggatc tcaagaagat cctttgatct tttctacggg gtctgacgct 6900
cagtggaacg aaaactcacg ttaagggatt ttggtcatga gattatcaaa aaggatcttc 6960
acctagatcc ttttaaatta aaaatgaagt tttaaatcaa tctaaagtat atatgagtaa 7020
acttggtctg acagttacca atgcttaatc agtgaggcac ctatctcagc gatctgtcta 7080
tttcgttcat ccatagttgc ctgactcccc gtcgtgtaga taactacgat acgggagggc 7140
ttaccatctg gccccagtgc tgcaatgata ccgcgagacc cacgctcacc ggctccagat 7200
ttatcagcaa taaaccagcc agccggaagg gccgagcgca gaagtggtcc tgcaacttta 7260
tccgcctcca tccagtctat taattgttgc cgggaagcta gagtaagtag ttcgccagtt 7320
aatagtttgc gcaacgttgt tgccattgct acaggcatcg tggtgtcacg ctcgtcgttt 7380
ggtatggctt cattcagctc cggttcccaa cgatcaaggc gagttacatg atcccccatg 7440
ttgtgcaaaa aagcggttag ctccttcggt cctccgatcg ttgtcagaag taagttggcc 7500
gcagtgttat cactcatggt tatggcagca ctgcataatt ctcttactgt catgccatcc 7560
gtaagatgct tttctgtgac tggtgagtac tcaaccaagt cattctgaga atagtgtatg 7620
cggcgaccga gttgctcttg cccggcgtca atacgggata ataccgcgcc acatagcaga 7680
actttaaaag tgctcatcat tggaaaacgt tcttcggggc gaaaactctc aaggatctta 7740
ccgctgttga gatccagttc gatgtaaccc actcgtgcac ccaactgatc ttcagcatct 7800
tttactttca ccagcgtttc tgggtgagca aaaacaggaa ggcaaaatgc cgcaaaaaag 7860
ggaataaggg cgacacggaa atgttgaata ctcatactct tcctttttca atattattga 7920
agcatttatc agggttattg tctcatgagc ggatacatat ttgaatgtat ttagaaaaat 7980
aaacaaatag gggttccgcg cacatttccc cgaaaagtgc cacctgatgc ggtgtgaaat 8040
accgcacaga tgcgtaagga gaaaataccg catcaggaaa ttgtaagcgt taatattttg 8100
ttaaaattcg cgttaaattt ttgttaaatc agctcatttt ttaaccaata ggccgaaatc 8160
ggcaaaatcc cttataaatc aaaagaatag accgagatag ggttgagtgt tgttccagtt 8220
tggaacaaga gtccactatt aaagaacgtg gactccaacg tcaaagggcg aaaaaccgtc 8280
tatcagggcg atggcccact acgtgaacca tcaccctaat caagtttttt ggggtcgagg 8340
tgccgtaaag cactaaatcg gaaccctaaa gggagccccc gatttagagc ttgacgggga 8400

-continued

```
aagccggcga acgtggcgag aaaggaaggg aagaaagcga aaggagcggg cgctagggcg   8460
ctggcaagtg tagcggtcac gctgcgcgta accaccacac ccgccgcgct taatgcgccg   8520
ctacagggcg cgtccattcg ccattcaggc tgcgcaactg ttgggaaggg cgatcggtgc   8580
gggcctcttc gctattacgc cagctggcga aaggggggatg tgctgcaagg cgattaagtt   8640
gggtaacgcc agggttttcc cagtcacgac gttgtaaaac gacggccagt gaattgtaat   8700
acgactcact atagggcgaa ttgggcccga cgtcgcatgc tacaagtatc gcaccatact   8760
tttgctgacg gcgcgccttc ttgcagtgat ataatcggtt tcttggagct gatggggtga   8820
gcatcataca agtatgagta cgagaagtcg cacttgtact ccaagtacaa atgcccggaa   8880
tggcagacac acaagtccta cgggtgttca gagactactg actggagatt gcaactacaa   8940
gtactgtaca cacagtacaa cacacaagtt aactcatcat tcataattat cataaactag   9000
acggccaaaa agtcgtggcc gctcctcagc gtcaatagcc gcgcttactt ggagcagtcc   9060
agaacgtatc gaccggcaat cttgccctcc tccatgagct tgtagacgga ttcgagctcg   9120
gagagaccaa caataatgat gggggacttg accagtcctc gggcaaagaa ctcaatggcc   9180
tcctgggagt cggctcggtt tccgacgtaa gagcccttga tctgaataga tcgagcaacc   9240
tgctggaaga tgggcgactt gcagacggca ccggcgggca gaccgaccag aacaacggtt   9300
cccagggttc gcacgtactc aacagactgg ttgacggcaa actcggagac agacacgttg   9360
atgacggcgt ggggtccgcc cttggtggcc tcctggacgt ccttgaccag atccttggac   9420
ttggcaaagt cgatgaagac ctcggcgccg agctccttgc acatcttctc cttgtcagcg   9480
ccagtgtcaa tggccagcac tcggttaatt aagttgcgac acatgtcttg atagtatctt   9540
gaattctctc tcttgagctt ttccataaca agttcttctg cctccaggaa gtccatcggt   9600
ggtttgatca tggttttggt gtagtggtag tgcagtggtg gtattgtgac tggggatgta   9660
gttgagaata agtcatacac aagtcagctt tcttcgagcc tcatataagt ataagtagtt   9720
caacgtatta gcactgtacc cagcatctcc gtatcgagaa acacaacaac atgccccatt   9780
ggacagatca tgcggataca caggttgtgc agtatcatac atactcgatc agacaggtcg   9840
tctgaccatc atacaagctg aacaagcgct ccatacttgc acgctctcta tatacacagt   9900
taaattacat atccatagtc taacctctaa cagttaatct tctggtaagc ctcccagcca   9960
gccttctggt atcgcttggc ctcctcaata ggatctcggt tctggccgta cagacctcgg  10020
ccgacaatta tgatatccgt tccggtagac atgacatcct caacagttcg gtactgctgt  10080
ccgagagcgt ctcccttgtc gtcaagaccc accccggggg tcagaataag ccagtcctca  10140
gagtcgccct taggtcggtt ctgggcaatg aagccaacca caaactcggg gtcggatcgg  10200
gcaagctcaa tggtctgctt ggagtactcg ccagtggcca gagagccctt gcaagacagc  10260
tcggccagca tgagcagacc tctggccagc ttctcgttgg gagaggggac taggaactcc  10320
ttgtactggg agttctcgta gtcagagacg tcctccttct tctgttcaga gacagtttcc  10380
tcggcaccag ctcgcaggcc agcaatgatt ccggttccgg gtacaccgtg ggcgttggtg  10440
atatcggacc actcggcgat tcggtgacac cggtactggt gcttgacagt gttgccaata  10500
tctgcgaact ttctgtcctc gaacaggaag aaaccgtgct taagagcaag ttccttgagg  10560
gggagcacag tgccggcgta ggtgaagtcg tcaatgatgt cgatatgggt tttgatcatg  10620
cacacataag gtccgacctt atcggcaagc tcaatgagct ccttggtggt ggtaacatcc  10680
agagaagcac acaggttggt tttcttggct gccacgagct tgagcactcg agcggcaaag  10740
gcggacttgt ggacgttagc tcgagcttcg taggagggca ttttggtggt gaagaggaga  10800
```

ctgaaataaa tttagtctgc agaacttttt atcggaacct tatctggggc agtgaagtat 10860
atgttatggt aatagttacg agttagttga acttatagat agactggact atacggctat 10920
cggtccaaat tagaaagaac gtcaatggct ctctgggcgt cgcctttgcc gacaaaaatg 10980
tgatcatgat gaaagccagc aatgacgttg cagctgatat tgttgtcggc caaccgcgcc 11040
gaaaacgcag ctgtcagacc cacagcctcc aacgaagaat gtatcgtcaa agtgatccaa 11100
gcacactcat agttggagtc gtactccaaa ggcggcaatg acgagtcaga cagatactcg 11160
tcgacctttt ccttgggaac caccaccgtc agcccttctg actcacgtat tgtagccacc 11220
gacacaggca acagtccgtg gatagcagaa tatgtcttgt cggtccattt ctcaccaact 11280
ttaggcgtca agtgaatgtt gcagaagaag tatgtgcctt cattgagaat cggtgttgct 11340
gatttcaata aagtcttgag atcagtttgg ccagtcatgt tgtgggggt aattggattg 11400
agttatcgcc tacagtctgt acaggtatac tcgctgccca ctttatactt tttgattccg 11460
ctgcacttga agcaatgtcg tttaccaaaa gtgagaatgc tccacagaac acaccccagg 11520
gtatggttga gcaaaaaata aacactccga tacggggaat cgaaccccgg tctccacggt 11580
tctcaagaag tattcttgat gagagcgtat cgatattctg aaactagagc catctcaaca 11640
caacagtctc tttgtgtagc tacttgtacc ctttttctct tcctctctcc agccagacat 11700
ctttgctagc gcctataatg taacccatca agacatgcac aggagatgct taatcggagt 11760
gtgtggtctg taggggagat cgagagagac tgcaattgac agagagatcg aagttggaat 11820
gagagagact gaaaattaag cgagcttggg tgtttgcccc tcccctcaca ccctcggata 11880
ctgtacctac atatccaggc cggtttggca cggcatcaaa agcctcctac aagaatgtat 11940
atgcgactct tctacaagta gatttccgcg cttgcaccaa cggctacgcc caagacgggg 12000
ctcgtacccg tccgtctatg gttcagccgc caacgaaaaa aaaaaaaagg atggctgtaa 12060
ttttattatg cttctgtgtt tgtgtttgtc ggtccgtttt tgcttttttc acccccaggc 12120
tgttattccg gggaataagg ctggtcatga tggggttgga aagtctaaat ttttgtggga 12180
caaagaaagc aggtatcgtg ccactaagaa aatagacttt taggcacccc agatttttgg 12240
aaaccttaat aggagactac ttccgtttcc taattaggac ttccgcgacc ccagacaaag 12300
cggcttggag taggcctcgt gtccggccta gggcagaaac agctccggaa ctcgattgag 12360
aagccgtact ctggaaagtc tagaggaagt tccaaggtcg agtctcttcg atataaaagg 12420
acgccatcga agctctgtag ttcgatatca aatactgaca acagtttcca aacacacaaa 12480
cacacacaca cacacacaca cacatacaac catggctgcc gtcatcgagg tggccaacga 12540
gttcgtcgct atcactgccg agacccttcc caaggtggac tatcagcgac tctggcgaga 12600
catctactcc tgcgagctcc tgtacttctc cattgctttc gtcatcctca agtttaccct 12660
tggcgagctc tcggattctg gcaaaaagat tctgcgagtg ctgttcaagt ggtacaacct 12720
cttcatgtcc gtcttttcgc tggtgtcctt cctctgtatg ggttacgcca tctacaccgt 12780
tggactgtac tccaacgaat gcgacagagc tttcgacaac agcttgttcc gatttgccac 12840
caaggtcttc tactattcca agtttctgga gtacatcgac tctttctacc ttcccctcat 12900
ggccaagcct ctgtcctttc tgcagttctt tcatcacttg ggagctccta tggacatgtg 12960
gctcttcgtg cagtactctg gcgaatccat ttggatcttt gtgttcctga acggattcat 13020
tcactttgtc atgtacggct actattggac acggctgatg aagttcaact ttcccatgcc 13080
caagcagctc attaccgcaa tgcagatcac ccagttcaac gttggcttct acctcgtgtg 13140

-continued

```
gtggtacaag gacattccct gttaccgaaa ggatcccatg cgaatgctgg cctggatctt  13200
caactactgg tacgtcggta ccgttcttct gctcttcatc aacttctttg tcaagtccta  13260
cgtgtttccc aagcctaaga ctgccgacaa aaaggtccag ggcgccggtc ccgctcgacc  13320
tgccggactt cctcccgcta cctactacga ctctctggcc gtcatgggat ccgtgaaggc  13380
ttctcgacag gctctgcccc tcgtcatcga cggaaaggtg tacgacgtct ccgcttgggt  13440
gaacttccac cctggtggag ctgaaatcat tgagaactac cagggacgag atgctactga  13500
cgccttcatg gttatgcact ctcaggaagc cttcgacaag ctcaagcgaa tgcccaagat  13560
caaccaggct tccgagctgc ctccccaggc tgccgtcaac gaagctcagg aggatttccg  13620
aaagctccga gaagagctga tcgccactgg catgtttgac gcctctcccc tctggtactc  13680
gtacaagatc ttgaccaccc tgggtcttgg cgtgcttgcc ttcttcatgc tggtccagta  13740
ccacctgtac ttcattggtg ctctcgtgct cggtatgcac taccagcaaa tgggatggct  13800
gtctcatgac atctgccacc accagacctt caagaaccga aactggaata acgtcctggg  13860
tctggtcttt ggcaacggac tccagggctt ctccgtgacc tggtggaagg acagacacaa  13920
cgcccatcat tctgctacca acgttcaggg tcacgatccc gacattgata acctgcctct  13980
gctcgcctgg tccgaggacg atgtcactcg agcttctccc atctcccgaa agctcattca  14040
gttccaacag tactatttcc tggtcatctg tattctcctg cgattcatct ggtgtttcca  14100
gtctgtgctg accgttcgat ccctcaagga ccgagacaac cagttctacc gatctcagta  14160
caagaaagag gccattggac tcgctctgca ctggactctc aagaccctgt tccacctctt  14220
ctttatgccc tccatcctga cctcgatgct ggtgttcttt gtttccgagc tcgtcggtgg  14280
cttcggaatt gccatcgtgg tcttcatgaa ccactaccct ctggagaaga tcggtgattc  14340
cgtctgggac ggacatggct tctctgtggg tcagatccat gagaccatga acattcgacg  14400
aggcatcatt actgactggt tctttggagg cctgaactac cagatcgagc accatctctg  14460
gcccaccctg cctcgacaca acctcactgc cgtttcctac caggtggaac agctgtgcca  14520
gaagcacaac ctcccctacc gaaaccctct gccccatgaa ggtctcgtca tcctgctccg  14580
atacctgtcc cagttcgctc gaatggccga gaagcagccc ggtgccaagg ctcagtaagc  14640
ggccgcacag cgaatggatc atcagcaact agctggtgca accgatacga tgagaacgga  14700
aaacaacata cttggtgcgc aacaaagacc aacaagtgag catcttcgat tctgaaagtc  14760
cgataagacg agggtatata tttaattgta ttgattagtt ttgagtattg tgtgagtagt  14820
cataaccaag atcaagttac agtaaatata caatacatag tcttcttgtt actacttgta  14880
gcagatatat acaattatat tcaatgatta taggtacaaa atataaatag gggaatgtac  14940
aatggttt                                                           14948
```

<210> SEQ ID NO 6
<211> LENGTH: 300
<212> TYPE: DNA
<213> ORGANISM: Yarrowia lipolytica

<400> SEQUENCE: 6

```
aaatagatta aggaagatgt tattgttgag agtgggtaga ctagagatac gccttggata     60
cgtcacgtga tgcgaggcaa tgagacagac agattttcgt gtacccgcac gttagtagac    120
gtaggaaacg tcgacgaata tgacagtgtg atccattcta tacaacgacc ttgttttcag    180
actacagtac agtacagtaa tcaacagttt cattatctat tcactgtcga aactctaagc    240
tcgcgatagc tgcaagttag tttataaaaa atggagtttc aaatttcaag acactctaca    300
```

<210> SEQ ID NO 7
<211> LENGTH: 300
<212> TYPE: DNA
<213> ORGANISM: Yarrowia lipolytica

<400> SEQUENCE: 7
acagcgaatg gatcatcagc aactagctgg tgcaaccgat acgatgagaa cggaaaacaa 60
catacttggt gcgcaacaaa gaccaacaag tgagcatctt cgattctgaa agtccgataa 120
gacgagggta tatatttaat tgtattgatt agttttgagt attgtgtgag tagtcataac 180
caagatcaag ttacagtaaa tatacaatac atagtcttct tgttactact tgtagcagat 240
atatacaatt atattcaatg attataggta caaaatataa atagggggaat gtacaatggt 300

<210> SEQ ID NO 8
<211> LENGTH: 2071
<212> TYPE: DNA
<213> ORGANISM: Yarrowia lipolytica

<400> SEQUENCE: 8
tgacgagggg tgtttgggcg ctggaagcgt aattttcgtc ttgaatgggc cgtcgagact 60
tggggttcga ccccgactaa atggcgcacc gctagattct cttttggcga ctttctcggg 120
attctagtca cccccgcaat gttccagctt acggtttgag acagtacacg actggctagg 180
cgagttgttg aagtcgtagc gtagagtggg aggcatgacg tcacgggaca gctgcgtgca 240
ccacgcgagc aggtcaattg acctcatttg agtggtgtgg cttggcgttc tagcggtggc 300
ggcgttgtcg agctccctct acttgtagtg agattatgtc gacgagcggg ggggacttcc 360
attgtgcttg ccactgctag tgcagtacaa ctgaaagcta aaccgcaatc aatcccaaac 420
tgcatgtccg ccttaactct gatatgttat caagagagtg gtgtggtgag gtgaggtgag 480
gtgacgtgga caagttgatg gggagttggg gcattgacaa aagggaaatt gcagggggat 540
tccgccggct atatatatct tatgtctgct caattcccag acggctccac acaaaaccaa 600
gataccacac catcatggtc acaccgggta cataactccc atccatctca tcccacttgc 660
atggcgaccg gagagagaaa gcccggggag agcacgtcgg cgcggtcccc agggcgacaa 720
ccaaaacaaa atcaccgagt gactccgaaa gccgcgttcc aacacccccc caaaatcccc 780
ccctcaaaca cgtcagccac ctgtcccccg aaaattaact tcactgacat ggcgcagcta 840
ttaaggctaa agtgaatgca tggctcatct ttgtttgctg gttgctactg tgactgaggt 900
aaaaaccctc gctcccaagt ctatatatac ctgggtgtgc tccctcgaac agacccgtca 960
cagtaaaact actacctcca tacacagcac cacctcaatc atgtctggac cttccaccct 1020
cgccacggga ctgcaccctc tccccacaga gaccccaaag ttccccacca acatcatgga 1080
ccgattctcc ctcaagggta aggttgcctc cgtcaccggc tcctcgtcag gtatcggcta 1140
ctgcgtggcc gaggcctacg cccaggccgg tgccgacgtg gccatctggt acaactccca 1200
ccccgccgac gcaaaggctg agcacctcgc taagacctac ggcgtcaagg ccaaggccta 1260
caagtgccct gtcaccgacg ccgccgccgt ggagtccacc atccagcaga tcgagaagga 1320
ctttggcacc attgacatct tcgtcgccaa cgctggtgtc ccctggaccg ccggccccat 1380
gatcgacgtg cccgacaaca aggagtggga caaggtcatc aacctggatc tcaacggtgc 1440
ctactactgc gccaagtacg ccggccagat cttcaagaag aagggcaagg gatccttcat 1500
cttcaccgcc tccatgtccg gccacattgt caacatcccc cagatgcagg cctgctacaa 1560

```
cgccgccaag gccgctctgc tgcacctgtc tcgatcgctg gccgtcgagt gggccggctt   1620

tgcccgatgc aacacagtct cccctggcta catggccacc gagatctccg actttgtccc   1680

caaggagacc aaggagaagt ggtggcagct cattcccatg ggccgagagg gagacccctc   1740

cgagctctac ctacctctac cttgcctctg atgctgccac ctacaccact ggtgccgaca   1800

ttatcgtcga tggtggctac tgcgctcctt agaggatgta tatagataat gattgtttat   1860

gattagacat tgattgagtg tagttggaca ttagcagtca gataggcaac gaagatcatc   1920

caagtctgaa tacataccca tacaaatcat acaagtaaat gatggaatta ctcatataag   1980

tatgtactta cttgtaccga attgccaatg aatgtcaatc agaacgcagt atgtacaagt   2040

actcgcacaa tatcataagg cactcgaatg t                                  2071


<210> SEQ ID NO 9
<211> LENGTH: 771
<212> TYPE: DNA
<213> ORGANISM: Yarrowia lipolytica

<400> SEQUENCE: 9

atgtctggac cttccaccct cgccacggga ctgcaccctc tccccacaga gaccccaaag     60

ttccccacca acatcatgga ccgattctcc ctcaagggta aggttgcctc cgtcaccggc    120

tcctcgtcag gtatcggcta ctgcgtggcc gaggcctacg cccaggccgg tgccgacgtg    180

gccatctggt acaactccca ccccgccgac gcaaaggctg agcacctcgc taagacctac    240

ggcgtcaagg ccaaggccta caagtgccct gtcaccgacg ccgccgccgt ggagtccacc    300

atccagcaga tcgagaagga ctttggcacc attgacatct tcgtcgccaa cgctggtgtc    360

ccctggaccg ccggccccat gatcgacgtg cccgacaaca aggagtggga caaggtcatc    420

aacctggatc tcaacggtgc ctactactgc gccaagtacg ccggccagat cttcaagaag    480

aagggcaagg gatccttcat cttcaccgcc tccatgtccg gccacattgt caacatcccc    540

cagatgcagg cctgctacaa cgccgccaag gccgctctgc tgcacctgtc tcgatcgctg    600

gccgtcgagt gggccggctt tgcccgatgc aacacagtct cccctggcta catggccacc    660

gagatctccg actttgtccc caaggagacc aaggagaagt ggtggcagct cattcccatg    720

ggccgagagg gagacccctc cgagctctac ctacctctac cttgcctctg a             771


<210> SEQ ID NO 10
<211> LENGTH: 256
<212> TYPE: PRT
<213> ORGANISM: Yarrowia lipolytica

<400> SEQUENCE: 10

Met Ser Gly Pro Ser Thr Leu Ala Thr Gly Leu His Pro Leu Pro Thr
1               5                   10                  15

Glu Thr Pro Lys Phe Pro Thr Asn Ile Met Asp Arg Phe Ser Leu Lys
            20                  25                  30

Gly Lys Val Ala Ser Val Thr Gly Ser Ser Ser Gly Ile Gly Tyr Cys
        35                  40                  45

Val Ala Glu Ala Tyr Ala Gln Ala Gly Ala Asp Val Ala Ile Trp Tyr
    50                  55                  60

Asn Ser His Pro Ala Asp Ala Lys Ala Glu His Leu Ala Lys Thr Tyr
65                  70                  75                  80

Gly Val Lys Ala Lys Ala Tyr Lys Cys Pro Val Thr Asp Ala Ala Ala
                85                  90                  95

Val Glu Ser Thr Ile Gln Gln Ile Glu Lys Asp Phe Gly Thr Ile Asp
```

-continued

```
            100                 105                 110

Ile Phe Val Ala Asn Ala Gly Val Pro Trp Thr Ala Gly Pro Met Ile
        115                 120                 125

Asp Val Pro Asp Asn Lys Glu Trp Asp Lys Val Ile Asn Leu Asp Leu
    130                 135                 140

Asn Gly Ala Tyr Tyr Cys Ala Lys Tyr Ala Gly Gln Ile Phe Lys Lys
145                 150                 155                 160

Lys Gly Lys Gly Ser Phe Ile Phe Thr Ala Ser Met Ser Gly His Ile
                165                 170                 175

Val Asn Ile Pro Gln Met Gln Ala Cys Tyr Asn Ala Ala Lys Ala Ala
            180                 185                 190

Leu Leu His Leu Ser Arg Ser Leu Ala Val Glu Trp Ala Gly Phe Ala
        195                 200                 205

Arg Cys Asn Thr Val Ser Pro Gly Tyr Met Ala Thr Glu Ile Ser Asp
    210                 215                 220

Phe Val Pro Lys Glu Thr Lys Glu Lys Trp Trp Gln Leu Ile Pro Met
225                 230                 235                 240

Gly Arg Glu Gly Asp Pro Ser Glu Leu Tyr Leu Pro Leu Pro Cys Leu
                245                 250                 255


<210> SEQ ID NO 11
<211> LENGTH: 2771
<212> TYPE: DNA
<213> ORGANISM: Yarrowia lipolytica

<400> SEQUENCE: 11

tgacgagggg tgtttgggcg ctggaagcgt aattttcgtc ttgaatgggc cgtcgagact      60

tggggttcga ccccgactaa atggcgcacc gctagattct cttttggcga ctttctcggg     120

attctagtca cccccgcaat gttccagctt acggtttgag acagtacacg actggctagg     180

cgagttgttg aagtcgtagc gtagagtggg aggcatgacg tcacgggaca gctgcgtgca     240

ccacgcgagc aggtcaattg acctcatttg agtggtgtgg cttggcgttc tagcggtggc     300

ggcgttgtcg agctccctct acttgtagtg agattatgtc gacgagcggg ggggacttcc     360

attgtgcttg ccactgctag tgcagtacaa ctgaaagcta aaccgcaatc aatcccaaac     420

tgcatgtccg ccttaactct gatatgttat caagagagtg gtgtggtgag gtgaggtgag     480

gtgacgtgga caagttgatg gggagttggg gcattgacaa aagggaaatt gcagggggat     540

tccgccggct atatatatct tatgtctgct caattcccag acggctccac acaaaaccaa     600

gataccacac catcatggtc acaccgggta cataactccc atccatctca tcccacttgc     660

atggcgaccg gagagagaaa gcccggggag agcacgtcgg cgcggtcccc agggcgacaa     720

ccaaaacaaa atcaccgagt gactccgaaa gccgcgttcc aacacccccc caaaatcccc     780

ccctcaaaca cgtcagccac ctgtcccccg aaaattaact tcactgacat ggcgcagcta     840

ttaaggctaa agtgaatgca tggctcatct ttgtttgctg gttgctactg tgactgaggt     900

aaaaaccctc gctcccaagt ctatatatac ctgggtgtgc tccctcgaac agacccgtca     960

cagtaaaact actacctcca tacacagcac cacctcaatc atgtctggac cttccaccct    1020

cgccacggga ctgcaccctc tccccacaga gaccccaaag ttccccacca acatcatgga    1080

ccgattctcc ctcaagggta aggttgcctc cgtcaccggc tcctcgtcag gtatcggcta    1140

ctgcgtggcc gaggcctacg cccaggccgg tgccgacgtg gccatctggt acaactccca    1200

ccccgccgac gcaaaggctg agcacctcgc taagacctac ggcgtcaagg ccaaggccta    1260
```

-continued

```
caagtgccct gtcaccgacg ccgccgccgt ggagtccacc atccagcaga tcgagaagga   1320
ctttggcacc attgacatct tcgtcgccaa cgctggtgtc ccctggaccg ccggccccat   1380
gatcgacgtg cccgacaaca aggagtggga caaggtcatc aacctggatc tcaacggtgc   1440
ctactactgc gccaagtacg ccggccagat cttcaagaag aagggcaagg gatccttcat   1500
cttcaccgcc tccatgtccg gccacattgt caacatcccc cagatgcagg cctgctacaa   1560
cgccgccaag gccgctctgc tgcacctgtc tcgatcgctg gccgtcgagt gggccggctt   1620
tgcccgatgc aacacagtct cccctggcta catggccacc gagatctccg actttgtccc   1680
caaggagacc aaggagaagt ggtggcagct cattcccatg ggccgagagg gagacccctc   1740
cgagctctac ctacctctac cttgcctctg atgctgccac ctacaccact ggtgccgaca   1800
ttatcgtcga tggtggctac tgcgctcctt agaggatgta tatagataat gattgtttat   1860
gattagacat tgattgagtg tagttggaca ttagcagtca gataggcaac gaagatcatc   1920
caagtctgaa tacataccca tacaaatcat acaagtaaat gatggaatta ctcatataag   1980
tatgtactta cttgtaccga attgccaatg aatgtcaatc agaacgcagt atgtacaagt   2040
actcgcacaa tatcataagg cactcgaatg ttcaagaagt catcattttg gtgattcggg   2100
gaaatacttg acacctttgt tgatgcaact tgactccata agtaggaaac ccatagtata   2160
tctttttgtc gctttatatt cacctgttcc cttctttcta tggactataa gttaatttag   2220
ttgaccttgt caagtaatac ctcaacaaac tgtaaagaaa taggagatta ttgcttttgg   2280
tttttgagaa gagatctgga tagcaccaca caaataatgc gtcaaaatca gttcaaaatc   2340
caacccacag aacaaccaac actccccgaa ccgctcataa cctgtatagg atgctgctcc   2400
actcacacct cttgtccagc cctaacctgc gatctaggtt ggggaaattt tgtatgcagg   2460
aaaaatatat gcaagatttg ggattttatt tgtgttcatc aaccacgtcg atttacacag   2520
ctatcatggt ccgagaacga tctggaacgg tggcgtacac gcccaaaaag cagcagaagc   2580
ctctggtgga cgacgcccac ttgtcctctg ctgaggagga cgatttcaag accccagaga   2640
gtgcaaagag caagaagcct gaagcgtcac aacaggagcc ggcggtgtca gaaacgccag   2700
tcaagggcaa ggccaagaag atcacctttg acgaggacgg aatgagtgcc gagcccatcg   2760
ttgagaagaa a                                                         2771
```

```
<210> SEQ ID NO 12
<211> LENGTH: 1434
<212> TYPE: DNA
<213> ORGANISM: Artificial sequence
<220> FEATURE:
<223> OTHER INFORMATION: Fusarium moniliforme delta-12 desaturase
      codon-omptimized for expression in Y. lipolytica

<400> SEQUENCE: 12

atggcctcca cctcggctct gcccaagcag aaccctgccc tccgacgaac cgtcacttcc     60
accactgtga ccgactcgga gtctgctgcc gtctctccct ccgattctcc cagacactcg    120
gcctcctcta catcgctgtc ttccatgtcc gaggtggaca ttgccaagcc caagtccgag    180
tacggtgtca tgctggatac ctacggcaac cagttcgaag ttcccgactt caccatcaag    240
gacatctaca acgctattcc caagcactgc ttcaagcgat ctgctctcaa gggatacggc    300
tacattcttc gagacattgt cctcctgact accactttca gcatctggta caactttgtg    360
acacccgagt acattccctc cactcctgct cgagccggtc tgtgggctgt gtacaccgtt    420
cttcagggac tcttcggtac tggactgtgg gtcattgccc acgagtgtgg acatggtgct    480
```

-continued

```
ttctccgatt cccgaatcat caacgacatt actggctggg tgcttcactc ttccctgctt    540

gttccctact tcagctggca aatctcccac cggaagcatc acaaggccac tggaaacatg    600

gagcgagaca tggtcttcgt tcctcgaacc cgagagcagc aagctactcg actcggcaag    660

atgacccacg aactcgccca tcttaccgag gaaactcctg ctttcaccct gctcatgctt    720

gtgcttcagc aactggtcgg ttggcccaac tatctcatta ccaacgttac tggacacaac    780

taccatgagc ggcagcgaga gggtcgaggc aagggaaagc acaacggtct tggcggtgga    840

gttaaccatt tcgatccccg atctcctctg tacgagaaca gcgacgccaa gctcatcgtg    900

ctctccgaca ttggcattgg tcttatggcc accgctctgt actttctcgt tcagaagttc    960

ggattctaca acatggccat ctggtacttc gttccctact tgtgggttaa ccactggctc   1020

gtcgccatta cctttctgca gcacacagat cctactcttc cccactacac caacgacgag   1080

tggaactttg tgcgaggtgc cgctgcaacc atcgaccgag agatgggctt cattggacgt   1140

catctgctcc acggcattat cgagactcac gtcctgcatc actacgtctc ttccattccc   1200

ttctacaatg cggacgaagc taccgaggcc atcaaaccta tcatgggcaa gcactatcga   1260

gctgatgtcc aggacggtcc tcgaggattc attcgagcca tgtaccgatc tgcacgaatg   1320

tgccagtggg ttgaaccctc cgctggtgcc gagggagctg gcaagggtgt cctgttcttt   1380

cgaaaccgaa acaatgtggg cactcctccc gctgtcatca agcccgttgc ctaa          1434


<210> SEQ ID NO 13
<211> LENGTH: 477
<212> TYPE: PRT
<213> ORGANISM: Fusarium moniliforme

<400> SEQUENCE: 13

Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205
```

-continued

```
Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475
```

<210> SEQ ID NO 14
<211> LENGTH: 1950
<212> TYPE: DNA
<213> ORGANISM: Artificial sequence
<220> FEATURE:
<223> OTHER INFORMATION: Y. lipolytica PDAT, but with an added alanine at amino acid position 2

<400> SEQUENCE: 14

```
atggccacac aacctgtgaa tcggaaggcg actgtcgagc gggtcgagcc agcagtggag      60

gtggctgact ccgagtccga ggccaagacc gacgtccacg ttcaccacca tcatcaccac     120

cacaagcgaa aatccgtcaa gggcaagatt ctcaacttct tcacccgaag tcgacgtatc     180

accttcgtcc tcggcgccgt ggtcggtgtg atagccgcgg gatactacgc tgcgccaccg     240

gagctcagca ttgatatcga cgctcttctc ggcgacttgc cctcgttcga ctttgacgct     300

ctatctctcg acaacttgtc gatggacagt gtgtcggact ttgtacaaga catgaaatcg     360

cggtttccga ccaagattct gcaggaggcg gccaagatcg agaagcacca gaaaagcgaa     420

cagaaggctg ccccttttgc tgtgggcaag gctatgaaga gcgagggact caacgccaag     480

tacccggtgg tgctggtgcc cggcgtcatc tccacgggac tggagagctg gtccctggag     540
```

```
ggaaccgagg agtgtcccac cgagtcgcac ttcagaaagc gaatgtgggg ctcctggtac    600

atgatccgag tcatgctgct ggacaagtac tgctggctgc agaacctgat gctggacaca    660

gagaccggtc tagaccctcc ccatttcaag ctgcgagccg cccagggatt tgcctccgcc    720

gacttcttta tggcaggcta ctggctgtgg aacaagctgc tcgagaacct ggctgttatt    780

ggatacgata cggatacaat gtctgctgcg gcctacgact ggagactgtc ctaccctgat    840

ttggagcacc gagacggata cttctccaag ctcaaagctt caatcgaaga gactaagcgt    900

atgacaggtg agaagacagt tctgacgggc cattcgatgg gctcccaggt catcttctac    960

ttcatgaagt gggctgaggc cgagggatat ggaggaggag gtcccaactg ggtcaatgac   1020

catattgaat cctttgtcga catttccggc tccatgctgg gtactcccaa gaccctggtt   1080

gctcttctgt ctggagaaat gaaggatacc gtgcagctga acgcgatggc tgtgtatgga   1140

ctggagcagt tcttctctcg acgagagcga gccgatctgc tgcgaacatg gggaggaatt   1200

gcttccatga ttcccaaggg tggtaaggct atctggggtg atcattctgg agcccctgat   1260

gacgagcccg gccagaatgt cacctttggc aacttcatca agttcaagga gtccttgacc   1320

gagtactctg ctaagaacct cactatggat gaaaccgttg acttcctgta ttctcagtct   1380

cccgagtggt ttgtgaaccg aaccgagggt gcttactcct ttggaattgc caagactcga   1440

aagcaggttg agcagaatga gaagcgacct tctacctgga gcaaccctct ggaagctgct   1500

ctccccaatg cccccgatct caagatctac tgcttctatg gagtcggtaa ggataccgag   1560

cgagcctact actaccagga tgagcccaat cccgagcaga ccaacttgaa cgtcagtatc   1620

gctggaaacg accctgatgg tgtgcttatg ggtcagggcg atggaaccgt ctcccttgtg   1680

acccatacca tgtgtcaccg atggaaggac gagaactcca agttcaaccc tggtaacgcc   1740

caggtcaagg ttgtggagat gttgcaccag cctgatcgac ttgatattcg aggcggtgct   1800

cagactgccg agcatgtgga cattctgggg cgttctgagt tgaacgagat ggttctgaag   1860

gtggctagtg gaaagggaaa tgagattgaa gagagagtca tctccaacat tgatgagtgg   1920

gtgtggaaga ttgatctcgg cagcaattag                                    1950
```

```
<210> SEQ ID NO 15
<211> LENGTH: 649
<212> TYPE: PRT
<213> ORGANISM: Artificial sequence
<220> FEATURE:
<223> OTHER INFORMATION: Y. lipolytica PDAT, but with an added alanine
      at amino acid position 2

<400> SEQUENCE: 15

Met Ala Thr Gln Pro Val Asn Arg Lys Ala Thr Val Glu Arg Val Glu
1               5                   10                  15

Pro Ala Val Glu Val Ala Asp Ser Glu Ser Glu Ala Lys Thr Asp Val
            20                  25                  30

His Val His His His His His His His Lys Arg Lys Ser Val Lys Gly
        35                  40                  45

Lys Ile Leu Asn Phe Phe Thr Arg Ser Arg Arg Ile Thr Phe Val Leu
    50                  55                  60

Gly Ala Val Val Gly Val Ile Ala Ala Gly Tyr Tyr Ala Ala Pro Pro
65                  70                  75                  80

Glu Leu Ser Ile Asp Ile Asp Ala Leu Leu Gly Asp Leu Pro Ser Phe
                85                  90                  95

Asp Phe Asp Ala Leu Ser Leu Asp Asn Leu Ser Met Asp Ser Val Ser
```

-continued

```
            100                 105                 110

Asp Phe Val Gln Asp Met Lys Ser Arg Phe Pro Thr Lys Ile Leu Gln
        115                 120                 125

Glu Ala Ala Lys Ile Glu Lys His Gln Lys Ser Glu Gln Lys Ala Ala
    130                 135                 140

Pro Phe Ala Val Gly Lys Ala Met Lys Ser Glu Gly Leu Asn Ala Lys
145                 150                 155                 160

Tyr Pro Val Val Leu Val Pro Gly Val Ile Ser Thr Gly Leu Glu Ser
                165                 170                 175

Trp Ser Leu Glu Gly Thr Glu Glu Cys Pro Thr Glu Ser His Phe Arg
            180                 185                 190

Lys Arg Met Trp Gly Ser Trp Tyr Met Ile Arg Val Met Leu Leu Asp
        195                 200                 205

Lys Tyr Cys Trp Leu Gln Asn Leu Met Leu Asp Thr Glu Thr Gly Leu
    210                 215                 220

Asp Pro Pro His Phe Lys Leu Arg Ala Ala Gln Gly Phe Ala Ser Ala
225                 230                 235                 240

Asp Phe Phe Met Ala Gly Tyr Trp Leu Trp Asn Lys Leu Leu Glu Asn
                245                 250                 255

Leu Ala Val Ile Gly Tyr Asp Thr Asp Thr Met Ser Ala Ala Ala Tyr
            260                 265                 270

Asp Trp Arg Leu Ser Tyr Pro Asp Leu Glu His Arg Asp Gly Tyr Phe
        275                 280                 285

Ser Lys Leu Lys Ala Ser Ile Glu Glu Thr Lys Arg Met Thr Gly Glu
    290                 295                 300

Lys Thr Val Leu Thr Gly His Ser Met Gly Ser Gln Val Ile Phe Tyr
305                 310                 315                 320

Phe Met Lys Trp Ala Glu Ala Glu Gly Tyr Gly Gly Gly Gly Pro Asn
                325                 330                 335

Trp Val Asn Asp His Ile Glu Ser Phe Val Asp Ile Ser Gly Ser Met
            340                 345                 350

Leu Gly Thr Pro Lys Thr Leu Val Ala Leu Leu Ser Gly Glu Met Lys
        355                 360                 365

Asp Thr Val Gln Leu Asn Ala Met Ala Val Tyr Gly Leu Glu Gln Phe
    370                 375                 380

Phe Ser Arg Arg Glu Arg Ala Asp Leu Leu Arg Thr Trp Gly Gly Ile
385                 390                 395                 400

Ala Ser Met Ile Pro Lys Gly Gly Lys Ala Ile Trp Gly Asp His Ser
                405                 410                 415

Gly Ala Pro Asp Asp Glu Pro Gly Gln Asn Val Thr Phe Gly Asn Phe
            420                 425                 430

Ile Lys Phe Lys Glu Ser Leu Thr Glu Tyr Ser Ala Lys Asn Leu Thr
        435                 440                 445

Met Asp Glu Thr Val Asp Phe Leu Tyr Ser Gln Ser Pro Glu Trp Phe
    450                 455                 460

Val Asn Arg Thr Glu Gly Ala Tyr Ser Phe Gly Ile Ala Lys Thr Arg
465                 470                 475                 480

Lys Gln Val Glu Gln Asn Glu Lys Arg Pro Ser Thr Trp Ser Asn Pro
                485                 490                 495

Leu Glu Ala Ala Leu Pro Asn Ala Pro Asp Leu Lys Ile Tyr Cys Phe
            500                 505                 510

Tyr Gly Val Gly Lys Asp Thr Glu Arg Ala Tyr Tyr Tyr Gln Asp Glu
        515                 520                 525
```

Pro Asn Pro Glu Gln Thr Asn Leu Asn Val Ser Ile Ala Gly Asn Asp
    530                 535                 540

Pro Asp Gly Val Leu Met Gly Gln Gly Asp Gly Thr Val Ser Leu Val
545                 550                 555                 560

Thr His Thr Met Cys His Arg Trp Lys Asp Glu Asn Ser Lys Phe Asn
                565                 570                 575

Pro Gly Asn Ala Gln Val Lys Val Val Glu Met Leu His Gln Pro Asp
            580                 585                 590

Arg Leu Asp Ile Arg Gly Gly Ala Gln Thr Ala Glu His Val Asp Ile
        595                 600                 605

Leu Gly Arg Ser Glu Leu Asn Glu Met Val Leu Lys Val Ala Ser Gly
    610                 615                 620

Lys Gly Asn Glu Ile Glu Glu Arg Val Ile Ser Asn Ile Asp Glu Trp
625                 630                 635                 640

Val Trp Lys Ile Asp Leu Gly Ser Asn
                645

<210> SEQ ID NO 16
<211> LENGTH: 2127
<212> TYPE: DNA
<213> ORGANISM: Artificial sequence
<220> FEATURE:
<223> OTHER INFORMATION: E389D9eS/EgD8M fusion

<400> SEQUENCE: 16
atggctgccg tcatcgaggt ggccaacgag ttcgtcgcta tcactgccga gacccttccc 60
aaggtggact atcagcgact ctggcgagac atctactcct gcgagctcct gtacttctcc 120
attgctttcg tcatcctcaa gtttaccctt ggcgagctct cggattctgg caaaaagatt 180
ctgcgagtgc tgttcaagtg gtacaacctc ttcatgtccg tcttttcgct ggtgtccttc 240
ctctgtatgg gttacgccat ctacaccgtt ggactgtact ccaacgaatg cgacagagct 300
ttcgacaaca gcttgttccg atttgccacc aaggtcttct actattccaa gtttctggag 360
tacatcgact ctttctacct tcccctcatg gccaagcctc tgtcctttct gcagttcttt 420
catcacttgg gagctcctat ggacatgtgg ctcttcgtgc agtactctgg cgaatccatt 480
tggatctttg tgttcctgaa cggattcatt cactttgtca tgtacggcta ctattggaca 540
cggctgatga agttcaactt tcccatgccc aagcagctca ttaccgcaat gcagatcacc 600
cagttcaacg ttggcttcta cctcgtgtgg tggtacaagg acattccctg ttaccgaaag 660
gatcccatgc gaatgctggc ctggatcttc aactactggt acgtcggtac cgttcttctg 720
ctcttcatca acttctttgt caagtcctac gtgtttccca agcctaagac tgccgacaaa 780
aaggtccagg gcgccggtcc cgctcgacct gccggacttc ctcccgctac ctactacgac 840
tctctggccg tcatgggatc cgtgaaggct tctcgacagg ctctgcccct cgtcatcgac 900
ggaaaggtgt acgacgtctc cgcttgggtg aacttccacc ctggtggagc tgaaatcatt 960
gagaactacc agggacgaga tgctactgac gccttcatgg ttatgcactc tcaggaagcc 1020
ttcgacaagc tcaagcgaat gcccaagatc aaccaggctt ccgagctgcc tccccaggct 1080
gccgtcaacg aagctcagga ggatttccga aagctccgag aagagctgat cgccactggc 1140
atgtttgacg cctctcccct ctggtactcg tacaagatct tgaccaccct gggtcttggc 1200
gtgcttgcct tcttcatgct ggtccagtac cacctgtact tcattggtgc tctcgtgctc 1260
ggtatgcact accagcaaat gggatggctg tctcatgaca tctgccacca ccagaccttc 1320
aagaaccgaa actggaataa cgtcctgggt ctggtctttg gcaacggact ccagggcttc 1380
tccgtgacct ggtggaagga cagacacaac gcccatcatt ctgctaccaa cgttcagggt 1440
cacgatcccg acattgataa cctgcctctg ctcgcctggt ccgaggacga tgtcactcga 1500
gcttctccca tctcccgaaa gctcattcag ttccaacagt actatttcct ggtcatctgt 1560
attctcctgc gattcatctg gtgtttccag tctgtgctga ccgttcgatc cctcaaggac 1620
cgagacaacc agttctaccg atctcagtac aagaaagagg ccattggact cgctctgcac 1680
tggactctca agaccctgtt ccacctcttc tttatgccct ccatcctgac ctcgatgctg 1740
gtgttctttg tttccgagct cgtcggtggc ttcggaattg ccatcgtggt cttcatgaac 1800
cactaccctc tggagaagat cggtgattcc gtctgggacg gacatggctt ctctgtgggt 1860
cagatccatg agaccatgaa cattcgacga ggcatcatta ctgactggtt ctttggaggc 1920
ctgaactacc agatcgagca ccatctctgg cccaccctgc ctcgacacaa cctcactgcc 1980
gtttcctacc aggtggaaca gctgtgccag aagcacaacc tcccctaccg aaaccctctg 2040
ccccatgaag gtctcgtcat cctgctccga tacctgtccc agttcgctcg aatggccgag 2100
aagcagcccg gtgccaaggc tcagtaa 2127

<210> SEQ ID NO 17
<211> LENGTH: 708
<212> TYPE: PRT
<213> ORGANISM: Artificial sequence
<220> FEATURE:
<223> OTHER INFORMATION: E389D9eS/EgD8M fusion

<400> SEQUENCE: 17

Met Ala Ala Val Ile Glu Val Ala Asn Glu Phe Val Ala Ile Thr Ala
1 5 10 15

Glu Thr Leu Pro Lys Val Asp Tyr Gln Arg Leu Trp Arg Asp Ile Tyr
20 25 30

Ser Cys Glu Leu Leu Tyr Phe Ser Ile Ala Phe Val Ile Leu Lys Phe
35 40 45

Thr Leu Gly Glu Leu Ser Asp Ser Gly Lys Lys Ile Leu Arg Val Leu
50 55 60

Phe Lys Trp Tyr Asn Leu Phe Met Ser Val Phe Ser Leu Val Ser Phe
65 70 75 80

Leu Cys Met Gly Tyr Ala Ile Tyr Thr Val Gly Leu Tyr Ser Asn Glu
85 90 95

Cys Asp Arg Ala Phe Asp Asn Ser Leu Phe Arg Phe Ala Thr Lys Val
100 105 110

Phe Tyr Tyr Ser Lys Phe Leu Glu Tyr Ile Asp Ser Phe Tyr Leu Pro
115 120 125

Leu Met Ala Lys Pro Leu Ser Phe Leu Gln Phe Phe His His Leu Gly
130 135 140

Ala Pro Met Asp Met Trp Leu Phe Val Gln Tyr Ser Gly Glu Ser Ile
145 150 155 160

Trp Ile Phe Val Phe Leu Asn Gly Phe Ile His Phe Val Met Tyr Gly
165 170 175

Tyr Tyr Trp Thr Arg Leu Met Lys Phe Asn Phe Pro Met Pro Lys Gln
180 185 190

Leu Ile Thr Ala Met Gln Ile Thr Gln Phe Asn Val Gly Phe Tyr Leu
195 200 205

Val Trp Trp Tyr Lys Asp Ile Pro Cys Tyr Arg Lys Asp Pro Met Arg
210 215 220

-continued

```
Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp Lys Lys Val Gln Gly Ala Gly Pro Ala Arg Pro Ala Gly
            260                 265                 270

Leu Pro Pro Ala Thr Tyr Tyr Asp Ser Leu Ala Val Met Gly Ser Val
        275                 280                 285

Lys Ala Ser Arg Gln Ala Leu Pro Leu Val Ile Asp Gly Lys Val Tyr
    290                 295                 300

Asp Val Ser Ala Trp Val Asn Phe His Pro Gly Gly Ala Glu Ile Ile
305                 310                 315                 320

Glu Asn Tyr Gln Gly Arg Asp Ala Thr Asp Ala Phe Met Val Met His
                325                 330                 335

Ser Gln Glu Ala Phe Asp Lys Leu Lys Arg Met Pro Lys Ile Asn Gln
            340                 345                 350

Ala Ser Glu Leu Pro Pro Gln Ala Ala Val Asn Glu Ala Gln Glu Asp
        355                 360                 365

Phe Arg Lys Leu Arg Glu Glu Leu Ile Ala Thr Gly Met Phe Asp Ala
    370                 375                 380

Ser Pro Leu Trp Tyr Ser Tyr Lys Ile Leu Thr Thr Leu Gly Leu Gly
385                 390                 395                 400

Val Leu Ala Phe Phe Met Leu Val Gln Tyr His Leu Tyr Phe Ile Gly
                405                 410                 415

Ala Leu Val Leu Gly Met His Tyr Gln Gln Met Gly Trp Leu Ser His
            420                 425                 430

Asp Ile Cys His His Gln Thr Phe Lys Asn Arg Asn Trp Asn Asn Val
        435                 440                 445

Leu Gly Leu Val Phe Gly Asn Gly Leu Gln Gly Phe Ser Val Thr Trp
    450                 455                 460

Trp Lys Asp Arg His Asn Ala His His Ser Ala Thr Asn Val Gln Gly
465                 470                 475                 480

His Asp Pro Asp Ile Asp Asn Leu Pro Leu Leu Ala Trp Ser Glu Asp
                485                 490                 495

Asp Val Thr Arg Ala Ser Pro Ile Ser Arg Lys Leu Ile Gln Phe Gln
            500                 505                 510

Gln Tyr Tyr Phe Leu Val Ile Cys Ile Leu Leu Arg Phe Ile Trp Cys
        515                 520                 525

Phe Gln Ser Val Leu Thr Val Arg Ser Leu Lys Asp Arg Asp Asn Gln
    530                 535                 540

Phe Tyr Arg Ser Gln Tyr Lys Lys Glu Ala Ile Gly Leu Ala Leu His
545                 550                 555                 560

Trp Thr Leu Lys Thr Leu Phe His Leu Phe Phe Met Pro Ser Ile Leu
                565                 570                 575

Thr Ser Met Leu Val Phe Phe Val Ser Glu Leu Val Gly Gly Phe Gly
            580                 585                 590

Ile Ala Ile Val Val Phe Met Asn His Tyr Pro Leu Glu Lys Ile Gly
        595                 600                 605

Asp Ser Val Trp Asp Gly His Gly Phe Ser Val Gly Gln Ile His Glu
    610                 615                 620

Thr Met Asn Ile Arg Arg Gly Ile Ile Thr Asp Trp Phe Phe Gly Gly
625                 630                 635                 640
```

-continued

```
Leu Asn Tyr Gln Ile Glu His His Leu Trp Pro Thr Leu Pro Arg His
                645                 650                 655

Asn Leu Thr Ala Val Ser Tyr Gln Val Glu Gln Leu Cys Gln Lys His
            660                 665                 670

Asn Leu Pro Tyr Arg Asn Pro Leu Pro His Glu Gly Leu Val Ile Leu
        675                 680                 685

Leu Arg Tyr Leu Ser Gln Phe Ala Arg Met Ala Glu Lys Gln Pro Gly
    690                 695                 700

Ala Lys Ala Gln
705
```

<210> SEQ ID NO 18
<211> LENGTH: 1269
<212> TYPE: DNA
<213> ORGANISM: Artificial sequence
<220> FEATURE:
<223> OTHER INFORMATION: mutant E. gracilis delta-8 desaturase

<400> SEQUENCE: 18

```
atggtgaagg cttctcgaca ggctctgccc ctcgtcatcg acggaaaggt gtacgacgtc      60

tccgcttggg tgaacttcca ccctggtgga gctgaaatca ttgagaacta ccagggacga     120

gatgctactg acgccttcat ggttatgcac tctcaggaag ccttcgacaa gctcaagcga     180

atgcccaaga tcaaccaggc ttccgagctg cctccccagg ctgccgtcaa cgaagctcag     240

gaggatttcc gaaagctccg agaagagctg atcgccactg gcatgtttga cgcctctccc     300

ctctggtact cgtacaagat cttgaccacc ctgggtcttg gcgtgcttgc cttcttcatg     360

ctggtccagt accacctgta cttcattggt gctctcgtgc tcggtatgca ctaccagcaa     420

atgggatggc tgtctcatga catctgccac caccagacct tcaagaaccg aaactggaat     480

aacgtcctgg gtctggtctt tggcaacgga ctccagggct tctccgtgac ctggtggaag     540

gacagacaca acgcccatca ttctgctacc aacgttcagg gtcacgatcc cgacattgat     600

aacctgcctc tgctcgcctg gtccgaggac gatgtcactc gagcttctcc catctcccga     660

aagctcattc agttccaaca gtactatttc ctggtcatct gtattctcct gcgattcatc     720

tggtgtttcc agtctgtgct gaccgttcga tccctcaagg accgagacaa ccagttctac     780

cgatctcagt acaagaaaga ggccattgga ctcgctctgc actggactct caagaccctg     840

ttccacctct tctttatgcc ctccatcctg acctcgatgc tggtgttctt tgtttccgag     900

ctcgtcggtg gcttcggaat tgccatcgtg gtcttcatga accactaccc tctggagaag     960

atcggtgatt ccgtctggga cggacatggc ttctctgtgg gtcagatcca tgagaccatg    1020

aacattcgac gaggcatcat tactgactgg ttctttggag gcctgaacta ccagatcgag    1080

caccatctct ggcccaccct gcctcgacac aacctcactg ccgtttccta ccaggtggaa    1140

cagctgtgcc agaagcacaa cctcccctac cgaaaccctc tgccccatga aggtctcgtc    1200

atcctgctcc gatacctgtc ccagttcgct cgaatggccg agaagcagcc cggtgccaag    1260

gctcagtaa                                                            1269
```

<210> SEQ ID NO 19
<211> LENGTH: 422
<212> TYPE: PRT
<213> ORGANISM: Artificial sequence
<220> FEATURE:
<223> OTHER INFORMATION: mutant E. gracilis delta-8 desaturase

<400> SEQUENCE: 19

```
Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Gln Ala Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Leu Thr Thr Leu Gly
            100                 105                 110

Leu Gly Val Leu Ala Phe Phe Met Leu Val Gln Tyr His Leu Tyr Phe
        115                 120                 125

Ile Gly Ala Leu Val Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Val Leu Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Met Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415

Pro Gly Ala Lys Ala Gln
```

420

<210> SEQ ID NO 20
<211> LENGTH: 1518
<212> TYPE: DNA
<213> ORGANISM: Artificial sequence
<220> FEATURE:
<223> OTHER INFORMATION: Rhizobium leguminosarum bv. viciae 3841 malonyl-CoA synthetase codon-omptimized for expression in Y. lipolytica

<400> SEQUENCE: 20

```
atggtctcca accacctgtt cgacgccatg cgagctgccg ctcccggaga cgcacctttc     60
attcgaatcg acaacgctcg gacctggact tacgatgacg ccattgctct ttccggtcga    120
atcgctggag ctatggacgc actcggcatt cgacccggag acagagttgc cgtgcaggtc    180
gagaagtctg ccgaggcgtt gattctctac ctggcctgtc ttcgaaccgg agctgtctac    240
ctgcctctca acactgccta caccctggcc gagctcgact acttcatcgg cgatgccgaa    300
ccgcgtctgg tggtcgttgc tcccgcagct cgaggtggcg tggagacaat tgccaagcga    360
cacggtgcta tcgtcgaaac cctcgacgcc gatggacgag gctccttgct ggaccttgct    420
agagatgagc ctgccgactt tgtcgatgct tcgcgatctg ccgacgatct ggctgctatt    480
ctctacactt ccggtacaac cggacgatcg aagggtgcca tgcttactca tggcaatctg    540
ctctccaacg ctctcacctt gcgagactat tggagagtta ccgcagacga tcgactcatc    600
catgccttgc caatctttca cactcatggt ctgttcgttg ctacgaacgt cacactgctt    660
gcaggagcct cgatgtttct gctctccaag ttcgatgccg acgaggtcgt ttctctcatg    720
ccacaggcca ccatgcttat gggcgtgccc acattctacg ttcgattgct gcagagtcct    780
cgactcgaga agggtgctgt ggccagcatc agactgttca tttctggatc agctcccttg    840
cttgccgaaa cccacgccga gtttcatgct cgtactggtc acgccattct cgagcgatac    900
ggcatgacgg aaaccaacat gaatacttcc aacccctacg agggcaagcg tattgccgga    960
accgttggtt ttcctctgcc cgacgtcact gtgcgagtca ccgatcccgc caccggtctc   1020
gttcttccac ctgaagagac tggcatgatc gagatcaagg gacccaacgt cttcaagggc   1080
tattggcgaa tgcccgaaaa gaccgctgcc gagtttaccg cagacggttt ctttatctct   1140
ggagatctcg gcaagatcga ccgagaaggt tacgttcaca ttgtgggacg aggcaaggac   1200
ctggtcattt ccggtggcta caacatctat cccaaagagg tcgaaggcga gatcgaccag   1260
atcgagggtg tggtcgagtc tgctgtcatt ggtgttcctc atcccgattt cggagaaggt   1320
gtcaccgctg ttgtcgtgtg caaacctggt gccgttctcg acgaaaagac catcgtgtct   1380
gctctgcagg accgtcttgc ccgatacaag caacccaagc ggattatctt tgccgacgat   1440
ctgcctcgaa acactatggg aaaggttcag aagaacattc ttcgacagca atacgccgat   1500
ctctacacca gacgataa                                                 1518
```

<210> SEQ ID NO 21
<211> LENGTH: 505
<212> TYPE: PRT
<213> ORGANISM: Artificial sequence
<220> FEATURE:
<223> OTHER INFORMATION: Rhizobium leguminosarum bv. viciae 3841 malonyl-CoA synthetase codon-omptimized for expression in Y. lipolytica

<400> SEQUENCE: 21

Met Val Ser Asn His Leu Phe Asp Ala Met Arg Ala Ala Ala Pro Gly

-continued

```
1               5                   10                  15

Asp Ala Pro Phe Ile Arg Ile Asp Asn Ala Arg Thr Trp Thr Tyr Asp
            20                  25                  30

Asp Ala Ile Ala Leu Ser Gly Arg Ile Ala Gly Ala Met Asp Ala Leu
        35                  40                  45

Gly Ile Arg Pro Gly Asp Arg Val Ala Val Gln Val Glu Lys Ser Ala
    50                  55                  60

Glu Ala Leu Ile Leu Tyr Leu Ala Cys Leu Arg Thr Gly Ala Val Tyr
65                  70                  75                  80

Leu Pro Leu Asn Thr Ala Tyr Thr Leu Ala Glu Leu Asp Tyr Phe Ile
                85                  90                  95

Gly Asp Ala Glu Pro Arg Leu Val Val Val Ala Pro Ala Ala Arg Gly
            100                 105                 110

Gly Val Glu Thr Ile Ala Lys Arg His Gly Ala Ile Val Glu Thr Leu
        115                 120                 125

Asp Ala Asp Gly Arg Gly Ser Leu Leu Asp Leu Ala Arg Asp Glu Pro
    130                 135                 140

Ala Asp Phe Val Asp Ala Ser Arg Ser Ala Asp Asp Leu Ala Ala Ile
145                 150                 155                 160

Leu Tyr Thr Ser Gly Thr Thr Gly Arg Ser Lys Gly Ala Met Leu Thr
                165                 170                 175

His Gly Asn Leu Leu Ser Asn Ala Leu Thr Leu Arg Asp Tyr Trp Arg
            180                 185                 190

Val Thr Ala Asp Asp Arg Leu Ile His Ala Leu Pro Ile Phe His Thr
        195                 200                 205

His Gly Leu Phe Val Ala Thr Asn Val Thr Leu Leu Ala Gly Ala Ser
    210                 215                 220

Met Phe Leu Leu Ser Lys Phe Asp Ala Asp Glu Val Val Ser Leu Met
225                 230                 235                 240

Pro Gln Ala Thr Met Leu Met Gly Val Pro Thr Phe Tyr Val Arg Leu
                245                 250                 255

Leu Gln Ser Pro Arg Leu Glu Lys Gly Ala Val Ala Ser Ile Arg Leu
            260                 265                 270

Phe Ile Ser Gly Ser Ala Pro Leu Leu Ala Glu Thr His Ala Glu Phe
        275                 280                 285

His Ala Arg Thr Gly His Ala Ile Leu Glu Arg Tyr Gly Met Thr Glu
    290                 295                 300

Thr Asn Met Asn Thr Ser Asn Pro Tyr Glu Gly Lys Arg Ile Ala Gly
305                 310                 315                 320

Thr Val Gly Phe Pro Leu Pro Asp Val Thr Val Arg Val Thr Asp Pro
                325                 330                 335

Ala Thr Gly Leu Val Leu Pro Pro Glu Glu Thr Gly Met Ile Glu Ile
            340                 345                 350

Lys Gly Pro Asn Val Phe Lys Gly Tyr Trp Arg Met Pro Glu Lys Thr
        355                 360                 365

Ala Ala Glu Phe Thr Ala Asp Gly Phe Phe Ile Ser Gly Asp Leu Gly
    370                 375                 380

Lys Ile Asp Arg Glu Gly Tyr Val His Ile Val Gly Arg Gly Lys Asp
385                 390                 395                 400

Leu Val Ile Ser Gly Gly Tyr Asn Ile Tyr Pro Lys Glu Val Glu Gly
                405                 410                 415

Glu Ile Asp Gln Ile Glu Gly Val Val Glu Ser Ala Val Ile Gly Val
            420                 425                 430
```

```
Pro His Pro Asp Phe Gly Glu Gly Val Thr Ala Val Val Val Cys Lys
        435                 440                 445

Pro Gly Ala Val Leu Asp Glu Lys Thr Ile Val Ser Ala Leu Gln Asp
    450                 455                 460

Arg Leu Ala Arg Tyr Lys Gln Pro Lys Arg Ile Ile Phe Ala Asp Asp
465                 470                 475                 480

Leu Pro Arg Asn Thr Met Gly Lys Val Gln Lys Asn Ile Leu Arg Gln
                485                 490                 495

Gln Tyr Ala Asp Leu Tyr Thr Arg Arg
            500                 505


<210> SEQ ID NO 22
<211> LENGTH: 849
<212> TYPE: DNA
<213> ORGANISM: Yarrowia lipolytica

<400> SEQUENCE: 22

atgtccgttg catccaagct cgtcttctac gtccgcgccg ccatcgccgt ggtcatcttt      60

gccgcctgtg ccacctacgg cgtgctggcg tccaccattc tcaccgccat cggcaagcag     120

ggcctggccc aatggaccgt tgccagagcc ttctactact cggtgcgcat cttcctgggt     180

atcagcatca agctgcgtag ccggcaggtg accggaaccg ccggtctgga tgcctccaag     240

atccaggtcg ccaacaccac caagcccatt gacgacatca ccaaacacct gccccgacca     300

tgcattctga tttccaacca ccagaacgaa atggacattc tggtgctcgg tcgcatcttc     360

ccccagtact gctccgtcac cgccaaaaag gccctcaagt ggtaccctct gctgggccag     420

ttcatggcgc tgtccggcac catcttcctg gaccgaaagg accgaaccaa gtccgtgcag     480

accctcggcg gcgccgtcaa gaccatccag agcggcaacg gaggcaaggg ccagagcgtc     540

ttcatgttcc ccgagggaac ccgatcctac tccaaggacg tcggcatcat gcccttcaag     600

aagggctgtt tccacctggc ggtccagtcg ggcgctccca ttgtccccgt ggtggtccag     660

aacacctccc gaatgttttc tttcggccga ggcaagctgg acgccggaga gatccttgtc     720

gacgtcctga gccccattga gaccaagggt ctggacgcca gcaacgtcga cgctctcatg     780

gccaccactt ataaggccat gtgcgagact gccgaccaga ttggctacgc tggccagaag     840

actcagtag                                                             849


<210> SEQ ID NO 23
<211> LENGTH: 282
<212> TYPE: PRT
<213> ORGANISM: Yarrowia lipolytica

<400> SEQUENCE: 23

Met Ser Val Ala Ser Lys Leu Val Phe Tyr Val Arg Ala Ala Ile Ala
1               5                   10                  15

Val Val Ile Phe Ala Ala Cys Ala Thr Tyr Gly Val Leu Ala Ser Thr
            20                  25                  30

Ile Leu Thr Ala Ile Gly Lys Gln Gly Leu Ala Gln Trp Thr Val Ala
        35                  40                  45

Arg Ala Phe Tyr Tyr Ser Val Arg Ile Phe Leu Gly Ile Ser Ile Lys
    50                  55                  60

Leu Arg Ser Arg Gln Val Thr Gly Thr Ala Gly Leu Asp Ala Ser Lys
65                  70                  75                  80

Ile Gln Val Ala Asn Thr Thr Lys Pro Ile Asp Asp Ile Thr Lys His
                85                  90                  95
```

```
Leu Pro Arg Pro Cys Ile Leu Ile Ser Asn His Gln Asn Glu Met Asp
            100                 105                 110

Ile Leu Val Leu Gly Arg Ile Phe Pro Gln Tyr Cys Ser Val Thr Ala
        115                 120                 125

Lys Lys Ala Leu Lys Trp Tyr Pro Leu Leu Gly Gln Phe Met Ala Leu
    130                 135                 140

Ser Gly Thr Ile Phe Leu Asp Arg Lys Asp Arg Thr Lys Ser Val Gln
145                 150                 155                 160

Thr Leu Gly Gly Ala Val Lys Thr Ile Gln Ser Gly Asn Gly Gly Lys
                165                 170                 175

Gly Gln Ser Val Phe Met Phe Pro Glu Gly Thr Arg Ser Tyr Ser Lys
            180                 185                 190

Asp Val Gly Ile Met Pro Phe Lys Lys Gly Cys Phe His Leu Ala Val
        195                 200                 205

Gln Ser Gly Ala Pro Ile Val Pro Val Val Val Gln Asn Thr Ser Arg
    210                 215                 220

Met Phe Ser Phe Gly Arg Gly Lys Leu Asp Ala Gly Glu Ile Leu Val
225                 230                 235                 240

Asp Val Leu Ser Pro Ile Glu Thr Lys Gly Leu Asp Ala Ser Asn Val
                245                 250                 255

Asp Ala Leu Met Ala Thr Thr Tyr Lys Ala Met Cys Glu Thr Ala Asp
            260                 265                 270

Gln Ile Gly Tyr Ala Gly Gln Lys Thr Gln
        275                 280


<210> SEQ ID NO 24
<211> LENGTH: 9085
<212> TYPE: DNA
<213> ORGANISM: Artificial sequence
<220> FEATURE:
<223> OTHER INFORMATION: Construct pZKMPn-YD58 for expressing mutant
      YlLPCAT (M136S_T389A)

<400> SEQUENCE: 24

gtacgactga tgtgtatgta agctcaatga gcagcgtgct cctcggtcta ctatatggcg     60

acatatctct tcgcttctgt ttacccttta catacggtac agctcttaca atgacattta    120

tccactggcg tcgatccata aaccacacga accctgtttt gttagtcacc atgaccgggg    180

cgtgtcgtgt tacgttccac cgtttcacct cagccggtta cgattcaact tgccgcgtca    240

ttctgcgttg ctagcggagc gagtacgagt aactagactt tcgataagct gaatgacttc    300

agggtgcatg agaggcgcag atcggtattt tcggacttgt tcttctagaa gactggtttg    360

agagcaatcg cggaagagtt gggaaccgct ggagagcaga atgggttagt acagagacta    420

tctgatctcc cccgcttgtg tctagcccca ctttatactc tatttggcag ttgttgcttg    480

ttattcaagc acagcatgtc tgctcgtatc actttggaga catccctaac ctctaaacct    540

ttatagatgc cttaccttct gagcttgcag agagcattcc acagcgaacc cagttgacat    600

tatcagttga catcttacgc tcacaccaca ttacgcatct cacacacaat cacacgcaca    660

agtacacacg caagcacatc atacaatggt caaggcgcgc cagctgcatt aatgaatcgg    720

ccaacgcgcg gggagaggcg gtttgcgtat tgggcgctct tccgcttcct cgctcactga    780

ctcgctgcgc tcggtcgttc ggctgcggcg agcggtatca gctcactcaa aggcggtaat    840

acggttatcc acagaatcag gggataacgc aggaaagaac atgtgagcaa aaggccagca    900

aaaggccagg aaccgtaaaa aggccgcgtt gctggcgttt ttccataggc tccgcccccc    960
```

-continued

```
tgacgagcat cacaaaaatc gacgctcaag tcagaggtgg cgaaacccga caggactata   1020
aagataccag gcgtttcccc ctggaagctc cctcgtgcgc tctcctgttc cgaccctgcc   1080
gcttaccgga tacctgtccg cctttctccc ttcgggaagc gtggcgcttt ctcatagctc   1140
acgctgtagg tatctcagtt cggtgtaggt cgttcgctcc aagctgggct gtgtgcacga   1200
accccccgtt cagcccgacc gctgcgcctt atccggtaac tatcgtcttg agtccaaccc   1260
ggtaagacac gacttatcgc cactggcagc agccactggt aacaggatta gcagagcgag   1320
gtatgtaggc ggtgctacag agttcttgaa gtggtggcct aactacggct acactagaag   1380
aacagtattt ggtatctgcg ctctgctgaa gccagttacc ttcggaaaaa gagttggtag   1440
ctcttgatcc ggcaaacaaa ccaccgctgg tagcggtggt ttttttgttt gcaagcagca   1500
gattacgcgc agaaaaaaag gatctcaaga agatcctttg atcttttcta cggggtctga   1560
cgctcagtgg aacgaaaact cacgttaagg gattttggtc atgagattat caaaaaggat   1620
cttcacctag atccttttaa attaaaaatg aagttttaaa tcaatctaaa gtatatatga   1680
gtaaacttgg tctgacagtt accaatgctt aatcagtgag gcacctatct cagcgatctg   1740
tctatttcgt tcatccatag ttgcctgact ccccgtcgtg tagataacta cgatacggga   1800
gggcttacca tctggcccca gtgctgcaat gataccgcga gacccacgct caccggctcc   1860
agatttatca gcaataaacc agccagccgg aagggccgag cgcagaagtg gtcctgcaac   1920
tttatccgcc tccatccagt ctattaattg ttgccgggaa gctagagtaa gtagttcgcc   1980
agttaatagt ttgcgcaacg ttgttgccat tgctacaggc atcgtggtgt cacgctcgtc   2040
gtttggtatg gcttcattca gctccggttc ccaacgatca aggcgagtta catgatcccc   2100
catgttgtgc aaaaaagcgg ttagctcctt cggtcctccg atcgttgtca gaagtaagtt   2160
ggccgcagtg ttatcactca tggttatggc agcactgcat aattctctta ctgtcatgcc   2220
atccgtaaga tgcttttctg tgactggtga gtactcaacc aagtcattct gagaatagtg   2280
tatgcggcga ccgagttgct cttgcccggc gtcaatacgg gataataccg cgccacatag   2340
cagaacttta aaagtgctca tcattggaaa acgttcttcg gggcgaaaac tctcaaggat   2400
cttaccgctg ttgagatcca gttcgatgta acccactcgt gcacccaact gatcttcagc   2460
atcttttact ttcaccagcg tttctgggtg agcaaaaaca ggaaggcaaa atgccgcaaa   2520
aaagggaata agggcgacac ggaaatgttg aatactcata ctcttccttt ttcaatatta   2580
ttgaagcatt tatcagggtt attgtctcat gagcggatac atatttgaat gtatttagaa   2640
aaataaacaa ataggggttc cgcgcacatt tccccgaaaa gtgccacctg atgcggtgtg   2700
aaataccgca cagatgcgta aggagaaaat accgcatcag gaaattgtaa gcgttaatat   2760
tttgttaaaa ttcgcgttaa atttttgtta aatcagctca ttttttaacc aataggccga   2820
aatcggcaaa atcccttata aatcaaaaga atagaccgag atagggttga gtgttgttcc   2880
agtttggaac aagagtccac tattaaagaa cgtggactcc aacgtcaaag ggcgaaaaac   2940
cgtctatcag ggcgatggcc cactacgtga accatcaccc taatcaagtt ttttggggtc   3000
gaggtgccgt aaagcactaa atcggaaccc taaagggagc ccccgattta gagcttgacg   3060
gggaaagccg gcgaacgtgg cgagaaagga agggaagaaa gcgaaaggag cgggcgctag   3120
ggcgctggca agtgtagcgg tcacgctgcg cgtaaccacc acacccgccg cgcttaatgc   3180
gccgctacag ggcgcgtcca ttcgccattc aggctgcgca actgttggga agggcgatcg   3240
gtgcgggcct cttcgctatt acgccagctg gcgaaagggg gatgtgctgc aaggcgatta   3300
```

-continued

```
agttgggtaa cgccagggtt ttcccagtca cgacgttgta aaacgacggc cagtgaattg   3360
taatacgact cactataggg cgaattgggc ccgacgtcgc atgctaggag agtctgtcgt   3420
tcgcgagtgg cgcgccaatg tcatgagtta cacctgattc aaatagtgaa taataatata   3480
acagccacaa atgaaagatg tatccacggg tagatatggc tttaattact gatgattgaa   3540
tgattatctg agtgctacag ttgtaacgag tacgagttat tacctgctac tattgtactc   3600
ctaaatcaaa gtactcgtac atgcaatgaa ttacttgtac ttgcgccaat cagatctatc   3660
ggttgtattg tatataatac tagtctattc ttttgcttac cagatggtgt aacctccatc   3720
gacaatgaga tcgtggccgg tcatgtagct ggaggcgtcg gaagccatga agacaatagg   3780
gcctccaaac tcctcgggct cagccattcg tcggaaagga attcgtcgct cccagtcgtt   3840
tcggagctct ccgtcagtct cgatgatgtg acgggtcaga ggagtaagaa tgtagccggg   3900
agacagagtg ttgactcgga tgttgtactg ggcccactcg gcagccagag acttggccat   3960
gtggatgaca cctgccttgg acatgttgta gggggtctgg ggctgggggt cgttgacaat   4020
ggagccactc atggatgcaa ccagaatcag agatccagga gactcgtcca ggacaagcga   4080
cttggccacc tcggtagcga agttgtagga tcccatgagg ttgacgtcca gcagtcgctt   4140
gacctggggg ttgggataat caaaggcagt catattctcg cagaatccgg cacagttaat   4200
taagttgcga cacatgtctt gatagtatct tgaattctct ctcttgagct tttccataac   4260
aagttcttct gcctccagga agtccatcgg tggtttgatc atggttttgg tgtagtggta   4320
gtgcagtggt ggtattgtga ctggggatgt agttgagaat aagtcataca caagtcagct   4380
ttcttcgagc ctcatataag tataagtagt tcaacgtatt agcactgtac ccagcatctc   4440
cgtatcgaga aacacaacaa catgccccat tggacagatc atgcggatac acaggttgtg   4500
cagtatcata catactcgat cagacaggtc gtctgaccat catacaagct gaacaagcgc   4560
tccatacttg cacgctctct atatacacag ttaaattaca tatccatagt ctaacctcta   4620
acagttaatc ttctggtaag cctcccagcc agccttctgg tatcgcttgg cctcctcaat   4680
aggatctcgg ttctggccgt acagacctcg gccgacaatt atgatatccg ttccggtaga   4740
catgacatcc tcaacagttc ggtactgctg tccgagagcg tctcccttgt cgtcaagacc   4800
caccccgggg gtcagaataa gccagtcctc agagtcgccc ttaggtcggt tctgggcaat   4860
gaagccaacc acaaactcgg ggtcggatcg ggcaagctca atggtctgct tggagtactc   4920
gccagtggcc agagagccct tgcaagacag ctcggccagc atgagcagac ctctggccag   4980
cttctcgttg ggagagggga ctaggaactc cttgtactgg gagttctcgt agtcagagac   5040
gtcctccttc ttctgttcag agacagtttc ctcggcacca gctcgcaggc cagcaatgat   5100
tccggttccg ggtacaccgt gggcgttggt gatatcggac cactcggcga ttcggtgaca   5160
ccggtactgg tgcttgacag tgttgccaat atctgcgaac tttctgtcct cgaacaggaa   5220
gaaaccgtgc ttaagagcaa gttccttgag ggggagcaca gtgccggcgt aggtgaagtc   5280
gtcaatgatg tcgatatggg ttttgatcat gcacacataa ggtccgacct tatcggcaag   5340
ctcaatgagc tccttggtgg tggtaacatc cagagaagca cacaggttgg ttttcttggc   5400
tgccacgagc ttgagcactc gagcggcaaa ggcggacttg tggacgttag ctcgagcttc   5460
gtaggagggc attttggtgg tgaagaggag actgaaataa atttagtctg cagaactttt   5520
tatcggaacc ttatctgggg cagtgaagta tatgttatgg taatagttac gagttagttg   5580
aacttataga tagactggac tatacggcta tcggtccaaa ttagaaagaa cgtcaatggc   5640
tctctgggcg tcgcctttgc cgacaaaaat gtgatcatga tgaaagccag caatgacgtt   5700
```

-continued

```
gcagctgata ttgttgtcgg ccaaccgcgc cgaaaacgca gctgtcagac ccacagcctc   5760
caacgaagaa tgtatcgtca aagtgatcca agcacactca tagttggagt cgtactccaa   5820
aggcggcaat gacgagtcag acagatactc gtcgaccttt tccttgggaa ccaccaccgt   5880
cagcccttct gactcacgta ttgtagccac cgacacaggc aacagtccgt ggatagcaga   5940
atatgtcttg tcggtccatt tctcaccaac tttaggcgtc aagtgaatgt tgcagaagaa   6000
gtatgtgcct tcattgagaa tcggtgttgc tgatttcaat aaagtcttga gatcagtttg   6060
gccagtcatg ttgtgggggg taattggatt gagttatcgc ctacagtctg tacaggtata   6120
ctcgctgccc actttatact ttttgattcc gctgcacttg aagcaatgtc gtttaccaaa   6180
agtgagaatg ctccacagaa cacaccccag ggtatggttg agcaaaaaat aaacactccg   6240
atacggggaa tcgaaccccg gtctccacgg ttctcaagaa gtattcttga tgagagcgta   6300
tcgatagttg gagcaaggga gaaatgtaga gtgtgaaaga ctcactatgg tccgggctta   6360
tctcgaccaa tagccaaagt ctggagtttc tgagagaaaa aggcaagata cgtatgtaac   6420
aaagcgacgc atggtacaat aataccggag gcatgtatca tagagagtta gtggttcgat   6480
gatggcactg gtgcctggta tgactttata cggctgacta catatttgtc ctcagacata   6540
caattacagt caagcactta cccttggaca tctgtaggta ccccccggcc aagacgatct   6600
cagcgtgtcg tatgtcggat tggcgtagct ccctcgctcg tcaattggct cccatctact   6660
ttcttctgct tggctacacc cagcatgtct gctatggctc gttttcgtgc cttatctatc   6720
ctcccagtat taccaactct aaatgacatg atgtgattgg gtctacactt tcatatcaga   6780
gataaggagt agcacagttg cataaaaagc ccaactctaa tcagcttctt cctttcttgt   6840
aattagtaca aaggtgatta gcgaaatctg gaagcttagt tggccctaaa aaaatcaaaa   6900
aaagcaaaaa acgaaaaacg aaaaaccaca gttttgagaa cagggaggta acgaaggatc   6960
gtatatatat atatatatat atatacccac ggatcccgag accggccttt gattcttccc   7020
tacaaccaac cattctcacc accctaattc acaaccatgg cctttccttg ggcagataag   7080
tgggcagccg atgcgtctgc atctacaggg ctgcctccgg acctcctcaa gattgcattc   7140
actctggtca tgtcttatcc gctgagttct ctcatgaaac ggctgccaga tgacgccaaa   7200
aacctcaaga tcatctatat catctccgtg tccatcttct acatggtggg tgtcttctcc   7260
ctctatggcg gagctgccac tctgctcttc tcctcaatgg gtaccttctt catcacccaa   7320
tggaagagcc cttacatgcc ctgggtcaat tttggttttg tcatgaccca tctcttcgtc   7380
aatcacctgc gttcgcagtt tttccccgaa acatacgacc ccaatgtcat tgacatcacc   7440
ggagcacaga tggttctgtg ttccaagcta tcgtcttttg gatggaacgt ctacgatgga   7500
tggcagattg agaagggtga gcagctcagc gagttccaga ctaaaagggc tgttctcaag   7560
caccccagtc ttatggactt cctagctttt gtgttctact tcccttccat tctgacaggt   7620
ccttcttacg actatatgga gttccataac tggctcgatc tcagcctgtt caaggagctg   7680
gagaaagata aggaccccaa gcgagctgct cgacgaaagc gacacaagat cccccgatct   7740
ggaatcgctg cttccaagaa actcgccgct ggtatcttct ggatcgttct gtggacccag   7800
gtggactctc gaatctccac cgcctacgct tactcagacg cattcaccaa ggagcacaac   7860
atctttggac gaattgtgta cctctacatg ctcggtttca tgtaccgact caagtactac   7920
ggagcctggt ccatttccga gggagcctgc atcttgtctg gcctcggatt ccacggcgtg   7980
gaccccaaaa ctggcaagta caagtgggac cgtgtccaga acgtggaccc gtggggattc   8040
```

-continued

```
gaaactggtc aaaacacaaa ggctctgctg gaggcctgga accagaacac taacaagtgg   8100

ctacgaaact atgtgtacct ccgagtggtg cccaaaggcc aaaagcctgg attccgagcc   8160

actatcttca catttgtggt ttccgccttc tggcatggaa ctcgacctgg ctactatctc   8220

gcctttgtga ccgctgccat gtaccagtct gttggtaagt tcttccgacg atacctgcga   8280

cccttcttca tggagtctga tggaaagact gccggtccct ataagatcta ctacgacatt   8340

gtgtgttgga tcgttgtcca aaccgcattt ggatacgcta cccagtcctt tatgattcta   8400

gacttctggc tgtcgctcaa gtgttggaag aactcctggt tcctgtacca cattgctctg   8460

ggcgccatct ttgcaatttc tagcccctac aaggcatggg cgattcccaa gatcaagaaa   8520

aagcaggctg gagccgtcac tgacaagaag gacgccaagg aggaggtgaa gaaggacacc   8580

atcaagacca agtaagcggc cgcatgagaa gataaatata taaatacatt gagatattaa   8640

atgcgctaga ttagagagcc tcatactgct cggagagaag ccaagacgag tactcaaagg   8700

ggattacacc atccatatcc acagacacaa gctggggaaa ggttctatat acactttccg   8760

gaataccgta gtttccgatg ttatcaatgg gggcagccag gatttcaggc acttcggtgt   8820

ctcggggtga aatggcgttc ttggcctcca tcaagtcgta ccatgtcttc atttgcctgt   8880

caaagtaaaa cagaagcaga tgaagaatga acttgaagtg aaggaattta aatgtaacga   8940

aactgaaatt tgaccagata ttgtgtccgc ggtggagctc cagcttttgt tccctttagt   9000

gagggttaat ttcgagcttg gcgtaatcat ggtcatagct gtttcctgtg tgaaattgtt   9060

atccgctcac aagcttccac acaac                                         9085
```

```
<210> SEQ ID NO 25
<211> LENGTH: 1539
<212> TYPE: DNA
<213> ORGANISM: Artificial sequence
<220> FEATURE:
<223> OTHER INFORMATION: Y. lipolytica LPCAT containing M136S and T389A
      mutations

<400> SEQUENCE: 25

atggcctttc cttgggcaga taagtgggca gccgatgcgt ctgcatctac agggctgcct     60

ccggacctcc tcaagattgc attcactctg gtcatgtctt atccgctgag ttctctcatg    120

aaacggctgc cagatgacgc caaaaacctc aagatcatct atatcatctc cgtgtccatc    180

ttctacatgg tgggtgtctt ctccctctat ggcggagctg ccactctgct cttctcctca    240

atgggtacct tcttcatcac ccaatggaag agcccttaca tgccctgggt caattttggt    300

tttgtcatga cccatctctt cgtcaatcac ctgcgttcgc agtttttccc cgaaacatac    360

gaccccaatg tcattgacat caccggagca cagatggttc tgtgttccaa gctatcgtct    420

tttggatgga acgtctacga tggatggcag attgagaagg gtgagcagct cagcgagttc    480

cagactaaaa gggctgttct caagcacccc agtcttatgg acttcctagc ttttgtgttc    540

tacttccctt ccattctgac aggtccttct tacgactata tggagttcca taactggctc    600

gatctcagcc tgttcaagga gctggagaaa gataaggacc ccaagcgagc tgctcgacga    660

aagcgacaca agatccccg atctggaatc gctgcttcca agaaactcgc cgctggtatc    720

ttctggatcg ttctgtggac ccaggtggac tctcgaatct ccaccgccta cgcttactca    780

gacgcattca ccaaggagca caacatcttt ggacgaattg tgtacctcta catgctcggt    840

ttcatgtacc gactcaagta ctacggagcc tggtccattt ccgagggagc ctgcatcttg    900

tctggcctcg gattccacgg cgtggacccc aaaactggca agtacaagtg ggaccgtgtc    960
```

-continued

```
cagaacgtgg acccgtgggg attcgaaact ggtcaaaaca caaaggctct gctggaggcc   1020

tggaaccaga acactaacaa gtggctacga aactatgtgt acctccgagt ggtgcccaaa   1080

ggccaaaagc ctggattccg agccactatc ttcacatttg tggtttccgc cttctggcat   1140

ggaactcgac ctggctacta tctcgccttt gtgaccgctg ccatgtacca gtctgttggt   1200

aagttcttcc gacgatacct gcgacccttc ttcatggagt ctgatggaaa gactgccggt   1260

ccctataaga tctactacga cattgtgtgt tggatcgttg tccaaaccgc atttggatac   1320

gctacccagt cctttatgat tctagacttc tggctgtcgc tcaagtgttg gaagaactcc   1380

tggttcctgt accacattgc tctgggcgcc atctttgcaa tttctagccc ctacaaggca   1440

tgggcgattc ccaagatcaa gaaaaagcag gctggagccg tcactgacaa gaaggacgcc   1500

aaggaggagg tgaagaagga caccatcaag accaagtaa                          1539
```

<210> SEQ ID NO 26
<211> LENGTH: 512
<212> TYPE: PRT
<213> ORGANISM: Artificial sequence
<220> FEATURE:
<223> OTHER INFORMATION: Y. lipolytica LPCAT containing M136S and T389A mutations

<400> SEQUENCE: 26

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Ser Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255
```

-continued

```
Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Ala Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 27
<211> LENGTH: 14825
<212> TYPE: DNA
<213> ORGANISM: Artificial sequence
<220> FEATURE:
<223> OTHER INFORMATION: Construct pZKT2-ML9DCB for expressing YlCPT1, YlD9, and MaLPAAT1S

<400> SEQUENCE: 27

```
aaaccacgcc aactgatatc cccttacgtt accccctcat cacctggtga ggcaaaactg      60

taaggtgaaa gctaaaaatg acatctcagc tgcacgaagg accggggctt aaaagacggg     120

ctggtgcttg tgatttaaaa ctggacaaat ctcagcttgc ttgaaatttt ggtctccaac     180

tgtttccgag cgaatcgcac acaaaccggg cttctctctg cagaccacgc ccccgaaact     240

ctttctccca ccaccaccaa cactcccttt ccattcccac accgttcctc tctcatcctt     300

gcgcaatcat cttcgtctgc gacatattgt acgacataca gtaccacgga acgtttcaga     360

ccgtcgacgt gaacacatct taggaacagc aacctgagct acagaaatct atctataggc     420

ggataaaaaa acgcacccac tgctcgtcct ccttgctcct cgaaaccgac tcctctacac     480

acgtcaaatc cgaggttgaa atcttcccca catttggcag ccaaaccagc acatcccagc     540

aacctcgcac agcgccgaaa tcgacctgtc gacttggcca caaaaaaaag caccggctct     600
```

-continued

```
gcaacagttc tcacgaccaa ttacgtacaa gtacgaaatc gttcgtggac cgtgactgat    660
aagctcccac tttttcttct aacaacaggc aacagacaag tcacacaaaa caaaagccat    720
ggtgaaaaac gtggaccaag tggatctctc gcaggtcgac accattgcct ccggccgaga    780
tgtcaactac aaggtcaagt acacctccgg cgttaagatg agccagggcg cctacgacga    840
caagggccgc cacatttccg agcagccctt cacctgggcc aactggcacc agcacatcaa    900
ctggctcaac ttcattctgg tgattgcgct gcctctgtcg tcctttgctg ccgctccctt    960
cgtctccttc aactggaaga ccgccgcgtt tgctgtcggc tattacatgt gcaccggtct   1020
cggtatcacc gccggctacc accgaatgtg ggcccatcga gcctacaagg ccgctctgcc   1080
cgttcgaatc atccttgctc tgtttggagg aggagctgtc gagggctcca tccgatggtg   1140
ggcctcgtct caccgagtcc accaccgatg gaccgactcc aacaaggacc cttacgacgc   1200
ccgaaaggga ttctggttct cccactttgg ctggatgctg cttgtgccca accccaagaa   1260
caagggccga actgacattt ctgacctcaa caacgactgg gttgtccgac tccagcacaa   1320
gtactacgtt tacgttctcg tcttcatggc cattgttctg cccaccctcg tctgtggctt   1380
tggctggggc gactggaagg gaggtcttgt ctacgccggt atcatgcgat acacctttgt   1440
gcagcaggtg actttctgtg tcaactccct tgcccactgg attggagagc agcccttcga   1500
cgaccgacga actccccgag accacgctct taccgccctg gtcacctttg gagagggcta   1560
ccacaacttc caccacgagt tcccctcgga ctaccgaaac gccctcatct ggtaccagta   1620
cgaccccacc aagtggctca tctggaccct caagcaggtt ggtctcgcct gggacctcca   1680
gaccttctcc cagaacgcca tcgagcaggg tctcgtgcag cagcgacaga agaagctgga   1740
caagtggcga aacaacctca actggggtat ccccattgag cagctgcctg tcattgagtt   1800
tgaggagttc caagagcagg ccaagacccg agatctggtt ctcatttctg gcattgtcca   1860
cgacgtgtct gcctttgtcg agcaccaccc tggtggaaag gccctcatta tgagcgccgt   1920
cggcaaggac ggtaccgctg tcttcaacgg aggtgtctac cgacactcca acgctggcca   1980
caacctgctt gccaccatgc gagtttcggt cattcgaggc ggcatggagg ttgaggtgtg   2040
gaagactgcc cagaacgaaa agaaggacca gaacattgtc tccgatgaga gtggaaaccg   2100
aatccaccga gctggtctcc aggccacccg ggtcgagaac cccggtatgt ctggcatggc   2160
tgcttaggcg gccgcatgag aagataaata tataaataca ttgagatatt aaatgcgcta   2220
gattagagag cctcatactg ctcggagaga agccaagacg agtactcaaa ggggattaca   2280
ccatccatat ccacagacac aagctgggga aaggttctat atacactttc cggaataccg   2340
tagtttccga tgttatcaat gggggcagcc aggatttcag gcacttcggt gtctcggggt   2400
gaaatggcgt tcttggcctc catcaagtcg taccatgtct tcatttgcct gtcaaagtaa   2460
aacagaagca gatgaagaat gaacttgaag tgaaggaatt taaattttcg agattttaca   2520
gatatttctc gcagtttttc acgtcccctt gtccttgtcc tattgtttca aataaactct   2580
cgtctactga tttcacatgg aacctttgct atttcgggga taacccccttt tgccattgca   2640
cgatggacgt ggcaaaagaa agatcgccct gcggggatac ttatcatgtg gtcacatgct   2700
gtgattagaa ataaagaaaa aggtgctttt ttggcgctgt gattaacatc tcgtctgccg   2760
tgctctacta gtcgcaatag caaaaactcg cttaatagtg tgcatagtgc ggggtagcag   2820
gatactgaac tacagtacga tttgcttgct actgcttgta gcaattacct ttactgtagg   2880
gaccacacct cctggtttca atgtctttcc tcgcctcgac aaagcaaaac tgtcacccaa   2940
tcacaccttg ttcatattca ttagtgcatc cgttaacctt gacatgacac ttctcatact   3000
```

-continued

```
agtgataggg ctgtagttga gacaagttga ttcacacgga tacatacaaa gcctcagaga   3060
gcaaatgtta tatactcagg gaccgaccaa tcaaaaaaac acactcctaa taaccaccat   3120
ttccatctac gcgtactcac tctgtcagct gccccacatt gcccaatgca caatgcacaa   3180
tgatgtgtgc aaacaacgca atcaaaagtc tatggatgct gaccaaactc tgatcaccaa   3240
gttgcgaaca tgaaaaagaa gacctgtgta tatataagta agggggagag ccctaactag   3300
atctttcgaa aaccccccga ccttcacctt ccacaaccat gatcatctta tacgttttgg   3360
ccgttgcggt ctccttcctc atcttcaaga gagtcaccta caccatggct tctattggtt   3420
cgtccaaccc cgtgctcttg gctgcgattc ccttcgtcta cctgtttgtc ctcccacgag   3480
tcctggcttt cctgcctcag aaggctcagt tcctggccaa atgtattgtg gtcctgattg   3540
ccacgcttat catgtccgtt gcaggctgct tcatctcgat cgtgtgcgct cttctggaca   3600
agagatacgt catcaattac gttgtgtcgc gattgttctc cttccttgcc gctcgaccgt   3660
gtggtgtgac ctataagatt gttggtgagg aacacctcga taagtaccct gctatcgtgg   3720
tctgtaacca tcaatcctct atggatatga tggttttggg acgagttttt ccaaagcact   3780
gcgttgtcat ggcgaagaag gaactcctgt actttccctt tttgggaatg tttatgaaac   3840
tgagcaacgc tatcttcatc gaccggaaga accacaagaa agccatcgag tctaccaccc   3900
aagccgtggc ggacatgaag aagcacaact ctggaatctg gattttccca gagggcaccc   3960
ggtctagact ggacaaggca gacctgctgc ccttcaagaa aggtgccttt catcttgcaa   4020
ttcaggccca gctccctatt ctccccatta tctcgcaggg ctattcccat atctacgact   4080
cttcgaagcg gtacttcccc ggtggagagc tcgagatcag agtcctggag cccattccta   4140
caactggcct cactactgat gatgtgaacg acctgatgga caagacacga aaccttatgc   4200
tcaagcactt gaaggagatg gattcccagt attcgtcgag cactgctgaa aatggatcca   4260
cgcacatcga cgccgatatt gccaagtcta cagccaccag cattggcaac actgacgacg   4320
caattacaaa acgtcgtacc cctaaggaat aagcggccgc aagtgtggat ggggaagtga   4380
gtgcccggtt ctgtgtgcac aattggcaat ccaagatgga tggattcaac acagggatat   4440
agcgagctac gtggtggtgc gaggatatag caacggatat ttatgtttga cacttgagaa   4500
tgtacgatac aagcactgtc caagtacaat actaaacata ctgtacatac tcatactcgt   4560
acccgggcaa cggtttcact tgagtgcagt ggctagtgct cttactcgta cagtgtgcaa   4620
tactgcgtat catagtcttt gatgtatatc gtattcattc atgttagttg cgtacgtcta   4680
cattgagtgg gttaagtatg ctttgcggtg gtgcgctttg tttgaatttt aaatggaagt   4740
gtgctgtgag cagaccagac gaacggcttg tggggcgtgt ctatttatcc gggcttgtgg   4800
gggggttccg gcagaaacga tgaggtcaat caattgcgcg ggcaattgac tacaacaagc   4860
cctccagacg gactcttgtc gcctctgttc acattggcca atccttcacc ttattttcct   4920
acaacgtgct gcacttggac atctgtcaca aaggctcaaa gtctacgttg ctactgactc   4980
atgcaactct aagctgttgg atgaagggtc cggaaaaact ctcggctgtg tgattggtga   5040
ataaatcccg ctagccgagg tatgcaagga cgagtgcaga gaaatcctcc ggtcgagcac   5100
gcgaggggtc ggatgtgaga ctggtcagta attgacctga cgtgaccatc gtttggtttt   5160
tatggtcctt ctcggcccca tgacaaagtg tctctagacc ttgttgtgaa cctctgaccg   5220
ggccgctgtc gcaactaaaa aattgaaaat ggtaggctca aacgaagaga acctccaatt   5280
ttgacacaat tgagtttgga cgttttgcga gtggaagagc aggaggggga tgaggaggag   5340
```

-continued

```
acgttgcggc gtggctgatg tggcggagaa tcagagggcg acagaatggt aggactgtat   5400
aagtgtacgc gagcccattt gtatattgtc caacccgtat cccaagacca ataaccacta   5460
ttcttgaaac caactaacgc ctctagtgcg accttatcgt gaccgttgag cgtgtgtgag   5520
ctgagtgagg cctttacaaa tggcctgttt tagtaccgtg ctgttggata caacataaaa   5580
aatggcgtca tgtgacagca tcatccgttg tcaccgttga atagccgttg gcagcttgcg   5640
tcaacaacat gccatagaaa acaaaccgct cttgtatgta gaggtcatcc aggtgtgaca   5700
tattcacatg actccctagc ctctatcaca tgatgcgtgg cggacagact cggcttgaca   5760
gtggatctgc gttgcccccg tcattccggt tcattctcgt gtttaaaatt cgccaaccag   5820
cattggatac tgtatgtacc atacagacac gtttttttcct cttcgtagta ggcacagaag   5880
acgtgcaata gatgtacata acctctgctt gtgaaaaaga aatgagcagc agcttaagcg   5940
gctgaattat gtgtgcactt tggcactact tgcacctggt atctttgttg acttcaatga   6000
gacaggatgt tacgcattca ccacttcaca ctaatccgat tgtaccgcag tggtggttgg   6060
acacactcta gaccgctgtt tccactcaca acacctatcc tcggcttatg aagagaaagg   6120
gtcggcttat gcaatgcagg acacgcgtga aagttgaaaa acttgcgatt cagtaagaac   6180
aggcgcgcca gctgcattaa tgaatcggcc aacgcgcggg gagaggcggt ttgcgtattg   6240
ggcgctcttc cgcttcctcg ctcactgact cgctgcgctc ggtcgttcgg ctgcggcgag   6300
cggtatcagc tcactcaaag gcggtaatac ggttatccac agaatcaggg gataacgcag   6360
gaaagaacat gtgagcaaaa ggccagcaaa aggccaggaa ccgtaaaaag gccgcgttgc   6420
tggcgttttt ccataggctc cgcccccctg acgagcatca caaaaatcga cgctcaagtc   6480
agaggtggcg aaacccgaca ggactataaa gataccaggc gtttccccct ggaagctccc   6540
tcgtgcgctc tcctgttccg accctgccgc ttaccggata cctgtccgcc tttctccctt   6600
cgggaagcgt ggcgctttct catagctcac gctgtaggta tctcagttcg gtgtaggtcg   6660
ttcgctccaa gctgggctgt gtgcacgaac cccccgttca gcccgaccgc tgcgccttat   6720
ccggtaacta tcgtcttgag tccaacccgg taagacacga cttatcgcca ctggcagcag   6780
ccactggtaa caggattagc agagcgaggt atgtaggcgg tgctacagag ttcttgaagt   6840
ggtggcctaa ctacggctac actagaagaa cagtatttgg tatctgcgct ctgctgaagc   6900
cagttacctt cggaaaaaga gttggtagct cttgatccgg caaacaaacc accgctggta   6960
gcggtggttt ttttgtttgc aagcagcaga ttacgcgcag aaaaaaagga tctcaagaag   7020
atcctttgat cttttctacg gggtctgacg ctcagtggaa cgaaaactca cgttaaggga   7080
ttttggtcat gagattatca aaaaggatct tcacctagat ccttttaaat taaaaatgaa   7140
gttttaaatc aatctaaagt atatatgagt aaacttggtc tgacagttac caatgcttaa   7200
tcagtgaggc acctatctca gcgatctgtc tatttcgttc atccatagtt gcctgactcc   7260
ccgtcgtgta gataactacg atacgggagg gcttaccatc tggccccagt gctgcaatga   7320
taccgcgaga cccacgctca ccggctccag atttatcagc aataaaccag ccagccggaa   7380
gggccgagcg cagaagtggt cctgcaactt tatccgcctc catccagtct attaattgtt   7440
gccgggaagc tagagtaagt agttcgccag ttaatagttt gcgcaacgtt gttgccattg   7500
ctacaggcat cgtggtgtca cgctcgtcgt ttggtatggc ttcattcagc tccggttccc   7560
aacgatcaag gcgagttaca tgatccccca tgttgtgcaa aaaagcggtt agctccttcg   7620
gtcctccgat cgttgtcaga agtaagttgg ccgcagtgtt atcactcatg gttatggcag   7680
cactgcataa ttctcttact gtcatgccat ccgtaagatg cttttctgtg actggtgagt   7740
```

```
actcaaccaa gtcattctga gaatagtgta tgcggcgacc gagttgctct tgcccggcgt   7800
caatacggga taataccgcg ccacatagca gaactttaaa agtgctcatc attggaaaac   7860
gttcttcggg gcgaaaactc tcaaggatct taccgctgtt gagatccagt tcgatgtaac   7920
ccactcgtgc acccaactga tcttcagcat cttttacttt caccagcgtt tctgggtgag   7980
caaaaacagg aaggcaaaat gccgcaaaaa agggaataag ggcgacacgg aaatgttgaa   8040
tactcatact cttccttttt caatattatt gaagcattta tcagggttat tgtctcatga   8100
gcggatacat atttgaatgt atttagaaaa ataaacaaat aggggttccg cgcacatttc   8160
cccgaaaagt gccacctgat gcggtgtgaa ataccgcaca gatgcgtaag gagaaaatac   8220
cgcatcagga aattgtaagc gttaatattt tgttaaaatt cgcgttaaat ttttgttaaa   8280
tcagctcatt ttttaaccaa taggccgaaa tcggcaaaat cccttataaa tcaaaagaat   8340
agaccgagat agggttgagt gttgttccag tttggaacaa gagtccacta ttaaagaacg   8400
tggactccaa cgtcaaaggg cgaaaaaccg tctatcaggg cgatggccca ctacgtgaac   8460
catcacccta atcaagtttt ttggggtcga ggtgccgtaa agcactaaat cggaacccta   8520
aagggagccc ccgatttaga gcttgacggg gaaagccggc gaacgtggcg agaaaggaag   8580
ggaagaaagc gaaaggagcg ggcgctaggg cgctggcaag tgtagcggtc acgctgcgcg   8640
taaccaccac acccgccgcg cttaatgcgc cgctacaggg cgcgtccatt cgccattcag   8700
gctgcgcaac tgttgggaag ggcgatcggt gcgggcctct tcgctattac gccagctggc   8760
gaaaggggga tgtgctgcaa ggcgattaag ttgggtaacg ccagggtttt cccagtcacg   8820
acgttgtaaa acgacggcca gtgaattgta atacgactca ctatagggcg aattgggccc   8880
gacgtcgcat gcaaggaagt cgatggcggt ggtggcatac tcgtacttca tagagtactt   8940
gcactcggca tcgaggtagg ggtaggggta caggattcgc ttaccctttg tgagagtaga   9000
ctgggggatc acaccgggtt cgggggtggg catctcagca agagaagcaa cggtgaaagc   9060
tcgagatccg tagttctcag aaaggtgctt agcaacctcg ggtcaaggt cctcctgctg    9120
gatcagatca atgtaagtga gaggagtcca gtccttagca ccgatgagct tgacgtctcg   9180
ggtgacggcc ttggcggaga tttcaggctt gagaccgaac ttggcaatgc aggcatcgac   9240
agtctcctca gccatctgtc ggtaagtggt ccactttccg ccagcaatgg tgacaagacc   9300
agactcggag taggtgatga gatggtttcg gacaagagac tcggtgttct tggcgtgggg   9360
gtcccggaca aggggtcgga ttccggacca ggcggccaga acgtcctctc gtcgcacatc   9420
aaccttgccc tcaacgtagt gtcggacctc gttgagaatg aagtcaatgt cctcctcgga   9480
ggggataggg ttagcagtga tcttggtagg ctggtcagta gtaccggcaa gggtgtttcc   9540
ctgccagggg aggaagaaga taactcggcc gtcagaagta gcggggtcaa ggagtcccat   9600
cttcttgggg gagtagtaac cggggagaat gatgtgaaca ccggaggaag gagcacagat   9660
ctccttggtg ttcttgtcgt ccatctgtcg cagagagtca gtgaagggtc cagtagcatt   9720
aacgacacac ttggccttga tgttgaagga tccagcgttt ccgtcagtat ccttggcaac   9780
aacaccgttg agctggccat tggcgccctt ggtgagctcg gtgacctcgc aatggttcag   9840
gatggtggca cccttctcaa cagcagtcat aataagagaa acgttcattc gagagtcgtt   9900
ctgggagcca tcatagtaga caatggcgcc cttgagcttg tcatcggaaa gcatggggaa   9960
ggcatcgaga gcacgggatc gggagagcat gtaagaggac tcgaggttct gtcggccggc  10020
aagcagatcg tagcacttga cacccatcca gaagtaggga agctgccacc aggtgtagac  10080
```

-continued

```
ggggatcatg atgggcagag caaaggtgag gtggggagca atgtcgagga agacctttcg  10140
ctcgtgcagg gcctccttga ccagctcgta ctggttgtag tcgaggttcc acacagcctt  10200
ctcgaggtat cggacacctc cgtggatgag cttggtggat cgggacgagg ttccgcagga  10260
gaaatcgtct cgctcgacca gagcaacctt gaggcctcgt gtgacagcgt cgagggcgat  10320
accggatccg gtagctcctc caccaacaac gacgagatca aactcctcgg tcttcatctt  10380
aattaagttg cgacacatgt cttgatagta tcttgaattc tctctcttga gcttttccat  10440
aacaagttct tctgcctcca ggaagtccat gggtggtttg atcatggttt tggtgtagtg  10500
gtagtgcagt ggtggtattg tgactgggga tgtagttgag aataagtcat acacaagtca  10560
gctttcttcg agcctcatat aagtataagt agttcaacgt attagcactg tacccagcat  10620
ctccgtatcg agaaacacaa caacatgccc cattggacag atcatgcgga tacacaggtt  10680
gtgcagtatc atacatactc gatcagacag gtcgtctgac catcatacaa gctgaacaag  10740
cgctccatac ttgcacgctc tctatataca cagttaaatt acatatccat agtctaacct  10800
ctaacagtta atcttctggt aagcctccca gccagccttc tggtatcgct tggcctcctc  10860
aataggatct cggttctggc cgtacagacc tcggccgaca attatgatat ccgttccggt  10920
agacatgaca tcctcaacag ttcggtactg ctgtccgaga gcgtctccct tgtcgtcaag  10980
acccaccccg gggtcagaa taagccagtc ctcagagtcg cccttaggtc ggttctgggc  11040
aatgaagcca accacaaact cggggtcgga tcgggcaagc tcaatggtct gcttggagta  11100
ctcgccagtg gccagagagc ccttgcaaga cagctcggcc agcatgagca gacctctggc  11160
cagcttctcg ttgggagagg ggactaggaa ctccttgtac tgggagttct cgtagtcaga  11220
gacgtcctcc ttcttctgtt cagagacagt ttcctcggca ccagctcgca ggccagcaat  11280
gattccggtt ccgggtacac cgtgggcgtt ggtgatatcg gaccactcgg cgattcggtg  11340
acaccggtac tggtgcttga cagtgttgcc aatatctgcg aactttctgt cctcgaacag  11400
gaagaaaccg tgcttaagag caagttcctt gagggggagc acagtgccgg cgtaggtgaa  11460
gtcgtcaatg atgtcgatat gggttttgat catgcacaca taaggtccga ccttatcggc  11520
aagctcaatg agctccttgg tggtggtaac atccagagaa gcacacaggt tggttttctt  11580
ggctgccacg agcttgagca ctcgagcggc aaaggcggac ttgtggacgt tagctcgagc  11640
ttcgtaggag ggcattttgg tggtgaagag gagactgaaa taaatttagt ctgcagaact  11700
ttttatcgga accttatctg gggcagtgaa gtatatgtta tggtaatagt tacgagttag  11760
ttgaacttat agatagactg gactatacgg ctatcggtcc aaattagaaa gaacgtcaat  11820
ggctctctgg gcgtcgcctt tgccgacaaa aatgtgatca tgatgaaagc cagcaatgac  11880
gttgcagctg atattgttgt cggccaaccg cgccgaaaac gcagctgtca gacccacagc  11940
ctccaacgaa gaatgtatcg tcaaagtgat ccaagcacac tcatagttgg agtcgtactc  12000
caaaggcggc aatgacgagt cagacagata ctcgtcgacc ttttccttgg gaaccaccac  12060
cgtcagccct tctgactcac gtattgtagc caccgacaca ggcaacagtc cgtggatagc  12120
agaatatgtc ttgtcggtcc atttctcacc aactttaggc gtcaagtgaa tgttgcagaa  12180
gaagtatgtg ccttcattga gaatcggtgt tgctgatttc aataaagtct tgagatcagt  12240
ttggccagtc atgttgtggg gggtaattgg attgagttat cgcctacagt ctgtacaggt  12300
atactcgctg cccactttat actttttgat tccgctgcac ttgaagcaat gtcgtttacc  12360
aaaagtgaga atgctccaca gaacacaccc cagggtatgg ttgagcaaaa aataaacact  12420
ccgatacggg gaatcgaacc ccggtctcca cggttctcaa gaagtattct tgatgagagc  12480
```

```
gtatcgatgg ttaatgctgc tgtgtgctgt gtgtgtgtgt tgtttggcgc tcattgttgc  12540
gttatgcagc gtacaccaca atattggaag cttattagcc tttctatttt ttcgtttgca  12600
aggcttaaca acattgctgt ggagagggat ggggatatgg aggccgctgg agggagtcgg  12660
agaggcgttt tggagcggct tggcctggcg cccagctcgc gaaacgcacc taggaccctt  12720
tggcacgccg aaatgtgcca cttttcagtc tagtaacgcc ttacctacgt cattccatgc  12780
gtgcatgttt gcgccttttt tcccttgccc ttgatcgcca cacagtacag tgcactgtac  12840
agtggaggtt ttgggggggt cttagatggg agctaaaagc ggcctagcgg tacactagtg  12900
ggattgtatg gagtggcatg gagcctaggt ggagcctgac aggacgcacg accggctagc  12960
ccgtgacaga cgatgggtgg ctcctgttgt ccaccgcgta caaatgtttg ggccaaagtc  13020
ttgtcagcct tgcttgcgaa cctaattccc aattttgtca cttcgcaccc ccattgatcg  13080
agccctaacc cctgcccatc aggcaatcca attaagctcg cattgtctgc cttgtttagt  13140
ttggctcctg cccgtttcgg cgtccacttg cacaaacaca aacaagcatt atatataagg  13200
ctcgtctctc cctcccaacc acactcactt ttttgcccgt cttcccttgc taacacaaaa  13260
gtcaagaaca caaacaacca ccccaacccc cttacacaca agacatatct acagcaatgg  13320
ccatgggcgt attcattaaa caggagcagc ttccggctct caagaagtac aagtactccg  13380
ccgaggatca ctcgttcatc tccaacaaca ttctgcgccc cttctggcga cagtttgtca  13440
aaatcttccc tctgtggatg gcccccaaca tggtgactct gctgggcttc ttctttgtca  13500
ttgtgaactt catcaccatg ctcattgttg atcccaccca cgaccgcgag cctcccagat  13560
gggtctacct cacctacgct ctgggtctgt tcctttacca gacatttgat gcctgtgacg  13620
gatcccatgc ccgacgaact ggccagagtg gaccccttgg agagctgttt gaccactgtg  13680
tcgacgccat gaatacctct ctgattctca cggtggtggt gtccaccacc catatgggat  13740
ataacatgaa gctactgatt gtgcagattg ccgctctcgg aaacttctac ctgtcgacct  13800
gggagaccta ccataccgga actctgtacc tttctggctt ctctggtcct gttgaaggta  13860
tcttgattct ggtggctctt ttcgtcctca ccttcttcac tggtcccaac gtgtacgctc  13920
tgaccgtcta cgaggctctt cccgagtcca tcacttcgct gctgcctgcc agcttcctgg  13980
acgtcaccat cacccagatc tacattggat tcggagtgct gggcatggtg ttcaacatct  14040
acggcgcctg cggaaacgtg atcaagtact acaacaacaa gggcaagagc gctctccccg  14100
ccattctcgg aatcgccccc tttggcatct tctacgtcgg cgtctttgcc tgggcccatg  14160
ttgctcctct gcttctctcc aagtacgcca tcgtctatct gtttgccatt ggggctgcct  14220
ttgccatgca agtcggccag atgattcttg cccatctcgt gcttgctccc tttccccact  14280
ggaacgtgct gctcttcttc ccctttgtgg gactggcagt gcactacatt gcacccgtgt  14340
ttggctggga cgccgatatc gtgtcggtta acactctctt cacctgtttt ggcgccaccc  14400
tctccattta cgccttcttt gtgcttgaga tcatcgacga gatcaccaac tacctcgata  14460
tctggtgtct gcgaatcaag taccctcagg agaagaagac cgaataagcg gccgcatgta  14520
catacaagat tatttataga aatgaatcgc gatcgaacaa agagtacgag tgtacgagta  14580
ggggatgatg ataaaagtgg aagaagttcc gcatctttgg atttatcaac gtgtaggacg  14640
atacttcctg taaaaatgca atgtctttac cataggttct gctgtagatg ttattaacta  14700
ccattaacat gtctacttgt acagttgcag accagttgga gtatagaatg gtacacttac  14760
caaaaagtgt tgatggttgt aactacgata tataaaactg ttgacgggat ctgcgtacac  14820
```

tgttt 14825

<210> SEQ ID NO 28
<211> LENGTH: 13236
<212> TYPE: DNA
<213> ORGANISM: Artificial sequence
<220> FEATURE:
<223> OTHER INFORMATION: Construct pZKLY-PP2YAP for expressing YlYAP1, Yl6PGL, and YlG6PDH

<400> SEQUENCE: 28
aaaccatcat ctaagggcct caaaactacc tcggaactgc tgcgctgatc tggacaccac 60
agaggttccg agcactttag gttgcaccaa atgtcccacc aggtgcaggc agaaaacgct 120
ggaacagcgt gtacagtttg tcttaacaaa aagtgagggc gctgaggtcg agcagggtgg 180
tgtgacttgt tatagccttt agagctgcga aagcgcgtat ggatttggct catcaggcca 240
gattgagggt ctgtggacac atgtcatgtt agtgtacttc aatcgccccc tggatatagc 300
cccgacaata ggccgtggcc tcattttttt gccttccgca catttccatt gctcggtacc 360
cacaccttgc ttctcctgca cttgccaacc ttaatactgg tttacattga ccaacatctt 420
acaagcgggg ggcttgtcta gggtatatat aaacagtggc tctcccaatc ggttgccagt 480
ctcttttttc ctttctttcc ccacagattc gaaatctaaa ctacacatca caccatggct 540
cccaaggtca tctctaagaa cgaatcgcaa ctggtcgctg aggctgctgc cgctgagatc 600
attcgactcc agaacgagtc aattgctgcc actggagctt tccatgttgc cgtatctgga 660
ggctctctgg tgtctgctct ccgaaagggt ctggtcaaca actcggagac caagttcccc 720
aagtggaaga ttttcttctc cgacgaacgg ctggtcaagc tggacgatgc cgactccaac 780
tacggtctcc tcaagaagga tctgctcgat cacatcccca aggatcagca accacaggtc 840
ttcaccgtca aggagtctct tctgaacgac tctgatgccg tctccaagga ctaccaggag 900
cagattgtca agaatgtgcc tctcaacggc cagggagtgc ctgttttcga tctcattctg 960
ctcggatgcg gtcctgatgg ccacacttgc tcgctgttcc ctggacacgc tctgctcaag 1020
gaggagacca agtttgtcgc caccattgag gactctccca agcctcctcc tcgacgaatc 1080
accatcactt tccccgttct caaggctgcc aaggccatcg ctttcgtcgc cgagggagcc 1140
ggaaaggccc ctgtcctcaa gcagatcttc gaggagcccg agcccactct tccctctgcc 1200
attgtcaaca aggtcgctac cggacccgtt ttctggtttg tttccgactc tgccgttgag 1260
ggcgtcaacc tctccaagat ctagcggccg catgagaaga taaatatata aatacattga 1320
gatattaaat gcgctagatt agagagcctc atactgctcg gagagaagcc aagacgagta 1380
ctcaaagggg attacaccat ccatatccac agacacaagc tggggaaagg ttctatatac 1440
actttccgga ataccgtagt ttccgatgtt atcaatgggg gcagccagga tttcaggcac 1500
ttcggtgtct cggggtgaaa tggcgttctt ggcctccatc aagtcgtacc atgtcttcat 1560
ttgcctgtca aagtaaaaca gaagcagatg aagaatgaac ttgaagtgaa ggaatttaaa 1620
tgcgtttgga tagcactagt ctatgaggag cgttttatgt tgcggtgagg gcgattggtg 1680
ctcatatggg ttcaattgag gtggcggaac gagcttagtc ttcaattgag gtgcgagcga 1740
cacaattggg tgtcacgtgg cctaattgac ctcgggtcgt ggagtcccca gttatacagc 1800
aaccacgagg tgcatgggta ggagacgtca ccagacaata gggttttttt tggactggag 1860
agggttgggc aaaagcgctc aacgggctgt ttggggagct gtgggggagg aattggcgat 1920
atttgtgagg ttaacggctc cgatttgcgt gttttgtcgc tcctgcatct ccccataccc 1980
atatcttccc tccccacctc tttccacgat aattttacgg atcagcaata aggttccttc 2040
tcctagtttc cacgtccata tatatctatg ctgcgtcgtc cttttcgtga catcaccaaa 2100
acacatacaa ccatggctgg caccttaccc aagttcggcg acggaaccac cattgtggtt 2160
cttggagcct ccggcgacct cgctaagaag aagaccgtga gtattgaacc agactgaggt 2220
caattgaaga gtaggagagt ctgagaacat tcgacggacc tgattgtgct ctggaccact 2280
caattgactc gttgagagcc ccaatgggtc ttggctagcc gagtcgttga cttgttgact 2340
tgttgagccc agaaccccca acttttgcca ccatacaccg ccatcaccat gacacccaga 2400
tgtgcgtgcg tatgtgagag tcaattgttc cgtggcaagg cacagcttat tccaccgtgt 2460
tccttgcaca ggtggtcttt acgctctccc actctatccg agcaataaaa gcggaaaaac 2520
agcagcaagt cccaacagac ttctgctccg aataaggcgt ctagcaagtg tgcccaaaac 2580
tcaattcaaa aatgtcagaa acctgatatc aacccgtctt caaaagctaa ccccagttcc 2640
ccgccctctt cggcctttac cgaaacggcc tgctgcccaa aaatgttgaa atcatcggct 2700
acgcacggtc gaaaatgact caggaggagt accacgagcg aatcagccac tacttcaaga 2760
cccccgacga ccagtccaag gagcaggcca agaagttcct tgagaacacc tgctacgtcc 2820
agggccctta cgacggtgcc gagggctacc agcgactgaa tgaaaagatt gaggagtttg 2880
agaagaagaa gcccgagccc cactaccgtc ttttctacct ggctctgccc cccagcgtct 2940
tccttgaggc tgccaacggt ctgaagaagt atgtctaccc cggcgagggc aaggcccgaa 3000
tcatcatcga gaagcccttt ggccacgacc tggcctcgtc acgagagctc caggacggcc 3060
ttgctcctct ctggaaggag tctgagatct tccgaatcga ccactacctc ggaaaggaga 3120
tggtcaagaa cctcaacatt ctgcgatttg gcaaccagtt cctgtccgcc gtgtgggaca 3180
agaacaccat ttccaacgtc cagatctcct tcaaggagcc ctttggcact gagggccgag 3240
gtggatactt caacgacatt ggaatcatcc gagacgttat tcagaaccat ctgttgcagg 3300
ttctgtccat tctagccatg gagcgacccg tcactttcgg cgccgaggac attcgagatg 3360
agaaggtcaa ggtgctccga tgtgtcgaca ttctcaacat tgacgacgtc attctcggcc 3420
agtacggccc ctctgaagac ggaaagaagc ccggatacac cgatgacgat ggcgttcccg 3480
atgactcccg agctgtgacc tttgctgctc tccatctcca gatccacaac gacagatggg 3540
agggtgttcc tttcatcctc cgagccggta aggctctgga cgagggcaag gtcgagatcc 3600
gagtgcagtt ccgagacgtg accaagggcg ttgtggacca tctgcctcga aatgagctcg 3660
tcatccgaat ccagccctcc gagtccatct acatgaagat gaactccaag ctgcctggcc 3720
ttactgccaa gaacattgtc accgacctgg atctgaccta caaccgacga tactcggacg 3780
tgcgaatccc tgaggcttac gagtctctca ttctggactg cctcaagggt gaccacacca 3840
actttgtgcg aaacgacgag ctggacattt cctggaagat tttcaccgat ctgctgcaca 3900
agattgacga ggacaagagc attgtgcccg agaagtacgc ctacggctct cgtggccccg 3960
agcgactcaa gcagtggctc cgagaccgag gctacgtgcg aaacggcacc gagctgtacc 4020
aatggcctgt caccaagggc tcctcgtgag cggccgcaag tgtggatggg gaagtgagtg 4080
cccggttctg tgtgcacaat tggcaatcca agatggatgg attcaacaca gggatatagc 4140
gagctacgtg gtggtgcgag gatatagcaa cggatattta tgtttgacac ttgagaatgt 4200
acgatacaag cactgtccaa gtacaatact aaacatactg tacatactca tactcgtacc 4260
cgggcaacgg tttcacttga gtgcagtggc tagtgctctt actcgtacag tgtgcaatac 4320
tgcgtatcat agtctttgat gtatatcgta ttcattcatg ttagttgcgt acgttgattg 4380

```
aggtggagcc agatgggcta ttgtttcata tatagactgg cagccacctc tttggcccag   4440
catgtttgta tacctggaag ggaaaactaa agaagctggc tagtttagtt tgattattat   4500
agtagatgtc ctaatcacta gagattagaa tgtcttggcg atgattagtc gtcgtcccct   4560
gtatcatgtc tagaccaact gtgtcatgaa gttggtgctg gtgttttacc tgtgtactac   4620
aagtaggtgt cctagatcta gtgtacagag ccgtttagac ccatgtggac ttcaccatta   4680
acgatggaaa atgttcatta tatgacagta tattacaatg gacttgctcc atttcttcct   4740
tgcatcacat gttctccacc tccatagttg atcaacacat catagtagct aaggctgctg   4800
ctctcccact acagtccacc acaagttaag tagcaccgtc agtacagcta aaagtacacg   4860
tctagtacgt ttcataacta gtcaagtagc ccctattaca gatatcagca ctatcacgca   4920
cgagtttttc tctgtgctat ctaatcaact tgccaagtat tcggagaaga tacactttct   4980
tggcatcagg tatacgaggg agcctatcag atgaaaaagg gtatattgga tccattcata   5040
tccacctaca cgttgtcata atctcctcat tcacgtgatt catttcgtga cactagtttc   5100
tcactttccc ccccgcacct atagtcaact tggcggacac gctacttgta gctgacgttg   5160
atttatagac ccaatcaaag cgggttatcg gtcaggtagc acttatcatt catcgttcat   5220
actacgatga gcaatctcgg gcatgtccgg aaaagtgtcg ggcgcgccag ctgcattaat   5280
gaatcggcca acgcgcgggg agaggcggtt tgcgtattgg gcgctcttcc gcttcctcgc   5340
tcactgactc gctgcgctcg gtcgttcggc tgcggcgagc ggtatcagct cactcaaagg   5400
cggtaatacg gttatccaca gaatcagggg ataacgcagg aaagaacatg tgagcaaaag   5460
gccagcaaaa ggccaggaac cgtaaaaagg ccgcgttgct ggcgtttttc cataggctcc   5520
gcccccctga cgagcatcac aaaaatcgac gctcaagtca gaggtggcga aacccgacag   5580
gactataaag ataccaggcg tttccccctg gaagctccct cgtgcgctct cctgttccga   5640
ccctgccgct taccggatac ctgtccgcct ttctcccttc gggaagcgtg gcgctttctc   5700
atagctcacg ctgtaggtat ctcagttcgg tgtaggtcgt tcgctccaag ctgggctgtg   5760
tgcacgaacc ccccgttcag cccgaccgct gcgccttatc cggtaactat cgtcttgagt   5820
ccaacccggt aagacacgac ttatcgccac tggcagcagc cactggtaac aggattagca   5880
gagcgaggta tgtaggcggt gctacagagt tcttgaagtg gtggcctaac tacggctaca   5940
ctagaagaac agtatttggt atctgcgctc tgctgaagcc agttaccttc ggaaaaagag   6000
ttggtagctc ttgatccggc aaacaaacca ccgctggtag cggtggtttt tttgtttgca   6060
agcagcagat tacgcgcaga aaaaaaggat ctcaagaaga tcctttgatc ttttctacgg   6120
ggtctgacgc tcagtggaac gaaaactcac gttaagggat tttggtcatg agattatcaa   6180
aaaggatctt cacctagatc cttttaaatt aaaaatgaag ttttaaatca atctaaagta   6240
tatatgagta aacttggtct gacagttacc aatgcttaat cagtgaggca cctatctcag   6300
cgatctgtct atttcgttca tccatagttg cctgactccc cgtcgtgtag ataactacga   6360
tacgggaggg cttaccatct ggccccagtg ctgcaatgat accgcgagac ccacgctcac   6420
cggctccaga tttatcagca ataaaccagc cagccggaag ggccgagcgc agaagtggtc   6480
ctgcaacttt atccgcctcc atccagtcta ttaattgttg ccgggaagct agagtaagta   6540
gttcgccagt taatagtttg cgcaacgttg ttgccattgc tacaggcatc gtggtgtcac   6600
gctcgtcgtt tggtatggct tcattcagct ccggttccca acgatcaagg cgagttacat   6660
gatcccccat gttgtgcaaa aaagcggtta gctccttcgg tcctccgatc gttgtcagaa   6720
```

-continued

```
gtaagttggc cgcagtgtta tcactcatgg ttatggcagc actgcataat tctcttactg   6780
tcatgccatc cgtaagatgc ttttctgtga ctggtgagta ctcaaccaag tcattctgag   6840
aatagtgtat gcggcgaccg agttgctctt gcccggcgtc aatacgggat aataccgcgc   6900
cacatagcag aactttaaaa gtgctcatca ttggaaaacg ttcttcgggg cgaaaactct   6960
caaggatctt accgctgttg agatccagtt cgatgtaacc cactcgtgca cccaactgat   7020
cttcagcatc ttttactttc accagcgttt ctgggtgagc aaaaacagga aggcaaaatg   7080
ccgcaaaaaa gggaataagg gcgacacgga aatgttgaat actcatactc ttcctttttc   7140
aatattattg aagcatttat cagggttatt gtctcatgag cggatacata tttgaatgta   7200
tttagaaaaa taaacaaata ggggttccgc gcacatttcc ccgaaaagtg ccacctgatg   7260
cggtgtgaaa taccgcacag atgcgtaagg agaaaatacc gcatcaggaa attgtaagcg   7320
ttaatatttt gttaaaattc gcgttaaatt tttgttaaat cagctcattt tttaaccaat   7380
aggccgaaat cggcaaaatc ccttataaat caaaagaata gaccgagata gggttgagtg   7440
ttgttccagt ttggaacaag agtccactat taaagaacgt ggactccaac gtcaaagggc   7500
gaaaaaccgt ctatcagggc gatggcccac tacgtgaacc atcaccctaa tcaagttttt   7560
tggggtcgag gtgccgtaaa gcactaaatc ggaaccctaa agggagcccc cgatttagag   7620
cttgacgggg aaagccggcg aacgtggcga gaaaggaagg gaagaaagcg aaaggagcgg   7680
gcgctagggc gctggcaagt gtagcggtca cgctgcgcgt aaccaccaca cccgccgcgc   7740
ttaatgcgcc gctacagggc gcgtccattc gccattcagg ctgcgcaact gttgggaagg   7800
gcgatcggtg cgggcctctt cgctattacg ccagctggcg aaagggggat gtgctgcaag   7860
gcgattaagt tgggtaacgc cagggttttc ccagtcacga cgttgtaaaa cgacggccag   7920
tgaattgtaa tacgactcac tatagggcga attgggcccg acgtcgcatg cattccgaca   7980
gcagcgactg ggcaccatga tcaagcgaaa caccttcccc cagctgccct ggcaaaccat   8040
caagaaccct actttcatca agtgcaagaa cggttctact cttctcacct ccggtgtcta   8100
cggctggtgc cgaaagccta actacaccgc tgatttcatc atgtgcctca cctgggctct   8160
catgtgcggt gttgcttctc ccctgcctta cttctacccg gtcttcttct tcctggtgct   8220
catccaccga gcttaccgag actttgagcg actggagcga aagtacggtg aggactacca   8280
ggagttcaag cgacaggtcc cttggatctt catcccttat gttttctaaa cgataagctt   8340
agtgagcgaa tggtgaggtt acttaattga gtggccagcc tatgggattg tataacagac   8400
agtcaatata ttactgaaaa gactgaacag ccagacggag tgaggttgtg agtgaatcgt   8460
agagggcggc tattacagca agtctactct acagtgtact aacacagcag agaacaaata   8520
caggtgtgca ttcggctatc tgagaattag ttggagagct cgagaccctc ggcgataaac   8580
tgctcctcgg ttttgtgtcc atacttgtac ggaccattgt aatggggcaa gtcgttgagt   8640
tctcgtcgtc cgacgttcag agcacagaaa ccaatgtaat caatgtagca gagatggttc   8700
tgcaaaagat tgatttgtgc gagcaggtta attaagttgc gacacatgtc ttgatagtat   8760
cttgaattct ctctcttgag cttttccata acaagttctt ctgcctccag gaagtccatg   8820
ggtggtttga tcatggtttt ggtgtagtgg tagtgcagtg gtggtattgt gactggggat   8880
gtagttgaga ataagtcata cacaagtcag ctttcttcga gcctcatata agtataagta   8940
gttcaacgta ttagcactgt acccagcatc tccgtatcga gaaacacaac aacatgcccc   9000
attggacaga tcatgcggat acacaggttg tgcagtatca tacatactcg atcagacagg   9060
tcgtctgacc atcatacaag ctgaacaagc gctccatact tgcacgctct ctatatacac   9120
```

-continued

```
agttaaatta catatccata gtctaacctc taacagttaa tcttctggta agcctcccag   9180
ccagccttct ggtatcgctt ggcctcctca ataggatctc ggttctggcc gtacagacct   9240
cggccgacaa ttatgatatc cgttccggta gacatgacat cctcaacagt tcggtactgc   9300
tgtccgagag cgtctccctt gtcgtcaaga cccaccccgg gggtcagaat aagccagtcc   9360
tcagagtcgc ccttaggtcg gttctgggca atgaagccaa ccacaaactc ggggtcggat   9420
cgggcaagct caatggtctg cttggagtac tcgccagtgg ccagagagcc cttgcaagac   9480
agctcggcca gcatgagcag acctctggcc agcttctcgt tgggagaggg gactaggaac   9540
tccttgtact gggagttctc gtagtcagag acgtcctcct tcttctgttc agagacagtt   9600
tcctcggcac cagctcgcag gccagcaatg attccggttc cgggtacacc gtgggcgttg   9660
gtgatatcgg accactcggc gattcggtga caccggtact ggtgcttgac agtgttgcca   9720
atatctgcga actttctgtc ctcgaacagg aagaaaccgt gcttaagagc aagttccttg   9780
agggggagca cagtgccggc gtaggtgaag tcgtcaatga tgtcgatatg ggttttgatc   9840
atgcacacat aaggtccgac cttatcggca agctcaatga gctccttggt ggtggtaaca   9900
tccagagaag cacacaggtt ggttttcttg gctgccacga gcttgagcac tcgagcggca   9960
aaggcggact tgtggacgtt agctcgagct tcgtaggagg gcattttggt ggtgaagagg  10020
agactgaaat aaatttagtc tgcagaactt tttatcggaa ccttatctgg ggcagtgaag  10080
tatatgttat ggtaatagtt acgagttagt tgaacttata gatagactgg actatacggc  10140
tatcggtcca aattagaaag aacgtcaatg gctctctggg cgtcgccttt gccgacaaaa  10200
atgtgatcat gatgaaagcc agcaatgacg ttgcagctga tattgttgtc ggccaaccgc  10260
gccgaaaacg cagctgtcag acccacagcc tccaacgaag aatgtatcgt caaagtgatc  10320
caagcacact catagttgga gtcgtactcc aaaggcggca atgacgagtc agacagatac  10380
tcgtcgacct tttccttggg aaccaccacc gtcagccctt ctgactcacg tattgtagcc  10440
accgacacag gcaacagtcc gtggatagca gaatatgtct tgtcggtcca tttctcacca  10500
actttaggcg tcaagtgaat gttgcagaag aagtatgtgc cttcattgag aatcggtgtt  10560
gctgatttca ataaagtctt gagatcagtt tggccagtca tgttgtgggg ggtaattgga  10620
ttgagttatc gcctacagtc tgtacaggta tactcgctgc ccactttata ctttttgatt  10680
ccgctgcact tgaagcaatg tcgtttacca aaagtgagaa tgctccacag aacacacccc  10740
agggtatggt tgagcaaaaa ataaacactc cgatacgggg aatcgaaccc cggtctccac  10800
ggttctcaag aagtattctt gatgagagcg tatcgatttc tcccaccacc accaacactc  10860
cctttccatt cccacaccgt tcctctctca tccttgcgca atcatcttcg tctgcgacat  10920
attgtacgac atacagtacc acggaacgtt tcagaccgtc gacgtgaaca catcttagga  10980
acagcaacct gagctacaga aatctatcta taggcggata aaaaaacgca cccactgctc  11040
gtcctccttg ctcctcgaaa ccgactcctc tacacacgtc aaatccgagg ttgaaatctt  11100
ccccacattt ggcagccaaa ccagcacatc ccagcaacct cgcacagcgc cgaaatcgac  11160
ctgtcgactt ggccacaaaa aaaagcaccg gctctgcaac agttctcacg accaattacg  11220
tacaagtacg aaatcgttcg tggaccgtga ctgataagct cccacttttt cttctaacaa  11280
caggcaacag acaagtcaca caaaacaaaa gccatgtact cagactacaa cattcctggt  11340
gccatgccgg cgtccatggc catgcctccg ttcaaacagg agtttgacta cgcccaatac  11400
gaccttaacc agcccctgcc cccgcagcag caacaacagc ctatcgacct gacccctgga  11460
```

gggcccctcc ccgtctcgga ttactcgacg tcgtcataca ccctggacaa cgactcacag 11520
aagcgaaaaa tgtccccggg agagtccacc agtgacggag gcgccgacga cgagtctcca 11580
gaaggagatg acggtgaggc cgaccccaag aagccccgaa agcccggccg aaagcccgaa 11640
accaccatcc ccgcgtccaa acgcaaggct cagaaccggg ctgcccaaag ggccttcaga 11700
gagcgaaagg aaaagcatct gcgcgacctg gaaaccaaaa tatctcagct cgagggcgag 11760
acggcagcca aaaactcgga aaacgagttc ctgcgcttcc aggtccagcg gcttcagaac 11820
gagctcaagc tttaccgtga gaagcctgcc ggcacttcgg gagcctctgg agtctctgga 11880
gccggagcac ccgcttcaaa cgtgcattcg gctcccatcc cggagatgtc gtccaaaccg 11940
ttcacgttcg agttcccctc gtacaacgtg cccaagccga ccgatgtgga gcgagaggca 12000
cgcgagcaac tgcaacgaga gcagatccga ggctacttgc agcgcaagcc ctcatctgtg 12060
gcctccgaca ccacttctcc tgcatctcaa acctcgtgca accagtctcc ctgcaccaac 12120
ccctcggcat acacttcgcc ccagagccag agtggaagtg tgagccagca gaagcccctg 12180
ttgggtgcta ccatcgctgc catgaacggc aagcccgacc cccatgctgt tgacttttgt 12240
gctgagctct ccaaggcctg tgtaaacaag gccgagctgc tgcagcgatc cgccacagcc 12300
agtgcatctc ccacaacctc caacacggtg gtaccgtccg cagctgcacc gggtagcact 12360
cagcagtcgg caggccagcc ctctgtatcc actcctacct cctccacaac tgcccctcct 12420
caattgtctg catctgtcgc tacagccggc tctgatcttc ccggatcgga cttcctgttt 12480
gacatgccct tcgacatgga ctttatgtcg taccgagacc ccgtttccga gacggcacat 12540
ctggacgact tttcgctgcc cgagctcacg acagaaacat ccatgtttga tcctctggac 12600
ccccattcca gcagcgacgt tatttctggc aagcctctgt ctaccatggg cgctacacac 12660
agtggtgtca acaacggaca gggaagtggt gctcccgaag tcaagaagga ggaggatgag 12720
gacctgctca tgttctccaa gcccaagacg ctcatgaact gcaccgctgt gtgggaccgt 12780
atcacgtcgc atcccaagtt tggcgatatc gacatcgagg gcctgtgttc ggagctgcga 12840
aacaaggcaa agtgcagtga gagtggcgtc gtgttgacgg agttggacgt ggatggtgtc 12900
ctgtcaacgt tccagtaagc ggccgcatgt acatacaaga ttatttatag aaatgaatcg 12960
cgatcgaaca aagagtacga gtgtacgagt aggggatgat gataaaagtg gaagaagttc 13020
cgcatctttg gatttatcaa cgtgtaggac gatacttcct gtaaaaatgc aatgtcttta 13080
ccataggttc tgctgtagat gttattaact accattaaca tgtctacttg tacagttgca 13140
gaccagttgg agtatagaat ggtacactta ccaaaaagtg ttgatggttg taactacgat 13200
atataaaact gttgacggga tctgcgtaca ctgttt 13236

<210> SEQ ID NO 29
<211> LENGTH: 843
<212> TYPE: DNA
<213> ORGANISM: Candida albicans

<400> SEQUENCE: 29
atgagcaaag aaacaacttc atataccaat gctaaattag gtccattacc aaccaaagca 60
gcaaccattc ctgataatat tttagatgca ttttcattaa aaggtaaagt tgcttctgta 120
actggttcct ctggaggaat tggttgggca gtagctgaag ggtatgcaca agctggtgct 180
gatgttgcca tctggtataa ttctcatcct gctgatgata aagctgaata tttaaccaag 240
acttatgggg ttaaatccaa agcatacaaa tgtaatgtta ctgatttcca agatgttgaa 300
aaagttgtca aacaaattga actggatttc ggtaccattg atatctttgt tgccaatgct 360

```
ggtgttgcct ggaccgaagg gcccgaaatt gatgtcaagg gagttgacaa atggaacaaa    420

gttgttgatg ttgatttaaa cagtgtttat tattgtgctc atgttgttgg tccaattttc    480

agaaaaaagg gtaaagggtc attcattttc actgccagta tgtcggcttc aattgttaat    540

gtcccacaat tacaagcagc ttacaacgct gctaaagctg ggtcaaaca tttgtccaaa    600

tcattgagtg ttgaatgggc accatttgct agagtcaatt ctgtttctcc aggttacatc    660

gctactcatc ttagtgaatt tgctgatcca gatgtcaaga gtaaatggtt gcaacttaca    720

ccacttggta gagaagccaa accaagagag cttgttggtg cctacttgta tttggcttcc    780

gatgctgcat cttatacaac tggtgctgat cttgctgttg atggtggtta cacagttgtt    840

taa                                                                  843
```

```
<210> SEQ ID NO 30
<211> LENGTH: 280
<212> TYPE: PRT
<213> ORGANISM: Candida albicans

<400> SEQUENCE: 30

Met Ser Lys Glu Thr Thr Ser Tyr Thr Asn Ala Lys Leu Gly Pro Leu
1               5                   10                  15

Pro Thr Lys Ala Ala Thr Ile Pro Asp Asn Ile Leu Asp Ala Phe Ser
            20                  25                  30

Leu Lys Gly Lys Val Ala Ser Val Thr Gly Ser Ser Gly Gly Ile Gly
        35                  40                  45

Trp Ala Val Ala Glu Gly Tyr Ala Gln Ala Gly Ala Asp Val Ala Ile
    50                  55                  60

Trp Tyr Asn Ser His Pro Ala Asp Asp Lys Ala Glu Tyr Leu Thr Lys
65                  70                  75                  80

Thr Tyr Gly Val Lys Ser Lys Ala Tyr Lys Cys Asn Val Thr Asp Phe
                85                  90                  95

Gln Asp Val Glu Lys Val Val Lys Gln Ile Glu Ser Asp Phe Gly Thr
            100                 105                 110

Ile Asp Ile Phe Val Ala Asn Ala Gly Val Ala Trp Thr Glu Gly Pro
        115                 120                 125

Glu Ile Asp Val Lys Gly Val Asp Lys Trp Asn Lys Val Val Asp Val
    130                 135                 140

Asp Leu Asn Ser Val Tyr Tyr Cys Ala His Val Val Gly Pro Ile Phe
145                 150                 155                 160

Arg Lys Lys Gly Lys Gly Ser Phe Ile Phe Thr Ala Ser Met Ser Ala
                165                 170                 175

Ser Ile Val Asn Val Pro Gln Leu Gln Ala Ala Tyr Asn Ala Ala Lys
            180                 185                 190

Ala Gly Val Lys His Leu Ser Lys Ser Leu Ser Val Glu Trp Ala Pro
        195                 200                 205

Phe Ala Arg Val Asn Ser Val Ser Pro Gly Tyr Ile Ala Thr His Leu
    210                 215                 220

Ser Glu Phe Ala Asp Pro Asp Val Lys Ser Lys Trp Leu Gln Leu Thr
225                 230                 235                 240

Pro Leu Gly Arg Glu Ala Lys Pro Arg Glu Leu Val Gly Ala Tyr Leu
                245                 250                 255

Tyr Leu Ala Ser Asp Ala Ala Ser Tyr Thr Thr Gly Ala Asp Leu Ala
            260                 265                 270

Val Asp Gly Gly Tyr Thr Val Val
```

275 280

<210> SEQ ID NO 31
<211> LENGTH: 648
<212> TYPE: PRT
<213> ORGANISM: Yarrowia lipolytica

<400> SEQUENCE: 31

Met Thr Gln Pro Val Asn Arg Lys Ala Thr Val Glu Arg Val Glu Pro
1 5 10 15

Ala Val Glu Val Ala Asp Ser Glu Ser Glu Ala Lys Thr Asp Val His
20 25 30

Val His His His His His His His Lys Arg Lys Ser Val Lys Gly Lys
35 40 45

Ile Leu Asn Phe Phe Thr Arg Ser Arg Arg Ile Thr Phe Val Leu Gly
50 55 60

Ala Val Val Gly Val Ile Ala Ala Gly Tyr Tyr Ala Ala Pro Pro Glu
65 70 75 80

Leu Ser Ile Asp Ile Asp Ala Leu Leu Gly Asp Leu Pro Ser Phe Asp
85 90 95

Phe Asp Ala Leu Ser Leu Asp Asn Leu Ser Met Asp Ser Val Ser Asp
100 105 110

Phe Val Gln Asp Met Lys Ser Arg Phe Pro Thr Lys Ile Leu Gln Glu
115 120 125

Ala Ala Lys Ile Glu Lys His Gln Lys Ser Glu Gln Lys Ala Ala Pro
130 135 140

Phe Ala Val Gly Lys Ala Met Lys Ser Glu Gly Leu Asn Ala Lys Tyr
145 150 155 160

Pro Val Val Leu Val Pro Gly Val Ile Ser Thr Gly Leu Glu Ser Trp
165 170 175

Ser Leu Glu Gly Thr Glu Glu Cys Pro Thr Glu Ser His Phe Arg Lys
180 185 190

Arg Met Trp Gly Ser Trp Tyr Met Ile Arg Val Met Leu Leu Asp Lys
195 200 205

Tyr Cys Trp Leu Gln Asn Leu Met Leu Asp Thr Glu Thr Gly Leu Asp
210 215 220

Pro Pro His Phe Lys Leu Arg Ala Ala Gln Gly Phe Ala Ser Ala Asp
225 230 235 240

Phe Phe Met Ala Gly Tyr Trp Leu Trp Asn Lys Leu Leu Glu Asn Leu
245 250 255

Ala Val Ile Gly Tyr Asp Thr Asp Thr Met Ser Ala Ala Ala Tyr Asp
260 265 270

Trp Arg Leu Ser Tyr Pro Asp Leu Glu His Arg Asp Gly Tyr Phe Ser
275 280 285

Lys Leu Lys Ala Ser Ile Glu Glu Thr Lys Arg Met Thr Gly Glu Lys
290 295 300

Thr Val Leu Thr Gly His Ser Met Gly Ser Gln Val Ile Phe Tyr Phe
305 310 315 320

Met Lys Trp Ala Glu Ala Glu Gly Tyr Gly Gly Gly Gly Pro Asn Trp
325 330 335

Val Asn Asp His Ile Glu Ser Phe Val Asp Ile Ser Gly Ser Met Leu
340 345 350

Gly Thr Pro Lys Thr Leu Val Ala Leu Leu Ser Gly Glu Met Lys Asp
355 360 365

-continued

```
Thr Val Gln Leu Asn Ala Met Ala Val Tyr Gly Leu Glu Gln Phe Phe
    370                 375                 380

Ser Arg Arg Glu Arg Ala Asp Leu Leu Arg Thr Trp Gly Gly Ile Ala
385                 390                 395                 400

Ser Met Ile Pro Lys Gly Gly Lys Ala Ile Trp Gly Asp His Ser Gly
                405                 410                 415

Ala Pro Asp Asp Glu Pro Gly Gln Asn Val Thr Phe Gly Asn Phe Ile
            420                 425                 430

Lys Phe Lys Glu Ser Leu Thr Glu Tyr Ser Ala Lys Asn Leu Thr Met
        435                 440                 445

Asp Glu Thr Val Asp Phe Leu Tyr Ser Gln Ser Pro Glu Trp Phe Val
    450                 455                 460

Asn Arg Thr Glu Gly Ala Tyr Ser Phe Gly Ile Ala Lys Thr Arg Lys
465                 470                 475                 480

Gln Val Glu Gln Asn Glu Lys Arg Pro Ser Thr Trp Ser Asn Pro Leu
                485                 490                 495

Glu Ala Ala Leu Pro Asn Ala Pro Asp Leu Lys Ile Tyr Cys Phe Tyr
            500                 505                 510

Gly Val Gly Lys Asp Thr Glu Arg Ala Tyr Tyr Tyr Gln Asp Glu Pro
        515                 520                 525

Asn Pro Glu Gln Thr Asn Leu Asn Val Ser Ile Ala Gly Asn Asp Pro
    530                 535                 540

Asp Gly Val Leu Met Gly Gln Gly Asp Gly Thr Val Ser Leu Val Thr
545                 550                 555                 560

His Thr Met Cys His Arg Trp Lys Asp Glu Asn Ser Lys Phe Asn Pro
                565                 570                 575

Gly Asn Ala Gln Val Lys Val Val Glu Met Leu His Gln Pro Asp Arg
            580                 585                 590

Leu Asp Ile Arg Gly Gly Ala Gln Thr Ala Glu His Val Asp Ile Leu
        595                 600                 605

Gly Arg Ser Glu Leu Asn Glu Met Val Leu Lys Val Ala Ser Gly Lys
    610                 615                 620

Gly Asn Glu Ile Glu Glu Arg Val Ile Ser Asn Ile Asp Glu Trp Val
625                 630                 635                 640

Trp Lys Ile Asp Leu Gly Ser Asn
                645
```

<210> SEQ ID NO 32
<211> LENGTH: 419
<212> TYPE: PRT
<213> ORGANISM: Yarrowia lipolytica

<400> SEQUENCE: 32

```
Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95
```

```
Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys


<210> SEQ ID NO 33
<211> LENGTH: 263
<212> TYPE: PRT
<213> ORGANISM: Eutreptiella sp. CCMP389

<400> SEQUENCE: 33

Met Ala Ala Val Ile Glu Val Ala Asn Glu Phe Val Ala Ile Thr Ala
1               5                   10                  15

Glu Thr Leu Pro Lys Val Asp Tyr Gln Arg Leu Trp Arg Asp Ile Tyr
            20                  25                  30

Ser Cys Glu Leu Leu Tyr Phe Ser Ile Ala Phe Val Ile Leu Lys Phe
        35                  40                  45
```

```
Thr Leu Gly Glu Leu Ser Asp Ser Gly Lys Lys Ile Leu Arg Val Leu
    50                  55                  60

Phe Lys Trp Tyr Asn Leu Phe Met Ser Val Phe Ser Leu Val Ser Phe
65                  70                  75                  80

Leu Cys Met Gly Tyr Ala Ile Tyr Thr Val Gly Leu Tyr Ser Asn Glu
                85                  90                  95

Cys Asp Arg Ala Phe Asp Asn Ser Leu Phe Arg Phe Ala Thr Lys Val
            100                 105                 110

Phe Tyr Tyr Ser Lys Phe Leu Glu Tyr Ile Asp Ser Phe Tyr Leu Pro
        115                 120                 125

Leu Met Ala Lys Pro Leu Ser Phe Leu Gln Phe Phe His His Leu Gly
    130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Val Met Tyr Gly
                165                 170                 175

Tyr Tyr Trp Thr Arg Leu Met Lys Phe Asn Phe Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
    210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp Lys Lys Val Gln
            260


<210> SEQ ID NO 34
<211> LENGTH: 24
<212> TYPE: PRT
<213> ORGANISM: Artificial sequence
<220> FEATURE:
<223> OTHER INFORMATION: Linker comprised in E389D9eS/EgD8M multizyme

<400> SEQUENCE: 34

Gly Ala Gly Pro Ala Arg Pro Ala Gly Leu Pro Pro Ala Thr Tyr Tyr
1               5                   10                  15

Asp Ser Leu Ala Val Met Gly Ser
            20


<210> SEQ ID NO 35
<211> LENGTH: 701
<212> TYPE: PRT
<213> ORGANISM: Artificial sequence
<220> FEATURE:
<223> OTHER INFORMATION: EgD9eS/EgD8M fusion

<400> SEQUENCE: 35

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
```

-continued

```
        50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln Gly Ala Gly Pro Ala Arg Pro Ala Gly Leu Pro Pro Ala Thr
            260                 265                 270

Tyr Tyr Asp Ser Leu Ala Val Met Val Lys Ala Ser Arg Gln Ala Leu
        275                 280                 285

Pro Leu Val Ile Asp Gly Lys Val Tyr Asp Val Ser Ala Trp Val Asn
    290                 295                 300

Phe His Pro Gly Gly Ala Glu Ile Ile Glu Asn Tyr Gln Gly Arg Asp
305                 310                 315                 320

Ala Thr Asp Ala Phe Met Val Met His Ser Gln Glu Ala Phe Asp Lys
                325                 330                 335

Leu Lys Arg Met Pro Lys Ile Asn Gln Ala Ser Glu Leu Pro Pro Gln
            340                 345                 350

Ala Ala Val Asn Glu Ala Gln Glu Asp Phe Arg Lys Leu Arg Glu Glu
        355                 360                 365

Leu Ile Ala Thr Gly Met Phe Asp Ala Ser Pro Leu Trp Tyr Ser Tyr
    370                 375                 380

Lys Ile Leu Thr Thr Leu Gly Leu Gly Val Leu Ala Phe Phe Met Leu
385                 390                 395                 400

Val Gln Tyr His Leu Tyr Phe Ile Gly Ala Leu Val Leu Gly Met His
                405                 410                 415

Tyr Gln Gln Met Gly Trp Leu Ser His Asp Ile Cys His His Gln Thr
            420                 425                 430

Phe Lys Asn Arg Asn Trp Asn Asn Val Leu Gly Leu Val Phe Gly Asn
        435                 440                 445

Gly Leu Gln Gly Phe Ser Val Thr Trp Trp Lys Asp Arg His Asn Ala
    450                 455                 460

His His Ser Ala Thr Asn Val Gln Gly His Asp Pro Asp Ile Asp Asn
465                 470                 475                 480
```

Leu Pro Leu Leu Ala Trp Ser Glu Asp Asp Val Thr Arg Ala Ser Pro
485 490 495

Ile Ser Arg Lys Leu Ile Gln Phe Gln Gln Tyr Tyr Phe Leu Val Ile
500 505 510

Cys Ile Leu Leu Arg Phe Ile Trp Cys Phe Gln Ser Val Leu Thr Val
515 520 525

Arg Ser Leu Lys Asp Arg Asp Asn Gln Phe Tyr Arg Ser Gln Tyr Lys
530 535 540

Lys Glu Ala Ile Gly Leu Ala Leu His Trp Thr Leu Lys Thr Leu Phe
545 550 555 560

His Leu Phe Phe Met Pro Ser Ile Leu Thr Ser Met Leu Val Phe Phe
565 570 575

Val Ser Glu Leu Val Gly Gly Phe Gly Ile Ala Ile Val Val Phe Met
580 585 590

Asn His Tyr Pro Leu Glu Lys Ile Gly Asp Ser Val Trp Asp Gly His
595 600 605

Gly Phe Ser Val Gly Gln Ile His Glu Thr Met Asn Ile Arg Arg Gly
610 615 620

Ile Ile Thr Asp Trp Phe Phe Gly Gly Leu Asn Tyr Gln Ile Glu His
625 630 635 640

His Leu Trp Pro Thr Leu Pro Arg His Asn Leu Thr Ala Val Ser Tyr
645 650 655

Gln Val Glu Gln Leu Cys Gln Lys His Asn Leu Pro Tyr Arg Asn Pro
660 665 670

Leu Pro His Glu Gly Leu Val Ile Leu Leu Arg Tyr Leu Ser Gln Phe
675 680 685

Ala Arg Met Ala Glu Lys Gln Pro Gly Ala Lys Ala Gln
690 695 700

<210> SEQ ID NO 36
<211> LENGTH: 702
<212> TYPE: PRT
<213> ORGANISM: Artificial sequence
<220> FEATURE:
<223> OTHER INFORMATION: EaD9eS/EaD8S fusion

<400> SEQUENCE: 36

Met Glu Ala Ala Lys Glu Leu Val Ser Ile Val Gln Glu Glu Leu Pro
1 5 10 15

Lys Val Asp Tyr Ala Gln Leu Trp Gln Asp Ala Ser Ser Cys Glu Val
20 25 30

Leu Tyr Leu Ser Val Ala Phe Val Ala Ile Lys Phe Met Leu Arg Pro
35 40 45

Leu Asp Leu Lys Arg Gln Ala Thr Leu Lys Lys Leu Phe Thr Ala Tyr
50 55 60

Asn Phe Leu Met Ser Ile Tyr Ser Phe Gly Ser Phe Leu Ala Met Ala
65 70 75 80

Tyr Ala Leu Ser Val Thr Gly Ile Leu Ser Gly Asp Cys Glu Thr Ala
85 90 95

Phe Asn Asn Asp Val Phe Arg Ile Thr Thr Gln Leu Phe Tyr Leu Ser
100 105 110

Lys Phe Val Glu Tyr Ile Asp Ser Phe Tyr Leu Pro Leu Met Asp Lys
115 120 125

Pro Leu Ser Phe Leu Gln Phe Phe His His Leu Gly Ala Pro Ile Asp
130 135 140

```
Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
            180                 185                 190

Met Gln Ile Ile Gln Phe Asn Val Gly Phe Tyr Ile Val Trp Lys Tyr
        195                 200                 205

Arg Asn Val Pro Cys Tyr Arg Gln Asp Gly Met Arg Met Phe Ala Trp
    210                 215                 220

Ile Phe Asn Tyr Trp Tyr Val Gly Thr Val Leu Leu Leu Phe Leu Asn
225                 230                 235                 240

Phe Tyr Val Gln Thr Tyr Ile Arg Lys Pro Arg Lys Asn Arg Gly Lys
                245                 250                 255

Lys Glu Gly Ala Gly Pro Ala Arg Pro Ala Gly Leu Pro Pro Ala Thr
            260                 265                 270

Tyr Tyr Asp Ser Leu Ala Val Met Gly Ser Met Val Lys Arg Pro Ala
        275                 280                 285

Leu Pro Leu Thr Val Asp Gly Val Thr Tyr Asp Val Ser Ala Trp Leu
    290                 295                 300

Asn His His Pro Gly Gly Ala Asp Ile Ile Glu Asn Tyr Arg Gly Arg
305                 310                 315                 320

Asp Ala Thr Asp Val Phe Met Val Met His Ser Glu Asn Ala Val Ser
                325                 330                 335

Lys Leu Arg Arg Met Pro Ile Met Glu Pro Ser Ser Pro Leu Thr Pro
            340                 345                 350

Thr Pro Pro Lys Pro Asn Ser Asp Glu Pro Gln Glu Asp Phe Arg Lys
        355                 360                 365

Leu Arg Asp Glu Leu Ile Ala Ala Gly Met Phe Asp Ala Ser Pro Met
    370                 375                 380

Trp Tyr Ala Tyr Lys Thr Leu Ser Thr Leu Gly Leu Gly Val Leu Ala
385                 390                 395                 400

Val Leu Leu Met Thr Gln Trp His Trp Tyr Leu Val Gly Ala Ile Val
                405                 410                 415

Leu Gly Ile His Phe Gln Gln Met Gly Trp Leu Ser His Asp Ile Cys
            420                 425                 430

His His Gln Leu Phe Lys Asp Arg Ser Ile Asn Asn Ala Ile Gly Leu
        435                 440                 445

Leu Phe Gly Asn Val Leu Gln Gly Phe Ser Val Thr Trp Trp Lys Asp
    450                 455                 460

Arg His Asn Ala His His Ser Ala Thr Asn Val Gln Gly His Asp Pro
465                 470                 475                 480

Asp Ile Asp Asn Leu Pro Leu Leu Ala Trp Ser Lys Glu Asp Val Glu
                485                 490                 495

Arg Ala Gly Pro Phe Ser Arg Arg Met Ile Lys Tyr Gln Gln Tyr Tyr
            500                 505                 510

Phe Phe Phe Ile Cys Ala Leu Leu Arg Phe Ile Trp Cys Phe Gln Ser
        515                 520                 525

Ile His Thr Ala Thr Gly Leu Lys Asp Arg Ser Asn Gln Tyr Tyr Arg
    530                 535                 540

Arg Gln Tyr Glu Lys Glu Ser Val Gly Leu Ala Leu His Trp Gly Leu
545                 550                 555                 560
```

-continued

```
Lys Ala Leu Phe Tyr Tyr Phe Tyr Met Pro Ser Phe Leu Thr Gly Leu
            565                 570                 575

Met Val Phe Phe Val Ser Glu Leu Leu Gly Gly Phe Gly Ile Ala Ile
            580                 585                 590

Val Val Phe Met Asn His Tyr Pro Leu Glu Lys Ile Gln Asp Ser Val
        595                 600                 605

Trp Asp Gly His Gly Phe Cys Ala Gly Gln Ile His Glu Thr Met Asn
    610                 615                 620

Val Gln Arg Gly Leu Val Thr Asp Trp Phe Phe Gly Gly Leu Asn Tyr
625                 630                 635                 640

Gln Ile Glu His His Leu Trp Pro Thr Leu Pro Arg His Asn Leu Thr
                645                 650                 655

Ala Ala Ser Ile Lys Val Glu Gln Leu Cys Lys Lys His Asn Leu Pro
            660                 665                 670

Tyr Arg Ser Pro Pro Met Leu Glu Gly Val Gly Ile Leu Ile Ser Tyr
        675                 680                 685

Leu Gly Thr Phe Ala Arg Met Val Ala Lys Ala Asp Lys Ala
    690                 695                 700
```

<210> SEQ ID NO 37
<211> LENGTH: 420
<212> TYPE: PRT
<213> ORGANISM: Euglena anabaena

<400> SEQUENCE: 37

```
Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
            20                  25                  30

Glu Asn Tyr Arg Gly Arg Asp Ala Thr Asp Val Phe Met Val Met His
        35                  40                  45

Ser Glu Asn Ala Val Ser Lys Leu Arg Arg Met Pro Ile Met Glu Pro
    50                  55                  60

Ser Ser Pro Leu Thr Pro Thr Pro Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95

Phe Asp Ala Ser Pro Met Trp Tyr Ala Tyr Lys Thr Leu Ser Thr Leu
            100                 105                 110

Gly Leu Gly Val Leu Ala Val Leu Leu Met Thr Gln Trp His Trp Tyr
        115                 120                 125

Leu Val Gly Ala Ile Val Leu Gly Ile His Phe Gln Gln Met Gly Trp
    130                 135                 140

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
                165                 170                 175

Val Thr Trp Trp Lys Asp Arg His Asn Ala His His Ser Ala Thr Asn
            180                 185                 190

Val Gln Gly His Asp Pro Asp Ile Asp Asn Leu Pro Leu Leu Ala Trp
        195                 200                 205

Ser Lys Glu Asp Val Glu Arg Ala Gly Pro Phe Ser Arg Arg Met Ile
    210                 215                 220

Lys Tyr Gln Gln Tyr Tyr Phe Phe Phe Ile Cys Ala Leu Leu Arg Phe
225                 230                 235                 240
```

```
Ile Trp Cys Phe Gln Ser Ile His Thr Ala Thr Gly Leu Lys Asp Arg
                245                 250                 255

Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
        275                 280                 285

Ser Phe Leu Thr Gly Leu Met Val Phe Phe Val Ser Glu Leu Leu Gly
    290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
        355                 360                 365

Pro Arg His Asn Leu Thr Ala Ala Ser Ile Lys Val Glu Gln Leu Cys
    370                 375                 380

Lys Lys His Asn Leu Pro Tyr Arg Ser Pro Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
            420
```

<210> SEQ ID NO 38
<211> LENGTH: 314
<212> TYPE: PRT
<213> ORGANISM: Mortierella alpina

<400> SEQUENCE: 38

```
Met Ser Ile Gly Ser Ser Asn Pro Val Leu Leu Ala Ala Ile Pro Phe
1               5                   10                  15

Val Tyr Leu Phe Val Leu Pro Arg Val Leu Ala Phe Leu Pro Gln Lys
            20                  25                  30

Ala Gln Phe Leu Ala Lys Cys Ile Val Val Leu Ile Ala Thr Leu Ile
        35                  40                  45

Met Ser Val Ala Gly Cys Phe Ile Ser Ile Val Cys Ala Leu Leu Asp
    50                  55                  60

Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu Glu His
                85                  90                  95

Leu Asp Lys Tyr Pro Ala Ile Val Val Cys Asn His Gln Ser Ser Met
            100                 105                 110

Asp Met Met Val Leu Gly Arg Val Phe Pro Lys His Cys Val Val Met
        115                 120                 125

Ala Lys Lys Glu Leu Leu Tyr Phe Pro Phe Leu Gly Met Phe Met Lys
    130                 135                 140

Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
                165                 170                 175

Ile Trp Ile Phe Pro Glu Gly Thr Arg Ser Arg Leu Asp Lys Ala Asp
```

```
            180                 185                 190

Leu Leu Pro Phe Lys Lys Gly Ala Phe His Leu Ala Ile Gln Ala Gln
        195                 200                 205

Leu Pro Ile Leu Pro Ile Ile Ser Gln Gly Tyr Ser His Ile Tyr Asp
    210                 215                 220

Ser Ser Lys Arg Tyr Phe Pro Gly Gly Glu Leu Glu Ile Arg Val Leu
225                 230                 235                 240

Glu Pro Ile Pro Thr Thr Gly Leu Thr Thr Asp Asp Val Asn Asp Leu
                245                 250                 255

Met Asp Lys Thr Arg Asn Leu Met Leu Lys His Leu Lys Glu Met Asp
            260                 265                 270

Ser Gln Tyr Ser Ser Ser Thr Ala Glu Asn Gly Ser Thr His Ile Asp
        275                 280                 285

Ala Asp Ile Ala Lys Ser Thr Ala Thr Ser Ile Gly Asn Thr Asp Asp
    290                 295                 300

Ala Ile Thr Lys Arg Arg Thr Pro Lys Glu
305                 310


<210> SEQ ID NO 39
<211> LENGTH: 1539
<212> TYPE: DNA
<213> ORGANISM: Yarrowia lipolytica

<400> SEQUENCE: 39

atggcctttc catgggcaga taagtgggca gccgatgcgt ctgcatctac agggctgcct     60

ccggacctcc tcaagattgc attcactctg gtcatgtctt atccgctgag ttctctcatg    120

aaacggctgc cagatgacgc caaaaacctc aagatcatct atatcatctc cgtgtccatc    180

ttctacatgg tgggtgtctt ctccctctat ggcggagctg ccactctgct cttctcctca    240

atgggtacct tcttcatcac ccaatggaag agcccttaca tgccctgggt caattttggt    300

tttgtcatga cccatctctt cgtcaatcac ctgcgttcgc agtttttccc cgaaacatac    360

gaccccaatg tcattgacat caccggagca cagatggttc tgtgtatgaa gctatcgtct    420

tttggatgga acgtctacga tggatggcag attgagaagg gtgagcagct cagcgagttc    480

cagactaaaa gggctgttct caagcacccc agtcttatgg acttcctagc ttttgtgttc    540

tacttccctt ccattctgac aggtccttct tacgactata tggagttcca taactggctc    600

gatctcagcc tgttcaagga gctggagaaa gataaggacc ccaagcgagc tgctcgacga    660

aagcgacaca agatccccccg atctggaatc gctgcttcca agaaactcgc cgctggtatc    720

ttctggatcg ttctgtggac ccaggtggac tctcgaatct ccaccgccta cgcttactca    780

gacgcattca ccaaggagca caacatcttt ggacgaattg tgtacctcta catgctcggt    840

ttcatgtacc gactcaagta ctacggagcc tggtccattt ccgagggagc ctgcatcttg    900

tctggcctcg gattccatgg cgtggacccc aaaactggca agtacaagtg ggaccgtgtc    960

cagaacgtgg acccgtgggg attcgaaact ggtcaaaaca caaaggctct gctggaggcc   1020

tggaaccaga acactaacaa gtggctacga aactatgtgt acctccgagt ggtgcccaaa   1080

ggccaaaagc ctggattccg agccactatc ttcacatttg tggtttccgc cttctggcat   1140

ggaactcgac ctggctacta tctcaccttt gtgaccgctg ccatgtacca gtctgttggt   1200

aagttcttcc gacgatacct gcgacccttc ttcatggagt ctgatggaaa gactgccggt   1260

ccctataaga tctactacga cattgtgtgt tggatcgttg tccaaaccgc atttggatac   1320

gctacccagt cctttatgat tctagacttc tggctgtcgc tcaagtgttg gaagaactcc   1380
```

```
tggttcctgt accacattgc tctgggcgcc atctttgcaa tttctagccc ctacaaggca   1440

tgggcgattc ccaagatcaa gaaaaagcag gctggagccg tcactgacaa gaaggacgcc   1500

aaggaggagg tgaagaagga caccatcaag accaagtaa                         1539


<210> SEQ ID NO 40
<211> LENGTH: 512
<212> TYPE: PRT
<213> ORGANISM: Yarrowia lipolytica

<400> SEQUENCE: 40

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
```

```
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 41
<211> LENGTH: 1539
<212> TYPE: DNA
<213> ORGANISM: Artificial sequence
<220> FEATURE:
<223> OTHER INFORMATION: YlLPCAT lacking two internal NcoI restriction
      sites with respect to SEQ ID NO:39, but encoding wild type YlLPCAT
      protein

<400> SEQUENCE: 41

atggcctttc cttgggcaga taagtgggca gccgatgcgt ctgcatctac agggctgcct     60

ccggacctcc tcaagattgc attcactctg gtcatgtctt atccgctgag ttctctcatg    120

aaacggctgc cagatgacgc caaaaacctc aagatcatct atatcatctc cgtgtccatc    180

ttctacatgg tgggtgtctt ctccctctat ggcggagctg ccactctgct cttctcctca    240

atgggtacct tcttcatcac ccaatggaag agcccttaca tgccctgggt caattttggt    300

tttgtcatga cccatctctt cgtcaatcac ctgcgttcgc agtttttccc cgaaacatac    360

gaccccaatg tcattgacat caccggagca cagatggttc tgtgtatgaa gctatcgtct    420

tttggatgga acgtctacga tggatggcag attgagaagg gtgagcagct cagcgagttc    480

cagactaaaa gggctgttct caagcacccc agtcttatgg acttcctagc ttttgtgttc    540

tacttccctt ccattctgac aggtccttct tacgactata tggagttcca taactggctc    600

gatctcagcc tgttcaagga gctggagaaa gataaggacc ccaagcgagc tgctcgacga    660

aagcgacaca agatccccccg atctggaatc gctgcttcca agaaactcgc cgctggtatc    720

ttctggatcg ttctgtggac ccaggtggac tctcgaatct ccaccgccta cgcttactca    780

gacgcattca ccaaggagca caacatcttt ggacgaattg tgtacctcta catgctcggt    840

ttcatgtacc gactcaagta ctacggagcc tggtccattt ccgagggagc ctgcatcttg    900

tctggcctcg gattccacgg cgtggacccc aaaactggca agtacaagtg ggaccgtgtc    960

cagaacgtgg acccgtgggg attcgaaact ggtcaaaaca caaaggctct gctggaggcc   1020

tggaaccaga acactaacaa gtggctacga aactatgtgt acctccgagt ggtgcccaaa   1080
```

```
ggccaaaagc ctggattccg agccactatc ttcacatttg tggtttccgc cttctggcat   1140

ggaactcgac ctggctacta tctcaccttt gtgaccgctg ccatgtacca gtctgttggt   1200

aagttcttcc gacgatacct gcgacccttc ttcatggagt ctgatggaaa gactgccggt   1260

ccctataaga tctactacga cattgtgtgt tggatcgttg tccaaaccgc atttggatac   1320

gctacccagt cctttatgat tctagacttc tggctgtcgc tcaagtgttg gaagaactcc   1380

tggttcctgt accacattgc tctgggcgcc atctttgcaa tttctagccc ctacaaggca   1440

tgggcgattc ccaagatcaa gaaaaagcag gctggagccg tcactgacaa gaaggacgcc   1500

aaggaggagg tgaagaagga caccatcaag accaagtaa                          1539
```

```
<210> SEQ ID NO 42
<211> LENGTH: 8518
<212> TYPE: DNA
<213> ORGANISM: Artificial sequence
<220> FEATURE:
<223> OTHER INFORMATION: Construct pY306-N, containing YlLPCAT*
      nucleotide sequence

<400> SEQUENCE: 42
```

```
catggccttt ccttgggcag ataagtgggc agccgatgcg tctgcatcta cagggctgcc     60

tccggacctc ctcaagattg cattcactct ggtcatgtct tatccgctga gttctctcat    120

gaaacggctg ccagatgacg ccaaaaacct caagatcatc tatatcatct ccgtgtccat    180

cttctacatg gtgggtgtct tctccctcta tggcggagct gccactctgc tcttctcctc    240

aatgggtacc ttcttcatca cccaatggaa gagcccttac atgccctggg tcaattttgg    300

ttttgtcatg acccatctct tcgtcaatca cctgcgttcg cagtttttcc ccgaaacata    360

cgaccccaat gtcattgaca tcaccggagc acagatggtt ctgtgtatga agctatcgtc    420

ttttggatgg aacgtctacg atggatggca gattgagaag ggtgagcagc tcagcgagtt    480

ccagactaaa agggctgttc tcaagcaccc cagtcttatg gacttcctag cttttgtgtt    540

ctacttccct tccattctga caggtccttc ttacgactat atggagttcc ataactggct    600

cgatctcagc ctgttcaagg agctggagaa agataaggac cccaagcgag ctgctcgacg    660

aaagcgacac aagatccccc gatctggaat cgctgcttcc aagaaactcg ccgctggtat    720

cttctggatc gttctgtgga cccaggtgga ctctcgaatc tccaccgcct acgcttactc    780

agacgcattc accaaggagc acaacatctt tggacgaatt gtgtacctct acatgctcgg    840

tttcatgtac cgactcaagt actacggagc ctggtccatt tccgagggag cctgcatctt    900

gtctggcctc ggattccacg gcgtggaccc caaaactggc aagtacaagt gggaccgtgt    960

ccagaacgtg gacccgtggg gattcgaaac tggtcaaaac acaaaggctc tgctggaggc   1020

ctggaaccag aacactaaca agtggctacg aaactatgtg tacctccgag tggtgcccaa   1080

aggccaaaag cctggattcc gagccactat cttcacattt gtggtttccg ccttctggca   1140

tggaactcga cctggctact atctcacctt tgtgaccgct gccatgtacc agtctgttgg   1200

taagttcttc cgacgatacc tgcgaccctt cttcatggag tctgatggaa agactgccgg   1260

tccctataag atctactacg acattgtgtg ttggatcgtt gtccaaaccg catttggata   1320

cgctacccag tcctttatga ttctagactt ctggctgtcg ctcaagtgtt ggaagaactc   1380

ctggttcctg taccacattg ctctgggcgc catctttgca atttctagcc cctacaaggc   1440

atgggcgatt cccaagatca agaaaaagca ggctggagcc gtcactgaca agaaggacgc   1500

caaggaggag gtgaagaagg acaccatcaa gaccaagtaa gcggccgcat gagaagataa   1560
```

atatataaat acattgagat attaaatgcg ctagattaga gagcctcata ctgctcggag 1620
agaagccaag acgagtactc aaaggggatt acaccatcca tatccacaga cacaagctgg 1680
ggaaaggttc tatatacact ttccggaata ccgtagtttc cgatgttatc aatgggggca 1740
gccaggattt caggcacttc ggtgtctcgg ggtgaaatgg cgttcttggc ctccatcaag 1800
tcgtaccatg tcttcatttg cctgtcaaag taaaacagaa gcagatgaag aatgaacttg 1860
aagtgaagga atttaaatgt aacgaaactg aaatttgacc agatattgtg tccgcggtgg 1920
agctccagct tttgttccct ttagtgaggg ttaatttcga gcttggcgta atcatggtca 1980
tagctgtttc ctgtgtgaaa ttgttatccg ctcacaagct tccacacaac gtacgagccg 2040
gaagcataaa gtgtaaagcc tggggtgcct aatgagtgag ctaactcaca ttaattgcgt 2100
tgcgctcact gcccgctttc cagtcgggaa acctgtcgtg ccagctgcat taatgaatcg 2160
gccaacgcgc ggggagaggc ggtttgcgta ttgggcgctc ttccgcttcc tcgctcactg 2220
actcgctgcg ctcggtcgtt cggctgcggc gagcggtatc agctcactca aaggcggtaa 2280
tacggttatc cacagaatca ggggataacg caggaaagaa catgtgagca aaaggccagc 2340
aaaaggccag gaaccgtaaa aaggccgcgt tgctggcgtt tttccatagg ctccgccccc 2400
ctgacgagca tcacaaaaat cgacgctcaa gtcagaggtg gcgaaacccg acaggactat 2460
aaagatacca ggcgtttccc cctggaagct ccctcgtgcg ctctcctgtt ccgaccctgc 2520
cgcttaccgg atacctgtcc gcctttctcc cttcgggaag cgtggcgctt tctcatagct 2580
cacgctgtag gtatctcagt tcggtgtagg tcgttcgctc caagctgggc tgtgtgcacg 2640
aaccccccgt tcagcccgac cgctgcgcct tatccggtaa ctatcgtctt gagtccaacc 2700
cggtaagaca cgacttatcg ccactggcag cagccactgg taacaggatt agcagagcga 2760
ggtatgtagg cggtgctaca gagttcttga agtggtggcc taactacggc tacactagaa 2820
ggacagtatt tggtatctgc gctctgctga agccagttac cttcggaaaa agagttggta 2880
gctcttgatc cggcaaacaa accaccgctg gtagcggtgg tttttttgtt tgcaagcagc 2940
agattacgcg cagaaaaaaa ggatctcaag aagatccttt gatcttttct acggggtctg 3000
acgctcagtg gaacgaaaac tcacgttaag ggattttggt catgagatta tcaaaaagga 3060
tcttcaccta gatcctttta aattaaaaat gaagttttaa atcaatctaa agtatatatg 3120
agtaaacttg gtctgacagt taccaatgct taatcagtga ggcacctatc tcagcgatct 3180
gtctatttcg ttcatccata gttgcctgac tccccgtcgt gtagataact acgatacggg 3240
agggcttacc atctggcccc agtgctgcaa tgataccgcg agacccacgc tcaccggctc 3300
cagatttatc agcaataaac cagccagccg gaagggccga gcgcagaagt ggtcctgcaa 3360
ctttatccgc ctccatccag tctattaatt gttgccggga agctagagta agtagttcgc 3420
cagttaatag tttgcgcaac gttgttgcca ttgctacagg catcgtggtg tcacgctcgt 3480
cgtttggtat ggcttcattc agctccggtt cccaacgatc aaggcgagtt acatgatccc 3540
ccatgttgtg caaaaaagcg gttagctcct tcggtcctcc gatcgttgtc agaagtaagt 3600
tggccgcagt gttatcactc atggttatgg cagcactgca taattctctt actgtcatgc 3660
catccgtaag atgcttttct gtgactggtg agtactcaac caagtcattc tgagaatagt 3720
gtatgcggcg accgagttgc tcttgcccgg cgtcaatacg ggataatacc gcgccacata 3780
gcagaacttt aaaagtgctc atcattggaa aacgttcttc ggggcgaaaa ctctcaagga 3840
tcttaccgct gttgagatcc agttcgatgt aacccactcg tgcacccaac tgatcttcag 3900

-continued

```
catcttttac tttcaccagc gtttctgggt gagcaaaaac aggaaggcaa aatgccgcaa   3960
aaaagggaat aagggcgaca cggaaatgtt gaatactcat actcttcctt tttcaatatt   4020
attgaagcat ttatcagggt tattgtctca tgagcggata catatttgaa tgtatttaga   4080
aaaataaaca aataggggtt ccgcgcacat ttccccgaaa agtgccacct gacgcgccct   4140
gtagcggcgc attaagcgcg gcgggtgtgg tggttacgcg cagcgtgacc gctacacttg   4200
ccagcgccct agcgcccgct cctttcgctt tcttcccttc ctttctcgcc acgttcgccg   4260
gctttccccg tcaagctcta aatcgggggc tccctttagg gttccgattt agtgctttac   4320
ggcacctcga ccccaaaaaa cttgattagg gtgatggttc acgtagtggg ccatcgccct   4380
gatagacggt ttttcgccct ttgacgttgg agtccacgtt ctttaatagt ggactcttgt   4440
tccaaactgg aacaacactc aaccctatct cggtctattc ttttgattta taagggattt   4500
tgccgatttc ggcctattgg ttaaaaaatg agctgattta acaaaaattt aacgcgaatt   4560
ttaacaaaat attaacgctt acaatttcca ttcgccattc aggctgcgca actgttggga   4620
agggcgatcg gtgcgggcct cttcgctatt acgccagctg gcgaaagggg gatgtgctgc   4680
aaggcgatta agttgggtaa cgccagggtt ttcccagtca cgacgttgta aaacgacggc   4740
cagtgaattg taatacgact cactataggg cgaattgggt accgggcccc ccctcgaggt   4800
cgatggtgtc gataagcttg atatcgaatt catgtcacac aaaccgatct tcgcctcaag   4860
gaaacctaat tctacatccg agagactgcc gagatccagt ctacactgat taattttcgg   4920
gccaataatt taaaaaaatc gtgttatata atattatatg tattatatat atacatcatg   4980
atgatactga cagtcatgtc ccattgctaa atagacagac tccatctgcc gcctccaact   5040
gatgttctca atatttaagg ggtcatctcg cattgtttaa taataaacag actccatcta   5100
ccgcctccaa atgatgttct caaaatatat tgtatgaact tatttttatt acttagtatt   5160
attagacaac ttacttgctt tatgaaaaac acttcctatt taggaaacaa tttataatgg   5220
cagttcgttc atttaacaat ttatgtagaa taaatgttat aaatgcgtat gggaaatctt   5280
aaatatggat agcataaatg atatctgcat tgcctaattc gaaatcaaca gcaacgaaaa   5340
aaatcccttg tacaacataa atagtcatcg agaaatatca actatcaaag aacagctatt   5400
cacacgttac tattgagatt attattggac gagaatcaca cactcaactg tctttctctc   5460
ttctagaaat acaggtacaa gtatgtacta ttctcattgt tcatacttct agtcatttca   5520
tcccacatat tccttggatt tctctccaat gaatgacatt ctatcttgca aattcaacaa   5580
ttataataag atataccaaa gtagcggtat agtggcaatc aaaaagcttc tctggtgtgc   5640
ttctcgtatt tatttttatt ctaatgatcc attaaaggta tatatttatt tcttgttata   5700
taatcctttt gtttattaca tgggctggat acataaaggt attttgattt aatttttttgc   5760
ttaaattcaa tccccccctcg ttcagtgtca actgtaatgg taggaaatta ccatactttt   5820
gaagaagcaa aaaaaatgaa agaaaaaaaa aatcgtattt ccaggttaga cgttccgcag   5880
aatctagaat gcggtatgcg gtacattgtt cttcgaacgt aaaagttgcg ctccctgaga   5940
tattgtacat ttttgctttt acaagtacaa gtacatcgta caactatgta ctactgttga   6000
tgcatccaca acagtttgtt ttgttttttt ttgttttttt tttttctaat gattcattac   6060
cgctatgtat acctacttgt acttgtagta agccgggtta ttggcgttca attaatcata   6120
gacttatgaa tctgcacggt gtgcgctgcg agttactttt agcttatgca tgctacttgg   6180
gtgtaatatt gggatctgtt cggaaatcaa cggatgctca atcgatttcg acagtaatta   6240
attaagtcat acacaagtca gctttcttcg agcctcatat aagtataagt agttcaacgt   6300
```

attagcactg tacccagcat ctccgtatcg agaaacacaa caacatgccc cattggacag 6360
atcatgcgga tacacaggtt gtgcagtatc atacatactc gatcagacag gtcgtctgac 6420
catcatacaa gctgaacaag cgctccatac ttgcacgctc tctatataca cagttaaatt 6480
acatatccat agtctaacct ctaacagtta atcttctggt aagcctccca gccagccttc 6540
tggtatcgct tggcctcctc aataggatct cggttctggc cgtacagacc tcggccgaca 6600
attatgatat ccgttccggt agacatgaca tcctcaacag ttcggtactg ctgtccgaga 6660
gcgtctccct tgtcgtcaag acccaccccg ggggtcagaa taagccagtc ctcagagtcg 6720
cccttaggtc ggttctgggc aatgaagcca accacaaact cggggtcgga tcgggcaagc 6780
tcaatggtct gcttggagta ctcgccagtg gccagagagc ccttgcaaga cagctcggcc 6840
agcatgagca gacctctggc cagcttctcg ttgggagagg ggactaggaa ctccttgtac 6900
tgggagttct cgtagtcaga gacgtcctcc ttcttctgtt cagagacagt ttcctcggca 6960
ccagctcgca ggccagcaat gattccggtt ccgggtacac cgtgggcgtt ggtgatatcg 7020
gaccactcgg cgattcggtg acaccggtac tggtgcttga cagtgttgcc aatatctgcg 7080
aactttctgt cctcgaacag gaagaaaccg tgcttaagag caagttcctt gagggggagc 7140
acagtgccgg cgtaggtgaa gtcgtcaatg atgtcgatat gggttttgat catgcacaca 7200
taaggtccga ccttatcggc aagctcaatg agctccttgg tggtggtaac atccagagaa 7260
gcacacaggt tggttttctt ggctgccacg agcttgagca ctcgagcggc aaaggcggac 7320
ttgtggacgt tagctcgagc ttcgtaggag ggcattttgg tggtgaagag gagactgaaa 7380
taaatttagt ctgcagaact ttttatcgga accttatctg gggcagtgaa gtatatgtta 7440
tggtaatagt tacgagttag ttgaacttat agatagactg gactatacgg ctatcggtcc 7500
aaattagaaa gaacgtcaat ggctctctgg gcgtcgcctt tgccgacaaa aatgtgatca 7560
tgatgaaagc cagcaatgac gttgcagctg atattgttgt cggccaaccg cgccgaaaac 7620
gcagctgtca gacccacagc ctccaacgaa gaatgtatcg tcaaagtgat ccaagcacac 7680
tcatagttgg agtcgtactc caaaggcggc aatgacgagt cagacagata ctcgtcgacc 7740
gtacgatagt tagtagacaa caatcgatag ttggagcaag ggagaaatgt agagtgtgaa 7800
agactcacta tggtccgggc ttatctcgac caatagccaa agtctggagt ttctgagaga 7860
aaaaggcaag atacgtatgt aacaaagcga cgcatggtac aataataccg gaggcatgta 7920
tcatagagag ttagtggttc gatgatggca ctggtgcctg gtatgacttt atacggctga 7980
ctacatattt gtcctcagac atacaattac agtcaagcac ttacccttgg acatctgtag 8040
gtacccccg gccaagacga tctcagcgtg tcgtatgtcg gattggcgta gctccctcgc 8100
tcgtcaattg gctcccatct actttcttct gcttggctac acccagcatg tctgctatgg 8160
ctcgttttcg tgccttatct atcctcccag tattaccaac tctaaatgac atgatgtgat 8220
tgggtctaca ctttcatatc agagataagg agtagcacag ttgcataaaa agcccaactc 8280
taatcagctt cttcctttct tgtaattagt acaaaggtga ttagcgaaat ctggaagctt 8340
agttggccct aaaaaaatca aaaaaagcaa aaaacgaaaa acgaaaaacc acagttttga 8400
gaacagggag gtaacgaagg atcgtatata tatatatata tatatatacc cacggatccc 8460
gagaccggcc tttgattctt ccctacaacc aaccattctc accaccctaa ttcacaac 8518

<210> SEQ ID NO 43
<211> LENGTH: 8518
<212> TYPE: DNA

<213> ORGANISM: Artificial sequence
<220> FEATURE:
<223> OTHER INFORMATION: Construct pY306, containing wild type YlLPCAT nucleotide sequence

<400> SEQUENCE: 43
ggccgcatga gaagataaat atataaatac attgagatat taaatgcgct agattagaga 60
gcctcatact gctcggagag aagccaagac gagtactcaa aggggattac accatccata 120
tccacagaca caagctgggg aaaggttcta tatacacttt ccggaatacc gtagtttccg 180
atgttatcaa tgggggcagc caggatttca ggcacttcgg tgtctcgggg tgaaatggcg 240
ttcttggcct ccatcaagtc gtaccatgtc ttcatttgcc tgtcaaagta aaacagaagc 300
agatgaagaa tgaacttgaa gtgaaggaat ttaaatgtaa cgaaactgaa atttgaccag 360
atattgtgtc cgcggtggag ctccagcttt tgttcccttt agtgagggtt aatttcgagc 420
ttggcgtaat catggtcata gctgtttcct gtgtgaaatt gttatccgct cacaagcttc 480
cacacaacgt acgagccgga agcataaagt gtaaagcctg gggtgcctaa tgagtgagct 540
aactcacatt aattgcgttg cgctcactgc ccgctttcca gtcgggaaac ctgtcgtgcc 600
agctgcatta atgaatcggc caacgcgcgg ggagaggcgg tttgcgtatt gggcgctctt 660
ccgcttcctc gctcactgac tcgctgcgct cggtcgttcg gctgcggcga gcggtatcag 720
ctcactcaaa ggcggtaata cggttatcca cagaatcagg ggataacgca ggaaagaaca 780
tgtgagcaaa aggccagcaa aaggccagga accgtaaaaa ggccgcgttg ctggcgtttt 840
tccataggct ccgcccccct gacgagcatc acaaaaatcg acgctcaagt cagaggtggc 900
gaaacccgac aggactataa agataccagg cgtttccccc tggaagctcc ctcgtgcgct 960
ctcctgttcc gaccctgccg cttaccggat acctgtccgc ctttctccct tcgggaagcg 1020
tggcgctttc tcatagctca cgctgtaggt atctcagttc ggtgtaggtc gttcgctcca 1080
agctgggctg tgtgcacgaa ccccccgttc agcccgaccg ctgcgcctta tccggtaact 1140
atcgtcttga gtccaacccg gtaagacacg acttatcgcc actggcagca gccactggta 1200
acaggattag cagagcgagg tatgtaggcg gtgctacaga gttcttgaag tggtggccta 1260
actacggcta cactagaagg acagtatttg gtatctgcgc tctgctgaag ccagttacct 1320
tcggaaaaag agttggtagc tcttgatccg gcaaacaaac caccgctggt agcggtggtt 1380
tttttgtttg caagcagcag attacgcgca gaaaaaaagg atctcaagaa gatcctttga 1440
tcttttctac ggggtctgac gctcagtgga acgaaaactc acgttaaggg attttggtca 1500
tgagattatc aaaaaggatc ttcacctaga tccttttaaa ttaaaaatga agttttaaat 1560
caatctaaag tatatatgag taaacttggt ctgacagtta ccaatgctta atcagtgagg 1620
cacctatctc agcgatctgt ctatttcgtt catccatagt tgcctgactc cccgtcgtgt 1680
agataactac gatacgggag ggcttaccat ctggccccag tgctgcaatg ataccgcgag 1740
acccacgctc accggctcca gatttatcag caataaacca gccagccgga agggccgagc 1800
gcagaagtgg tcctgcaact ttatccgcct ccatccagtc tattaattgt tgccgggaag 1860
ctagagtaag tagttcgcca gttaatagtt tgcgcaacgt tgttgccatt gctacaggca 1920
tcgtggtgtc acgctcgtcg tttggtatgg cttcattcag ctccggttcc caacgatcaa 1980
ggcgagttac atgatccccc atgttgtgca aaaaagcggt tagctccttc ggtcctccga 2040
tcgttgtcag aagtaagttg gccgcagtgt tatcactcat ggttatggca gcactgcata 2100
attctcttac tgtcatgcca tccgtaagat gcttttctgt gactggtgag tactcaacca 2160

```
agtcattctg agaatagtgt atgcggcgac cgagttgctc ttgcccggcg tcaatacggg   2220
ataataccgc gccacatagc agaactttaa aagtgctcat cattggaaaa cgttcttcgg   2280
ggcgaaaact ctcaaggatc ttaccgctgt tgagatccag ttcgatgtaa cccactcgtg   2340
cacccaactg atcttcagca tcttttactt tcaccagcgt ttctgggtga gcaaaaacag   2400
gaaggcaaaa tgccgcaaaa aagggaataa gggcgacacg gaaatgttga atactcatac   2460
tcttcctttt tcaatattat tgaagcattt atcagggtta ttgtctcatg agcggataca   2520
tatttgaatg tatttagaaa aataaacaaa taggggttcc gcgcacattt ccccgaaaag   2580
tgccacctga cgcgccctgt agcggcgcat taagcgcggc gggtgtggtg gttacgcgca   2640
gcgtgaccgc tacacttgcc agcgccctag cgcccgctcc tttcgctttc ttcccttcct   2700
ttctcgccac gttcgccggc tttccccgtc aagctctaaa tcgggggctc cctttagggt   2760
tccgatttag tgctttacgg cacctcgacc ccaaaaaact tgattagggt gatggttcac   2820
gtagtgggcc atcgccctga tagacggttt ttcgcccttt gacgttggag tccacgttct   2880
ttaatagtgg actcttgttc caaactggaa caacactcaa ccctatctcg gtctattctt   2940
ttgatttata agggattttg ccgatttcgg cctattggtt aaaaaatgag ctgatttaac   3000
aaaaatttaa cgcgaatttt aacaaaatat taacgcttac aatttccatt cgccattcag   3060
gctgcgcaac tgttgggaag ggcgatcggt gcgggcctct tcgctattac gccagctggc   3120
gaaaggggga tgtgctgcaa ggcgattaag ttgggtaacg ccagggtttt cccagtcacg   3180
acgttgtaaa acgacggcca gtgaattgta atacgactca ctatagggcg aattgggtac   3240
cgggcccccc ctcgaggtcg atggtgtcga taagcttgat atcgaattca tgtcacacaa   3300
accgatcttc gcctcaagga aacctaattc tacatccgag agactgccga gatccagtct   3360
acactgatta attttcgggc caataattta aaaaaatcgt gttatataat attatatgta   3420
ttatatatat acatcatgat gatactgaca gtcatgtccc attgctaaat agacagactc   3480
catctgccgc ctccaactga tgttctcaat atttaagggg tcatctcgca ttgtttaata   3540
ataaacagac tccatctacc gcctccaaat gatgttctca aaatatattg tatgaactta   3600
tttttattac ttagtattat tagacaactt acttgcttta tgaaaaacac ttcctattta   3660
ggaaacaatt tataatggca gttcgttcat ttaacaattt atgtagaata aatgttataa   3720
atgcgtatgg gaaatcttaa atatggatag cataaatgat atctgcattg cctaattcga   3780
aatcaacagc aacgaaaaaa atcccttgta caacataaat agtcatcgag aaatatcaac   3840
tatcaaagaa cagctattca cacgttacta ttgagattat tattggacga gaatcacaca   3900
ctcaactgtc tttctctctt ctagaaatac aggtacaagt atgtactatt ctcattgttc   3960
atacttctag tcatttcatc ccacatattc cttggatttc tctccaatga atgacattct   4020
atcttgcaaa ttcaacaatt ataataagat ataccaaagt agcggtatag tggcaatcaa   4080
aaagcttctc tggtgtgctt ctcgtattta tttttattct aatgatccat taaaggtata   4140
tatttatttc ttgttatata atccttttgt ttattacatg ggctggatac ataaaggtat   4200
tttgatttaa ttttttgctt aaattcaatc ccccctcgtt cagtgtcaac tgtaatggta   4260
ggaaattacc atacttttga agaagcaaaa aaaatgaaag aaaaaaaaaa tcgtatttcc   4320
aggttagacg ttccgcagaa tctagaatgc ggtatgcggt acattgttct tcgaacgtaa   4380
aagttgcgct ccctgagata ttgtacattt ttgcttttac aagtacaagt acatcgtaca   4440
actatgtact actgttgatg catccacaac agtttgtttt gttttttttt gttttttttt   4500
tttctaatga ttcattaccg ctatgtatac ctacttgtac ttgtagtaag ccgggttatt   4560
```

ggcgttcaat taatcataga cttatgaatc tgcacggtgt gcgctgcgag ttacttttag 4620
cttatgcatg ctacttgggt gtaatattgg gatctgttcg gaaatcaacg gatgctcaat 4680
cgatttcgac agtaattaat taagtcatac acaagtcagc tttcttcgag cctcatataa 4740
gtataagtag ttcaacgtat tagcactgta cccagcatct ccgtatcgag aaacacaaca 4800
acatgcccca ttggacagat catgcggata cacaggttgt gcagtatcat acatactcga 4860
tcagacaggt cgtctgacca tcatacaagc tgaacaagcg ctccatactt gcacgctctc 4920
tatatacaca gttaaattac atatccatag tctaacctct aacagttaat cttctggtaa 4980
gcctcccagc cagccttctg gtatcgcttg gcctcctcaa taggatctcg gttctggccg 5040
tacagacctc ggccgacaat tatgatatcc gttccggtag acatgacatc ctcaacagtt 5100
cggtactgct gtccgagagc gtctcccttg tcgtcaagac ccaccccggg ggtcagaata 5160
agccagtcct cagagtcgcc cttaggtcgg ttctgggcaa tgaagccaac cacaaactcg 5220
gggtcggatc gggcaagctc aatggtctgc ttggagtact cgccagtggc cagagagccc 5280
ttgcaagaca gctcggccag catgagcaga cctctggcca gcttctcgtt gggagagggg 5340
actaggaact ccttgtactg ggagttctcg tagtcagaga cgtcctcctt cttctgttca 5400
gagacagttt cctcggcacc agctcgcagg ccagcaatga ttccggttcc gggtacaccg 5460
tgggcgttgg tgatatcgga ccactcggcg attcggtgac accggtactg gtgcttgaca 5520
gtgttgccaa tatctgcgaa ctttctgtcc tcgaacagga agaaaccgtg cttaagagca 5580
agttccttga gggggagcac agtgccggcg taggtgaagt cgtcaatgat gtcgatatgg 5640
gttttgatca tgcacacata aggtccgacc ttatcggcaa gctcaatgag ctccttggtg 5700
gtggtaacat ccagagaagc acacaggttg gttttcttgg ctgccacgag cttgagcact 5760
cgagcggcaa aggcggactt gtggacgtta gctcgagctt cgtaggaggg cattttggtg 5820
gtgaagagga gactgaaata aatttagtct gcagaacttt ttatcggaac cttatctggg 5880
gcagtgaagt atatgttatg gtaatagtta cgagttagtt gaacttatag atagactgga 5940
ctatacggct atcggtccaa attagaaaga acgtcaatgg ctctctgggc gtcgcctttg 6000
ccgacaaaaa tgtgatcatg atgaaagcca gcaatgacgt tgcagctgat attgttgtcg 6060
gccaaccgcg ccgaaaacgc agctgtcaga cccacagcct ccaacgaaga atgtatcgtc 6120
aaagtgatcc aagcacactc atagttggag tcgtactcca aaggcggcaa tgacgagtca 6180
gacagatact cgtcgaccgt acgatagtta gtagacaaca atcgatagtt ggagcaaggg 6240
agaaatgtag agtgtgaaag actcactatg gtccgggctt atctcgacca atagccaaag 6300
tctggagttt ctgagagaaa aaggcaagat acgtatgtaa caaagcgacg catggtacaa 6360
taataccgga ggcatgtatc atagagagtt agtggttcga tgatggcact ggtgcctggt 6420
atgactttat acggctgact acatatttgt cctcagacat acaattacag tcaagcactt 6480
acccttggac atctgtaggt acccccccggc caagacgatc tcagcgtgtc gtatgtcgga 6540
ttggcgtagc tccctcgctc gtcaattggc tcccatctac tttcttctgc ttggctacac 6600
ccagcatgtc tgctatggct cgttttcgtg ccttatctat cctcccagta ttaccaactc 6660
taaatgacat gatgtgattg ggtctacact ttcatatcag agataaggag tagcacagtt 6720
gcataaaaag cccaactcta atcagcttct tcctttcttg taattagtac aaaggtgatt 6780
agcgaaatct ggaagcttag ttggccctaa aaaaatcaaa aaaagcaaaa aacgaaaaac 6840
gaaaaaccac agttttgaga acagggaggt aacgaaggat cgtatatata tatatatata 6900
tatataccca cggatcccga gaccggcctt tgattcttcc ctacaaccaa ccattctcac 6960
caccctaatt cacaaccatg gcctttccat gggcagataa gtgggcagcc gatgcgtctg 7020
catctacagg gctgcctccg gacctcctca agattgcatt cactctggtc atgtcttatc 7080
cgctgagttc tctcatgaaa cggctgccag atgacgccaa aaacctcaag atcatctata 7140
tcatctccgt gtccatcttc tacatggtgg gtgtcttctc cctctatggc ggagctgcca 7200
ctctgctctt ctcctcaatg ggtaccttct tcatcaccca atggaagagc ccttacatgc 7260
cctgggtcaa ttttggtttt gtcatgaccc atctcttcgt caatcacctg cgttcgcagt 7320
ttttccccga aacatacgac cccaatgtca ttgacatcac cggagcacag atggttctgt 7380
gtatgaagct atcgtctttt ggatggaacg tctacgatgg atggcagatt gagaagggtg 7440
agcagctcag cgagttccag actaaaaggg ctgttctcaa gcaccccagt cttatggact 7500
tcctagcttt tgtgttctac ttcccttcca ttctgacagg tccttcttac gactatatgg 7560
agttccataa ctggctcgat ctcagcctgt tcaaggagct ggagaaagat aaggacccca 7620
agcgagctgc tcgacgaaag cgacacaaga tcccccgatc tggaatcgct gcttccaaga 7680
aactcgccgc tggtatcttc tggatcgttc tgtggaccca ggtggactct cgaatctcca 7740
ccgcctacgc ttactcagac gcattcacca aggagcacaa catctttgga cgaattgtgt 7800
acctctacat gctcggtttc atgtaccgac tcaagtacta cggagcctgg tccatttccg 7860
agggagcctg catcttgtct ggcctcggat tccatggcgt ggaccccaaa actggcaagt 7920
acaagtggga ccgtgtccag aacgtggacc cgtggggatt cgaaactggt caaaacacaa 7980
aggctctgct ggaggcctgg aaccagaaca ctaacaagtg gctacgaaac tatgtgtacc 8040
tccgagtggt gcccaaaggc caaaagcctg gattccgagc cactatcttc acatttgtgg 8100
tttccgcctt ctggcatgga actcgacctg gctactatct cacctttgtg accgctgcca 8160
tgtaccagtc tgttggtaag ttcttccgac gatacctgcg acccttcttc atggagtctg 8220
atggaaagac tgccggtccc tataagatct actacgacat tgtgtgttgg atcgttgtcc 8280
aaaccgcatt tggatacgct acccagtcct ttatgattct agacttctgg ctgtcgctca 8340
agtgttggaa gaactcctgg ttcctgtacc acattgctct gggcgccatc tttgcaattt 8400
ctagccccta caaggcatgg gcgattccca agatcaagaa aaagcaggct ggagccgtca 8460
ctgacaagaa ggacgccaag gaggaggtga agaaggacac catcaagacc aagtaagc 8518

<210> SEQ ID NO 44
<211> LENGTH: 512
<212> TYPE: PRT
<213> ORGANISM: Artificial sequence
<220> FEATURE:
<223> OTHER INFORMATION: Mutant YlLPCAT_M132X
<220> FEATURE:
<221> NAME/KEY: MISC_FEATURE
<222> LOCATION: (132)..(132)
<223> OTHER INFORMATION: Xaa = Ala [A], Asn [N], Cys [C], Gly [G], Gln [Q], His [H], Ile [I], Leu [L], Phe [F], Pro [P], Ser [S], Thr [T], Trp [W], Tyr [Y] or Val [V]

<400> SEQUENCE: 44

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

```
Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Xaa Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
```

-continued 465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys
500 505 510

<210> SEQ ID NO 45
<211> LENGTH: 512
<212> TYPE: PRT
<213> ORGANISM: Artificial sequence
<220> FEATURE:
<223> OTHER INFORMATION: Mutant YlLPCAT_V133X
<220> FEATURE:
<221> NAME/KEY: MISC_FEATURE
<222> LOCATION: (133)..(133)
<223> OTHER INFORMATION: Xaa = Ala [A], Asn [N], Cys [C], Gly [G], Gln [Q], His [H], Leu [L], Met [M], Phe [F], Pro [P], Ser [S], Thr [T], Trp [W] or Tyr [Y]

<400> SEQUENCE: 45

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val
50 55 60

Gly Val Phe Ser Leu Tyr Gly Gly Ala Ala Thr Leu Leu Phe Ser Ser
65 70 75 80

Met Gly Thr Phe Phe Ile Thr Gln Trp Lys Ser Pro Tyr Met Pro Trp
85 90 95

Val Asn Phe Gly Phe Val Met Thr His Leu Phe Val Asn His Leu Arg
100 105 110

Ser Gln Phe Phe Pro Glu Thr Tyr Asp Pro Asn Val Ile Asp Ile Thr
115 120 125

Gly Ala Gln Met Xaa Leu Cys Met Lys Leu Ser Ser Phe Gly Trp Asn
130 135 140

Val Tyr Asp Gly Trp Gln Ile Glu Lys Gly Glu Gln Leu Ser Glu Phe
145 150 155 160

Gln Thr Lys Arg Ala Val Leu Lys His Pro Ser Leu Met Asp Phe Leu
165 170 175

Ala Phe Val Phe Tyr Phe Pro Ser Ile Leu Thr Gly Pro Ser Tyr Asp
180 185 190

Tyr Met Glu Phe His Asn Trp Leu Asp Leu Ser Leu Phe Lys Glu Leu
195 200 205

Glu Lys Asp Lys Asp Pro Lys Arg Ala Ala Arg Arg Lys Arg His Lys
210 215 220

Ile Pro Arg Ser Gly Ile Ala Ala Ser Lys Lys Leu Ala Ala Gly Ile
225 230 235 240

Phe Trp Ile Val Leu Trp Thr Gln Val Asp Ser Arg Ile Ser Thr Ala
245 250 255

Tyr Ala Tyr Ser Asp Ala Phe Thr Lys Glu His Asn Ile Phe Gly Arg
260 265 270

Ile Val Tyr Leu Tyr Met Leu Gly Phe Met Tyr Arg Leu Lys Tyr Tyr
275 280 285

Gly Ala Trp Ser Ile Ser Glu Gly Ala Cys Ile Leu Ser Gly Leu Gly

```
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 46
<211> LENGTH: 512
<212> TYPE: PRT
<213> ORGANISM: Artificial sequence
<220> FEATURE:
<223> OTHER INFORMATION: Mutant YlLPCAT_L134X
<220> FEATURE:
<221> NAME/KEY: MISC_FEATURE
<222> LOCATION: (134)..(134)
<223> OTHER INFORMATION: Xaa = Ala [A], Asn [N], Cys [C], Gly [G], Gln [Q], His [H], Met [M], Phe [F], Pro [P], Ser [S], Thr [T], Trp [W], Tyr [Y] or Val [V]

<400> SEQUENCE: 46

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
```

```
        115                 120                 125

Gly Ala Gln Met Val Xaa Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 47
<211> LENGTH: 512
<212> TYPE: PRT
<213> ORGANISM: Artificial sequence
```

```
<220> FEATURE:
<223> OTHER INFORMATION: Mutant YlLPCAT_C135X
<220> FEATURE:
<221> NAME/KEY: MISC_FEATURE
<222> LOCATION: (135)..(135)
<223> OTHER INFORMATION: Xaa = Arg [R], Asn [N], Asp [D], Glu [E],
      Gly [G], Gln [Q], His [H], Ile [I], Leu [L], Lys [K], Met [M],
      Phe [F], Pro [P], Ser [S], Trp [W] or Tyr [Y]

<400> SEQUENCE: 47

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Xaa Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365
```

Thr Ile Phe Thr Phe Val Val Ser Ala Phe Trp His Gly Thr Arg Pro
370 375 380

Gly Tyr Tyr Leu Thr Phe Val Thr Ala Ala Met Tyr Gln Ser Val Gly
385 390 395 400

Lys Phe Phe Arg Arg Tyr Leu Arg Pro Phe Phe Met Glu Ser Asp Gly
405 410 415

Lys Thr Ala Gly Pro Tyr Lys Ile Tyr Tyr Asp Ile Val Cys Trp Ile
420 425 430

Val Val Gln Thr Ala Phe Gly Tyr Ala Thr Gln Ser Phe Met Ile Leu
435 440 445

Asp Phe Trp Leu Ser Leu Lys Cys Trp Lys Asn Ser Trp Phe Leu Tyr
450 455 460

His Ile Ala Leu Gly Ala Ile Phe Ala Ile Ser Ser Pro Tyr Lys Ala
465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys
500 505 510

<210> SEQ ID NO 48
<211> LENGTH: 512
<212> TYPE: PRT
<213> ORGANISM: Artificial sequence
<220> FEATURE:
<223> OTHER INFORMATION: Mutant YlLPCAT_M136X
<220> FEATURE:
<221> NAME/KEY: MISC_FEATURE
<222> LOCATION: (136)..(136)
<223> OTHER INFORMATION: Xaa = Ala [A], Asn [N], Cys [C], Gly [G], His [H], Ile [I], Phe [F], Pro [P], Ser [S], Thr [T], Trp [W], Tyr [Y] or Val [V]

<400> SEQUENCE: 48

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val
50 55 60

Gly Val Phe Ser Leu Tyr Gly Gly Ala Ala Thr Leu Leu Phe Ser Ser
65 70 75 80

Met Gly Thr Phe Phe Ile Thr Gln Trp Lys Ser Pro Tyr Met Pro Trp
85 90 95

Val Asn Phe Gly Phe Val Met Thr His Leu Phe Val Asn His Leu Arg
100 105 110

Ser Gln Phe Phe Pro Glu Thr Tyr Asp Pro Asn Val Ile Asp Ile Thr
115 120 125

Gly Ala Gln Met Val Leu Cys Xaa Lys Leu Ser Ser Phe Gly Trp Asn
130 135 140

Val Tyr Asp Gly Trp Gln Ile Glu Lys Gly Glu Gln Leu Ser Glu Phe
145 150 155 160

Gln Thr Lys Arg Ala Val Leu Lys His Pro Ser Leu Met Asp Phe Leu
165 170 175

Ala Phe Val Phe Tyr Phe Pro Ser Ile Leu Thr Gly Pro Ser Tyr Asp
180 185 190

```
Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 49
<211> LENGTH: 512
<212> TYPE: PRT
<213> ORGANISM: Artificial sequence
<220> FEATURE:
<223> OTHER INFORMATION: Mutant YlLPCAT_K137X
<220> FEATURE:
<221> NAME/KEY: MISC_FEATURE
<222> LOCATION: (137)..(137)
<223> OTHER INFORMATION: Xaa = Ala [A], Arg [R], Asn [N], Gly [G],
His [H], Pro [P], Ser [S], Thr [T] or Tyr [Y]

<400> SEQUENCE: 49

```
Met Ala Phe Pro Trp Ala Asp Lys Trp Ala Ala Asp Ala Ser Ala Ser
1               5                   10                  15
```

-continued

```
Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Xaa Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
```

```
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 50
<211> LENGTH: 512
<212> TYPE: PRT
<213> ORGANISM: Artificial sequence
<220> FEATURE:
<223> OTHER INFORMATION: Mutant YlLPCAT_L138X
<220> FEATURE:
<221> NAME/KEY: MISC_FEATURE
<222> LOCATION: (138)..(138)
<223> OTHER INFORMATION: Xaa = Ala [A], Asn [N], Cys [C], Gly [G],
      Gln [Q], His [H], Ile [I], Met [M], Phe [F], Pro [P], Ser [S],
      Thr [T], Trp [W] or Tyr [Y]

<400> SEQUENCE: 50

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Xaa Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
```

```
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 51
<211> LENGTH: 512
<212> TYPE: PRT
<213> ORGANISM: Artificial sequence
<220> FEATURE:
<223> OTHER INFORMATION: Mutant YlLPCAT_S139X
<220> FEATURE:
<221> NAME/KEY: MISC_FEATURE
<222> LOCATION: (139)..(139)
<223> OTHER INFORMATION: Xaa = Ala [A], Asn [N], Cys [C], Gly [G],
      His [H], Leu [L], Met [M], Phe [F], Pro [P], Trp [W] or Val [V]

<400> SEQUENCE: 51

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95
```

```
Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Xaa Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 52
<211> LENGTH: 512
<212> TYPE: PRT
<213> ORGANISM: Artificial sequence
<220> FEATURE:
<223> OTHER INFORMATION: Mutant YlLPCAT_S140X
<220> FEATURE:
<221> NAME/KEY: MISC_FEATURE
<222> LOCATION: (140)..(140)
<223> OTHER INFORMATION: Xaa = Asn [N], Cys [C], His [H], Ile [I],
Leu [L], Phe [F], Pro [P], Trp [W], Tyr [Y] or Val [V]

<400> SEQUENCE: 52

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Xaa Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
```

```
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 53
<211> LENGTH: 512
<212> TYPE: PRT
<213> ORGANISM: Artificial sequence
<220> FEATURE:
<223> OTHER INFORMATION: Mutant YlLPCAT_F141X
<220> FEATURE:
<221> NAME/KEY: MISC_FEATURE
<222> LOCATION: (141)..(141)
<223> OTHER INFORMATION: Xaa = Ala [A], Asn [N], Gly [G], His [H],
      Ile [I], Met [M], Pro [P], Ser [S], Thr [T], Trp [W] or Val [V]

<400> SEQUENCE: 53

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Xaa Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175
```

```
Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

```
<210> SEQ ID NO 54
<211> LENGTH: 512
<212> TYPE: PRT
<213> ORGANISM: Artificial sequence
<220> FEATURE:
<223> OTHER INFORMATION: Mutant YlLPCAT_G142X
<220> FEATURE:
<221> NAME/KEY: MISC_FEATURE
<222> LOCATION: (142)..(142)
<223> OTHER INFORMATION: Xaa = Asn [N], His [H], Ile [I], Leu [L],
      Met [M], Phe [F], Pro [P], Thr [T], Trp [W], Tyr [Y] or Val [V]

<400> SEQUENCE: 54
```

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Xaa Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
```

```
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 55
<211> LENGTH: 512
<212> TYPE: PRT
<213> ORGANISM: Artificial sequence
<220> FEATURE:
<223> OTHER INFORMATION: Mutant YlLPCAT_W143X
<220> FEATURE:
<221> NAME/KEY: MISC_FEATURE
<222> LOCATION: (143)..(143)
<223> OTHER INFORMATION: Xaa = Ala [A], Gly [G], His [H], Leu [L],
      Lys [K], Pro [P], Ser [S], Thr [T] or Val [V]

<400> SEQUENCE: 55

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Xaa Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255
```

```
Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 56
<211> LENGTH: 512
<212> TYPE: PRT
<213> ORGANISM: Artificial sequence
<220> FEATURE:
<223> OTHER INFORMATION: Mutant YlLPCAT_N144X
<220> FEATURE:
<221> NAME/KEY: MISC_FEATURE
<222> LOCATION: (144)..(144)
<223> OTHER INFORMATION: Xaa = Ala [A], Arg [R], Gly [G], His [H], Lys [K], Phe [F], Pro [P], Thr [T] or Val [V]

<400> SEQUENCE: 56

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80
```

-continued

```
Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Xaa
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
```

500 505 510

<210> SEQ ID NO 57
<211> LENGTH: 512
<212> TYPE: PRT
<213> ORGANISM: Artificial sequence
<220> FEATURE:
<223> OTHER INFORMATION: Mutant YlLPCAT_V145X
<220> FEATURE:
<221> NAME/KEY: MISC_FEATURE
<222> LOCATION: (145)..(145)
<223> OTHER INFORMATION: Xaa = Ala [A], Cys [C], Gly [G], Glu [E], His [H], Met [M], Phe [F], Pro [P], Ser [S], Thr [T] or Trp [W]

<400> SEQUENCE: 57

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val
50 55 60

Gly Val Phe Ser Leu Tyr Gly Gly Ala Ala Thr Leu Leu Phe Ser Ser
65 70 75 80

Met Gly Thr Phe Phe Ile Thr Gln Trp Lys Ser Pro Tyr Met Pro Trp
85 90 95

Val Asn Phe Gly Phe Val Met Thr His Leu Phe Val Asn His Leu Arg
100 105 110

Ser Gln Phe Phe Pro Glu Thr Tyr Asp Pro Asn Val Ile Asp Ile Thr
115 120 125

Gly Ala Gln Met Val Leu Cys Met Lys Leu Ser Ser Phe Gly Trp Asn
130 135 140

Xaa Tyr Asp Gly Trp Gln Ile Glu Lys Gly Glu Gln Leu Ser Glu Phe
145 150 155 160

Gln Thr Lys Arg Ala Val Leu Lys His Pro Ser Leu Met Asp Phe Leu
165 170 175

Ala Phe Val Phe Tyr Phe Pro Ser Ile Leu Thr Gly Pro Ser Tyr Asp
180 185 190

Tyr Met Glu Phe His Asn Trp Leu Asp Leu Ser Leu Phe Lys Glu Leu
195 200 205

Glu Lys Asp Lys Asp Pro Lys Arg Ala Ala Arg Arg Lys Arg His Lys
210 215 220

Ile Pro Arg Ser Gly Ile Ala Ala Ser Lys Lys Leu Ala Ala Gly Ile
225 230 235 240

Phe Trp Ile Val Leu Trp Thr Gln Val Asp Ser Arg Ile Ser Thr Ala
245 250 255

Tyr Ala Tyr Ser Asp Ala Phe Thr Lys Glu His Asn Ile Phe Gly Arg
260 265 270

Ile Val Tyr Leu Tyr Met Leu Gly Phe Met Tyr Arg Leu Lys Tyr Tyr
275 280 285

Gly Ala Trp Ser Ile Ser Glu Gly Ala Cys Ile Leu Ser Gly Leu Gly
290 295 300

Phe His Gly Val Asp Pro Lys Thr Gly Lys Tyr Lys Trp Asp Arg Val
305 310 315 320

Gln Asn Val Asp Pro Trp Gly Phe Glu Thr Gly Gln Asn Thr Lys Ala
325 330 335

```
Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 58
<211> LENGTH: 512
<212> TYPE: PRT
<213> ORGANISM: Artificial sequence
<220> FEATURE:
<223> OTHER INFORMATION: Mutant YlLPCAT_Y146X
<220> FEATURE:
<221> NAME/KEY: MISC_FEATURE
<222> LOCATION: (146)..(146)
<223> OTHER INFORMATION: Xaa = Arg [R], Asn [N], Asp [D], Gly [G],
      Glu [E], Gln [Q], Ile [I], Leu [L], Met [M], Phe [F], Pro [P],
      Trp [W]] or Val [V]

<400> SEQUENCE: 58

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Xaa Asp Gly Trp Gln Ile Glu Lys Gly Glu Gln Leu Ser Glu Phe
145                 150                 155                 160
```

```
Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 59
<211> LENGTH: 512
<212> TYPE: PRT
<213> ORGANISM: Artificial sequence
<220> FEATURE:
<223> OTHER INFORMATION: Mutant YlLPCAT_D147X
<220> FEATURE:
<221> NAME/KEY: MISC_FEATURE
<222> LOCATION: (147)..(147)
<223> OTHER INFORMATION: Xaa = Ala [A], Asn [N], Gly [G], Glu [E],
      Gln [Q], His [H], Phe [F], Ser [S] or Thr [T]
```

<400> SEQUENCE: 59

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val
50 55 60

Gly Val Phe Ser Leu Tyr Gly Gly Ala Ala Thr Leu Leu Phe Ser Ser
65 70 75 80

Met Gly Thr Phe Phe Ile Thr Gln Trp Lys Ser Pro Tyr Met Pro Trp
85 90 95

Val Asn Phe Gly Phe Val Met Thr His Leu Phe Val Asn His Leu Arg
100 105 110

Ser Gln Phe Phe Pro Glu Thr Tyr Asp Pro Asn Val Ile Asp Ile Thr
115 120 125

Gly Ala Gln Met Val Leu Cys Met Lys Leu Ser Ser Phe Gly Trp Asn
130 135 140

Val Tyr Xaa Gly Trp Gln Ile Glu Lys Gly Glu Gln Leu Ser Glu Phe
145 150 155 160

Gln Thr Lys Arg Ala Val Leu Lys His Pro Ser Leu Met Asp Phe Leu
165 170 175

Ala Phe Val Phe Tyr Phe Pro Ser Ile Leu Thr Gly Pro Ser Tyr Asp
180 185 190

Tyr Met Glu Phe His Asn Trp Leu Asp Leu Ser Leu Phe Lys Glu Leu
195 200 205

Glu Lys Asp Lys Asp Pro Lys Arg Ala Ala Arg Arg Lys Arg His Lys
210 215 220

Ile Pro Arg Ser Gly Ile Ala Ala Ser Lys Lys Leu Ala Ala Gly Ile
225 230 235 240

Phe Trp Ile Val Leu Trp Thr Gln Val Asp Ser Arg Ile Ser Thr Ala
245 250 255

Tyr Ala Tyr Ser Asp Ala Phe Thr Lys Glu His Asn Ile Phe Gly Arg
260 265 270

Ile Val Tyr Leu Tyr Met Leu Gly Phe Met Tyr Arg Leu Lys Tyr Tyr
275 280 285

Gly Ala Trp Ser Ile Ser Glu Gly Ala Cys Ile Leu Ser Gly Leu Gly
290 295 300

Phe His Gly Val Asp Pro Lys Thr Gly Lys Tyr Lys Trp Asp Arg Val
305 310 315 320

Gln Asn Val Asp Pro Trp Gly Phe Glu Thr Gly Gln Asn Thr Lys Ala
325 330 335

Leu Leu Glu Ala Trp Asn Gln Asn Thr Asn Lys Trp Leu Arg Asn Tyr
340 345 350

Val Tyr Leu Arg Val Val Pro Lys Gly Gln Lys Pro Gly Phe Arg Ala
355 360 365

Thr Ile Phe Thr Phe Val Val Ser Ala Phe Trp His Gly Thr Arg Pro
370 375 380

Gly Tyr Tyr Leu Thr Phe Val Thr Ala Ala Met Tyr Gln Ser Val Gly
385 390 395 400

Lys Phe Phe Arg Arg Tyr Leu Arg Pro Phe Phe Met Glu Ser Asp Gly

```
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 60
<211> LENGTH: 512
<212> TYPE: PRT
<213> ORGANISM: Artificial sequence
<220> FEATURE:
<223> OTHER INFORMATION: Mutant YlLPCAT_G148X
<220> FEATURE:
<221> NAME/KEY: MISC_FEATURE
<222> LOCATION: (148)..(148)
<223> OTHER INFORMATION: Xaa = Ala [A], Asn [N], His [H], Leu [L],
      Met [M], Phe [F], Ser [S], Thr [T] or Val [V]

<400> SEQUENCE: 60

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240
```

```
Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 61
<211> LENGTH: 512
<212> TYPE: PRT
<213> ORGANISM: Artificial sequence
<220> FEATURE:
<223> OTHER INFORMATION: Mutant YlLPCAT_S376X
<220> FEATURE:
<221> NAME/KEY: MISC_FEATURE
<222> LOCATION: (376)..(376)
<223> OTHER INFORMATION: Xaa = Ala [A], Gly [G], His [H], Leu [L],
      Phe [F], Pro [P], Thr [T] or Val [V]

<400> SEQUENCE: 61

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60
```

-continued

```
Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Xaa Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
```

```
                485                 490                 495

Lys Lys Asp Ala Lys Glu Glu Val Lys Lys Asp Thr Ile Lys Thr Lys
            500                 505                 510


<210> SEQ ID NO 62
<211> LENGTH: 512
<212> TYPE: PRT
<213> ORGANISM: Artificial sequence
<220> FEATURE:
<223> OTHER INFORMATION: Mutant YlLPCAT_A377X
<220> FEATURE:
<221> NAME/KEY: MISC_FEATURE
<222> LOCATION: (377)..(377)
<223> OTHER INFORMATION: Xaa = Asn [N], Gly [G], His [H], Leu [L],
      Phe [F], Pro [P], Ser [S], Thr [T] or Val [V]

<400> SEQUENCE: 62

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320
```

```
Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Xaa Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 63
<211> LENGTH: 512
<212> TYPE: PRT
<213> ORGANISM: Artificial sequence
<220> FEATURE:
<223> OTHER INFORMATION: Mutant YlLPCAT_F378X
<220> FEATURE:
<221> NAME/KEY: MISC_FEATURE
<222> LOCATION: (378)..(378)
<223> OTHER INFORMATION: Xaa = Ala [A], Asn [N], Cys [C], Gly [G],
      His [H], Leu [L], Pro [P], Ser [S], Thr [T], Trp [W] or Tyr [Y]

<400> SEQUENCE: 63

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140
```

```
Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Xaa Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 64
<211> LENGTH: 512
<212> TYPE: PRT
<213> ORGANISM: Artificial sequence
<220> FEATURE:
<223> OTHER INFORMATION: Mutant YlLPCAT_T382X
<220> FEATURE:
<221> NAME/KEY: MISC_FEATURE
<222> LOCATION: (382)..(382)

```
<223> OTHER INFORMATION: Xaa = Ala [A], Asn [N], Gly [G], Gln [Q],
      His [H], Ile [I], Met [M], Pro [P], Ser [S], Trp [W] or Tyr [Y]

<400> SEQUENCE: 64

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Xaa Arg Pro
    370                 375                 380

Gly Tyr Tyr Leu Thr Phe Val Thr Ala Ala Met Tyr Gln Ser Val Gly
385                 390                 395                 400
```

```
Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 65
<211> LENGTH: 512
<212> TYPE: PRT
<213> ORGANISM: Artificial sequence
<220> FEATURE:
<223> OTHER INFORMATION: Mutant YlLPCAT_R383X
<220> FEATURE:
<221> NAME/KEY: MISC_FEATURE
<222> LOCATION: (383)..(383)
<223> OTHER INFORMATION: Xaa = Ala [A], Asn [N], Asp [D], Gly [G], Glu [E], Gln [Q], His [H], Ile [I], Leu [L], Lys [K], Met [M], Phe [F], Pro [P], Thr [T], Trp [W] or Val [V]

<400> SEQUENCE: 65

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220
```

```
Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Xaa Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 66
<211> LENGTH: 512
<212> TYPE: PRT
<213> ORGANISM: Artificial sequence
<220> FEATURE:
<223> OTHER INFORMATION: Mutant YlLPCAT_P384X
<220> FEATURE:
<221> NAME/KEY: MISC_FEATURE
<222> LOCATION: (384)..(384)
<223> OTHER INFORMATION: Xaa = Ala [A], Arg [R], Gly [G], His [H], Ile [I], Leu [L], Lys [K], Met [M], Phe [F], Ser [S], Thr [T], Trp [W], Tyr [Y] or Val [V]

<400> SEQUENCE: 66

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45
```

```
Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Xaa
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460
```

```
His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 67
<211> LENGTH: 512
<212> TYPE: PRT
<213> ORGANISM: Artificial sequence
<220> FEATURE:
<223> OTHER INFORMATION: Mutant YlLPCAT_G385X
<220> FEATURE:
<221> NAME/KEY: MISC_FEATURE
<222> LOCATION: (385)..(385)
<223> OTHER INFORMATION: Xaa = Ala [A], Asn [N], Cys [C], Gly [G],
      His [H], Ile [I], Leu [L], Lys [K], Met [M], Phe [F], Ser [S],
      Thr [T], Trp [W], Tyr [Y] or Val [V]

<400> SEQUENCE: 67

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285
```

```
Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Xaa Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 68
<211> LENGTH: 512
<212> TYPE: PRT
<213> ORGANISM: Artificial sequence
<220> FEATURE:
<223> OTHER INFORMATION: Mutant YlLPCAT_Y386X
<220> FEATURE:
<221> NAME/KEY: MISC_FEATURE
<222> LOCATION: (386)..(386)
<223> OTHER INFORMATION: Xaa = Ala [A], Gly [G], His [H], Leu [L],
      Phe [F], Pro [P], Ser [S], Thr [T] or Val [V]

<400> SEQUENCE: 68

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
```

```
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Xaa Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 69
<211> LENGTH: 512
<212> TYPE: PRT
<213> ORGANISM: Artificial sequence

```
<220> FEATURE:
<223> OTHER INFORMATION: Mutant YlLPCAT_Y387X
<220> FEATURE:
<221> NAME/KEY: MISC_FEATURE
<222> LOCATION: (387)..(387)
<220> FEATURE:
<221> NAME/KEY: MISC_FEATURE
<222> LOCATION: (387)..(387)
<223> OTHER INFORMATION: Xaa = Ala [A], Gly [G], His [H], Leu [L],
      Phe [F], Pro [P], Ser [S], Thr [T], Trp [W] or Val [V]

<400> SEQUENCE: 69

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350
```

Val Tyr Leu Arg Val Val Pro Lys Gly Gln Lys Pro Gly Phe Arg Ala
355 360 365

Thr Ile Phe Thr Phe Val Val Ser Ala Phe Trp His Gly Thr Arg Pro
370 375 380

Gly Tyr Xaa Leu Thr Phe Val Thr Ala Ala Met Tyr Gln Ser Val Gly
385 390 395 400

Lys Phe Phe Arg Arg Tyr Leu Arg Pro Phe Phe Met Glu Ser Asp Gly
405 410 415

Lys Thr Ala Gly Pro Tyr Lys Ile Tyr Tyr Asp Ile Val Cys Trp Ile
420 425 430

Val Val Gln Thr Ala Phe Gly Tyr Ala Thr Gln Ser Phe Met Ile Leu
435 440 445

Asp Phe Trp Leu Ser Leu Lys Cys Trp Lys Asn Ser Trp Phe Leu Tyr
450 455 460

His Ile Ala Leu Gly Ala Ile Phe Ala Ile Ser Ser Pro Tyr Lys Ala
465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys
500 505 510

<210> SEQ ID NO 70
<211> LENGTH: 512
<212> TYPE: PRT
<213> ORGANISM: Artificial sequence
<220> FEATURE:
<223> OTHER INFORMATION: Mutant YlLPCAT_L388X
<220> FEATURE:
<221> NAME/KEY: MISC_FEATURE
<222> LOCATION: (388)..(388)
<223> OTHER INFORMATION: Xaa = Ala [A], Gly [G], His [H], Pro [P], Ser [S], Thr [T], Trp [W], Tyr [Y] or Val [V]

<400> SEQUENCE: 70

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val
50 55 60

Gly Val Phe Ser Leu Tyr Gly Gly Ala Ala Thr Leu Leu Phe Ser Ser
65 70 75 80

Met Gly Thr Phe Phe Ile Thr Gln Trp Lys Ser Pro Tyr Met Pro Trp
85 90 95

Val Asn Phe Gly Phe Val Met Thr His Leu Phe Val Asn His Leu Arg
100 105 110

Ser Gln Phe Phe Pro Glu Thr Tyr Asp Pro Asn Val Ile Asp Ile Thr
115 120 125

Gly Ala Gln Met Val Leu Cys Met Lys Leu Ser Ser Phe Gly Trp Asn
130 135 140

Val Tyr Asp Gly Trp Gln Ile Glu Lys Gly Glu Gln Leu Ser Glu Phe
145 150 155 160

Gln Thr Lys Arg Ala Val Leu Lys His Pro Ser Leu Met Asp Phe Leu
165 170 175

Ala Phe Val Phe Tyr Phe Pro Ser Ile Leu Thr Gly Pro Ser Tyr Asp

```
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Xaa Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 71
<211> LENGTH: 512
<212> TYPE: PRT
<213> ORGANISM: Artificial sequence
<220> FEATURE:
<223> OTHER INFORMATION: Mutant YlLPCAT_T389X
<220> FEATURE:
<221> NAME/KEY: MISC_FEATURE
<222> LOCATION: (389)..(389)
<223> OTHER INFORMATION: Xaa = Ala [A], Cys [C], Gly [G], His [H],
      Ile [I], Leu [L], Met [M], Phe [F], Pro [P], Ser [S], Trp [W],
      Tyr [Y] or Val [V]

<400> SEQUENCE: 71

Met Ala Phe Pro Trp Ala Asp Lys Trp Ala Ala Asp Ala Ser Ala Ser
```

-continued

```
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Xaa Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430
```

```
Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 72
<211> LENGTH: 512
<212> TYPE: PRT
<213> ORGANISM: Artificial sequence
<220> FEATURE:
<223> OTHER INFORMATION: Mutant YlLPCAT_F390X
<220> FEATURE:
<221> NAME/KEY: MISC_FEATURE
<222> LOCATION: (390)..(390)
<223> OTHER INFORMATION: Ala [A], Asn [N], Cys [C], Gly [G], His [H],
      Leu [L], Met [M], Pro [P], Ser [S], Thr [T] or Val [V]

<400> SEQUENCE: 72

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255
```

```
Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 73
<211> LENGTH: 512
<212> TYPE: PRT
<213> ORGANISM: Artificial sequence
<220> FEATURE:
<223> OTHER INFORMATION: Mutant YlLPCAT protein generic
<220> FEATURE:
<221> NAME/KEY: MISC_FEATURE
<222> LOCATION: (133)..(133)
<223> OTHER INFORMATION: Xaa = Val [V] or Cys [C]
<220> FEATURE:
<221> NAME/KEY: MISC_FEATURE
<222> LOCATION: (134)..(134)
<223> OTHER INFORMATION: Xaa = Leu [L] or Ala [A] or Cys [C] or Gly [G]
<220> FEATURE:
<221> NAME/KEY: MISC_FEATURE
<222> LOCATION: (135)..(135)
<223> OTHER INFORMATION: Xaa = Cys [C] or Asp [D] or Ile [I] or Phe [F]
<220> FEATURE:
<221> NAME/KEY: MISC_FEATURE
<222> LOCATION: (136)..(136)
<223> OTHER INFORMATION: Xaa = Met [M] or Gly [G] or Pro [P] or Ser [S]
      or Val [V] or Asn [N] or Thr [T]
<220> FEATURE:
<221> NAME/KEY: MISC_FEATURE
<222> LOCATION: (137)..(137)
<223> OTHER INFORMATION: Xaa = Lys [K] or Asn [N] or Gly [G] or His [H]
      or Tyr [Y]
<220> FEATURE:
<221> NAME/KEY: MISC_FEATURE
```

<222> LOCATION: (138)..(138)
<223> OTHER INFORMATION: Xaa = Leu [L] or Ala [A] or His [H] or Met [M]
or Gly [G] or Ile [I] or Asn [N]
<220> FEATURE:
<221> NAME/KEY: MISC_FEATURE
<222> LOCATION: (139)..(139)
<223> OTHER INFORMATION: Xaa = Ser [S] or Leu [L] or Trp [W] or Gly [G]
or Asn [N]
<220> FEATURE:
<221> NAME/KEY: MISC_FEATURE
<222> LOCATION: (140)..(140)
<223> OTHER INFORMATION: Xaa = Ser [S] or Asn [N] or His [H] or Pro [P]
or Trp [W] or Tyr [Y] or Ile [I]
<220> FEATURE:
<221> NAME/KEY: MISC_FEATURE
<222> LOCATION: (141)..(141)
<223> OTHER INFORMATION: Xaa = Phe [F] or Ala [A] or Met [M] or Trp [W]
or Val [V]
<220> FEATURE:
<221> NAME/KEY: MISC_FEATURE
<222> LOCATION: (142)..(142)
<223> OTHER INFORMATION: Xaa = Gly [G] or His [H] or Ile [I] or Val [V]
<220> FEATURE:
<221> NAME/KEY: MISC_FEATURE
<222> LOCATION: (143)..(143)
<223> OTHER INFORMATION: Xaa = Trp [W] or Leu [L] or His [H]
<220> FEATURE:
<221> NAME/KEY: MISC_FEATURE
<222> LOCATION: (144)..(144)
<223> OTHER INFORMATION: Xaa = Asn [N] or Ala [A] or Lys [K] or Phe [F]
or Thr [T] or Val [V]
<220> FEATURE:
<221> NAME/KEY: MISC_FEATURE
<222> LOCATION: (145)..(145)
<223> OTHER INFORMATION: Xaa = Val [V] or Ala [A] or Gly [G] or Glu [E]
or Met [M] or Phe [F] or Trp [W]
<220> FEATURE:
<221> NAME/KEY: MISC_FEATURE
<222> LOCATION: (146)..(146)
<223> OTHER INFORMATION: Xaa = Tyr (Y) or Gly [G] or Leu [L] or Met [M]
<220> FEATURE:
<221> NAME/KEY: MISC_FEATURE
<222> LOCATION: (147)..(147)
<223> OTHER INFORMATION: Xaa = Asp [D] or Asn [N] or Gln [Q] or His [H]
or Glu [E]
<220> FEATURE:
<221> NAME/KEY: MISC_FEATURE
<222> LOCATION: (148)..(148)
<223> OTHER INFORMATION: Xaa = Gly [G] or Ala [A] or Asn [N] or Val [V]
<220> FEATURE:
<221> NAME/KEY: MISC_FEATURE
<222> LOCATION: (378)..(378)
<223> OTHER INFORMATION: Xaa = Phe [F] or Tyr [Y]
<220> FEATURE:
<221> NAME/KEY: MISC_FEATURE
<222> LOCATION: (382)..(382)
<223> OTHER INFORMATION: Xaa = Thr [T] or Ile [I] or Pro [P] or Tyr [Y]
<220> FEATURE:
<221> NAME/KEY: MISC_FEATURE
<222> LOCATION: (383)..(383)
<223> OTHER INFORMATION: Xaa = Arg [R] or Ala [A] or Met [M]
<220> FEATURE:
<221> NAME/KEY: MISC_FEATURE
<222> LOCATION: (388)..(388)
<223> OTHER INFORMATION: Xaa = Leu [L] or Gly [G] or Tyr [Y] or His [H]
or Thr [T]
<220> FEATURE:
<221> NAME/KEY: MISC_FEATURE
<222> LOCATION: (389)..(389)
<223> OTHER INFORMATION: Xaa = Thr [T] or Ala [A] or Cys [C] or Ser [S]
<220> FEATURE:
<221> NAME/KEY: MISC_FEATURE
<222> LOCATION: (390)..(390)
<223> OTHER INFORMATION: Xaa = Phe [F] or Cys [C] or Gly [G] or Asn [N]
or Ser [S] or Thr [T]

<400> SEQUENCE: 73

Met Ala Phe Pro Trp Ala Asp Lys Trp Ala Ala Asp Ala Ser Ala Ser

-continued

```
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Xaa Xaa Xaa Xaa Xaa Xaa Xaa Xaa Xaa Xaa Xaa Xaa
    130                 135                 140

Xaa Xaa Xaa Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Xaa Trp His Gly Xaa Xaa Pro
    370                 375                 380

Gly Tyr Tyr Xaa Xaa Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430
```

```
Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

```
<210> SEQ ID NO 74
<211> LENGTH: 512
<212> TYPE: PRT
<213> ORGANISM: Artificial sequence
<220> FEATURE:
<223> OTHER INFORMATION: Mutant YlLPCAT protein double generic
<220> FEATURE:
<221> NAME/KEY: MISC_FEATURE
<222> LOCATION: (134)..(134)
<223> OTHER INFORMATION: Xaa = Leu [L] or Ala [A] or Gly [G]
<220> FEATURE:
<221> NAME/KEY: MISC_FEATURE
<222> LOCATION: (136)..(136)
<223> OTHER INFORMATION: Xaa = Met [M] or Ser [S] or Val [V]
<220> FEATURE:
<221> NAME/KEY: MISC_FEATURE
<222> LOCATION: (137)..(137)
<223> OTHER INFORMATION: Xaa = Lys [K] or Asn [N] or His [H]
<220> FEATURE:
<221> NAME/KEY: MISC_FEATURE
<222> LOCATION: (140)..(140)
<223> OTHER INFORMATION: Xaa = Ser [S] or His [H] or Trp [W]
<220> FEATURE:
<221> NAME/KEY: MISC_FEATURE
<222> LOCATION: (141)..(141)
<223> OTHER INFORMATION: Xaa = Phe [F] or Met [M] or Trp [W]
<220> FEATURE:
<221> NAME/KEY: MISC_FEATURE
<222> LOCATION: (144)..(144)
<223> OTHER INFORMATION: Xaa = Asn [N] or Ala [A] or Thr [T]
<220> FEATURE:
<221> NAME/KEY: MISC_FEATURE
<222> LOCATION: (145)..(145)
<223> OTHER INFORMATION: Xaa = Val [V] or Met [M] or Trp [W]
<220> FEATURE:
<221> NAME/KEY: MISC_FEATURE
<222> LOCATION: (147)..(147)
<223> OTHER INFORMATION: Xaa = Asp [D] or Gln [Q] or His [H]
<220> FEATURE:
<221> NAME/KEY: MISC_FEATURE
<222> LOCATION: (148)..(148)
<223> OTHER INFORMATION: Xaa = Gly [G] or Ala [A] or Asn [N]
<220> FEATURE:
<221> NAME/KEY: MISC_FEATURE
<222> LOCATION: (378)..(378)
<223> OTHER INFORMATION: Xaa = Phe [F] or Tyr [Y]
<220> FEATURE:
<221> NAME/KEY: MISC_FEATURE
<222> LOCATION: (382)..(382)
<223> OTHER INFORMATION: Xaa = Thr [T] or Ile [I] or Pro [P] or Tyr [Y]
<220> FEATURE:
<221> NAME/KEY: MISC_FEATURE
<222> LOCATION: (383)..(383)
<223> OTHER INFORMATION: Xaa = Arg [R] or Met [M]
<220> FEATURE:
<221> NAME/KEY: MISC_FEATURE
<222> LOCATION: (384)..(384)
<223> OTHER INFORMATION: Xaa = Pro [P] or Ala [A] or Gly [G]
<220> FEATURE:
<221> NAME/KEY: MISC_FEATURE
<222> LOCATION: (388)..(388)
<223> OTHER INFORMATION: Xaa = Leu [L] or Gly [G] or Tyr [Y] or Thr [T]
```

```
<220> FEATURE:
<221> NAME/KEY: MISC_FEATURE
<222> LOCATION: (389)..(389)
<223> OTHER INFORMATION: Xaa = Thr [T] or Ala [A] or Cys [C] or Ser [S]
<220> FEATURE:
<221> NAME/KEY: MISC_FEATURE
<222> LOCATION: (390)..(390)
<223> OTHER INFORMATION: Xaa = Phe [F] or Gly [G] or Ser [S] or Thr [T]

<400> SEQUENCE: 74

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Xaa Cys Xaa Xaa Leu Ser Xaa Xaa Gly Trp Xaa
    130                 135                 140

Xaa Tyr Xaa Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365
```

```
Thr Ile Phe Thr Phe Val Val Ser Ala Xaa Trp His Gly Xaa Xaa Xaa
    370                 375                 380

Gly Tyr Tyr Xaa Xaa Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 75
<211> LENGTH: 512
<212> TYPE: PRT
<213> ORGANISM: Artificial sequence
<220> FEATURE:
<223> OTHER INFORMATION: Y. lipolytica LPCAT containing M136S and T389C
      mutations

<400> SEQUENCE: 75

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Ser Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
```

```
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Cys Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 76
<211> LENGTH: 512
<212> TYPE: PRT
<213> ORGANISM: Artificial sequence
<220> FEATURE:
<223> OTHER INFORMATION: Y. lipolytica LPCAT containing M136S and T389S mutations

<400> SEQUENCE: 76

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60
```

```
Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Ser Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Ser Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
```

```
                485                 490                 495

Lys Lys Asp Ala Lys Glu Glu Val Lys Lys Asp Thr Ile Lys Thr Lys
            500                 505                 510
```

```
<210> SEQ ID NO 77
<211> LENGTH: 512
<212> TYPE: PRT
<213> ORGANISM: Artificial sequence
<220> FEATURE:
<223> OTHER INFORMATION: Y. lipolytica LPCAT containing M136V and T389C
      mutations

<400> SEQUENCE: 77

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Val Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335
```

```
Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Cys Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 78
<211> LENGTH: 512
<212> TYPE: PRT
<213> ORGANISM: Artificial sequence
<220> FEATURE:
<223> OTHER INFORMATION: Y. lipolytica LPCAT containing N144A and F390S
      mutations

<400> SEQUENCE: 78

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Ala
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190
```

Tyr Met Glu Phe His Asn Trp Leu Asp Leu Ser Leu Phe Lys Glu Leu
195 200 205

Glu Lys Asp Lys Asp Pro Lys Arg Ala Ala Arg Arg Lys Arg His Lys
210 215 220

Ile Pro Arg Ser Gly Ile Ala Ala Ser Lys Lys Leu Ala Ala Gly Ile
225 230 235 240

Phe Trp Ile Val Leu Trp Thr Gln Val Asp Ser Arg Ile Ser Thr Ala
245 250 255

Tyr Ala Tyr Ser Asp Ala Phe Thr Lys Glu His Asn Ile Phe Gly Arg
260 265 270

Ile Val Tyr Leu Tyr Met Leu Gly Phe Met Tyr Arg Leu Lys Tyr Tyr
275 280 285

Gly Ala Trp Ser Ile Ser Glu Gly Ala Cys Ile Leu Ser Gly Leu Gly
290 295 300

Phe His Gly Val Asp Pro Lys Thr Gly Lys Tyr Lys Trp Asp Arg Val
305 310 315 320

Gln Asn Val Asp Pro Trp Gly Phe Glu Thr Gly Gln Asn Thr Lys Ala
325 330 335

Leu Leu Glu Ala Trp Asn Gln Asn Thr Asn Lys Trp Leu Arg Asn Tyr
340 345 350

Val Tyr Leu Arg Val Val Pro Lys Gly Gln Lys Pro Gly Phe Arg Ala
355 360 365

Thr Ile Phe Thr Phe Val Val Ser Ala Phe Trp His Gly Thr Arg Pro
370 375 380

Gly Tyr Tyr Leu Thr Ser Val Thr Ala Ala Met Tyr Gln Ser Val Gly
385 390 395 400

Lys Phe Phe Arg Arg Tyr Leu Arg Pro Phe Phe Met Glu Ser Asp Gly
405 410 415

Lys Thr Ala Gly Pro Tyr Lys Ile Tyr Tyr Asp Ile Val Cys Trp Ile
420 425 430

Val Val Gln Thr Ala Phe Gly Tyr Ala Thr Gln Ser Phe Met Ile Leu
435 440 445

Asp Phe Trp Leu Ser Leu Lys Cys Trp Lys Asn Ser Trp Phe Leu Tyr
450 455 460

His Ile Ala Leu Gly Ala Ile Phe Ala Ile Ser Ser Pro Tyr Lys Ala
465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys
500 505 510

<210> SEQ ID NO 79
<211> LENGTH: 512
<212> TYPE: PRT
<213> ORGANISM: Artificial sequence
<220> FEATURE:
<223> OTHER INFORMATION: Y. lipolytica LPCAT containing G148A and F390S mutations

<400> SEQUENCE: 79

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys

-continued

```
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Ala Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Ser Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460
```

His Ile Ala Leu Gly Ala Ile Phe Ala Ile Ser Ser Pro Tyr Lys Ala
465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys
500 505 510

<210> SEQ ID NO 80
<211> LENGTH: 512
<212> TYPE: PRT
<213> ORGANISM: Artificial sequence
<220> FEATURE:
<223> OTHER INFORMATION: Y. lipolytica LPCAT containing G148N and T382I mutations

<400> SEQUENCE: 80

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val
50 55 60

Gly Val Phe Ser Leu Tyr Gly Gly Ala Ala Thr Leu Leu Phe Ser Ser
65 70 75 80

Met Gly Thr Phe Phe Ile Thr Gln Trp Lys Ser Pro Tyr Met Pro Trp
85 90 95

Val Asn Phe Gly Phe Val Met Thr His Leu Phe Val Asn His Leu Arg
100 105 110

Ser Gln Phe Phe Pro Glu Thr Tyr Asp Pro Asn Val Ile Asp Ile Thr
115 120 125

Gly Ala Gln Met Val Leu Cys Met Lys Leu Ser Ser Phe Gly Trp Asn
130 135 140

Val Tyr Asp Asn Trp Gln Ile Glu Lys Gly Glu Gln Leu Ser Glu Phe
145 150 155 160

Gln Thr Lys Arg Ala Val Leu Lys His Pro Ser Leu Met Asp Phe Leu
165 170 175

Ala Phe Val Phe Tyr Phe Pro Ser Ile Leu Thr Gly Pro Ser Tyr Asp
180 185 190

Tyr Met Glu Phe His Asn Trp Leu Asp Leu Ser Leu Phe Lys Glu Leu
195 200 205

Glu Lys Asp Lys Asp Pro Lys Arg Ala Ala Arg Arg Lys Arg His Lys
210 215 220

Ile Pro Arg Ser Gly Ile Ala Ala Ser Lys Lys Leu Ala Ala Gly Ile
225 230 235 240

Phe Trp Ile Val Leu Trp Thr Gln Val Asp Ser Arg Ile Ser Thr Ala
245 250 255

Tyr Ala Tyr Ser Asp Ala Phe Thr Lys Glu His Asn Ile Phe Gly Arg
260 265 270

Ile Val Tyr Leu Tyr Met Leu Gly Phe Met Tyr Arg Leu Lys Tyr Tyr
275 280 285

Gly Ala Trp Ser Ile Ser Glu Gly Ala Cys Ile Leu Ser Gly Leu Gly
290 295 300

Phe His Gly Val Asp Pro Lys Thr Gly Lys Tyr Lys Trp Asp Arg Val

```
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Ile Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 81
<211> LENGTH: 512
<212> TYPE: PRT
<213> ORGANISM: Artificial sequence
<220> FEATURE:
<223> OTHER INFORMATION: Y. lipolytica LPCAT containing G148N and F390S
      mutations

<400> SEQUENCE: 81

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Asn Trp Gln Ile Glu Lys Gly Glu Gln Leu Ser Glu Phe
145                 150                 155                 160
```

-continued

Gln Thr Lys Arg Ala Val Leu Lys His Pro Ser Leu Met Asp Phe Leu
165 170 175

Ala Phe Val Phe Tyr Phe Pro Ser Ile Leu Thr Gly Pro Ser Tyr Asp
180 185 190

Tyr Met Glu Phe His Asn Trp Leu Asp Leu Ser Leu Phe Lys Glu Leu
195 200 205

Glu Lys Asp Lys Asp Pro Lys Arg Ala Ala Arg Arg Lys Arg His Lys
210 215 220

Ile Pro Arg Ser Gly Ile Ala Ala Ser Lys Lys Leu Ala Ala Gly Ile
225 230 235 240

Phe Trp Ile Val Leu Trp Thr Gln Val Asp Ser Arg Ile Ser Thr Ala
245 250 255

Tyr Ala Tyr Ser Asp Ala Phe Thr Lys Glu His Asn Ile Phe Gly Arg
260 265 270

Ile Val Tyr Leu Tyr Met Leu Gly Phe Met Tyr Arg Leu Lys Tyr Tyr
275 280 285

Gly Ala Trp Ser Ile Ser Glu Gly Ala Cys Ile Leu Ser Gly Leu Gly
290 295 300

Phe His Gly Val Asp Pro Lys Thr Gly Lys Tyr Lys Trp Asp Arg Val
305 310 315 320

Gln Asn Val Asp Pro Trp Gly Phe Glu Thr Gly Gln Asn Thr Lys Ala
325 330 335

Leu Leu Glu Ala Trp Asn Gln Asn Thr Asn Lys Trp Leu Arg Asn Tyr
340 345 350

Val Tyr Leu Arg Val Val Pro Lys Gly Gln Lys Pro Gly Phe Arg Ala
355 360 365

Thr Ile Phe Thr Phe Val Val Ser Ala Phe Trp His Gly Thr Arg Pro
370 375 380

Gly Tyr Tyr Leu Thr Ser Val Thr Ala Ala Met Tyr Gln Ser Val Gly
385 390 395 400

Lys Phe Phe Arg Arg Tyr Leu Arg Pro Phe Phe Met Glu Ser Asp Gly
405 410 415

Lys Thr Ala Gly Pro Tyr Lys Ile Tyr Tyr Asp Ile Val Cys Trp Ile
420 425 430

Val Val Gln Thr Ala Phe Gly Tyr Ala Thr Gln Ser Phe Met Ile Leu
435 440 445

Asp Phe Trp Leu Ser Leu Lys Cys Trp Lys Asn Ser Trp Phe Leu Tyr
450 455 460

His Ile Ala Leu Gly Ala Ile Phe Ala Ile Ser Ser Pro Tyr Lys Ala
465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys
500 505 510

<210> SEQ ID NO 82
<211> LENGTH: 17
<212> TYPE: PRT
<213> ORGANISM: Yarrowia lipolytica

<400> SEQUENCE: 82

Met Val Leu Cys Met Lys Leu Ser Ser Phe Gly Trp Asn Val Tyr Asp
1 5 10 15

Gly

<210> SEQ ID NO 83
<211> LENGTH: 15
<212> TYPE: PRT
<213> ORGANISM: Yarrowia lipolytica

<400> SEQUENCE: 83

Ser Ala Phe Trp His Gly Thr Arg Pro Gly Tyr Tyr Leu Thr Phe
1 5 10 15

<210> SEQ ID NO 84
<211> LENGTH: 512
<212> TYPE: PRT
<213> ORGANISM: Artificial sequence
<220> FEATURE:
<223> OTHER INFORMATION: Mutant YlLPCAT protein generic Xaa only
<220> FEATURE:
<221> NAME/KEY: MISC_FEATURE
<222> LOCATION: (133)..(148)
<223> OTHER INFORMATION: Xaa can be any naturally occurring amino acid
<220> FEATURE:
<221> NAME/KEY: MISC_FEATURE
<222> LOCATION: (378)..(378)
<223> OTHER INFORMATION: Xaa can be any naturally occurring amino acid
<220> FEATURE:
<221> NAME/KEY: MISC_FEATURE
<222> LOCATION: (382)..(383)
<223> OTHER INFORMATION: Xaa can be any naturally occurring amino acid
<220> FEATURE:
<221> NAME/KEY: MISC_FEATURE
<222> LOCATION: (385)..(385)
<223> OTHER INFORMATION: Xaa can be any naturally occurring amino acid
<220> FEATURE:
<221> NAME/KEY: MISC_FEATURE
<222> LOCATION: (388)..(390)
<223> OTHER INFORMATION: Xaa can be any naturally occurring amino acid

<400> SEQUENCE: 84

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val
50 55 60

Gly Val Phe Ser Leu Tyr Gly Gly Ala Ala Thr Leu Leu Phe Ser Ser
65 70 75 80

Met Gly Thr Phe Phe Ile Thr Gln Trp Lys Ser Pro Tyr Met Pro Trp
85 90 95

Val Asn Phe Gly Phe Val Met Thr His Leu Phe Val Asn His Leu Arg
100 105 110

Ser Gln Phe Phe Pro Glu Thr Tyr Asp Pro Asn Val Ile Asp Ile Thr
115 120 125

Gly Ala Gln Met Xaa Xaa Xaa Xaa Xaa Xaa Xaa Xaa Xaa Xaa Xaa Xaa
130 135 140

Xaa Xaa Xaa Xaa Trp Gln Ile Glu Lys Gly Glu Gln Leu Ser Glu Phe
145 150 155 160

Gln Thr Lys Arg Ala Val Leu Lys His Pro Ser Leu Met Asp Phe Leu
165 170 175

Ala Phe Val Phe Tyr Phe Pro Ser Ile Leu Thr Gly Pro Ser Tyr Asp
180 185 190

Tyr Met Glu Phe His Asn Trp Leu Asp Leu Ser Leu Phe Lys Glu Leu
195 200 205

-continued

```
Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Xaa Trp His Gly Xaa Xaa Pro
    370                 375                 380

Xaa Tyr Tyr Xaa Xaa Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

RECOMBINANT MICROBIAL CELLS THAT PRODUCE AT LEAST 28% EICOSAPENTAENOIC ACID AS DRY CELL WEIGHT

This application claims the benefit of U.S. Provisional Application Nos. 61/740,502 and 61/740,506, each filed Dec. 21, 2012, both of which are incorporated herein by reference in their entireties.

FIELD OF THE INVENTION

This invention is in the field of biotechnology. More specifically, this invention pertains to recombinant microbial cells such as recombinant oleaginous yeast cells that can produce at least 28% eicosapentaenoic acid (EPA) as dry cell weight.

BACKGROUND OF THE INVENTION

A variety of different hosts including plants, algae, fungi, stramenopiles and yeast have been and continue to be investigated as means for commercial production of polyunsaturated fatty acids (PUFA). Genetic engineering has demonstrated that the natural abilities of some hosts, even those natively limited to linoleic acid (LA, 18:2 omega-6) or alpha-linolenic acid (ALA, 18:3 omega-3) fatty acid production, can be substantially altered to result in high-level production of various long-chain omega-3/omega-6 PUFAs.

Although the literature reports a number of recent examples whereby various portions of the omega-3/omega-6 PUFA biosynthetic pathway responsible for eicosapentaenoic acid (EPA) production have been introduced into plants and non-oleaginous yeast, significant efforts have focused on the use of the oleaginous yeast, *Yarrowia lipolytica* (U.S. Pat. Nos. 7,238,482 and 7,932,077; U.S. Pat. Appl. Publ. Nos. 2009-0093543 and 2010-0317072). Oleaginous yeast are defined as those yeast that are naturally capable of oil synthesis and accumulation, wherein oil accumulation is at least 25% of the cellular dry weight, or those yeast genetically engineered such that they become capable of oil synthesis and accumulation, wherein oil accumulation is at least 25% of the cellular dry weight.

Emphasis has been placed on the development of transgenic oleaginous *Y. lipolytica* strains that can produce enhanced amounts of EPA. This focus on EPA production is due in part to the recognized salutary effects of EPA. For example, EPA has been shown to play a role in maintaining brain, retina and cardiovascular health. EPA is also known to have anti-inflammatory properties and may be useful in treating or preventing diseases linked to inflammation, such as cardiovascular disease and arthritis. Thus, the clinical and pharmaceutical value of EPA is well known (U.S. Pat. Appl. Publ. No. 2009-0093543). Similarly, the advantages of producing EPA in microbes using recombinant means, as opposed to producing EPA from natural microbial sources or via isolation from fish oil and marine plankton, are also well recognized. Interest in EPA production in yeast has also been due to the drive to develop sustainable sources of EPA as alternatives to producing EPA from fish, which would help alleviate problems associated with overfishing.

Enhanced EPA production in *Y. lipolytica* has been targeted in two general ways. First, attempts have been made to increase the amount of EPA present in the oil produced by *Y. lipolytica*. Such oil, which may not necessarily constitute a large percentage of the dry cell weight of *Y. lipolytica* biomass, can be purified away from the biomass, then used in EPA dietary supplements and/or used for further concentration for pharmaceutical applications. Attempts have also been made to increase the amount of EPA in the dry cell weight of *Y. lipolytica*. This entails trying to (i) increase the level of oil in *Y. lipolytica* while also (ii) increasing the amount of EPA present in the oil. The resulting biomass can be used directly in feeding schemes to deliver a high quantity of EPA in the diet while side-stepping issues of oil purification. Of course, such biomass can also serve as a source of oil in EPA supplements and the oil can also be used for further concentration for pharmaceutical applications, requiring less biomass per unit of EPA produced compared to *Y. lipolytica* biomass containing a lower amount of oil.

U.S. Pat. Appl. Publ. No. 2010-0317072 discloses a transgenic *Y. lipolytica* strain that produces oil containing 61.8% by weight EPA of the total fatty acids of the oil. However, this strain contains 26.5% oil on a dry cell weight basis. So, while the EPA content in the oil is high (61.8%), the EPA content in the disclosed *Y. lipolytica* strain on a dry cell weight basis is lower at about 16.4%.

A transgenic *Y. lipolytica* strain is disclosed in U.S. Pat. Appl. Publ. No. 2012-0052537 that produces oil containing 58.7% by weight EPA of the total fatty acids of the oil. This strain contains 38.3% oil on a dry cell weight basis. So, while the EPA content in the oil is high (58.7%), the EPA content in the disclosed *Y. lipolytica* strain on a dry cell weight basis is lower at about 22.5%.

U.S. Pat. Appl. Publ. No. 2012-0052537 also discloses a transgenic *Y. lipolytica* strain that produces oil containing 48.3% by weight EPA of the total fatty acids of the oil. On a dry cell weight basis, this strain contains 56.2% oil and an EPA content of about 27.1%.

These disclosed examples indicate that as improvements are made in developing transgenic *Y. lipolytica* strains for enhanced EPA and/or oil production, an inverse correlation arises between the total amount of oil produced and the amount of EPA present in the total fatty acids of the oil. Strains engineered to produce higher amounts of oil on a dry cell basis generally have lower amounts of EPA as a percentage of the fatty acids in the oil.

Increases in the total amount of EPA produced on a dry cell weight basis have been realized, even though there has been an inverse relationship between oil production and the amount of EPA produced as a percentage of the total fatty acids in oil. Despite this achievement, there is still a need to develop *Y. lipolytica* strains that can produce greater total amounts of EPA. Achieving this goal will likely entail the development of new strain modifications that enhance the amount of EPA as a percentage of the total fatty acids in oil, while not compromising the total amount of oil produced by the strain.

Polynucleotide sequences encoding the Sou2 sorbitol utilization protein have been identified by others. Information regarding the function of this protein, however, appears to be limited. For example, Jami et al. (2010, *Molecular & Cellular Proteomics* 9:2729-2744) disclosed that a "probable" Sou2 protein was present in the extra-cellular fraction of the filamentous fungus *Penicillium chrysogenum*. The characterization of several amino acid sequences in online databases as Sou2 sorbitol utilization protein appears to be based on sequence homology only without the disclosure of functional studies. The amino acid sequence of the Sou2 protein in *Candida albicans* is about 72% identical to the amino acid sequence of *C. albicans* Sou1 protein, which has been disclosed by Janbon et al. (1998, *Proc. Natl. Acad. Sci. U.S.A.* 95:5150-5155) and Greenberg et al. (2005, *Yeast* 22:957-969) to be a sorbose reductase required for L-sorbose utilization. However, despite the homology between *C. albicans* Sou1 and -2 proteins, Janbon et al. disclosed that the Sou2 protein is not required for sorbose utilization. The roles of the Sou1 and Sou2 proteins in lipid metabolism, if any, are believed to be unknown.

Studies are disclosed herein detailing the development of *Y. lipolytica* strains that can produce more than 28% EPA as dry cell weight. The modifications used to generate such strains included down-regulating a gene encoding Sou2 sorbitol utilization protein.

SUMMARY OF THE INVENTION

In one embodiment, the invention concerns a recombinant microbial cell that produces an oil comprising at least 28 percent eicosapentaenoic acid (EPA) measured as a weight percent of dry cell weight. This cell comprises at least one polynucleotide sequence encoding an acyl-CoA:lysophosphatidylcholine acyltransferase (LPCAT) comprising at least one amino acid mutation in a membrane-bound O-acyltransferase motif, wherein the LPCAT has LPCAT activity, and the polynucleotide encoding LPCAT is operably linked to at least one regulatory sequence.

In a second embodiment, the LPCAT is a *Yarrowia lipolytica* LPCAT. In a third embodiment, the *Yarrowia lipolytica* LPCAT comprises mutations at (i) amino acid position 136 changing methionine to a different amino acid, and (ii) amino acid position 389 changing threonine to a different amino acid.

In a fourth embodiment, the recombinant microbial cell further comprises a down-regulation of an endogenous polynucleotide sequence encoding Sou2 sorbitol utilization protein. In a fifth embodiment, this down-regulation is due to a mutation of the endogenous polynucleotide sequence encoding Sou2 sorbitol utilization protein, wherein the mutation is selected from the group consisting of a substitution, deletion and insertion.

In a sixth embodiment, the Sou2 sorbitol utilization protein encoded by the endogenous polynucleotide sequence comprises an amino acid sequence that is at least 95% identical to SEQ ID NO:10.

In a seventh embodiment, the down-regulation of the endogenous polynucleotide sequence encoding Sou2 sorbitol utilization protein decreases the total amount of sugar alcohols produced by the recombinant microbial cell.

In an eighth embodiment, the recombinant microbial cell further comprises: (a) at least one polynucleotide sequence encoding phospholipid:diacylglycerol acyltransferase (PDAT), (b) at least one polynucleotide sequence encoding delta-12 desaturase, and (c) at least one polynucleotide sequence encoding a dihomo-gamma-linolenic acid (DGLA) synthase multizyme; wherein each of the polynucleotide sequences of (a)-(c) is operably linked to at least one regulatory sequence. In a ninth embodiment, the DGLA synthase multizyme encoded by the polynucleotide sequence of (c) comprises a delta-9 elongase linked to a delta-8 desaturase.

In a tenth embodiment, the recombinant microbial cell further comprises: (a) at least one polynucleotide sequence encoding delta-8 desaturase, (b) at least one polynucleotide sequence encoding malonyl-CoA synthetase (MCS), and (c) at least one polynucleotide sequence encoding acyl-CoA: lysophosphatidic acid acyltransferase (LPAAT); wherein each of the polynucleotide sequences of (a)-(c) is operably linked to at least one regulatory sequence.

In an eleventh embodiment, the oil produced by recombinant microbial cell comprises at least 30 percent EPA measured as a weight percent of the dry cell weight of the host cell.

In a twelfth embodiment, the recombinant microbial cell is an oleaginous yeast cell. In a thirteenth embodiment, this oleaginous yeast cell is a *Yarrowia* cell.

In a fourteenth embodiment, the invention concerns a method of producing a microbial oil comprising eicosapentaenoic acid. This method comprises: a) culturing a recombinant microbial cell of the invention, wherein a microbial oil comprising eicosapentaenoic acid is produced; and b) optionally recovering the microbial oil of step (a).

BIOLOGICAL DEPOSITS

The following biological material has been deposited with the American Type Culture Collection (ATCC), 10801 University Boulevard, Manassas, Va. 20110-2209, and bears the following designation, accession number and date of deposit.

| Biological Material | Accession No. | Date of Deposit |
|---|---|---|
| *Yarrowia lipolytica* Y8412 | ATCC PTA-10026 | May 14, 2009 |

The biological material listed above was deposited under the terms of the Budapest Treaty on the International Recognition of the Deposit of Microorganisms for the Purposes of Patent Procedure. The listed deposit will be maintained in the indicated international depository for at least 30 years and will be made available to the public upon the grant of a patent disclosing it. The availability of a deposit does not constitute a license to practice the subject invention in derogation of patent rights granted by government action.

*Y. lipolytica* strain Y9502 was derived from *Y. lipolytica* strain Y8412 as described in U.S. Pat. Appl. Publ. No. 2010-0317072, which is incorporated herein by reference. *Y. lipolytica* strain Z5585 was derived from *Y. lipolytica* strain Y9502 as described in U.S. Pat. Appl. Publ. No. 2012-0052537, which is incorporated herein by reference.

BRIEF DESCRIPTION OF THE DRAWINGS AND SEQUENCES

FIG. 1: Biosynthetic pathways for producing omega-3 and omega-6 fatty acids in *Yarrowia* are shown.

FIG. 2: Diagrammed are (A) the steps of developing *Y. lipolytica* strain Y9502 from wild type strain ATCC #20362, and (B) the steps of developing *Y. lipolytica* strains Z5627 and Z5585 from strain Y9502. The percent fatty acid (E.g., EPA) values listed under certain strains represent the percentage of the particular fatty acid in the fatty acids of the oil produced by the strain. The percent oil values listed under certain strains represent the oil as a percent of dry cell weight of the strain.

Figure 3:
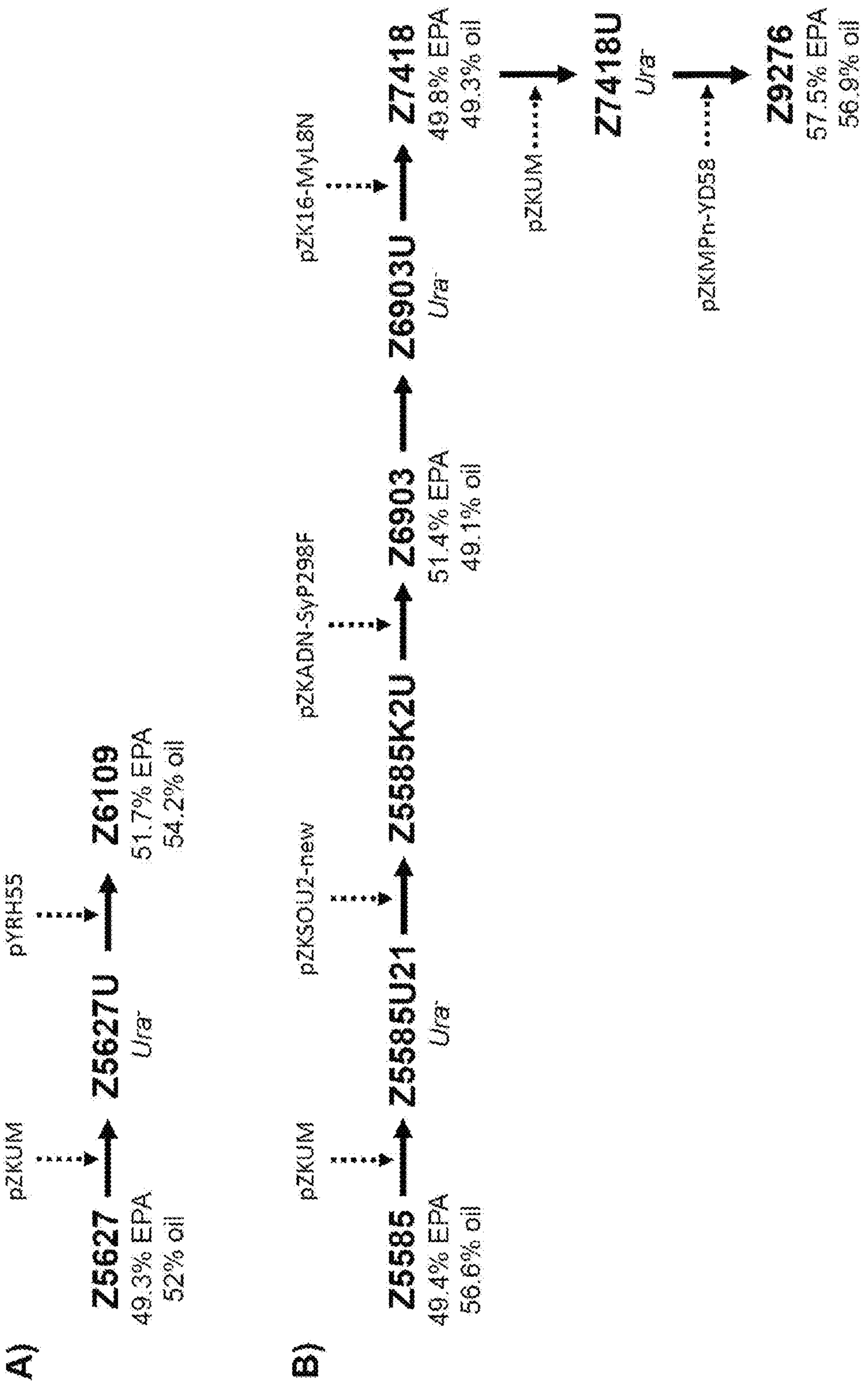

FIG. 3: Diagrammed are (A) the steps of developing *Y. lipolytica* strain Z6109 from strain Z5627, and (B) the steps of developing *Y. lipolytica* strain Z9276 from strain Z5585. The percent EPA values listed under certain strains represent the percentage of the EPA in the fatty acids of the oil produced by the strain. The percent oil values listed under certain strains represent the oil as a percent of dry cell weight of the strain.

FIG. 4: Diagrammed are plasmid constructs (A) pYRH55 and (B) pZKSOU2-New.

FIG. 5: Genomic DNA sequence (SEQ ID NO:8) containing the *Y. lipolytica* SOU2 gene locus (GenBank Accession No. XM_503010, YALI0D18964g) is shown. The Sou2 amino acid coding region (SEQ ID NO:9) is indicated with bold, underlined text. Two adjacent cytosine residues, which are located at positions 2400349 and 2400350 of chromosome D, are shown in large bold font and are just downstream an apparent TATA box (bold). The mutational insertion observed in strain Z3041 impairing Sou2 expression occurred between these two cytosine residues. The sequence indicated between the two opposing triangles was targeted for removal by the 5'- and 3'-homology sequences of plasmid pZKSOU2-New.

Figure 6:
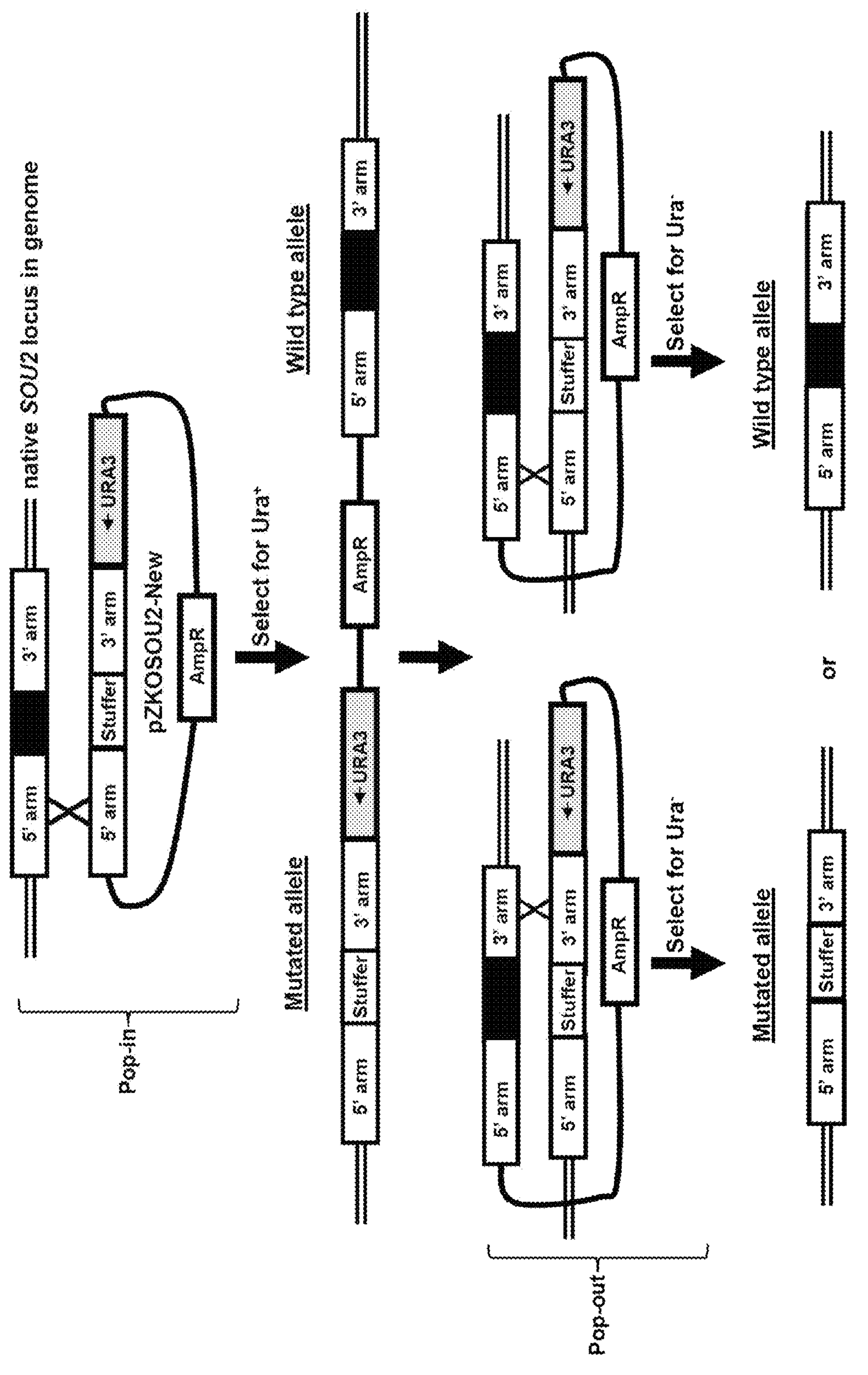

FIG. 6: Diagrammed is the genetic targeting strategy used to knock-out the endogenous SOU2 gene in *Y. lipolytica* using construct pZKSOU2-New. The "X"s shown between certain 5'- and 3'-homology arm sequences denotes sites of homologous recombination. The pop-in event resulting from homologous recombination at the 5'-homology arms results in the juxtaposition of a mutated SOU2 allele with the wild type SOU2 allele. Two different pop-out events are shown. The left-hand pop-out event occurs as a result of homologous recombination at the 3'-homology arms of the gene structure formed from the 5'-arm pop-in event. This process results in a mutated SOU2 allele and removal of the wild type allele. The right-hand pop-out event occurs as a result of homologous recombination at the 5'-homology arms. This pop-out event results in the wild type SOU2 allele.

FIG. 7: Diagrammed are plasmid constructs (A) pZKADn-SyP298F and (B) pZKMPn-YD58.

Figure 8:
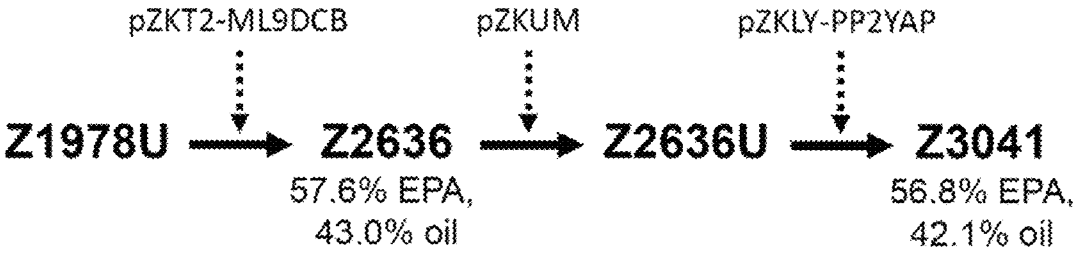

FIG. 8: Diagrammed are the steps of developing *Y. lipolytica* strain Z3041 from strain Z1978U. The percent EPA values listed under certain strains represent the percentage of the EPA in the fatty acids of the oil produced by the strain. The percent oil values listed under certain strains represent the oil as a percent of dry cell weight of the strain.

FIG. 9: Diagrammed are plasmid constructs (A) pZKT2-ML9DCB and (B) pZKLY-PP2YAP.

Figure 10:
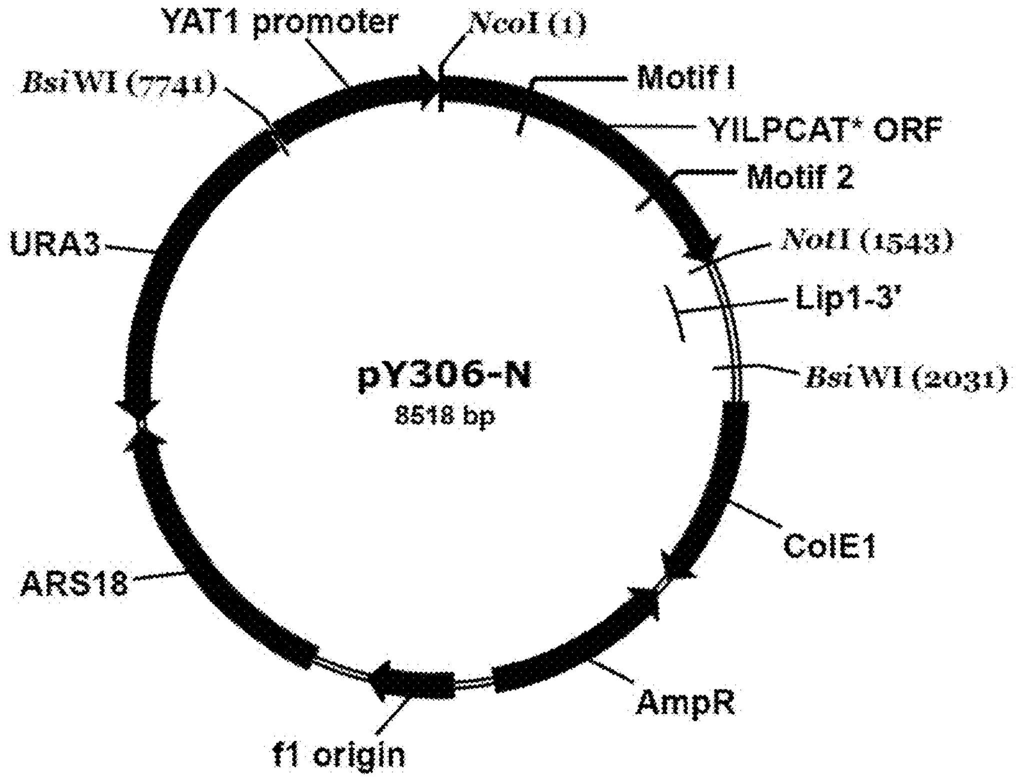

FIG. 10: Diagrammed is the plasmid construct pY306-N.

TABLE 1

Summary of Gene and Protein SEQ ID Numbers

| Description | Nucleic acid SEQ ID NO. | Protein SEQ ID NO. |
|---|---|---|
| Construct pYRH55 for expressing codon-optimized *Arabidopsis thaliana* caleosin-1 (AtClo1S) | 1 | |
| AtClo1S, *A. thaliana* caleosin-1 codon-optimized for expression in *Y. lipolytica* (U.S. Appl. Publ. No. 2012-0301932) | 2 | 3 (245 aa) |
| Construct pZKSOU2-New for down-regulating endogenous *Y. lipolytica* SOU2 expression | 4 | |
| Construct pZKADn-SyP298F for expressing YlPDAT, FmD12S, and E389D9eS/EgD8M | 5 | |
| Erp, terminator sequence from *Y. lipolytica* ERP gene | 6 | |
| Glo terminator sequence from *Y. lipolytica* GLO gene | 7 | |
| Genomic DNA sequence containing the *Y. lipolytica* SOU2 gene locus, FIG. 5, 2071-bp (1000-bp upstream Sou2 ATG start codon, 771-bp Sou2 coding sequence, 300-bp downstream Sou2 TGA stop codon) | 8 | |
| *Y. lipolytica* Sou2 sorbitol utilization protein | 9 | 10 (256 aa) |
| Genomic DNA sequence containing the *Y. lipolytica* SOU2 gene locus, 2771-bp (1000-bp upstream Sou2 ATG start codon, 771-bp Sou2 coding sequence, 1000-bp downstream Sou2 TGA stop codon) | 11 | |
| FmD12S, *Fusarium moniliforme* delta-12 desaturase (U.S. Pat. No. 7,504,259) codon-optimized for expression in *Y. lipolytica* | 12 | 13 (477 aa) |
| YlPDAT, *Y. lipolytica* PDAT (U.S. Pat. Appl. Publ. No. 2012-0052537), but with an added alanine at amino acid position 2 | 14 | 15 (649 aa) |
| E389D9eS/EgD8M: gene fusion comprising a codon-optimized delta-9 elongase derived from *Eutreptiella* sp. CCMP389 (E389D9eS), a linker, and a codon-optimized mutant delta-8 desaturase derived from *Euglena gracilis* (EgD8M) (U.S. Pat. Appl. Publ. No. 2008-0254191) | 16 | 17 (708 aa) |
| EgD8M, mutant *E. gracilis* delta-8 desaturase (U.S. Pat. No. 7,709,239) | 18 | 19 (422 aa) |
| MCS, *Rhizobium leguminosarum* bv. *viciae* 3841 malonyl-CoA synthetase (U.S. Pat. Appl. Publ. No. 2010/0159558) codon-optimized for expression in *Y. lipolytica* | 20 | 21 (505 aa) |
| YlLPAAT1, *Y. lipolytica* LPAAT1 (U.S. Pat. Appl. Publ. No. 2012-0052537) | 22 | 23 (282 aa) |
| Construct pZKMPn-YD58 for expressing mutant YlLPCAT (M136S_T389A) | 24 | |
| Mutant YlLPCAT (M136S_T389A), *Y. lipolytica* LPCAT containing M136S and T389A mutations | 25 | 26 (512 aa) |
| Construct pZKT2-ML9DCB for expressing YlCPT1, YlD9, and MaLPAAT1S | 27 | |
| Construct pZKLY-PP2YAP for expressing YlYAP1, Yl6PGL, and YlG6PDH | 28 | |

TABLE 1-continued

| Summary of Gene and Protein SEQ ID Numbers | | |
|---|---|---|
| Description | Nucleic acid SEQ ID NO. | Protein SEQ ID NO. |
| *Candida albicans* Sou2 sorbitol utilization protein | 29 | 30 (280 aa) |
| YlPDAT, *Y. lipolytica* PDAT (U.S. Pat. No. 7,267,976) | | 31 (648 aa) |
| YlD12, *Y. lipolytica* delta-12 desaturase (U.S. Pat. No. 7,504,259) | | 32 (419 aa) |
| E389D9eS, delta-9 elongase derived from *Eutreptiella* sp. CCMP389 (E389D9eS) (U.S. Pat. Appl. Publ. No. 2008-0254191) | | 33 (263 aa) |
| Linker comprised in E389D9eS/EgD8M multizyme | | 34 (24 aa) |
| EgD9eS/EgD8M: gene fusion comprising a delta-9 elongase derived from *Euglena gracilis* (EgD9eS), a linker, and a mutant delta-8 desaturase derived from *Euglena gracilis* (EgD8M) (U.S. Pat. Appl. Publ. No. 2008-0254191) | | 35 (701 aa) |
| EaD9eS/EaD8S: gene fusion comprising a delta-9 elongase derived from *Euglena anabaena* (EaD9eS), a linker, and a delta-8 desaturase derived from *Euglena anabaena* (EaD8S) (U.S. Pat. Appl. Publ. No. 2008-0254191) | | 36 (702 aa) |
| EaD8, *E. anabaena* delta-8 desaturase (U.S. Pat. No. 7,790,156) | | 37 (420 aa) |
| MaLPAAT1, *M. alpina* lysophosphatidic acid acyltransferase-1 (U.S. Pat. No. 7,879,591) | | 38 (314 aa) |
| YlLPCAT, wild type *Y. lipolytica* LPCAT (YALI0F19514p, GenBank Accession No. XP_505624) | 39 | 40 (512 aa) |
| YlLPCAT*, YlLPCAT lacking two internal NcoI restriction sites with respect to SEQ ID NO: 39, but encoding wild type YlLPCAT protein | 41 | 40 (512 aa) |
| Construct pY306-N, containing YlLPCAT* nucleotide sequence | 42 | |
| Construct pY306, containing wild type YlLPCAT nucleotide sequence | 43 | |
| Mutant YlLPCAT_M132X, comprising M132A, M132N, M132C, M132G, M132Q, M132H, M132I, M132L, M132F, M132P, M132S, M132T, M132W, M132Y or M132V mutation in Motif I | | 44 (512 aa) |
| Mutant YlLPCAT_V133X, comprising V133A, V133N, V133C, V133G, V133Q, V133H, V133L, V133M, V133F, V133P, V133S, V133T, V133W or V133Y mutation in Motif I | | 45 (512 aa) |
| Mutant YlLPCAT_L134X, comprising L134A, L134N, L134C, L134G, L134Q, L134H, L134M, L134F, L134P, L134S, L134T, L134W, L134Y or L134V mutation in Motif I | | 46 (512 aa) |
| Mutant YlLPCAT_C135X, comprising C135R, C135N, C135D, C135G, C135E, C135Q, C135H, C135I, C135L, C135K, C135M, C135F, C135P, C135S, C135W or C135Y mutation in Motif I | | 47 (512 aa) |
| Mutant YlLPCAT_M136X, comprising M136A, M136N, M136C, M136G, M136H, M136I, M136F, M136P, M136S, M136T, M136W, M136Y or M136V mutation in Motif I | | 48 (512 aa) |
| Mutant YlLPCAT_K137X, comprising K137A, K137R, K137N, K137G, K137H, K137P, K137S, K137T, or K137Y mutation in Motif I | | 49 (512 aa) |
| Mutant YlLPCAT_L138X, comprising L138A, L138N, L138C, L138G, L138Q, L138H, L138I, L138M, L138F, L138P, L138S, L138T, L138W, or L138Y mutation in Motif I | | 50 (512 aa) |
| Mutant YlLPCAT_S139X, comprising S139A, S139N, S139C, S139G, S139H, S139L, S139M, S139F, S139P, S139W, or S139V mutation in Motif I | | 51 (512 aa) |
| Mutant YlLPCAT_S140X, comprising S140N, S140C, S140H, S140I, S140L, S140F, S140P, S140W, S140Y or S140V mutation in Motif I | | 52 (512 aa) |
| Mutant YlLPCAT_F141X, comprising F141A, F141N, F141G, F141H, F141I, F141M, F141P, F141S, F141T, F141W, or F141V mutation in Motif I | | 53 (512 aa) |
| Mutant YlLPCAT_G142X, comprising G142N, G142H, G142I, G142L, G142M, G142F, G142P, G142T, G142W, G142Y or G142V mutation in Motif I | | 54 (512 aa) |

TABLE 1-continued

| Summary of Gene and Protein SEQ ID Numbers | | |
|---|---|---|
| Description | Nucleic acid SEQ ID NO. | Protein SEQ ID NO. |
| Mutant YlLPCAT_W143X, comprising W143A, W143G, W143H, W143L, W143K, W143P, W143S, W143T or W143V mutation in Motif I | | 55 (512 aa) |
| Mutant YlLPCAT_N144X, comprising N144A, N144R, N144G, N144H, N144K, N144F, N144P, N144T or N144V mutation in Motif I | | 56 (512 aa) |
| Mutant YlLPCAT_V145X, comprising V145A, V145C, V145G, V145E, V145H, V145M, V145F, V145P, V145S, V145T, or V145W mutation in Motif I | | 57 (512 aa) |
| Mutant YlLPCAT_Y146X, comprising Y146R, Y146N, Y146D, Y146G, Y146E, Y146Q, Y146I, Y146L, Y146M, Y146F, Y146P, Y146W or Y146V mutation in Motif I | | 58 (512 aa) |
| Mutant YlLPCAT_D147X, comprising D147A, D147N, D147G, D147E, D147Q, D147H, D147F, D147S, or D147T mutation in Motif I | | 59 (512 aa) |
| Mutant YlLPCAT_G148X, comprising G148A, G148N, G148H, G148L, G148M, G148F, G148S, G148T or G148V mutation in Motif I | | 60 (512 aa) |
| Mutant YlLPCAT_S376X, comprising S376A, S376G, S376H, S376L, S376F, S376P, S376T or S376V mutation in Motif II | | 61 (512 aa) |
| Mutant YlLPCAT_A377X, comprising A377N, A377G, A377H, A377L, A377F, A377P, A377S, A377T or A377V mutation in Motif II | | 62 (512 aa) |
| Mutant YlLPCAT_F378X, comprising F378A, F378N, F378C, F378G, F378H, F378L, F378P, F378S, F378T, F378W, or F378Y mutation in Motif II | | 63 (512 aa) |
| Mutant YlLPCAT_T382X, comprising T382A, T382N, T382G, T382Q, T382H, T382I, T382M, T382P, T382S, T382W or T382Y mutation in Motif II | | 64 (512 aa) |
| Mutant YlLPCAT_R383X, comprising R383A, R383N, R383D, R383G, R383E, R383Q, R383H, R383I, R383L, R383K, R383M, R383F, R383P, R383T, R383W or R383V mutation in Motif II | | 65 (512 aa) |
| Mutant YlLPCAT_P384X, comprising P384A, P384R, P384G, P384H, P384I, P384L, P384K, P384M, P384F, P384S, P384T, P384W, P384Y or P384V mutation in Motif II | | 66 (512 aa) |
| Mutant YlLPCAT_G385X, comprising G385A, G385N, G385C, G385G, G385H, G385I, G385L, G385K, G385M, G385F, G385S, G385T, G385W, G385Y or G385V mutation in Motif II | | 67 (512 aa) |
| Mutant YlLPCAT_Y386X, comprising Y386A, Y386G, Y386H, Y386L, Y386F, Y386P, Y386S, Y386T or Y386V mutation in Motif II | | 68 (512 aa) |
| Mutant YlLPCAT_Y387X, comprising Y387A, Y387G, Y387H, Y387L, Y387F, Y387P, Y387S, Y387T, Y387W or Y387V mutation in Motif II | | 69 (512 aa) |
| Mutant YlLPCAT_L388X, comprising L388A, L388G, L388H, L388P, L388S, L388T, L388W, L388Y or L388V mutation in Motif II | | 70 (512 aa) |
| Mutant YlLPCAT_T389X, comprising T389A, T389C, T389G, T389H, T389I, T389L, T389M, T389F, T389P, T389S, T389W, T389Y or T389V mutation in Motif II | | 71 (512 aa) |
| Mutant YlLPCAT_F390X, comprising F390A, F390N, F390C, F390G, F390H, F390L, F390M, F390P, F390S, F390T or F390V mutation in Motif II | | 72 (512 aa) |
| Mutant YlLPCAT, comprising single mutations in Motif I and/or Motif II | | 73 (512 aa) |
| Mutant YlLPCAT, comprising a single mutation in Motif I and a single mutation in Motif II | | 74 (512 aa) |
| Mutant YlLPCAT (M136S_T389C), *Y. lipolytica* LPCAT containing M136S and T389C mutations | | 75 (512 aa) |
| Mutant YlLPCAT (M136S_T389S), *Y. lipolytica* LPCAT containing M136S and T389S mutations | | 76 (512 aa) |
| Mutant YlLPCAT (M136V_T389C), *Y. lipolytica* LPCAT containing M136V and T389C mutations | | 77 (512 aa) |
| Mutant YlLPCAT (N144A_F390S), *Y. lipolytica* LPCAT containing N144A and F390S mutations | | 78 (512 aa) |
| Mutant YlLPCAT (G148A_F390S), *Y. lipolytica* LPCAT containing G148A and F390S mutations | | 79 (512 aa) |
| Mutant YlLPCAT (G148N_T382I), *Y. lipolytica* LPCAT containing G148N and T382I mutations | | 80 (512 aa) |

TABLE 1-continued

| Summary of Gene and Protein SEQ ID Numbers | | |
|---|---|---|
| Description | Nucleic acid SEQ ID NO. | Protein SEQ ID NO. |
| Mutant YlLPCAT (G148N_F390S), *Y. lipolytica* LPCAT containing G148N and F390S mutations | | 81 (512 aa) |
| MBOAT Motif I of YlLPCAT | | 82 (17 aa) |
| MBOAT Motif II of YlLPCAT | | 83 (15 aa) |
| Mutant YlLPCAT, comprising a mutant Motif I and/or a mutant Motif II | | 84 (512 aa) |

DETAILED DESCRIPTION OF THE INVENTION

All patents, patent applications, and publications cited are incorporated herein by reference in their entirety.

As used herein the term "invention" or "present invention" is intended to refer to all aspects and embodiments of the invention as described in the claims and specification herein and should not be read so as to be limited to any particular embodiment or aspect.

The terms "SOU2", "SOU2 gene" and "endogenous polynucleotide sequence encoding Sou2 sorbitol utilization protein" are used interchangeably herein. The "Sou2 sorbitol utilization protein" (Sou2p) is encoded by the SOU2 gene.

The Sou2 sorbitol utilization protein of *Y. lipolytica* (SEQ ID NO:10) has about 66% amino acid sequence identity (according to a BLAST alignment) with *Candida albicans* Sou2 sorbitol utilization protein (SEQ ID NO:30). Thus, a Sou2 sorbitol utilization protein in certain embodiments has at least 60% amino acid sequence identity with SEQ ID NO:30. A Sou2 sorbitol utilization protein may alternatively have at least 65%, 70%, 75%, or 80% amino acid sequence identity with SEQ ID NO:30.

The term "lipids" as used herein refers to any fat-soluble (i.e., lipophilic), naturally-occurring molecule. A general overview of lipids is provided in U.S. Pat. Appl. Publ. No. 2009-0093543 (see Table 2 therein).

The term "oil" as used herein refers to a lipid substance that is liquid at 25° C.; oil is hydrophobic and soluble in organic solvents. In oleaginous organisms, oil constitutes a major part of the total lipids. Oil is composed primarily of triacylglycerols, but may also contain other neutral lipids, phospholipids and free fatty acids. The fatty acid composition in the oil and the fatty acid composition of the total lipids are generally similar; thus, an increase or decrease in the concentration of fatty acids in the total lipids will correspond with an increase or decrease in the concentration of fatty acids in the oil, and vice versa. The terms "oil", "total lipids", "total lipid content", "total fatty acids", and "total fatty acid methyl esters" are used interchangeable herein.

The term "triacylglycerols" (TAG or TAGs) as used herein refers to neutral lipids composed of three fatty acyl residues esterified to a glycerol molecule. TAGs can contain long-chain polyunsaturated and saturated fatty acids, as well as shorter chain unsaturated and saturated fatty acids.

The term "total fatty acids" (TFA or TFAs) as used herein refers to the sum of all cellular fatty acids that can be derivatized to fatty acid methyl esters (FAME or FAMES) by base transesterification of a given sample, which may be biomass or oil, for example. Thus, total fatty acids include fatty acids from neutral lipids (monoacylglycerols, diacylglycerols, TAGs) and polar lipids (e.g., phosphatidylcholine, phosphatidylethanolamine).

The term "total lipid content" of cells as used herein refers to a measure of TFAs as a percent of the dry cell weight (DCW) and can be expressed as "TFAs % DCW"; e.g., milligrams TFA per 100 milligrams of DCW. For example, 50 TFAs % DCW means that 50% of the dry cell weight is lipid or oil. Total lipid content can be approximated as a measure of FAMEs as a percent of the DCW (FAMEs % DCW).

The concentration of a fatty acid in the total lipids is expressed herein as a weight percent of TFAs (% TFAs); e.g., milligrams of a given fatty acid per 100 milligrams of TFAs. Unless otherwise specifically stated herein, reference to the percent of a given fatty acid with respect to total lipids or oil is equivalent to the concentration of the fatty acid as % TFAs (e.g., % EPA of total lipids or oil is equivalent to EPA % TFAs). For example, 50% by weight of EPA in the total fatty acids of an oil is expressed as 50 EPA % TFAs.

It can also useful to express the content of a given fatty acid(s) in a cell as its weight percent of the dry cell weight (% DCW). A measure of total EPA production (EPA % DCW), for example, can be determined using the formula: (EPA % TFAs)*(TFAs % DCW)]/100. A measurement of 30% by weight EPA in the dry cell weight, for example, is expressed by 30 EPA % DCW. The content of a fatty acid(s) such as EPA in the dry cell weight can be approximated using the formula: (EPA % FAMEs)*(FAMEs % DCW)]/100.

The terms "lipid profile", "lipid composition", and "fatty acid profile" are used interchangeably herein and refer to the amount of each individual fatty acid contained in the total lipids or oil, wherein the amount is expressed as a wt % of TFAs. The sum of each individual fatty acid present in the mixture should be 100.

The term "oleaginous" as used herein describes those organisms that tend to store their energy source in the form of lipid (Weete, In: Fungal Lipid Biochemistry, 2nd Ed., Plenum, 1980). An oleaginous microorganism can comprise, or can accumulate or produce, about 25% or more of its dry cell weight as oil (i.e., ≥25 TFAs % DCW).

The term "oleaginous yeast" as used herein refers to those microorganisms classified as yeasts that can produce a high amount of oil. Examples of oleaginous yeast include, for example, the genera *Yarrowia, Candida, Rhodotorula, Rhodosporidium, Cryptococcus, Trichosporon* and *Lipomyces*. Preferably, an oleaginous yeast can accumulate in excess of about 25% of its dry cell weight as oil.

The term "fatty acids" as used herein refers to long-chain aliphatic acids (alkanoic acids) of varying chain lengths, from about $C_{12}$ to $C_{22}$. The predominant chain lengths are between $C_{16}$ and $C_{22}$. The structure of a fatty acid is represented by a simple notation system of "X:Y", where X is the total number of carbon (C) atoms in the fatty acid and Y is the number of double bonds. Additional details concerning the differentiation between "saturated fatty acids" versus "unsaturated fatty acids", "monounsaturated fatty acids" versus "polyunsaturated fatty acids" (PUFAs), and "omega-6 fatty acids" (n−6) versus "omega-3 fatty acids" (n−3) are provided in U.S. Pat. No. 7,238,482, which is incorporated herein by reference.

The nomenclature used to describe PUFAs herein is given in Table 2. In the "Shorthand Notation" column, the omega-reference system is used to indicate the number of carbons, the number of double bonds and the position of the double bond closest to the omega carbon, counting from the omega carbon. The remainder of Table 2 summarizes the common names of omega-3 and omega-6 fatty acids, abbreviations that will be used throughout the specification, and the chemical name of each compound.

TABLE 2

Nomenclature of Polyunsaturated Fatty Acids

| Common Name | Abbreviation | Chemical Name | Shorthand Notation |
|---|---|---|---|
| Myristic | — | tetradecanoic | 14:0 |
| Palmitic | — | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 n-6 |
| gamma-Linolenic | GLA | cis-6,9,12-octadecatrienoic | 18:3 n-6 |
| Eicosadienoic | EDA | cis-11,14-eicosadienoic | 20:2 n-6 |
| Dihomo-gamma-Linolenic | DGLA | cis-8,11,14-eicosatrienoic | 20:3 n-6 |
| Arachidonic | ARA | cis-5,8,11,14-eicosatetraenoic | 20:4 n-6 |
| alpha-Linolenic | ALA | cis-9,12,15-octadecatrienoic | 18:3 n-3 |
| Stearidonic | STA | cis-6,9,12,15-octadecatetraenoic | 18:4 n-3 |
| Eicosatrienoic | ETrA | cis-11,14,17-eicosatrienoic | 20:3 n-3 |
| Eicosatetraenoic | ETA | cis-8,11,14,17-eicosatetraenoic | 20:4 n-3 |
| Eicosapentaenoic | EPA | cis-5,8,11,14,17-eicosapentaenoic | 20:5 n-3 |
| Docosatetraenoic | DTA | cis-7,10,13,16-docosatetraenoic | 22:4 n-6 |
| Docosapentaenoic | DPAn-6 | cis-4,7,10,13,16-docosapentaenoic | 22:5 n-6 |
| Docosapentaenoic | DPA | cis-7,10,13,16,19-docosapentaenoic | 22:5 n-3 |
| Docosahexaenoic | DHA | cis-4,7,10,13,16,19-docosahexaenoic | 22:6 n-3 |

The term "PUFA biosynthetic pathway" as used herein refers to a metabolic pathway or process that converts oleic acid to omega-6 fatty acids such as LA, EDA, GLA, DGLA, ARA, DTA and DPAn-6 and omega-3 fatty acids such as ALA, STA, ETrA, ETA, EPA, DPA and DHA. This pathway is described in the literature (e.g., U.S. Pat. No. 7,932,077; U.S. Pat. Appl. Publ. No. 2009-0093543-A1). Briefly, a PUFA biosynthetic pathway involves elongation of the carbon chain through the addition of carbon atoms and desaturation of the molecule through the addition of double bonds, via a series of special elongation and desaturation enzymes termed "PUFA biosynthetic pathway enzymes". More specifically, "PUFA biosynthetic pathway enzymes" refer to any of the following enzymes (and genes encoding these enzymes) associated with the biosynthesis of a PUFA, including: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase and/or $C_{20/22}$ elongase. FIG. 1 illustrates certain PUFA biosynthetic pathways.

A PUFA biosynthetic pathway may be "engineered" in certain embodiments. Such a pathway would comprise one or more foreign or heterologous PUFA biosynthetic pathway enzymes. Such enzymes could be expressed in the cell through the introduction of one or more transgenes encoding the enzymes.

The terms "conversion efficiency" and "percent substrate conversion" herein refer to the efficiency by which a particular enzyme, such as a desaturase or elongase, can convert its respective substrate to product. The conversion efficiency is measured according to the following formula: ([product]/[substrate+product])*100, where "product" refers to the immediate product and all products derived from it. More specifically, since each PUFA biosynthetic pathway enzyme rarely functions with 100% efficiency to convert substrate to product, the final lipid profile of unpurified oils produced in a host cell will typically be a mixture of various PUFAs consisting of the desired omega-3/omega-6 fatty acid, as well as various upstream intermediary PUFAs.

The term "$C_{18}$ to $C_{20}$ elongation conversion efficiency" refers herein to the efficiency by which $C_{18/20}$ elongases can convert $C_{18}$ substrates (i.e., LA, ALA, GLA, STA, etc.) to $C_{20}$ products (i.e., EDA, ETrA, DGLA, ETA, EPA, etc.). These $C_{18/20}$ elongases can be either delta-9 elongases or delta-6 elongases.

The terms "delta-9 elongation conversion efficiency" and "delta-9 elongase conversion efficiency" herein refer to the efficiency by which delta-9 elongase can convert $C_{18}$ substrates (e.g., LA, ALA) to $C_{20}$ products (e.g., EDA, ETrA, DGLA, ETA, ARA, EPA). Delta-9 elongase conversion efficiency is referred to herein as "% Conv." or "d9e CE (%)".

The terms "membrane-bound O-acyltransferase motif" and "MBOAT motif" are used interchangeably herein. MBOAT motifs are contained in LPLATs such as LPCAT and play a role in the enzymatic activity of these proteins (Shindou et al., 2009, *Biochem. Biophys. Res. Comm.* 383: 320-325; U.S. Pat. No. 7,732,155; U.S. Pat. Appl. Publ. Nos. 2008-0145867 and 2010-0317882).

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "isolated" as used herein refers to a polynucleotide or polypeptide molecule that has been completely or partially purified from its native source. In some instances, the isolated polynucleotide or polypeptide molecule is part of a greater composition, buffer system or reagent mix. For example, the isolated polynucleotide or polypeptide molecule can be comprised within a cell or organism in a heterologous manner.

The term "gene" as used herein refers to a polynucleotide sequence that expresses a protein, and which may refer to the coding region alone or may include regulatory sequences upstream and/or downstream to the coding region (e.g., 5' untranslated regions upstream of the transcription start site of the coding region). A gene that is "native" or "endogenous" refers to a gene as found in nature with its own regulatory sequences; this gene is located in its natural location in the genome of an organism. An "endogenous polynucleotide encoding" a particular protein is an example of an endogenous gene. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene herein refers to a gene that is introduced into the host organism by gene transfer. Foreign genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a transformation procedure. A "codon-optimized gene" is a gene having its frequency of codon usage designed to mimic the frequency of preferred codon usage of the host cell.

"Coding sequence" as used herein refers to a DNA sequence that codes for a specific amino acid sequence. "Regulatory sequences" as used herein refer to nucleotide sequences located upstream of the coding sequence's transcription start site, 5' untranslated regions and 3' non-coding regions, and which may influence the transcription, RNA processing or stability, or translation of the associated coding sequence. Regulatory sequences may include promoters, enhancers, silencers, 5' untranslated leader sequence, introns, polyadenylation recognition sequences, RNA processing sites, effector binding sites, stem-loop structures and other elements involved in regulation of gene expression.

A "promoter" as used herein refers to a DNA sequence capable of controlling the expression of a coding sequence or functional RNA. In general, a promoter sequence is 5' upstream of the transcription start site of a gene. Promoters may be derived in their entirety from a native gene, or be composed of different elements derived from different promoters found in nature, or even comprise synthetic DNA segments. Promoters that cause a gene to be expressed in most cell types at most times are commonly referred to as "constitutive promoters".

The terms "3' non-coding sequence", "transcription terminator" and "terminator" as used herein refer to DNA sequences located 3' downstream of a coding sequence. This includes polyadenylation recognition sequences and other sequences encoding regulatory signals capable of affecting mRNA processing or gene expression.

The term "expression" as used herein refers to the transcription from a gene to produce RNA such as messenger RNA (mRNA). This term can also refer to translation of mRNA into a polypeptide.

When used to describe the expression of a gene or polynucleotide sequence, the terms "down-regulation", "disruption", and "inhibition" are used interchangeably herein to refer to instances when the transcription of the polynucleotide sequence is reduced or eliminated. This results in the reduction or elimination of RNA transcripts from the polynucleotide sequence, which results in a reduction or elimination of protein expression derived from the polynucleotide sequence. Alternatively, down-regulation can refer to instances where protein translation from transcripts produced by the polynucleotide sequence is reduced or eliminated. Alternatively still, down-regulation can refer to instances where a protein expressed by the polynucleotide sequence has reduced activity. The reduction in any of the above processes (transcription, translation, protein activity) in a cell can by about 40%, 50%, 60%, 70%, 80%, 90%, 95%, or 100% relative to the transcription, translation, or protein activity of a suitable control cell. Down-regulation can be the result of a mutation as disclosed herein (e.g., knock-out) or through the use of antisense or RNAi technology, for example.

The terms "control cell" and "suitable control cell" are used interchangeably herein and may be referenced with respect to a cell in which a particular modification (e.g., over-expression of a polynucleotide, down-regulation of a polynucleotide) has been made (i.e., an "experimental cell"). A control cell may be any cell that does not have or does not express the particular modification of the experimental cell. Thus, a control cell may be an untransformed wild type cell or may be genetically transformed but does not express the genetic transformation. For example, a control cell may be a direct parent of the experimental cell, which direct parent cell does not have the particular modification that is in the experimental cell. Alternatively, a control cell may be a parent of the experimental cell that is removed by one or more generations. Alternatively still, a control cell may be a sibling of the experimental cell, which sibling does not comprise the particular modification that is present in the experimental cell. A sibling cell that could serve as a control cell could be a cell in which a plasmid for protein over-expression is inserted, but not expressed, in the sibling cell, whereas the plasmid is expressed in the experimental cell. It is well within the skill in the art to determine if a cell can be a control cell.

The term "increased" as used herein means having a greater quantity, for example a quantity only slightly greater than the original quantity, or for example a quantity in large excess compared to the original quantity, and including all quantities in between. Alternatively, "increased" may refer to a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared. The terms "increased", "greater than", and "improved" are used interchangeably herein. The term "increased" can be used to characterize the expression of a polynucleotide encoding a protein, for example, where "increased expression" can also mean "over-expression".

The term "operably linked" as used herein refers to the association of two or more nucleic acid sequences such that that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences in sense or antisense orientation.

The term "recombinant" as used herein refers to an artificial combination of two otherwise separated segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

The term "transformation" as used herein refers to the transfer of a nucleic acid molecule into a host organism. The nucleic acid molecule may be a plasmid that replicates autonomously, or it may integrate into the genome of the host organism. Host organisms containing the transformed nucleic acid fragments are referred to as "transgenic" or "recombinant" or "transformed" organisms or "transformants".

The terms "microbial cell" and "microbial organism" are used interchangeably herein and refer to a microorganism capable of receiving foreign or heterologous genes and capable of expressing those genes. A "recombinant microbial cell" refers to a microbial cell that has been recombinantly engineered.

The term "expression cassette" as used herein refers to a polynucleotide sequence comprising a promoter and the coding sequence of a selected gene as well as some other regulatory sequences preceding (5' non-coding sequences) and following (3' non-coding sequences) the coding sequence that are required for expression of the selected gene product. Thus, an expression cassette is typically composed of: 1) a promoter; 2) a coding sequence (i.e., open reading frame [ORF]); and 3) a terminator that usually contains a polyadenylation site. Different expression cassettes can be transformed into different organisms including bacteria, yeast, plants and mammalian cells, as long as the correct regulatory sequences are used for each host. As used herein, an "open reading frame" refers to a sequence of DNA or RNA that encodes the amino acid sequence of a polypeptide. The open reading frame begins at the translation initiation start codon (ATG) and ends at the codon immediately 5' to the translation termination codon (stop codon).

The terms "sequence identity" or "identity" as used herein with respect to nucleic acid or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4.

Various polypeptide amino acid sequences and polynucleotide sequences are disclosed herein as features of certain embodiments of the disclosed invention. Variants of these sequences that are at least about 70-85%, 85-90%, or 90%-95% identical to the sequences disclosed herein may be used in certain embodiments. Alternatively, a variant amino acid sequence or polynucleotide sequence in certain embodiments can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function of the disclosed sequence, or at least about 85%, 86%, 87%, 88%, 89%, 90%, 91%, 92%, 93%, 94%, 95%, 96%, 97%, 98%, or 99% of the function of the disclosed sequence.

As discussed in the Background section (above), previous work has shown that as improvements are made in developing transgenic *Y. lipolytica* strains for enhanced EPA and/or oil production, an inverse correlation generally arises between the total amount of oil produced and the amount of EPA present in the total fatty acids of the oil. Strains that have been engineered to produce higher amounts of oil on a dry cell weight basis generally have lower amounts of EPA as a percentage of the fatty acids in the oil.

The Examples disclosed herein show that certain modifications in *Y. lipolytica* strains maintain or increase total oil content in a manner that does not decrease the EPA content in the total fatty acids of the oil. Interestingly, such modified *Y. lipolytica* strains are capable of producing oil comprising at least about 28 percent EPA measured as a weight percent of the dry cell weight of each strain (i.e., 28 EPA % DCW).

Thus, one aspect of the disclosed invention is drawn to a recombinant microbial cell that produces an oil comprising at least about 28 percent EPA measured as a weight percent of dry cell weight. The recombinant microbial cell can be a cell of a yeast, mold, fungus, oomycete, bacteria, algae, stramenopile, or protist (e.g., euglenoid). In certain embodiments, the recombinant microbial cell is an oleaginous microbial cell, such as an oleaginous yeast cell. Examples of oleaginous yeast include species of the genera *Yarrowia, Candida, Rhodotorula, Rhodosporidium, Cryptococcus, Trichosporon* and *Lipomyces*. More specific examples of oleaginous yeast include *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus* and *R. graminis*, for example. Examples of fungal cells in certain embodiments include species of the genera *Fusarium* (e.g., *Fusarium lateritium*), *Mortierella* (e.g., *Mortierella alpina*) and *Mucor* (e.g., *Mucor rouxii* and *Mucor circinelloides*). The microbial cell can be of the genera *Entomophthora, Pythium* and *Porphyridium* in other embodiments of the disclosed invention.

A *Yarrowia* cell can be the oleaginous yeast cell in certain embodiments of the disclosed invention. Examples of *Yarrowia* cells that can be modified to produce an oil with at least 28% EPA as a percent of dry cell weight include the following wild type *Y. lipolytica* isolates available from the American Type Culture Collection (ATCC, Manassas, Va.): strain designations ATCC #20362, #8862, #8661, #8662, #9773, #15586, #16617, #16618, #18942, #18943, #18944, #18945, #20114, #20177, #20182, #20225, #20226, #20228,

#20327, #20255, #20287, #20297, #20315, #20320, #20324, #20336, #20341, #20346, #20348, #20363, #20364, #20372, #20373, #20383.

The recombinant microbial cell in certain embodiments may be one that has been genetically engineered to produce an increased amount of total lipids and/or fatty acids such as PUFAs. For example, a fatty acid or PUFA biosynthetic pathway, or portion thereof, may be introduced to the organism by inserting coding sequences for certain pathway enzymes, such as fatty acid desaturases and elongases. Examples of PUFA biosynthetic pathways that can be used herein are shown in FIG. 1. One or a combination of the following enzymes may be genetically introduced to the oleaginous yeast cell to provide a PUFA biosynthetic pathway therein: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase, $C_{20/22}$ elongase. One or more of these enzymes may be from a heterologous source. Example PUFA biosynthetic pathways may contain both a delta-9 elongase and delta-8 desaturase (e.g., refer to U.S. Pat. Appl. Publ. No. 2011-0055973, herein incorporated by reference), or both a delta-6 desaturase and delta-6 elongase. Alternatively, the recombinant microbial cell may be modified to have increased total lipids and/or PUFA levels by introducing or deleting genes, other than those encoding desaturases or elongases, that regulate fatty acid biosynthesis.

The PUFAs generated by the PUFA biosynthetic pathway expressed by a recombinant microbial cell of the disclosed invention may include omega-3 and/or omega-6 PUFAs; examples of such PUFAs are linoleic acid (LA), gamma-linolenic acid (GLA), dihomo-gamma-linolenic acid (DGLA), arachidonic acid (ARA), alpha-linolenic acid (ALA), stearidonic acid (STA), eicosatetraenoic acid (ETA), eicosapentaenoic acid (EPA), omega-6 docosapentaenoic acid (DPAn-6), omega-3 docosapentaenoic acid (DPAn-3), eicosadienoic acid (EDA), eicosatrienoic acid (ETrA), docosatetraenoic acid (DTA) and docosahexaenoic acid (DHA). One or more of these PUFAs in the recombinant microbial cell may be produced from a substrate that is endogenously produced by the recombinant microbial cell or exogenously supplied to the recombinant microbial cell.

The recombinant microbial cell of the disclosed invention may be a *Yarrowia* strain containing a PUFA biosynthetic pathway that produces a PUFA in addition to linoleic acid. For example, the *Yarrowia* cell may contain enzymes for producing alpha-linolenic acid, gamma-linolenic acid, and/or eicosadienoic acid, none of which PUFAs are produced in wild type *Yarrowia*. Beyond the fatty acid biosynthetic pathway enzymes normally expressed in *Yarrowia* to generate linoleic acid, a delta-9 elongase, delta-6 desaturase, and/or delta-15 desaturase may be exogenously expressed for production of eicosadienoic acid, gamma-linolenic acid, and/or alpha-linolenic acid, respectively. These three PUFAs can be further modified (desaturation and/or elongation) to produce downstream PUFAs by expressing additional PUFA pathway enzymes.

The recombinant microbial cell used in certain embodiments of the disclosed invention may be one that has been genetically engineered to produce an elevated amount of lipids compared to its wild type form. Examples of such genetically engineered cells are certain *Yarrowia* strains disclosed in U.S. Pat. Appl. Publ. Nos. 2009-0093543, 2010-0317072 and 2012-0052537, which are herein incorporated by reference.

The recombinant microbial cell in certain embodiments of the disclosed invention comprises or produces an oil comprising at least about 28% EPA measured as a weight percent of the dry cell weight of the microbial cell. Alternatively, the recombinant microbial cell comprises or produces an oil comprising at least about 30% EPA measured as a weight percent of the dry cell weight of the microbial cell. Still, in other embodiments of the disclosed invention, the recombinant microbial cell produces an oil comprising at least about 28%, 28.5%, 29%, 29.5%, 30%, 30.5%, 31%, 31.5%, 32%, 32.5%, 33%, 33.5%, 34%, 34.5%, or 35% EPA measured as a weight percent of the dry cell weight of the microbial cell.

An increase in the level of EPA measured as a weight percent of the dry cell weight (EPA % DCW) of the recombinant microbial cell in certain embodiments may be at least about 1%, 2%, 3%, 4%, 5%, 6%, 7%, 8%, 9%, 10%, 11%, 12%, 13%, 14%, 15%, 16%, 17%, or 18% over the EPA % DCW of a control cell. In certain embodiments, this increase in EPA % DCW is coupled with a maintenance or increase in oil content (TFAs % DCW) relative to the oil content of a control cell. A maintenance in oil content in certain embodiments refers to less than about a −3%, −2%, −1%, or 0% change in oil content of the recombinant microbial cell relative to the oil content of a control cell. An increase in oil content in certain embodiments refers to an increase of more than about 3%, 4%, 5%, 6%, 7%, 8%, 9%, or 10% over the oil content of a control cell.

The recombinant microbial cell in certain embodiments of the disclosed invention has an oil content (TFAs % DCW) of at least about 50%, 51%, 52%, 53%, 54%, 55%, 56%, 57%, 58%, 59%, 60%, 61%, 62%, 63%, 64%, or 65% of the dry cell weight of the microbial cell.

The recombinant microbial cell in certain embodiments of the disclosed invention has an EPA content in the total fatty acids of the oil (EPA % TFAs) of at least about 50%, 51%, 52%, 53%, 54%, 55%, 56%, 57%, 58%, 59%, 60%, 61%, 62%, 63%, 64%, or 65% by weight.

The recombinant microbial cell in certain embodiments of the disclosed invention produces oil that is devoid of gamma-linolenic acid (GLA). By devoid, it is meant that GLA is below the threshold of detection in the oil, or alternatively, it is meant that the amount of GLA in the oil is less than 0.1% by weight of the TFAs of the oil.

The recombinant microbial cell in certain embodiments of the disclosed invention has a stearic acid (C18:0) content in the total fatty acids of the oil (18:0% TFAs) that is less than about 2.5%, 2.4%, 2.3%, 2.2%, 2.1%, 1.9%, 1.8%, 1.7%, 1.6%, 1.5%, 1.4%, 1.3%, 1.2%, 1.1%, or 1.0% by weight of the TFAs of the oil.

In certain embodiments of the disclosed invention, the dry cell weight of the recombinant microbial cell grown in a culture is at least about 5.5 grams per liter of the culture. Alternatively, the dry cell weight of the recombinant microbial cell grown in a culture is at least 5.0, 5.2, 5.4, 5.6, 5.8, 6.0, 6.2, 6.4, 6.6, 6.8, 7.0, or 7.2 grams per liter of the culture. The dry cell weight of the microbial cell can be measured in certain embodiments by growing the microbial cell in a culture that is nitrogen-limited for a period of about 120 hours. Such a culture may comprise glucose as the only carbon source or as the predominant carbon source (e.g., other carbon sources less than 5% by weight of the culture). The starting inoculum of the culture for determining dry cell weight of the recombinant microbial cell can be from a culture in which the cells have grown to an $OD_{600}$ of about 0.3. All the cells of a certain volume (e.g., 6 mL) of this $OD_{600}$ ~0.3 culture are then used to inoculate a volume (e.g., 25 mL) of a nitrogen-limited culture medium. This culture is then incubated for a period of about 120 hours, after which the dry cell weight of the culture is determined.

An increase in the dry cell weight of the recombinant microbial cell in certain embodiments may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, or 38% over the dry cell weight of a control cell. The dry cell weights can be measured as above, for example, in making this comparison.

The recombinant microbial cell in certain embodiments of the disclosed invention comprises at least one polynucleotide sequence encoding an acyl-CoA:lysophosphatidylcholine acyltransferase (LPCAT) comprising at least one amino acid mutation in a membrane-bound O-acyltransferase (MBOAT) motif, wherein the LPCAT has LPCAT activity. The polynucleotide encoding the LPCAT is operably linked to at least one regulatory sequence. Thus, certain embodiments are drawn to a recombinant microbial cell that produces an oil comprising at least 28 percent eicosapentaenoic acid (EPA) measured as a weight percent of dry cell weight, wherein the cell comprises at least one polynucleotide sequence encoding an LPCAT comprising at least one amino acid mutation in an MBOAT motif, wherein the LPCAT has LPCAT activity.

The term "acyl-CoA:lysophosphatidylcholine acyltransferase" (LPCAT, EC 2.3.1.23) as used herein refers to an enzyme that catalyzes the following enzymatic reaction: acyl-CoA+1-acyl-sn-glycero-3-phosphocholine=CoA+1,2-diacyl-sn-glycero-3-phosphocholine. LPCAT activity has been described in two structurally distinct protein families, namely the LPAAT protein family (Hishikawa et al., 2008, *Proc. Natl. Acad. Sci. U.S.A.* 105:2830-2835; Intl. App. Publ. No. WO 2004/076617) and the Ale1 protein family (Tamaki et al., Stahl et al., Chen et al., Benghezal et al., Riekhof et al.).

Polynucleotide sequences encoding mutant LPCAT enzymes as disclosed in U.S. Pat. Appl. No. 61/661,623 (incorporated herein by reference) may be used in certain embodiments disclosed herein. The mutant LPCAT is non-naturally occurring.

Membrane-bound O-acyltransferase (MBOAT) motifs are contained in LPLATs such as LPCAT and play a role in the enzymatic activity of these proteins. Examples of MBOAT motifs that can be mutated in certain embodiments of the disclosed invention are disclosed in Shindou et al. (2009, *Biochem. Biophys. Res. Comm.* 383:320-325), U.S. Pat. No. 7,732,155, and U.S. Pat. Appl. Publ. Nos. 2008-0145867 and 2010-0317882, which are incorporated herein by reference. In certain embodiments, either one or two MBOAT motifs of the LPCAT enzyme are mutated. Since the mutant LPCAT has LPCAT activity, the mutation(s) in the MBOAT motif(s) should not significantly reduce the activity of the enzyme.

The mutated LPCAT in certain embodiments of the disclosed invention is a *Yarrowia lipolytica* LPCAT (YILPCAT, SEQ ID NO:40) that has been mutated. The terms "Motif I" and "Motif II" are used herein to refer to two different MBOAT motifs of YILPCAT that can be mutated in certain embodiments. Motif I is represented by the amino acid sequence MVLCMKLSSFGWNVYDG (SEQ ID NO:82), which is located at positions 132-148 of SEQ ID NO:40, whereas Motif II is represented by the amino acid sequence SAFWHGTRPGYYLTF (SEQ ID NO:83), which is located at positions 376-390 of SEQ ID NO:40; both these sequences are contained in wild type YILPCAT.

Motif I and/or Motif II of YILPCAT (SEQ ID NO:40) can be mutated in certain embodiments. Alternatively, Motif I and/or Motif II can be mutated and be comprised within an amino acid sequence that is at least 90%, or 95%, identical to SEQ ID NO:40 and has LPCAT activity. The mutations may be, for example, one or more amino acid substitutions, deletions, and/or insertions in Motif I (SEQ ID NO:40 residues 132, 133, 134, 135, 136, 137, 138, 139, 140, 141, 142, 143, 144, 145, 146, 147, 148) and/or Motif II (SEQ ID NO:40 residues 376, 377, 378, 382, 383, 384, 385, 386, 387, 389, 390). Substitution mutations may be any of those described herein, for example. In alternative embodiments, mutations in Motif II can be to residues 376 to 378 and 382-390 of SEQ ID NO:40. Preferably, the activity of a mutant LPCAT polypeptide encoded by a polynucleotide in certain embodiments is equal to or greater than the activity of wild type YILPCAT (e.g., SEQ ID NO:40). Such activity can be determined by comparing the EPA % TFAs and/or d9e CE (%) in a recombinant microbial cell over-expressing a mutant LPCAT with the EPA % TFAs and/or d9e CE (%) in a control cell.

In the below examples, YILPCAT mutants having equivalent or increased activity were generated by mutating amino acid residues 133, 134, 135, 136, 137, 138, 139, 140, 141, 142, 143, 144, 145, 146, 147 or 148 within Motif I, thereby demonstrating that only the methionine residue at position 132 of SEQ ID NO:40 may be unable to tolerate variation. Similarly, YILPCAT mutants having equivalent or increased activity were generated by mutating amino acid residues 378, 382, 383, 385, 388, 389 or 390 within Motif II, thereby demonstrating that the serine, alanine, proline and both tyrosines of SEQ ID NO:83 may be unable to tolerate variation. The amino acids at residues 379-381 (i.e., WHG) of SEQ ID NO:40 were not subjected to mutation, since the histidine of other LPCATs corresponding to H380 of YILPCAT has been reported to be a likely active site residue (Lee et al., 2008, *Mol. Biol. Cell* 19:1174-1184).

Thus, in certain embodiments of the disclosed invention, the mutant LPCAT comprises an amino acid sequence as set forth in SEQ ID NO:84, wherein SEQ ID NO:84 differs from SEQ ID NO:40 (YILPCAT) by at least one amino acid mutation, wherein:

(i) the amino acid mutation is an amino acid substitution at a residue selected from the group consisting of: residue 133, residue 134, residue 135, residue 136, residue 137, residue 138, residue 139, residue 140, residue 141, residue 142, residue 143, residue 144, residue 145, residue 146, residue 147 and residue 148;

(ii) the amino acid mutation is in an amino acid substitution at a residue selected from the group consisting of: residue 378, residue 382, residue 383, residue 385, residue 388, residue 389 and residue 390; or (iii) there are at least two amino acid mutations, wherein a first amino acid mutation is an amino acid substitution selected from the group set forth in part (i), and the second amino acid mutation is an amino acid substitution selected from the group set forth in part (ii).

A mutant YILPCAT in certain embodiments can comprise an amino acid sequence as set forth in SEQ ID NO:73, wherein SEQ ID NO:73 differs from SEQ ID NO:40 by at least one amino acid mutation selected from the group consisting of: V133C, L134A, L134C, L134G, C135F, C135D, C135I, M136T, M136N, M136G, M136P, M136S, M136V, K137N, K137G, K137H, K137Y, L138G, L138I, L138N, L138A, L138H, L138M, S139G, S139N, S139L, S139W, S140Y, S140I, S140N, S140H, S140P, S140W, F141V, F141A, F141M, F141W, G142I, G142V, G142H, W143H, W143L, N144A, N144K, N144F, N144T, N144V, V145A, V145G, V145E, V145M, V145F, V145W, Y146G, Y146L, Y146M, D147E, D147N, D147Q, D147H, G148V, G148A, G148N, F378Y, T382Y, T382I, T382P, R383A, R383M, L388H, L388T, L388G, L388Y, T389A, T389C, T389S, F390C, F390G, F390N, F390T and F390S.

A mutant YILPCAT in certain embodiments can comprise a mutated MBOAT motif. Examples of mutated MBOAT motifs are mutated variants of motifs I (SEQ ID NO:82) and II (SEQ ID NO:83). In certain embodiments, a YILPCAT comprises a Motif I having one or more of the following amino acid substitutions: V2C, L3A, L3C, L3G, K6H, K6G, K6N, K6Y, L7A, L7N, L7G, L7H, L7I, L7M, D16Q, D16N, D16H, G17A, G17V and G17N; and/or a Motif II having one or more of the following amino acid substitutions: F15N, F15C, F15G and F15T.

The mutated YILPCAT in certain embodiments of the disclosed invention comprises mutations at (i) amino acid position 136 changing methionine to a different amino acid, and (ii) amino acid position 389 changing threonine to a different amino acid. An example of such a mutated YILPCAT is one in which the position 136 methionine is changed to a serine and the position 389 threonine is changed to an alanine (SEQ ID NO:26). Alternatively, the mutated YILPCAT may comprise the amino acid sequence of any one of SEQ ID NOs:75-81, which contain other combinations of mutations in both Motifs I and II. Alternatively, a mutated YILPCAT in certain embodiments may comprise an amino acid sequence that is at least about 90%, 91%, 92%, 93%, 94%, 95%, 96%, 97%, 98%, or 99% identical to any one of SEQ ID NOs:26, 75-81 (or any other mutant LPCAT disclosed herein) and have LPCAT function (above). Alternatively still, a mutated YILPCAT may comprise an amino acid sequence that (i) is at least about 90%, 91%, 92%, 93%, 94%, 95%, 96%, 97%, 98%, or 99% identical to any one of SEQ ID NOs:26, 75-81; (ii) contains both mutations listed in Table 1 for the mutated YILPCAT of (i); and (iii) has LPCAT function (above). For example, a mutated YILPCAT may comprise an amino acid sequence that is at least about 90%, 91%, 92%, 93%, 94%, 95%, 96%, 97%, 98%, or 99% identical to SEQ ID NO:26, where the amino acid sequence has a serine at position 136 and an alanine at position 389.

Further regarding mutations in both Motifs I and II, a mutant YILPCAT in certain embodiments can comprise an amino acid sequence as set forth in SEQ ID NO:74, wherein SEQ ID NO:74 differs from SEQ ID NO:40 by at least one of the pairs of mutations set forth in Table 3 (e.g., an L134A mutation in Motif I may be combined with either a T382I mutation, L388G mutation, F390G mutation or F390T mutation in Motif II, thereby generating mutants L134A_T382I, L134A_L388G, L134A_F390G and L134A_F390T, respectively).

TABLE 3

YILPCAT Double Mutations Demonstrating Equivalent or Improved EPA % TFAs and/or Equivalent or Improved % Delta-9 Conversion

| Amino Acid Mutation in Motif I | Amino Acid Mutation in Motif II |
|---|---|
| L134A | T382I[b], L388G, F390G[a], F390T |
| L134G | L388G[a], F390G[a], F390T[a] |
| M136S | F378Y, T382I, T382P, T382Y, R383M, P384A, L388Y, T389A, T389C, T389S |
| M136V | T382P, T382Y, P384A, L388Y, T389A, T389C, T389S |
| K137H | T382I[a], P384G, L388G[b], L388T, F390G[a], F390S, F390T |
| K137N | F378Y, T382P, R383M, P384G, L388G, L388T, T389A, T389C[b], T389S, F390G[b], F390S, F390T |
| S140H | T382I[b], P384G, L388G[b], L388T, F390G, F390S |
| S140W | T382I, T382P, T382Y, R383M, P384A, L388Y, T389A, T389C, T389S[a] |
| F141M | F378Y, T382P[b], T382Y, R383M, P384A, T389A[a], T389C |
| F141W | F378Y, T382I[b], T382P, T382Y, R383M, P384A, L388Y[b], T389A, T389C, T389S |
| N144A | T382I[a], P384G, L388G, L388T, F390G, F390S, F390T |
| N144T | F378Y, T382P, T382Y, R383M, P384A, L388Y, T389A, T389C, T389S |
| V145M | F378Y[b], T382Y[b], T382I, R383M, T389A, T389C |
| V145W | F378Y[b], T382I, T389A[a], T389S[a] |
| D147H | T382I[b], L388G, L388T, F390S, F390T[a] |
| D147Q | T382I, L388G[a], L388T[a], F390S |
| G148A | F378Y, T382I, T382Y, R383M, P384A[b], P384G, L388G, L388Y, T389A, T389C, F390S, F390T |
| G148N | T382I, P384G[a], L388T, F390G, F390S |

Notes:
Pairs of mutations comprising a first mutation in Motif I and a second mutation in Motif II lacking a superscript (a or b) resulted in equivalent or improved EPA % TFAs and equivalent or improved % Conv.
[a]Indicates a pair of mutations comprising a first mutation in Motif I and a second mutation in Motif II that resulted in equivalent or improved EPA % TFAs (but not equivalent or improved % Conv.).
[b]Indicates a pair of mutations comprising a first mutation in Motif I and a second mutation in Motif II that resulted in equivalent or improved % Conv. (but not equivalent or improved EPA % TFAs).

Although certain combinations of LPCAT amino acid mutations are disclosed herein, one of skill in the art would readily recognize that other combinations of the Motif I and Motif II mutations disclosed herein may be combined as well. Accordingly, one or more of the disclosed Motif I mutations may be used in combination with one or more of the disclosed Motif II mutations in preparing a polynucleotide encoding a mutant LPCAT polypeptide.

In certain embodiments of the disclosed invention, the recombinant microbial cell comprising a polynucleotide sequence encoding an active LPCAT enzyme with at least one amino acid mutation in an MBOAT motif also comprises:

(a) an amount of at least one long-chain polyunsaturated fatty acid measured as a weight percent of total fatty acids that is at least the same as or greater than the amount produced by a control cell, and/or (b) a $C_{18}$ to $C_{20}$ elongation conversion efficiency (e.g., delta-9 elongase conversion efficiency or delta-6 elongase conversion efficiency) that is at least the same as or greater than the conversion efficiency of a control cell.

An increase in the amount of the at least one long-chain PUFA (e.g., EPA) measured as a weight percent of total fatty acids of the recombinant cell over-expressing a mutant LPCAT (containing a mutation in Motif I and/or Motif II) may be at least about 1%, 2%, 3%, 4%, 5%, 6%, 7%, 8%, 9%, 10%, 11%, 12%, 13%, 14%, 15%, 16%, 17%, 18%, 19%, or 20% over the amount of the at least one long-chain PUFA measured as a weight percent of total fatty acids of a control cell.

An increase in the $C_{18}$ to $C_{20}$ elongation conversion efficiency, delta-9 elongase conversion efficiency, and/or delta-6 elongase conversion efficiency of the recombinant cell over-expressing a mutant LPCAT (containing a mutation in Motif I and/or Motif II) may be at least about 1%, 2%, 3%, 4%, 5%, 6%, 7%, 8%, 9%, 10%, 11%, 12%, 13%, 14%, or 15% over the $C_{18}$ to $C_{20}$ elongation conversion efficiency, delta-9 elongase conversion efficiency, and/or delta-6 elongase conversion efficiency, respectively, of a control cell.

The control cell in certain embodiments may be a wild type or recombinant cell that corresponds to the recombinant cell, but that does not comprise, or does not over-express, a polynucleotide encoding an active LPCAT enzyme comprising a mutated MBOAT motif. For example, the control cell does not over-express a mutant LPCAT by virtue of not comprising recombinant polynucleotide sequences encoding mutant LPCAT. Also for example, the control cell does not over-express mutant LPCAT by virtue of comprising, but not expressing, a polynucleotide sequence encoding mutant LPCAT. The control cell may be the recombinant cell as it existed before it was modified to over-express a mutant LPCAT polypeptide (i.e., a parent cell), or may be a recombinant cell that has been modified to contain a recombinant polynucleotide encoding mutant LPCAT, but does not over-express the mutant LPCAT polypeptide (e.g., a cell prepared in parallel with the recombinant cell that over-expresses a mutant LPCAT).

The recombinant microbial cell in certain embodiments of the disclosed invention comprises a down-regulation of an endogenous polynucleotide sequence encoding Sou2 sorbitol utilization protein. In other embodiments, the recombinant microbial cell comprises (i) a down-regulation of an endogenous polynucleotide sequence encoding Sou2 sorbitol utilization protein, and (ii) a PUFA biosynthetic pathway. The down-regulation of the endogenous polynucleotide sequence encoding the Sou2 sorbitol utilization protein in certain embodiments increases the lipid content of the recombinant microbial cell and/or decreases the total amount of sugar alcohols produced by the cell.

The Sou2 sorbitol utilization protein is encoded by the SOU2 gene. The terms "SOU2", "SOU2 gene" and "endogenous polynucleotide sequence encoding Sou2 sorbitol utilization protein" are used interchangeably herein.

The Sou2 sorbitol utilization protein (Sou2p) of *Y. lipolytica* (SEQ ID NO:10) has about 66% amino acid sequence identity (according to a BLAST alignment) with *Candida albicans* Sou2 sorbitol utilization protein (SEQ ID NO:30). *C. albicans* Sou2 sorbitol utilization protein was described by Janbon et al. (1998, *Proc. Natl. Acad. Sci. U.S.A.* 95:5150-5155) as being similar to Sou1 sorbitol utilization protein (Sou1p), but as not being required for sorbose utilization. Sou1 sorbitol utilization protein has been described by Janbon et al. and Greenberg et al. (2005, *Yeast* 22:957-969) to be a sorbose reductase required for L-sorbose utilization. The amino acid sequences of *C. albicans* Sou1 and Sou2 proteins have about 72% identity with each other. Given this degree of similarity, it was proposed by Greenberg et al. that Sou2 protein "is probably an oxidoreductase which utilizes NADP(H) as a co-factor and overlaps with Sou1p in substrate specificity.

Examples of microbial cell Sou2 sorbitol utilization protein sequences that can be down-regulated in certain embodiments include the sequences disclosed in the following GenBank Accession Nos.: P87218 (*Candida albicans*), EAZ63262 (*Scheffersomyces stipitis*), CAX42453 (*Candida dubliniensis*), EHK97934 (*Glarea lozoyensis*), ZP_08499267 (*Enterobacter hormaechei*), CCG21852 (*Candida orthopsilosis*), YP_887907 (*Mycobacterium smegmatis*), EJT74900 (*Gaeumannomyces graminis*), EGZ74878 (*Neurospora tetrasperma*), EFY96110 (*Metarhizium anisopliae*), EGX88960 (*Cordyceps militaris*), EFY85020 (*Metarhizium acridum*), EGY16179 (*Verticillium dahliae*), EEH42615 (*Paracoccidioides brasiliensis*), EHA51546 (*Magnaporthe oryzae*), EEP78930 (*Uncinocarpus reesii*), XP_961192 (*Neurospora crassa*), XP_001523181 (*Lodderomyces elongisporus*), CAK39371 (*Aspergillus niger*), XP_002556984 (*Penicillium chrysogenum*), CAG81202 (*Yarrowia lipolytica*), CAG84844 (*Debaryomyces hansenii*), CCE43891 (*Candida parapsilosis*) and ZP_02917979 (*Bifidobacterium dentium*).

In certain embodiments of the disclosed invention, the down-regulation of the endogenous polynucleotide sequence encoding Sou2 sorbitol utilization protein is due to a mutation of the polynucleotide sequence. This mutation is a substitution, deletion or an insertion in certain embodiments. A deletion in certain embodiments removes (i) one or more nucleotides from an open reading frame encoding the Sou2 sorbitol utilization protein, and/or (ii) one or more nucleotides of a non-protein-coding sequence located within 500 base pairs of the 5'-end of the open reading frame encoding the Sou2 sorbitol utilization protein.

Examples of a deletion in an SOU2 open reading frame are those removing one or two nucleotides, thereby resulting in a frame-shift mutation; the amino acid sequence encoded downstream such a deletion would be different from the endogenous amino acid sequence. One of ordinary skill in the art would understand that other deletions can be made to create a frame-shift mutation (e.g., any deletion removing a number of base pairs that is not divisible by three). Other deletion examples include those removing the entire SOU2 open reading frame or a portion thereof (e.g., a "knock-out" of SOU2). Where a portion of the SOU2 open reading frame is deleted, or removed by virtue of introducing a frame-shift, down-regulation may occur if the deleted amino acids are necessary for proper Sou2 protein function and/or localization. Alternatively, a deletion in the SOU2 open reading frame may affect proper transcription and/or translation of SOU2. In certain embodiments, the deletion in the SOU2 open reading frame is at least 50, 100, 150, 200, 250, 300, 350, 400, 450, 500, 550, 600, 650, 700, 750, or 800 base pairs. The deletion may be made beginning at the first codon or any downstream codon (e.g., a 250-bp deletion could begin at the tenth codon).

Deletions in certain embodiments of the disclosed invention remove portions of the 5'- and/or 3'-regulatory, non-translated sequences of SOU2. Certain deletions may remove sequences from both of these regulatory sequences; such deletions in most instances would remove the entire SOU2 open reading frame. Other deletions may affect one SOU2 regulatory region and the open reading frame (e.g., deletion of certain 5'-regulatory sequence and 5'-end of the open reading frame). Deletions affecting a 5'-regulatory sequence may down-regulate SOU2 by disrupting proper promoter activity, thereby reducing or eliminating SOU2 transcription. Deletions affecting a 3'-regulatory sequence may down-regulate SOU2 by disrupting proper transcription termination and/or transcript stability.

A deletion in certain embodiments removes one or more nucleotides of a non-protein-coding sequence located within 500 base pairs of the 5'-end of the SOU2 open reading frame. Such a deletion removes sequence from the 5'-non-translated region of the SOU2 transcribed sequence and/or the SOU2 promoter, and may down-regulate SOU2 by reducing transcription and/or translation. The deletion in certain embodiments removes base pairs −10 to −1, −20 to −1, −30 to −1, −40 to −1, −50 to −1, −60 to −1, −70 to −1, −80 to −1, −90 to −1, −100 to −1, −150 to −1, −200 to −1, −250 to −1, −300 to −1, −350 to −1, −400 to −1, −450 to −1, or −500 to −1 of the non-protein-coding sequence upstream the SOU2 open reading frame, where the −1 position is the nucleotide immediately 5'-adjacent the SOU2 start codon (ATG). A deletion in other embodiments removes about 10, 20, 30, 40, 50, 60, 70, 80, 90, 100, 150, 200, 250, 300, 350, 400, or 450 consecutive base pairs from any one of these aforementioned regions (e.g., 300 consecutive base pairs deleted within the −500 to −1 region).

In other embodiments a deletion removes one or more regulatory elements in the SOU2 promoter such as a TATA box consensus sequence or a TATA-like sequence (Basehoar et al., 2004, Cell 116:699-709, which is incorporated by reference). This type of promoter consensus sequence is usually located within 100 base pairs of the non-protein-coding sequence upstream of the SOU2 open reading frame. Where such a deletion is made to the SOU2 gene promoter in a *Yarrowia* cell, for example, the TATA box consensus could be removed by deleting one or more base pairs of the −79 to −72 region with respect to the SOU2 start codon (FIG. 5).

In those embodiments in which the recombinant microbial cell is a *Yarrowia* cell, the down-regulated endogenous polynucleotide sequence may encode a Sou2 sorbitol utilization protein that comprises an amino acid sequence that is at least 95% identical to SEQ ID NO:10. In alternative embodiments, the Sou2 sorbitol utilization protein comprises an amino acid sequence that is at least 96%, 97%, 98%, or 99% identical to SEQ ID NO:10, or the amino acid sequence comprises SEQ ID NO:10. In other embodiments, the down-regulated endogenous polynucleotide sequence encoding a Sou2 sorbitol utilization protein comprises a nucleotide sequence that is at least 95% identical to SEQ ID NO:9. The polynucleotide sequence may alternatively comprise a nucleotide sequence that is at least 96%, 97%, 98%, or 99% identical to SEQ ID NO:9, or the polynucleotide sequence comprises SEQ ID NO:9.

*Y. lipolytica* in the below Examples was genetically modified to have a deletion that removed the first 287 base pairs of an endogenous SOU2 open reading frame, as well as 235 base pairs of non-protein coding sequence immediately upstream the SOU2 start codon (i.e., positions −235 to −1 were deleted). SEQ ID NO:8 (FIG. 5) is an example of genomic DNA sequence containing the *Y. lipolytica* SOU2 gene locus. This sequence contains 1000 base pairs of non-protein coding sequence upstream the SOU2 start codon, 771 base pairs of SOU2 open reading frame (corresponding to SEQ ID NO:9), and 300 base pairs of non-protein coding sequence downstream of the SOU2 stop codon.

Thus, any of the deletions disclosed herein that can be used to down-regulate SOU2 in *Yarrowia* may be characterized with respect to nucleotide positions in SEQ ID NOs:8 or 9, or a polynucleotide sequence having at least 95%, 96%, 97%, 98%, or 99% identity thereto (accounting for natural sequence variability that might exist across different *Yarrowia* strains). Such deletions may similarly be characterized with respect to amino acid positions in SEQ ID NO:10, or an amino acid sequence having at least 95%, 96%, 97%, 98%, or 99% identity thereto. For example, a deletion can remove at least nucleotide positions 1-768 (an entire *Yarrowia* SOU2 open reading frame removed) or 1-287 of SEQ ID NO:9 (i.e., base pairs 1-287 of a *Yarrowia* SOU2 open reading frame), or alternatively a deletion can remove at least nucleotide positions 1001-1768 (an entire *Yarrowia* SOU2 open reading frame removed) or 1001-1287 of SEQ ID NO:8 (i.e., base pairs 1-287 of a *Yarrowia* SOU2 open reading frame). As another example, a deletion can remove at least nucleotide positions 501-1000 of SEQ ID NO:8 (i.e., −500 to −1 with respect to a *Yarrowia* SOU2 start codon) or 766-1000 (i.e., −235 to −1 with respect to a *Yarrowia SOU*2 start codon). As yet another example, a deletion can remove at least nucleotide positions 766-1287 of SEQ ID NO:8 (i.e., −235 to +287, corresponding to the deletion noted in FIG. 5).

An insertion in certain embodiments occurs within (i) an open reading frame encoding the Sou2 sorbitol utilization protein, or (ii) a non-protein-coding sequence located within 500 base pairs of the 5'-end of the open reading frame. As used herein, the terms "insertion" and "integration" are used interchangeably herein to refer to one or more consecutive nucleotides inserted into a genetic sequence. If an insertion is in an open reading frame, it will be disrupted during transcription and/or translation. This may result in an altered sequence of amino acids, extra amino acids in a chain, or premature termination. The newly synthesized protein produced from such a mutated open reading frame may be abnormally short, abnormally long, and/or contain the wrong amino acids, and will most likely not be functional.

In certain embodiments, an insertion in an SOU2 open reading frame adds one or two nucleotides, thereby resulting in a frame-shift mutation; the amino acid sequence encoded downstream such an insertion would be different from the endogenous amino acid sequence. One of ordinary skill in the art would understand that other insertions can be made to create a frame-shift mutation (e.g., any insertion adding a number of base pairs that is not divisible by three). Down-regulation of SOU2 may occur if the amino acids affected by the insertion are necessary for proper Sou2 protein function and/or localization. Alternatively, an insertion in the SOU2 open reading frame may affect proper transcription and/or translation of SOU2. In certain embodiments, the insertion in the SOU2 open reading frame can be of any length that results in down-regulation of the SOU2 gene. Alternatively, the length of the insertion can be at least 50, 100, 150, 200, 250, 300, 350, 400, 450, 500, 550, 600, 650, 700, 750, 800, 850, 900, 950, or 1000 base pairs. The insertion may be made immediately after the first codon or any downstream codon (e.g., a 250-bp insertion immediately after the tenth codon).

An insertion in certain embodiments adds one or more nucleotides into a non-protein-coding sequence located within 500 base pairs of the 5'-end of the SOU2 open reading frame. Such an insertion can affect the 5'-non-translated region of the SOU2 transcribed sequence and/or the SOU2 promoter, and may down-regulate SOU2 by reducing transcription and/or translation. The insertion in certain embodiments is within the −10 to −1, −20 to −1, −30 to −1, −40 to −1, −50 to −1, −60 to −1, −70 to −1, −80 to −1, −90 to −1, −100 to −1, −150 to −1, −200 to −1, −250 to −1, −300 to −1, −350 to −1, −400 to −1, −450 to −1, or −500 to −1 region of the non-protein-coding sequence upstream the SOU2 open reading frame, where the −1 position is the nucleotide immediately 5'-adjacent the SOU2 start codon (ATG). The insertion in any of these aforementioned regions can be at least 50, 100, 150, 200, 250, 300, 350, 400, 450, 500, 550, 600, 650, 700, 750, 800, 850, 900, 950, or 1000 base pairs, for example (e.g., 300-bp insertion within the −100 to −1 region). Alternatively, the insertion can be of any length that results in down-regulation of the SOU2 gene.

*Y. lipolytica* in the below Examples was genetically modified to have an insertion between positions −71 to −70 with respect to the ATG start codon of an SOU2 gene. This particular insertion, as well as any of the insertions disclosed herein that can be used to down-regulate SOU2 in *Yarrowia*, may be characterized with respect to nucleotide positions in SEQ ID NOs:8 or 9, or a polynucleotide sequence having at least 95%, 96%, 97%, 98%, or 99% identity thereto (accounting for natural sequence variability that might exist across different *Yarrowia* strains). For example, an insertion between positions −71 to −70 with respect to the ATG start codon of a *Yarrowia* SOU2 gene can be described as an insertion between nucleotide positions 930 and 931 of SEQ ID NO:8. As another example, an insertion between base pairs 10 and 11 of a *Yarrowia* SOU2 open reading frame can be described as an insertion between nucleotide positions 1010 and 1011 of SEQ ID NO:8, or alternatively as an insertion between nucleotide positions 10 and 11 of SEQ ID NO:9.

Other types of mutations aside from the aforementioned deletions and insertions can be used to down-regulate the endogenous polynucleotide sequence encoding Sou2 sorbitol utilization protein in alternative embodiments of the disclosed invention. For example, one or more point mutations, which exchange a single nucleotide for another (i.e., a nucleotide substitution), may be used. The point mutation may be a transition point mutation (i.e., a purine in place of another purine, or a pyrimidine in place of another pyrimidine) or transversion point mutation (i.e., a purine in place of a pyrimidine, or a pyrimidine in place of a purine). An example transition mutation is where an adenine is in place of a guanine. An example transversion mutation is where an adenine is in place of a cytosine. Any of these mutations may result, for example, in an amino acid substitution that down-regulates the function of the Sou2 protein.

In certain embodiments, the mutation may be a nonsense mutation within the SOU2 open reading frame; such a mutation changes an amino acid codon to a nonsense codon. Depending on the position of the nonsense mutation in the SOU2 open reading frame, the encoded Sou2 sorbitol utilization protein may be truncated at its carboxy terminus by one more amino acids. Such a truncation may remove at least 1, 5, 25, 50, 75, 100, 125, 150, 175, 200, 225, 250, or 275 amino acids from the carboxy terminus, for example.

The mutation in certain embodiments may be a missense mutation within the SOU2 open reading frame, where a codon is mutated to encode a different amino acid. Such a mutation may down-regulate SOU2 by virtue of reducing or eliminating the wild type function of the Sou2 sorbitol utilization protein. For example, the proper localization and/or enzymatic activity of the Sou2 protein may be impaired.

A mutation in a codon of the SOU2 open reading frame that does not change the amino acid encoded by the codon (i.e., a silent mutation) is not a mutation as described herein that down-regulates SOU2. Nor is a mutation as described herein one that changes the amino acid encoded by a codon to a related amino acid that does not alter the wild type function of the Sou2 protein. Related amino acids in certain embodiments have side groups that share structure and/or charge, and can be grouped as follows: aliphatic (glycine, alanine, valine, leucine, isoleucine), aromatic (phenylalanine, tyrosine, tryptophan), hydroxyl group-containing (serine, threonine), sulfur group-containing (cysteine, methionine), carboxylic acid group-containing (aspartate, glutamate), amide group-containing (asparagine, glutamine), and amino group-containing (histidine, lysine, arginine).

It would be understood by one of ordinary skill in the art that any of the disclosed mutations to the endogenous SOU2 sequence can be determined to constitute a mutation by referring to the endogenous SOU2 sequence in a microbial cell that has not be modified to mutate the endogenous SOU2 sequence. For example, the SOU2 sequence in a modified *Y. lipolytica* strain can be compared to the endogenous SOU2 sequence of the counterpart wild type *Y. lipolytica* strain from which the modified strain was derived.

Any of the above deletions and insertions, as well as any other mutation described herein, may be introduced to an endogenous SOU2 sequence of a recombinant microbial cell using any means known in the art. Genetic targeting techniques may be used, for example, such as those described for modifying yeast (Longtine et al., *Yeast* 14:953-961), fungi (Meyer et al., *J. Biotechnol.* 128:770-775), algae (Zorin et al., *Gene,* 432:91-96), and bacteria (Zhong et al., *Nucleic Acids Res.* 31:1656-1664). Alternatively, random mutagenesis techniques may be used.

The down-regulation of an endogenous polynucleotide sequence encoding Sou2 sorbitol utilization protein in certain embodiments is a reduction in the transcription and/or translation of the endogenous polynucleotide sequence by at least about 20%, 30%, 40%, 50%, 60%, 70%, 80%, 90%, 95%, or 100% relative to the transcription and/or translation of a control cell. In other embodiments, the down-regulation of an endogenous polynucleotide sequence encoding Sou2 sorbitol utilization protein is reflected by a reduction of at least about 20%, 30%, 40%, 50%, 60%, 70%, 80%, 90%, 95%, or 100% in the function (e.g., protein localization and/or enzymatic activity) of the encoded Sou2 sorbitol utilization protein relative to the function of the Sou2 protein in a control cell.

The down-regulation of the endogenous polynucleotide sequence encoding the Sou2 sorbitol utilization protein in certain embodiments of the disclosed invention increases the lipid content of the recombinant microbial cell. This increase in lipid content (TFAs % DCW) can be at least about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35% over the lipid content of a control cell.

The down-regulation of the endogenous polynucleotide sequence encoding the Sou2 sorbitol utilization protein in certain embodiments of the disclosed invention decreases the total amount of sugar alcohols produced by the microbial cell. The sugar alcohols may comprise arabitol and/or mannitol, for example. The decrease of the total amount of sugar alcohols can be at least about 20%, 30%, 40%, 50%, 60%, or 70% below the total amount of sugar alcohols in a control cell. The decrease of arabitol and/or mannitol can be at least about 20%, 30%, 40%, 50%, 60%, 70%, 80%, 90%, or 100% below the amount of arabitol and/or mannitol in a control cell. A 100% decrease in certain embodiments represents that arabitol and/or mannitol are below the threshold of detection.

The control cell in certain embodiments has an endogenous polynucleotide sequence encoding Sou2 sorbitol utilization protein that does not have any of the mutations disclosed herein. Such non-mutation in the control cell can be determined by comparing its polynucleotide sequence encoding Sou2 sorbitol utilization protein with that of a counterpart wild type cell. For example, where the control cell is a particular recombinant *Yarrowia* cell that has not been modified to have a mutation in an endogenous polynucleotide sequence encoding Sou2 sorbitol utilization protein, this polynucleotide sequence in the control cell should be the same or very similar to (e.g., containing silent a mutation) the polynucleotide sequence in the counterpart wild type *Yarrowia* cell from which the control was derived. Other aspects of a control cell that can be used in certain embodiments are described above.

A recombinant microbial cell that does not comprise an endogenous polynucleotide sequence encoding Sou2 sorbitol utilization protein should not be considered to comprise a down-regulation of this polynucleotide if the wild type counterpart cell from which the recombinant microbial cell was derived likewise does not comprise an endogenous polynucleotide sequence encoding Sou2 sorbitol utilization protein.

The recombinant microbial cell in certain embodiments of the disclosed invention comprises (a) at least one heterologous polynucleotide sequence encoding phospholipid:diacylglycerol acyltransferase (PDAT), (b) at least one heterologous polynucleotide sequence encoding delta-12 desaturase, and (c) at least one polynucleotide sequence encoding a dihomo-gamma-linolenic acid (DGLA) synthase multizyme. Each of these polynucleotide sequences (a-c) is operably linked to at least one regulatory sequence.

The term "phospholipid:diacylglycerol acyltransferase" (PDAT; EC 2.3.1.158) as used herein refers to an enzyme that is capable of transferring an acyl group from the sn-2 position of phospholipids such as phosphatidylcholine (PC) and phosphatidylethanolamine (PE) to the sn-3 position of 1,2-diacylglycerol (DAG). This reaction results in lysophospholipids such as lysophosphatidylcholine (LPC) and lysophosphatidylethanolamine (LPE). Although both PDAT and acyl-CoA:diacylglycerol acyltransferases (DGAT; E.C. 2.3.1.20) are involved in the terminal step of TAG biosynthesis, only PDAT may synthesize TAGs via an acyl-CoA-independent mechanism.

Dahlqvist et al. (2000, *Proc. Natl. Acad. Sci. U.S.A.* 97:6487-6492) and Oelkers et al. (2000, *J. Biol. Chem.* 275:15609-15612) were the first to appreciate that TAG synthesis can occur in the absence of acyl-CoA, via the acyl-CoA-independent PDAT enzyme (structurally related to the lecithin:cholesterol acyltransferase family of proteins). Following this work, U.S. Pat. No. 7,267,976 (incorporated herein by reference) described the cloning, overexpression and knockout of the *Y. lipolytica* ATCC #90812 gene encoding PDAT (SEQ ID NO:31 herein), which was determined to share 47.1% amino acid sequence identity with ScPDAT. A single-amino acid insertion variant (SEQ ID NO:15 herein) of this YIPDAT was disclosed in U.S. Pat. Appl. Publ. No. 2012-0052537.

The heterologous polynucleotide sequence encoding PDAT in certain embodiments of the disclosed invention may encode an amino acid sequence comprising a *Yarrowia* PDAT. Such a PDAT may comprise the amino acid sequence of SEQ ID NO:15 or 31, for example. Alternatively, a PDAT in certain embodiments may comprise an amino acid sequence that is at least about 90%, 91%, 92%, 93%, 94%, 95%, 96%, 97%, 98%, or 99% identical to SEQ ID NO:15 or 31 and have PDAT function (above).

The term "delta-12 desaturase" (D12; EC 1.14.19.6) as used herein refers to an enzyme that is capable of introducing a carbon-carbon double bond between the 12th and 13th carbons as numbered from the carboxyl end of a fatty acid.

The heterologous polynucleotide sequence encoding delta-12 desaturase in certain embodiments of the disclosed invention may encode an amino acid sequence comprising a delta-12 desaturase as disclosed in U.S. Pat. No. 7,214,491 and U.S. Pat. Appl. Publ. No. 2007-0254299, both of which are incorporated herein by reference. Alternatively, the amino acid sequence may comprise a delta-12 desaturase from *Fusarium moniliforme* (e.g., SEQ ID NO:13), *Y. lipolytica* (e.g., SEQ ID NO:32), *Aspergillus nidulans, Magnaporthe grisea, Neurospora crassa, Fusarium graminearium, Aspergillus fumigatus* or *Aspergillus flavus*, all of which are disclosed in U.S. Pat. No. 7,504,259 (incorporated herein by reference). Alternatively, a delta-12 desaturase in certain embodiments may comprise an amino acid sequence that is at least about 90%, 91%, 92%, 93%, 94%, 95%, 96%, 97%, 98%, or 99% identical to SEQ ID NO:13 or 32 and have delta-12 desaturase function (above).

The terms "multizyme" and "fusion protein" are used interchangeably in embodiments herein and refer to a single polypeptide having at least two independent and separable enzymatic activities, wherein the first enzymatic activity is preferably linked to the second enzymatic activity (U.S. Pat. Appl. Publ. No. 2008-0254191, incorporated herein by reference). The multizyme in certain embodiments comprises two independent and separate enzymes. The "linker" between the two independent and separable enzymatic activities may be comprised of a single peptide bond, although the linker may also be comprised of one amino acid residue, such as a proline, or a polypeptide comprising at least one proline. Examples of linkers that can be used in certain embodiments are disclosed as SEQ ID NOs:4-10 in U.S. Pat. Appl. Publ. No. 2008-0254191.

A "DGLA synthase multizyme" in certain embodiments of the disclosed invention comprises a delta-9 elongase linked to a delta-8 desaturase. The DGLA synthase multizyme can convert LA to DGLA by virtue of containing both delta-9 elongase activity (converts LA to EDA) and delta-8 desaturase activity (converts EDA to DGLA). The DGLA synthase multizyme can also convert ALA to ETA, since its delta-9 elongase activity can convert ALA to ETrA and its delta-8 desaturase activity can convert ETrA to ETA.

Examples of delta-9 elongase amino acid sequences that can be comprised within the DGLA synthase multizyme are disclosed as SEQ ID NOs:254 (*Euglena anabaena* D9e, EaD9e), 319 (*Euglena gracilis* D9e, EgD9e) and 359 (*Eutreptiella* sp. CCMP389 D9e, E389D9e) in U.S. Pat. Appl. Publ. No. 2008-0254191. Examples of delta-8 desaturase amino acid sequences that can be comprised within the DGLA synthase multizyme are disclosed as SEQ ID NOs: 328 (mutant *Euglena gracilis* D8, EgD8M), 430 (*Euglena anabaena* D8, EaD8) and 514 (*Tetruetreptia pornquetensis* CCMP1491 D8, TpomD8) in U.S. Pat. Appl. Publ. No. 2008-0254191. Each of these delta-9 elongases and delta-8 desaturases, or a variant thereof having at least about 90%, 91%, 92%, 93%, 94%, 95%, 96%, 97%, 98%, or 99% amino acid identity thereto and having either delta-9 elongase or delta-8 desaturase function, may be comprised in the DGLA synthase multizyme, for example.

In certain embodiments, the DGLA synthase multizyme comprises E389D9eS/EgD8M (SEQ ID NO:17 herein). This multizyme comprises E389D9e (SEQ ID NO:33 herein) linked to most of the amino acid sequence of EgD8M (SEQ ID NO:19 herein). Specifically, E389D9eS/EgD8M comprises, in the direction of the amino terminus to the carboxy terminus, SEQ ID NO:33—linker GAGPARPAGLPPATYYDSLAVMGS (SEQ ID NO:34)—positions 2-422 of SEQ ID NO:19. The DGLA synthase multizyme in other embodiments may be any of those disclosed in U.S. Pat. Appl. Publ. No. 2008-0254191 (e.g., EgD9eS/EgD8M, SEQ ID NO:35 herein; EgD9eS/EaD8S; EaD9eS/EgD8M; EaD9eS/EaD8S, SEQ ID NO:36 herein; EgD9e/TpomD8; EaD9e/TpomD8). Alternatively, the DGLA synthase multizyme in certain embodiments may comprise an amino acid sequence that is at least about 90%, 91%, 92%, 93%, 94%, 95%, 96%, 97%, 98%, or 99% identical to SEQ ID NO:17, 35, or 36 (or any of the other above DGLA synthases) and have DGLA synthase function (above). The delta-9 elongase is located at the amino-terminus (N-terminus) of the multizyme polypeptide in certain embodiments.

The recombinant microbial cell in certain embodiments of the disclosed invention comprises (a) at least one heterologous polynucleotide sequence encoding delta-8 desaturase, (b) at least one heterologous polynucleotide sequence encoding malonyl-CoA synthetase (MCS), and (c) at least one heterologous polynucleotide sequence encoding acyl-CoA:lysophosphatidic acid acyltransferase (LPAAT). Each of these polynucleotide sequences (a-c) is operably linked to at least one regulatory sequence.

The term "delta-8 desaturase" (D8; EC 1.14.19.4) as used herein refers to an enzyme that is capable of introducing a carbon-carbon double bond between the 8th and 9th carbons as numbered from the carboxyl end of a fatty acid.

The heterologous polynucleotide sequence encoding delta-8 desaturase in certain embodiments of the disclosed invention may encode an amino acid sequence comprising a delta-8 desaturase sequence as disclosed in U.S. Pat. Appl. Publ. No. 2005-0273885 or U.S. Pat. Nos. 7,550,651; 7,256,033; 7,790,156; 7,943,823; 7,863,502; or 6,825,017, all of which are incorporated herein by reference. Alternatively, the amino acid sequence may comprise a delta-8 desaturase from *Euglena gracilis* (e.g., SEQ ID NO:19) or *Euglena anabaena* (e.g., SEQ ID NO:37), for example. Alternatively, a delta-8 desaturase in certain embodiments may comprise an amino acid sequence that is at least about 90%, 91%, 92%, 93%, 94%, 95%, 96%, 97%, 98%, or 99% identical to SEQ ID NO:19 or 37 and have delta-8 desaturase function (above).

The term "malonyl-CoA synthetase" (MCS, EC 6.2.1.14) as used herein refers to an enzyme that catalyzes the following enzymatic reaction: malonate+ATP+CoA malonyl-CoA+AMP+pyrophosphate. The enzyme was first purified from malonate-grown *Pseudomonas fluorescens* (1985, Kim and Bang, *J. Biol. Chem.* 260:5098-5104), although various *Rhizobia* homologs have since been isolated from bacteroides within legume nodules (e.g., Kim and Chae, 1991, *Biochem. J.* 273:511-516; Kim and Kang, 1994 *Biochem. J.* 297:327-333). By converting malonate into malonyl-CoA, MCS can provide malonyl-CoA substrate for use in fatty acid synthesis. Thus, in addition to reducing the byproduction of malonates in a cell, MCS expression also helps to avoid carbon and energy waste within the cell, reduce the amount of base required to maintain an optimal pH range during the fermentation process, and reduce the amount of byproduct organic acids that require neutralization within the fermentation waste steam.

The heterologous polynucleotide sequence encoding MCS in certain embodiments of the disclosed invention may encode an amino acid sequence comprising an MCS sequence as disclosed in U.S. Pat. Appl. Publ. No. 2010-0159558, which is incorporated herein by reference. For example, the amino acid sequence may comprise an MCS from *Rhizobium leguminosarum* (e.g., SEQ ID NO:21). Alternatively, an MCS in certain embodiments may comprise an amino acid sequence that is at least about 90%, 91%, 92%, 93%, 94%, 95%, 96%, 97%, 98%, or 99% identical to SEQ ID NO:21 and have MCS function (above).

The term "acyl-CoA:lysophospholipid acyltransferase" or "lysophospholipid acyltransferase" ("LPLAT") herein refers to a broad class of acyltransferases that can acylate a variety of lysophospholipid substrates at the sn-2 position. More specifically, LPLATs include lysophosphatidic acid (LPA) acyltransferase (LPAAT), which can catalyze conversion of LPA to PA; LPC acyltransferase (LPCAT), which can catalyze conversion of LPC to PC; LPE acyltransferase (LPEAT), which can catalyze conversion of LPE to PE; LPS acyltransferase (LPSAT), which can catalyze conversion of LPS to PS; and LPG acyltransferase (LPGAT), which can catalyze conversion of LPG to PG. Various other designations for LPLATs are used in the art. For example, LPAAT has also been referred to as acyl-CoA:1-acyl-sn-glycerol-3-phosphate 2-O-acyltransferase, 1-acyl-sn-glycerol-3-phosphate acyltransferase, or 1-acylglycerolphosphate acyltransferase. LPCAT has also been referred to as acyl-CoA:1-acyl lysophosphatidylcholine acyltransferase. Certain LPLATs, such as *Saccharomyces cerevisiae* Ale1, have broad specificity and thus a single enzyme may be capable of catalyzing several LPLAT reactions, including LPAAT, LPCAT and LPEAT reactions (Tamaki et al., 2007, *J. Biol. Chem.* 282:34288-34298; Stahl et al., 2008, *FEBS Letters* 582:305-309; Chen et al., 2007, *FEBS Letters* 581:5511-5516; Benghezal et al., 2007, *J. Biol. Chem.* 282:30845-30855; Riekhof et al., 2007, *J. Biol. Chem.* 282:28344-28352).

The term "lysophosphatidic acid acyltransferase" (LPAAT, EC 2.3.1.51) as used herein refers to an enzyme that catalyzes the following reaction: acyl-CoA+1-acyl-sn-glycerol 3-phosphate=CoA+1,2-diacyl-sn-glycerol 3-phosphate.

The heterologous polynucleotide sequence encoding LPAAT in certain embodiments of the disclosed invention may encode an amino acid sequence comprising an LPAAT sequence as disclosed in U.S. Pat. Appl. Publ. No. 2010-0317882 or U.S. Pat. Nos. 7,189,559 and 7,879,591, all of which are incorporated herein by reference. For example, the amino acid sequence may comprise an LPAAT from *Mortierella alpina* (e.g., SEQ ID NO:38) or *Y. lipolytica* (e.g., SEQ ID NO:23). Alternatively, an LPAAT in certain embodiments may comprise an amino acid sequence that is at least about 90%, 91%, 92%, 93%, 94%, 95%, 96%, 97%, 98%, or 99% identical to SEQ ID NO:38 or 23 and have LPAAT function (above).

Thus, a recombinant microbial cell in certain embodiments of the disclosed invention comprises one or more of the following features as described above:

(i) at least one polynucleotide sequence encoding an active LPCAT comprising at least one amino acid mutation in a membrane-bound O-acyltransferase motif;

(ii) a down-regulation of an endogenous polynucleotide sequence encoding Sou2 sorbitol utilization protein;

(iii) at least one polynucleotide sequence encoding PDAT;

(iv) at least one polynucleotide sequence encoding delta-12 desaturase;

(v) at least one polynucleotide sequence encoding a DGLA synthase multizyme;

(vi) at least one polynucleotide sequence encoding delta-8 desaturase;

(vii) at least one polynucleotide sequence encoding MCS;

(viii) at least one polynucleotide sequence encoding LPAAT; wherein each of the polynucleotide sequences of (i) and (iii)-(viii) is operably linked to at least one regulatory sequence. Each of the polynucleotides of (i) and (iii)-(viii) may be heterologous. The recombinant microbial cell in each embodiment may comprise or produce an oil comprising at least 28 percent EPA measured as a weight percent of the dry cell weight. Certain embodiments of the recombinant microbial cell comprise feature(s):

(i);

(ii);

(i) and (ii);

(i), (ii), (iii), (iv) and (v);

(i), (ii), (vi), (vii) and (viii); or (i)-(viii).

For example, certain embodiments of the invention that have both features (i) and (ii) refer to recombinant microbial cells (e.g., recombinant *Yarrowia* cells) that produce an oil comprising at least 28 percent EPA measured as a weight percent of the dry cell weight and that comprise a down-regulation of an endogenous polynucleotide sequence encoding Sou2 sorbitol utilization protein, and at least one polynucleotide sequence encoding an active LPCAT enzyme comprising at least one amino acid mutation in a membrane-bound O-acyltransferase motif.

As described in U.S. Pat. Appl. Publ. No. 2010-0317072 (incorporated herein by reference), *Y. lipolytica* strain Y9502 was derived from strain Y8412, which in turn was derived from wild type strain ATCC #20362. *Y. lipolytica* strain Z5585 was derived from strain Y9502 as described in U.S. Pat. Appl. Publ. No. 2012-0052537, which is incorporated herein by reference. Certain of the recombinant *Y. lipolytica* strains disclosed in the below Examples are derived from Z5585, such as the strains listed in Table 13 (e.g. Z9276). Thus, in certain embodiments of the disclosed invention, the recombinant microbial cell is a *Y. lipolytica* comprising one of, a combination of, or all of the following heterologous features: down-regulation of a Pex protein-encoding polynucleotide (e.g., Pex3), down-regulation of a Sou2p-encoding polynucleotide, at least 3 polynucleotides encoding $C_{16118}$ elongase (e.g., ME3), at least 5 polynucleotides encoding delta-9 elongase (e.g., EgD9e), at least 6 polynucleotides encoding delta-8 desaturase (e.g., EgD8, EgD8M, or EaD8), at least 4 polynucleotides encoding DGLA synthase (e.g., E389D9eS/EgD8M, E389D9eS/EgD8M, EgD9eS/EgD8M, EaD9eS/EaD8S), at least 2 polynucleotides encoding delta-9 desaturase (e.g., YID9), at least 5 polynucleotides encoding delta-12 desaturase (e.g., FmD12), at least 4 polynucleotides encoding delta-5 desaturase (e.g., EgD5M), at least 3 polynucleotides encoding delta-17 desaturase (e.g., PaD17), at least 2 polynucleotides encoding diacylglycerol cholinephosphotransferase (e.g., YICPT1), at least 3 polynucleotides encoding malonyl-CoA synthetase (e.g., MCS), at least 1 polynucleotide encoding choline-phosphate cytidylyl-transferase (e.g., YIPCT), at least 5 polynucleotides encoding acyl-CoA:lysophosphatidic acid acyltransferase (e.g., MaLPAAT1 or YILPAAT1), at least 3 polynucleotides encoding phospholipid:diacylglycerol acyltransferase (e.g., YIPDAT), at least 1 polynucleotide encoding a mutant acyl CoA:lysophosphatidylcholine acyltransferase (e.g., YILPCAT (M136X/T389X). Alternatively, the cell may comprise one copy of some or all of these polynucleotides.

Constructs or vectors comprising the polynucleotides described herein may be introduced into a host cell by any standard technique. These techniques include transformation (e.g., lithium acetate transformation [*Methods in Enzymology,* 194:186-187 (1991)]), biolistic impact, electroporation, and microinjection, for example. As an example, U.S. Pat. Nos. 4,880,741 and 5,071,764, and Chen et al. (1997, *Appl. Microbiol. Biotechnol.* 48:232-235), describe integration techniques for *Y. lipolytica*, based on linearized fragments of DNA.

Preferred selection methods for use herein are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate [5-FOA]) is used for selection of yeast $Ura^-$ mutants (U.S. Pat. Appl. Publ. No. 2009-0093543), or a native acetohydroxyacid synthase (or acetolactate synthase; E.C. 4.1.3.18) that confers sulfonyl urea herbicide resistance (Intl. Appl. Publ. No. WO 2006/052870) is utilized for selection of transformants. A unique method of "recycling" a pair of preferred selection markers for their use in multiple sequential transformations, by use of site-specific recombinase systems, is also taught in U.S. Pat. Appl. Publ. No. 2009-0093543.

It may be desirable to manipulate a number of different genetic elements in the disclosed embodiments that control aspects of transcription, RNA stability, translation, protein stability and protein location, oxygen limitation and secretion from the host cell. More specifically, gene expression may be controlled by altering the following: the nature of the relevant promoter and terminator sequences; the number of copies of the cloned gene; whether the gene is plasmid-borne or integrated into the genome of the host cell; the final cellular location of the synthesized foreign protein; the efficiency of translation in the host organism; the intrinsic stability of the cloned gene protein within the host cell; and the codon usage within the cloned gene, such that its frequency approaches the frequency of preferred codon usage of the host cell.

Promoters useful to drive expression of heterologous genes in microbial host cells are numerous and known to those skilled in the art. Expression can be accomplished in an induced or constitutive fashion. Induced expression can be accomplished by inducing the activity of a regulatable promoter operably linked to the gene of interest, while constitutive expression can be achieved by the use of a constitutive promoter operably linked to the gene of interest. Virtually any promoter (i.e., native, synthetic, or chimeric) capable of directing expression of a gene is suitable, although transcriptional and translational regulatory regions from the host species may be particularly useful.

In general, the terminator can be derived from the 3' region of the gene from which the promoter was obtained or from a different gene. A large number of terminators are known and function satisfactorily in a variety of hosts, when utilized both in the same and different genera and species from which they were derived. The terminator usually is selected more as a matter of convenience rather than because of any particular property. Preferably, the terminator is derived from a yeast gene. The terminator can also be synthetic, as one of skill in the art can utilize available information to design and synthesize a terminator. A terminator may be unnecessary, but it is preferred.

Although not intended to be limiting, preferred promoters and terminators for use in a recombinant microbial host cell of the genus *Yarrowia* are those taught in U.S. Pat. Appl. Publ. Nos. 2009-0093543, 2010-0068789, 2011-0059496, 2012-0252079, 2012-0252093, 2013-0089910 and 2013-0089911, all of which are incorporated herein by reference.

Additional copies (i.e., more than one copy) of the PUFA biosynthetic pathway desaturases, elongases, etc. genes may be introduced into the recombinant microbial host cell to increase EPA production and accumulation. Specifically, additional copies of genes may be cloned within a single expression construct; and/or additional copies of the cloned gene(s) may be introduced into the host cell by increasing the plasmid copy number or by multiple integration of the cloned gene into the genome.

In general, once a DNA cassette (e.g., comprising a chimeric gene comprising a promoter, ORF and terminator) suitable for expression in a recombinant microbial host cell has been obtained, it is either placed in a plasmid vector capable of autonomous replication in the host cell or directly integrated into the genome of the host cell. Integration of expression cassettes can occur randomly within the host genome or can be targeted through the use of constructs containing regions of homology with the host genome sufficient to target recombination with the host locus. Although not relied on herein, all or some of the transcriptional and translational regulatory regions can be provided by the endogenous locus where constructs are targeted to an endogenous locus.

With respect to engineered recombinant *Y. lipolytica* host cells, the preferred method of expressing genes in this microbial host is by integration of a linear DNA fragment into the genome of the host. Integration into multiple locations within the genome can be particularly useful when high level expression of genes is desired. Preferred loci include those taught in U.S. Pat. Appl. Publ. No. 2009-0093543, for example.

Another aspect of the disclosed invention concerns a method for producing a microbial oil comprising a polyunsaturated fatty acid (PUFA). This method comprises:

a) culturing a recombinant microbial cell as described herein, wherein a microbial oil comprising a PUFA is produced; and b) optionally recovering the microbial oil of step (a).

In certain embodiments, the microbial oil produced by the method comprises EPA. Depending on the species of the microbial cell used in the method, the oil may be a fungal oil or yeast oil, for example. The oil in certain embodiments may be recovered or obtained from the recombinant microbial cell after about 12, 24, 36, 48, 60, 72, 84, 96, 100, 105, 110, 115, 120, 125, 130, 135, 140, 145, 150, 160, 170, 180, or 200 hours of culturing the microbial cell.

The recombinant microbial cell of the present disclosure can be grown under conditions that optimize expression of the disclosed polynucleotides and produce the greatest and the most economical yield of one or more PUFAs. In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest.

Fermentation media for growing the recombinant microbial cell described herein must contain a suitable carbon source, such as described in U.S. Pat. No. 7,238,482 and U.S. Pat. Appl. Publ. No. 2011-0059204. Preferred growth media include, for example, common commercially prepared media such as Yeast Nitrogen Base, corn steep liquors, or corn steep solids. Other defined or synthetic growth media may also be used. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, where microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process can be used for the production of EPA in *Yarrowia lipolytica*. This approach is described in U.S. Pat. No. 7,238,482, as are various suitable fermentation process designs (i.e., batch, fed-batch and continuous) and considerations during growth. In a two-stage approach, the first stage of the fermentation is for the accumulation of cell mass and is characterized by rapid cell growth and division; a standard amount of nitrogen is included in this stage of fermentation. In the second stage of the fermentation, nitrogen deprivation in the culture promotes a high level of lipid production and accumulation. The first stage may be performed for about 12, 24, 36, 48, or 60 hours, while the second stage (oleaginous) may be performed for about 12-150 hours, depending on the desired level of oil production.

The conditions of growing the disclosed recombinant microbial cell may be oleaginous; for example, oleaginous growth conditions for *Yarrowia* are described in U.S. Appl. Publ. No. 2009-0093543, which is incorporated herein by reference. Oleaginous growth conditions differ from standard growth conditions mainly in that nitrogen is absent or very limited (nitrogen-limited), but while still providing an ample or high amount of a fermentable carbon source. Example fermentable carbon sources are monosaccharides (e.g., glucose, fructose), disaccharides (e.g., sucrose), invert sucrose, oligosaccharides, polysaccharides, alkanes, fatty acids (e.g., 10-22 carbons), esters of fatty acids, glycerol, monoglycerides, diglycerides, and triglycerides. An example of an oleaginous growth medium lacking nitrogen has about 80 g/L glucose, 2.58 g/L $KH_2PO_4$ and 5.36 g/L $K_2HPO_4$. Another example is a medium in which no nitrogen-containing salt is directly added when preparing the medium. Since an oleaginous medium is nitrogen-limited, it may have at most about 0.050, 0.100, 0.125 0.150, 0.175, 0.200, 0.225, 0.250, 0.275, or 0.300 g/L of a nitrogen-containing salt (e.g., ammonium-containing salt such as $(NH_4)_2HPO_4$, $(NH_4)_2HSO_4$, $NH_4NO_3$, or $NH_4Cl$; a nitrate-containing salt such as $KNO_3$ or $NaNO_3$), amino acid, or urea. The amount of glucose in an oleaginous growth medium may be at least about 20, 30, 40, 50, 60, 70, 80, 90, 100, 110, 120, 130, 140, 150, 160, 170, 180, 190, or 200 g/L.

EXAMPLES

The present invention is further defined in the following Examples. It should be understood that these Examples, while indicating preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used herein are well known in the art and are described by Sambrook, J. and Russell, D., *Molecular Cloning: A Laboratory Manual,* 3rd Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et. al., *Short Protocols in Molecular Biology,* 5th Ed. Current Protocols, John Wiley and Sons, Inc., N.Y., 2002. Unless otherwise indicated herein comparisons of genetic sequences were performed using DNASTAR software (DNASTAR Inc., Madison, Wis.).

Materials and methods suitable for the maintenance and growth of microbial cultures are well known in the art. Techniques suitable for use in the following examples may be found as set out in *Manual of Methods for General Bacteriology* (P. Gerhardt, R. G. E. Murray, R. N. Costilow, E. W. Nester, W. A. Wood, N. R. Krieg and G. B. Phillips, Eds.), American Society for Microbiology: Washington, D.C. (1994)); or in *Manual of Industrial Microbiology and*

*Biotechnology,* 3rd Edition (R. H. Baltz, J. E. Davies, and A. L. Demain, Eds.), ASM Press, Washington, D.C., 2010.

All reagents, restriction enzymes and materials used for the growth and maintenance of microbial cells were obtained from Aldrich Chemicals (Milwaukee, Wis.), DIFCO Laboratories (Detroit, Mich.), New England Biolabs, Inc. (Beverly, Mass.), GIBCO/BRL (Gaithersburg, Md.), or Sigma Chemical Company (St. Louis, Mo.), unless otherwise specified.

The structure of each genetic expression cassette disclosed herein is represented by the simple notation system of "X::Y::Z". Specifically, X describes the promoter, Y describes the protein-coding sequence, and Z describes the terminator. X is operably linked to Y, and Y is operably linked to Z.

Transformation and Cultivation of *Y. lipolytica*

*Y. lipolytica* strains were routinely grown at 30° C. in several media, according to the recipes shown below.

High Glucose Medium (HGM) (per liter): 80 g glucose, 2.58 g $KH_2PO_4$ and 5.36 g $K_2HPO_4$, pH 7.5 (do not need to adjust).

Synthetic Dextrose Medium (SD) (per liter): 6.7 g yeast nitrogen base with ammonium sulfate and without amino acids, and 20 g glucose.

Fermentation medium (FM) (per liter): 6.7 g yeast nitrogen base with ammonium sulfate and without amino acids, 6.0 g $KH_2PO_4$, 2.0 g $K_2HPO_4$, 1.5 g $MgSO_4.7H_2O$, 20 g glucose, and 5.0 g yeast extract (BBL, BD Diagnostic Systems, Sparks, Md.).

Transformation of *Y. lipolytica* was performed as described in U.S. Pat. Appl. Publ. No. 2009-0093543, which is incorporated herein by reference. In general, for transformation of $Ura3^-$ cells, cells were transfected with a plasmid or fragment thereof carrying a URA3 gene, and then selected for transformation on plates lacking uracil.

Fatty Acid Analysis of Y. *Lipolytica*

For fatty acid analysis, cells were collected by centrifugation and lipids were extracted as described in Bligh, E. G. & Dyer, W. J. (*Can. J. Biochem. Physiol.,* 37:911-917 (1959)). Fatty acid methyl esters (FAMEs) were prepared by transesterification of the lipid extract with sodium methoxide (Roughan, G., and Nishida I., *Arch Biochem Biophys.,* 276(1):38-46 (1990)) and subsequently analyzed with an Agilent Technologies 6890N gas chromatograph fitted with a 30-m×0.25 mm (i.d.) SUPELCO Omegawax320 (Agilent Technologies) column. The oven temperature was ramped from 160° C. to 240° C. at 30° C./min and then held for 3.8 min at 240° C.

For direct base transesterification, a *Y. lipolytica* culture (1 mL) was harvested by centrifugation (13,000×g) for 1 min. Sodium methoxide (500 μL of a 1% solution) was added to the sample, and then the sample was vortexed and rocked for 45 min. Then, 100 μL of 1.0 M NaCl and 500 μL of hexane were added, and the sample was vortexed and spun. The upper layer was removed and analyzed by gas chromatography as described above.

In general, initial fatty acid screening of new transformants of *Yarrowia* strains was performed as follows. Single colonies that were grown on minimal medium (MM) plates at 30° C. for 5 to 6 days were re-streaked onto MM plates, grown for two days at 30° C., and then inoculated into liquid MM in a multi-well plate (e.g., 24-well, 3 mL MM) and shaken at 250 rpm at 30° C. for 2 days. The cells from each well were collected by centrifugation, resuspended in HGM, and then shaken at 250 rpm for 5 days. Cells were then processed for fatty acid analysis as described above. Transformants exhibiting a desired fatty acid trait were further analyzed by "flask assay" as described below.

Analysis of Total Lipid Content and Composition in *Y. lipolytica* (Flask Assay)

For a detailed analysis of the total lipid content and composition in a particular strain of *Y. lipolytica*, flask assays were conducted as follows. Specifically, cultures were grown at a starting $OD_{600}$ of ~0.3 in 25 mL of SD medium in a 125-mL flask for 48 h. 6 mL of the culture was harvested by centrifugation for 5 min at 4300 rpm in a 50-mL conical tube. The supernatant was discarded and the cells were resuspended in 25 mL of HGM in another 125 mL flask; this culture was incubated for 120 hours (except as otherwise noted) in a shaker incubator at 250 rpm and 30° C. A 1-mL aliquot of the culture was then used for fatty acid analysis (as described above) following centrifugation for 1 min at 13,000 rpm, and a 5-mL aliquot of the culture was dried for dry cell weight determination. All flask assays referenced herein were performed following this methodology, except those performed using the "one-step flask assay".

For DCW determination, 10 mL of culture was harvested by centrifugation for 5 min at 4300 rpm. The pellet was resuspended in 10 mL of sterile water and re-harvested as above. The washed pellet was re-suspended in 1 mL of water (three times) and transferred to a pre-weighed aluminum pan. The cell suspension was dried overnight in a vacuum oven at 80° C. The weight of the cells was determined (g/L).

Total lipid content of cells (TFAs % DCW) was calculated and considered in conjunction with data tabulating the concentration of each fatty acid as a weight percent of TFAs (% TFAs) and the EPA content as a percent of the dry cell weight (EPA % DCW). Data from flask assays are presented in table format summarizing the total DCW of the cells, the total lipid content of cells (TFAs % DCW), the concentration of each fatty acid as a weight percent of TFAs (% TFAs) and the EPA content as a percent of the dry cell weight (EPA % DCW).

*Y. lipolytica* Strains Z5627 and Z5585

The generation of *Y. lipolytica* strains Z5627 and Z5585 is described in U.S. Pat. Appl. Publ. No. 2012-0052537, which is incorporated herein by reference. As described in Examples 1-4, Z5627 and Z5585 were used to derive certain strains of the disclosed invention.

Figure 2A:
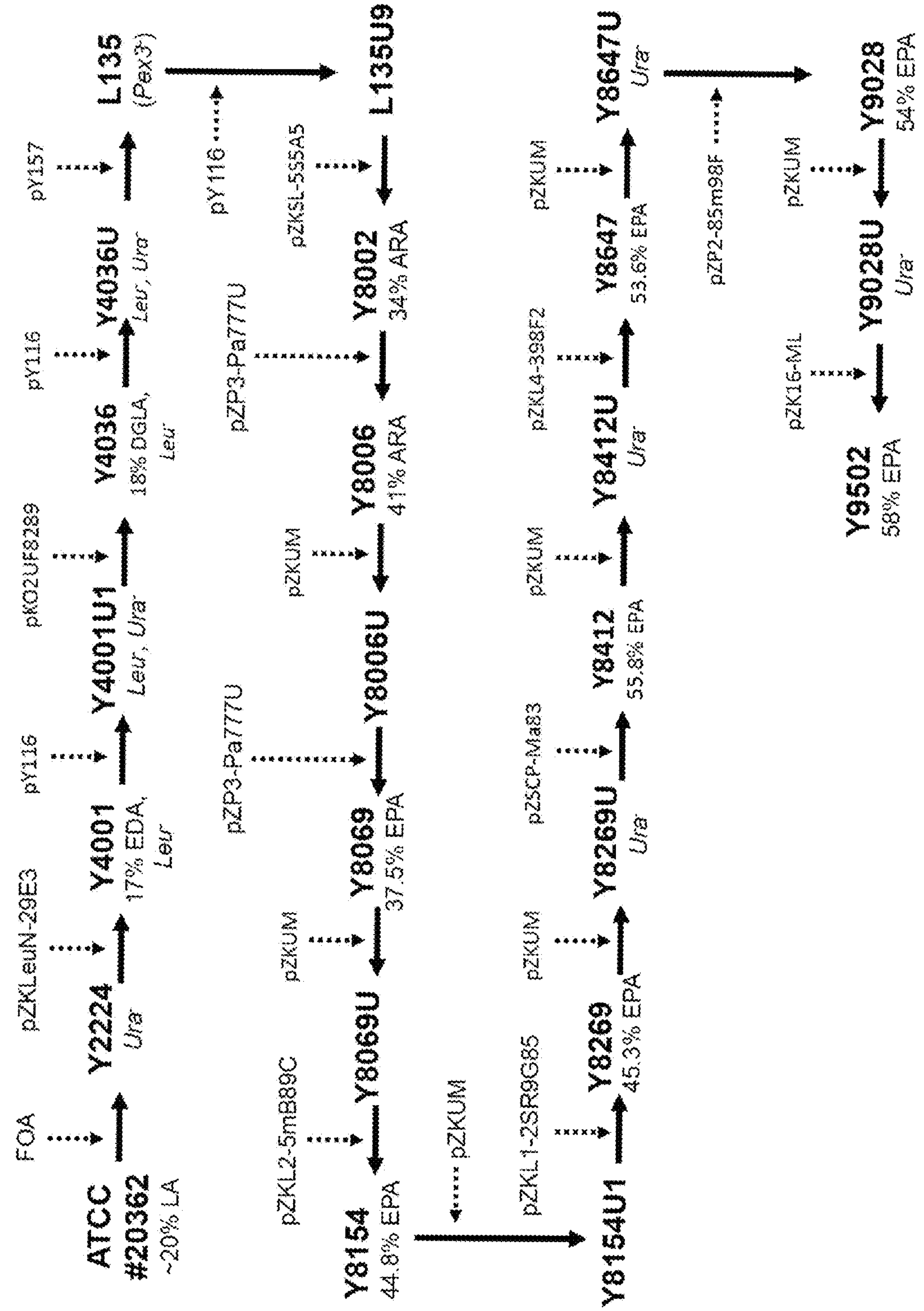
Figure 2B:
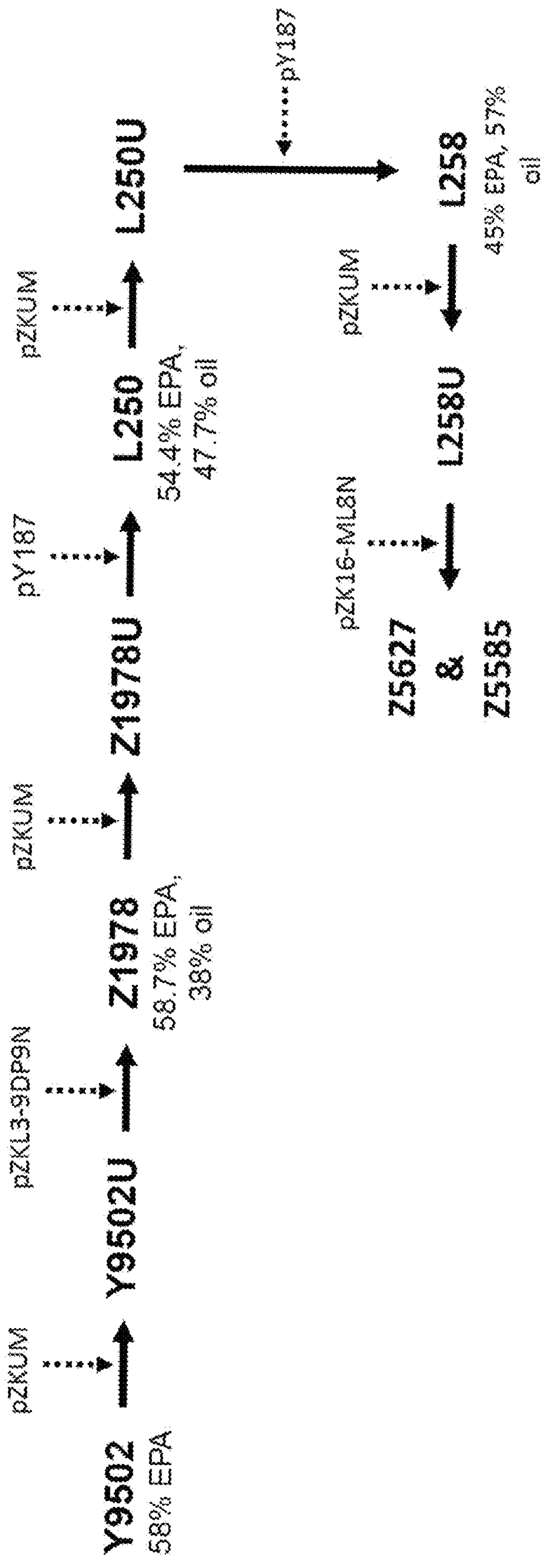

*Y. lipolytica* strains Z5627 and Z5585 were derived from multiple genetic modifications of strain Y9502, which in turn was derived after multiple genetic modifications of wild type *Y. lipolytica* strain ATCC #20362. The modification steps and intermediate strains used for generating strains Z5627 and Z5585 are shown in FIGS. 2A (ATCC #20362 to Y9502) and 2B (Y9502 to Z5627 and Z5585).

The genotype of both strains Z5627 and Z5585 with respect to wild type *Y. lipolytica* ATCC #20362 is: $Ura^+$, $Pex3^-$, unknown $1^-$, unknown $2^-$, unknown $3^-$, unknown $4^-$, $YALI0E12947g^-$, unknown $6^-$, $YALI0B21890g^-$, unknown $8^-$, unknown $10^-$, unknown $11^-$, unknown $12^-$, unknown $13^-$, unknown $14^-$, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M::Aco, FBAINm::EaD9eS/EaD8S::Lip2, DGAT2M::YlD9::Lip1, GPDIN::YlD9::Lip1, GPD::FmD12::Pex20, YAT1::FmD12::Oct, EXP1::FmD12S::Aco, GPDIN::FmD12::Pex16, EXP1::EgD5M::Pex16, FBAIN::EgD5SM::Pex20, EXP1::

EgD5SM::Lip1, YAT1::EaD5SM::Oct, FBAINm::PaD17::Aco, EXP1::PaD17::Pex16, YAT1::PaD17S::Lip1, YAT1::YICPT1::Aco, EXP1::YICPT1::Oct, YAT1::MCS::Lip1, FBA::MCS::Lip1, EXP1::YIPCT::Pex16, YAT1::MaLPAAT1S::Pex16, ALK2LM1::MaLPAAT1S::Pex20, FBAINm::YILPAAT1::Lip1 (2 copies), YAT1::YIPDAT::Lip1 (2 copies).

The abbreviations listed in the above genotype are as follows: FmD12 is a *Fusarium moniliforme* delta-12 desaturase gene and FmD12S is a codon-optimized form thereof (U.S. Pat. No. 7,504,259); ME3S is a codon-optimized *Mortierella alpina* $C_{16/18}$ elongase gene (U.S. Pat. No. 7,470,532); EgD9e is a *Euglena gracilis* delta-9 elongase gene and EgD9eS is a codon-optimized form thereof (U.S. Pat. No. 7,645,604); EgD9eS-L35G is a mutant form of EgD9eS (U.S. Pat. Appl. Publ. No. 2012/0226062); EgD8M is a synthetic mutant *E. gracilis* delta-8 desaturase gene (U.S. Pat. No. 7,709,239); EaD8S is a codon-optimized *Euglena anabaena* delta-8 desaturase gene (U.S. Pat. No. 7,790,156); E389D9eS/EgD8M is a DGLA synthase created by linking a codon-optimized delta-9 elongase gene (E389D9eS) from *Eutreptiella* sp. CCMP389 (U.S. Pat. No. 7,645,604) to EgD8M (U.S. Pat. Appl. Publ. No. 2008/0254191); EgD9eS/EgD8M is a DGLA synthase created by linking EgD9eS to EgD8M (U.S. Pat. Appl. Publ. No. 2008/0254191); EaD9eS/EaD8S is a DGLA synthase created by linking a codon-optimized *E. anabaena* delta-9 elongase gene (EaD9eS) (U.S. Pat. No. 7,794,701) to EaD8S (U.S. Pat. No. 7,790,156); YID9 is a *Y. lipolytica* delta-9 desaturase gene (U.S. Pat. Appl. Publ. No. 2012/0052537); EgD5M and EgD5SM are synthetic mutant *E. gracilis* delta-5 desaturase genes comprising a mutant HPGS motif (U.S. Pat. Appl. Publ. No. 2010/0075386); EaD5SM is a synthetic mutant *E. anabaena* delta-5 desaturase gene comprising a mutant HAGG motif (U.S. Pat. Appl. Publ. No. 2010/0075386); PaD17 is a *Pythium aphanidermatum* delta-17 desaturase gene and PaD17S is a codon-optimized form thereof (U.S. Pat. No. 7,556,949); YICPT1 is a *Y. lipolytica* diacylglycerol cholinephosphotransferase gene (U.S. Pat. No. 7,932,077); MCS is a codon-optimized malonyl-CoA synthetase gene from *Rhizobium leguminosarum* bv. viciae 3841 (U.S. Pat. Appl. Publ. No. 2010/0159558); YIPCT is a *Y. lipolytica* choline-phosphate cytidylyl-transferase gene (U.S. Pat. Appl. Publ. No. 2012-0052537 and GenBank Accession No. XM_502978); MaLPAAT1S is a codon-optimized *M. alpina* lysophosphatidic acid acyltransferase gene (U.S. Pat. No. 7,879,591); YILPAAT1 is a *Y. lipolytica* lysophosphatidic acid acyltransferase gene (U.S. Pat. Appl. Publ. No. 2012-0052537); YIPDAT is a *Y. lipolytica* phospholipid:diacylglycerol acyltransferase gene (U.S. Pat. Appl. Publ. No. 2012-0052537); YAT1 is a *Y. lipolytica* YAT1 gene promoter (U.S. Pat. Appl. Publ. No. 2010/0068789); Pex16 is a *Y. lipolytica Pex*16 gene terminator (GenBank Accession No. U75433); GPD is a *Y. lipolytica* glyceraldehyde-3-phosphate dehydrogenase gene promoter (U.S. Pat. No. 7,459,546); GPDIN is a *Y. lipolytica* GPD gene promoter plus intron (U.S. Pat. No. 7,459,546); Pex20 is a *Y. lipolytica* Pex20 gene terminator (GenBank Accession No. AF054613); Lip1 is a *Y. lipolytica* Lip1 gene terminator (GenBank Accession No. Z50020); Lip2 is a *Y. lipolytica* Lip2 gene terminator (GenBank Accession No. AJ012632); FBA is a *Y. lipolytica* fructose-bisphosphate aldolase promoter sequence, and FBAIN and FBAINm are *Y. lipolytica* FBA promoter plus intron sequences (U.S. Pat. No. 7,202,356); DGAT2M is a *Y. lipolytica* diacylglycerol acyltransferase-2 (DGAT2) promoter sequence (U.S. Pat. Appl. Publ. No. 2012-0052537); EXP1 is a *Y. lipolytica* export protein (EXP1) gene promoter sequence (Intl. Appl. Publ. No. WO06/052870); GPAT is a *Y. lipolytica* GPAT promoter (Intl. Appl. Publ. No. WO 2006/031937); Aco is a *Y. lipolytica* Aco gene terminator (GenBank Accession No. AJ001300); Oct is a *Y. lipolytica* Oct gene terminator (GenBank Accession No. X69988); and ALK2LM1 is a *Y. lipolytica* n-alkane-hydroxylating cytochrome P450 gene (ALK2) promoter sequence plus N-terminal 66-bp coding region of the *Y. lipolytica* ALK2 gene (U.S. Pat. Appl. Publ. No. 2012-0052537).

As shown below in Table 4, which is also disclosed in U.S. Pat. Appl. Publ. No. 2012-0052537, strain Z5627 can produce oil containing about 49.5% EPA in the fatty acids of the oil. This strain can also produce, as a percentage of DCW, about 52% oil and 25.6% EPA.

As shown in Table 4, strain Z5585 can produce oil containing about 49.4% EPA in the fatty acids of the oil. This strain can also produce, as a percentage of DCW, about 56.6% oil and 28% EPA.

TABLE 4

Total Lipid Content and Composition in Various Recombinant *Y. lipolytica* Strains by Flask Assay (U.S. Pat. Appl. Publ. No. 2012-0052537)[g]

| Strain | DCW (g/L) | TFAs % DCW | % TFAs 16:0 | 16:1 | 18:0 | 18:1 | 18:2 | ALA | EDA | DGLA | ARA | ETrA | ETA | EPA | EPA % DCW |
|---|---|---|---|---|---|---|---|---|---|---|---|---|---|---|---|
| Z1977 | 3.8 | 34.3 | 2 | 0.5 | 1.9 | 4.6 | 11.2 | 0.7 | 3.1 | 3.3 | 0.9 | 0.7 | 2.2 | 59.1 | 20.3 |
| Z1978 | 3.9 | 38.3 | 2.4 | 0.4 | 2.4 | 4.8 | 11.1 | 0.7 | 3.2 | 3.3 | 0.8 | 0.6 | 2.1 | 58.7 | 22.5 |
| Z1979 | 3.7 | 33.7 | 2.3 | 0.4 | 2.4 | 4.1 | 10.5 | 0.6 | 3.2 | 3.6 | 0.9 | 0.6 | 2.2 | 59.4 | 20 |
| Z1980 | 3.6 | 32.7 | 2.1 | 0.4 | 2.2 | 4 | 10.8 | 0.6 | 3.1 | 3.5 | 0.9 | 0.7 | 2.2 | 59.5 | 19.5 |
| Z1981 | 3.5 | 34.3 | 2.2 | 0.4 | 2.1 | 4.2 | 10.6 | 0.6 | 3.3 | 3.4 | 1 | 0.8 | 2.2 | 58.5 | 20.1 |
| Genotype Additions with Respect to Strain Z1978: YILPAAT1, YIPDAT | | | | | | | | | | | | | | | |
| L250 | 4.4 | 51.5 | 2 | 0.7 | 2.8 | 6.1 | 16.7 | 0.9 | 3.3 | 4.9 | 0.7 | 0.6 | 3.2 | 50.4 | 26 |
| Genotype Additions with Respect to Strain Z1978: 2 YILPAAT1, 2 YIPDAT | | | | | | | | | | | | | | | |
| L258[a] | 5 | 57.1 | 2.3 | 0.9 | 3.4 | 7.8 | 18.7 | 0.9 | 4 | 5.3 | 0.8 | 0.6 | 3.2 | 45.2 | 25.8 |
| Genotype Additions with Respect to Strain Z1978: 2 YILPAAT1, 2 YIPDAT, EgD8M, MCS, MaLPAAT1S | | | | | | | | | | | | | | | |
| Z5565[b] | 4.8 | 56.1 | 2.1 | 0.8 | 2.8 | 6.8 | 17.3 | 0.8 | 3.8 | 5.2 | 1.1 | 0.8 | 3.4 | 47.4 | 26.6 |
| Z5567[b] | 4.9 | 56.2 | 1.9 | 0.7 | 2.6 | 6.2 | 16.7 | 0.7 | 3.8 | 5.6 | 1.1 | 1 | 3.6 | 48.3 | 27.1 |
| Z5575[b] | 4.7 | 53.8 | 1.8 | 0.7 | 2.4 | 5.7 | 15.3 | 0.6 | 3.6 | 5.9 | 1.2 | 1 | 3.6 | 50.4 | 27.1 |
| Z5576[b] | 4.9 | 55.6 | 2.3 | 0.9 | 2.8 | 6.9 | 16.9 | 0.7 | 3.6 | 5.5 | 1.2 | 0.9 | 3.3 | 47.2 | 26.2 |

TABLE 4-continued

Total Lipid Content and Composition in Various Recombinant *Y. lipolytica* Strains by Flask Assay (U.S. Pat. Appl. Publ. No. 2012-0052537)[g]

| Strain | DCW (g/L) | TFAs % DCW | % TFAs 16:0 | 16:1 | 18:0 | 18:1 | 18:2 | ALA | EDA | DGLA | ARA | ETrA | ETA | EPA | EPA % DCW |
|---|---|---|---|---|---|---|---|---|---|---|---|---|---|---|---|
| Genotype Additions with Respect to Strain Z1978: 3 YILPAAT1, 2 YIPDAT, EgD8M, MCS | | | | | | | | | | | | | | | |
| Z5620[c] | 4.5 | 52.8 | 2.1 | 0.7 | 2.8 | 6.6 | 16.1 | 0.7 | 3.6 | 5.7 | 1.1 | 0.7 | 3.3 | 49 | 25.9 |
| Z5623[c] | 4.3 | 51.7 | 2.3 | 0.8 | 2.4 | 6 | 15.9 | 0.7 | 3.8 | 5.2 | 1.1 | 0.7 | 3.1 | 50 | 25.8 |
| Z5625[c] | 4.6 | 52.7 | 2.1 | 0.7 | 2.7 | 6.2 | 16.6 | 0.7 | 3.9 | 5.4 | 1.1 | 0.8 | 3.2 | 49.1 | 25.9 |
| Genotype Additions with Respect to Strain Z1978: 2 YILPAAT1, 2 YIPDAT, ME3S, MCS, MaLPAAT1S | | | | | | | | | | | | | | | |
| Z5581[d] | 4.7 | 56.3 | 1.9 | 0.7 | 2.6 | 6.1 | 16.5 | 0.7 | 3.7 | 5.6 | 1.2 | 1 | 3.5 | 48.7 | 27.4 |
| Z5582[d] | 4.8 | 55.6 | 1.9 | 0.7 | 2.5 | 6.1 | 16.4 | 0.7 | 3.7 | 5.7 | 1.1 | 0.9 | 3.6 | 48.9 | 27.2 |
| Z5583[d] | 4.9 | 56.8 | 2 | 0.7 | 2.6 | 6.2 | 16.7 | 0.8 | 3.7 | 5.4 | 1 | 1 | 3.7 | 48.4 | 27.5 |
| Z5584[d] | 4.9 | 55.3 | 2 | 0.7 | 2.7 | 6.5 | 16.1 | 0.7 | 3.7 | 5.7 | 1.1 | 1 | 3.6 | 48.6 | 26.8 |
| Genotype Additions with Respect to Strain Z1978: 2 YILPAAT1, 2 YIPDAT, YIPCT, YID9, MaLPAAT1S | | | | | | | | | | | | | | | |
| Z5570[e] | 4.8 | 55 | 2 | 0.8 | 2.5 | 6.1 | 16.4 | 0.7 | 3.7 | 5.5 | 1.2 | 1 | 3.4 | 48.6 | 26.8 |
| Z5571[e] | 4.8 | 54.1 | 2.2 | 0.8 | 2.4 | 6.5 | 16.7 | 0.7 | 3.8 | 5.5 | 1.1 | 0.9 | 3.2 | 48.3 | 26.2 |
| Z5572[e] | 4.9 | 54 | 2.1 | 0.8 | 2.5 | 6.5 | 16.7 | 0.7 | 3.7 | 5.5 | 1.1 | 0.9 | 3.3 | 48.4 | 26.1 |
| Z5574[e] | 5 | 53.8 | 1.8 | 0.7 | 2.4 | 5.7 | 15.3 | 0.6 | 3.6 | 5.9 | 1.2 | 1 | 3.6 | 50.4 | 27.1 |
| Genotype Additions with Respect to Strain Z1978: 2 YILPAAT1, 2 YIPDAT, YICPT1, YID9, MaLPAAT1S | | | | | | | | | | | | | | | |
| Z5585[f] | 4.6 | 56.6 | 1.9 | 0.7 | 2.6 | 5.6 | 16.4 | 0.7 | 3.5 | 5.5 | 1.1 | 1 | 3.5 | 49.4 | 28 |
| Z5627[f] | 4.8 | 52 | 1.9 | 0.7 | 2.6 | 6.2 | 16.1 | 0.6 | 4 | 5.6 | 1.2 | 0.9 | 3.2 | 49.3 | 25.6 |

[a]Strain L258 was used to derive L258U (FIG. 2B), which is $Ura3^-$.
[b]Each of strains Z5565, Z5567, Z5575 and Z5576 was derived through the one-step introduction to strain L258U of gene cassettes for expressing EgD8M, MCS and MaLPAAT1S.
[c]Each of strains Z5620, Z5623 and Z5625 was derived through the one-step introduction to strain L258U of gene cassettes for expressing YILPAAT1, EgD8M and MCS.
[d]Each of strains Z5581, Z5582, Z5583 and Z5584 was derived through the one-step introduction to strain L258U of gene cassettes for expressing ME3S, MCS and MaLPAAT1S.
[e]Each of strains Z5570, Z5571, Z5572 and Z5574 was derived through the one-step introduction to strain L258U of gene cassettes for expressing YIPCT, YID9 and MaLPAAT1S.
[f]Each of strains Z5585 and Z5627 was derived through the one-step introduction to strain L258U of gene cassettes for expressing YICPT1, YID9 and MaLPAAT1S.
[g]The values shown in the table were measured in each strain after growth in HGM for 120 hours.

Table 4 lists other strains beside Z5627 and Z5585 that were derived through multiple genetic modifications of wild type *Y. lipolytica* strain ATCC #20362. The strains in this table can produce approximately 20%-28% EPA as a percentage of DCW. Several of the strains listed in Table 4, specifically strains L250 on down to Z5627, are all descendants of intermediate strain Z1978. The genetic modifications ("genotype additions") made in each strain with respect to Z1978 are shown in Table 4. Strains Z5565 on down to Z5627 in Table 4 were directly derived through certain one-step genetic modifications of strain L258U, which is a $Ura3^-$ transformant of strain L258 (see table footnotes).

It is apparent from Table 4 that the different genetic modifications made to strain Z1978 to yield each of descendent strains Z5565 to Z5627 raised the total oil content (TFAs % DCW) from 38.3% to a range of 51.7%-56.6%. This rise in oil content was associated with an overall decrease in the percentage of EPA in the fatty acids of the oil, from 58.7% in Z1978 to a range of 47.2%-50.4% in descendent strains Z5565 to Z5627.

Thus, the increase in the total amounts of EPA produced on a dry cell weight basis obtained in strains Z5565 to Z5627 (25.6 to 28 EPA % DCW, Table 4) through the genetic modifications of strain Z1978 (22.5 EPA % DCW, Table 4) was achieved through substantially increasing oil production. Despite this significant achievement, it was not apparent from the studies disclosed in U.S. Pat. Appl. Publ. No. 2012-0052537 how to further increase total EPA content on a dry cell weight basis. For example, the steps to maintain or increase oil content while increasing the amount of EPA in the fatty acids of the oil, which would boost EPA % DCW, were unknown.

Thus, there is still a need to increase oil production while also increasing EPA content (EPA % TFAs).

Example 1

Generation of Strain Z6109 Producing at Least about 51.7% EPA of Total Fatty Acids with at Least about 54.2% Total Lipid Content This Example describes the generation of *Y. lipolytica* strain Z6109 through genetic modification of strain Z5627. The genetic modification entailed introducing an expression cassette encoding *Arabidopsis thaliana* caleosin-1 (AtClo1) into Z5627. FIG. 3A shows the modification steps and intermediate strain used for generating strain Z6109.

In order to introduce AtClo1 to Z5627, it was necessary to first render this strain to be $Ura3^-$ for subsequent selection purposes. Z5627 carries an intact URA3 coding sequence within the integrated plasmid construct pZKMP-ML9DCB, which was previously used to introduce sequences allowing for expression of MaLPAAT1S, YID9 and YICPT1 (see U.S. Pat. Appl. Publ. No. 2012-0052537). To disrupt the URA3 coding sequence of Z5627, construct pZKUM was used to integrate a $Ura3^-$ mutant sequence into the intact URA3 sequence. The construction and use of plasmid pZKUM to obtain $Ura^-$ *Y. lipolytica* cells has been described (U.S. Pat. Appl. Publ. No. 2009-0093543, see Table 15 therein, which is incorporated herein by reference).

Z5627 pZKUM-transformants with a $Ura^-$ phenotype were selected on minimal media (MM) plates containing 5-fluoroorotic acid (5-FOA) (U.S. Pat. Appl. Publ. No. 2009-0093543). A total of eight transformants were grown and identified to possess a Ura⁻ phenotype. These transformants were subjected to an initial fatty acid screening process as described above.

Gas chromatography (GC) analyses showed the presence of 33.5%, 35.7%, 35.9% and 34% EPA of TFAs in Z5627 pZKUM-transformants #2, #3, #4 and #6 cells from FOA-plates, respectively. These four transformants were designated as strains Z5627U1, Z5627U2, Z5627U3 and Z5627U5, respectively, and were collectively designated as strain Z5627U.

Plasmid pYRH55 (FIG. 4A, SEQ ID NO:1) was generated to integrate one synthetic *Arabidopsis thaliana* caleosin-1 (AtClo1) gene into the *Yarrowia lipase* 7 gene locus (GenBank Accession No. AJ549519). The AtClo1 coding sequence (SEQ ID NO:2, encoding SEQ ID NO:3) in pYRH55 was derived from GenBank Accession No. AEE85247 and is codon-optimized for expression in *Y. lipolytica* (see U.S. Appl. Publ. No. 2012-0301932, which is incorporated herein by reference). This codon-optimized AtClo1 is herein referred to as AtClo1S. Table 5 describes the components contained in pYRH55.

TABLE 5

Description of Plasmid pYRH55 (SEQ ID NO: 1)

| RE[a] Sites and Nucleotide Positions | Description of Fragment and Chimeric Gene Components |
|---|---|
| AscI/BsiWI (1212-318) | 887-bp 5' portion of *Yarrowia* lipase 7 locus (GenBank Accession No. AJ549519, labeled as LipY-5' in FIG. 4A) |
| PacI/SphI (4682-3920) | 756-bp 3' portion of *Yarrowia* lipase 7 locus (GenBank Accession No. AJ549519, labeled as LipY-3' in FIG. 4A) |
| SwaI/BsiWI (6219-318) | FBAINm::AtClo1S::Pex20, comprising: FBAINm: *Y. lipolytica* FBAIN promoter (U.S. Pat. No. 7,202,356); AtClo1S: codon-optimized *Arabidopsis thaliana* caleosin-1 coding sequence (SEQ ID NO: 2) Pex20: Pex20 terminator sequence from *Yarrowia* Pex20 gene (GenBank Accession No. AF054613) |
| PmeI/PacI (6183-4682) | *Yarrowia* URA3 gene (GenBank Accession No. AJ306421) |

[a]RE, restriction endonuclease

The pYRH55 plasmid was digested with AscI/SphI, and then used to transform strain Z5627U5. The transformed cells were plated onto uracil-minus MM plates and maintained at 30° C. for 5 to 6 days. Single colonies were grown as described above for initial fatty acid screening.

GC analyses showed that almost all of the selected 72 strains of Z5627U5 transformed with pYRH55 produced more than 49% EPA of TFAs. Eleven strains (#1, #11, #15, #16, #20, #21, #30, #34, #51, #53 and #54) produced about 55.3%, 50.1%, 50.9%, 51.7%, 50.8%, 49.7%, 53.4%, 54.8%, 50.3%, 53.9% and 50.6% EPA of TFAs and were designated as Z6103, Z6104, Z6105, Z6106, Z6107, Z6108, Z6109, Z6110, Z6111, Z6112 and Z6113, respectively.

Knockout of the Lip7 locus in above strains Z6103 to Z6113 was not confirmed. The genotype of strains Z6109 and its ten siblings with respect to wild type *Y. lipolytica* ATCC #20362 was: Ura⁺, Pex3⁻, unknown 1⁻, unknown 7, unknown 3⁻, unknown 4⁻, YALI0E12947g⁻, unknown 6⁻, YALI0B21890g⁻, unknown 8⁻, unknown 10⁻, unknown 11⁻, unknown 17, unknown 13⁻, unknown 14⁻, unknown 15⁻, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M::Aco, FBAINm::EaD9eS/EaD8S::Lip2, DGAT2M::YID9::Lip1, GPDIN::YID9::Lip1, GPD::FmD12::Pex20, YAT1::FmD12::Oct, EXP1::FmD12S::Aco, GPDIN::FmD12::Pex16, EXP1::EgD5M::Pex16, FBAIN::EgD5SM::Pex20, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, EXP1::YICPT1::Oct, YAT1::MCS::Lip1, FBA::MCS::Lip1, EXP1::YIPCT::Pex16, YAT1::MaLPAAT1S::Pex16, ALK2LM1::MaLPAAT1S::Pex20, FBAINm::YILPAAT1::Lip1 (2 copies), YAT1::YIPDAT::Lip1 (2 copies), FBAINm::AtClo1S::Pex20.

Analysis of Total Lipid Content and Composition by Flask Assay

Cells of strains Z6109 and its siblings were grown and analyzed for total lipid content and fatty acid composition by the flask assay described above. Table 6 summarizes the DCW, the TFAs % DCW, the amount of each fatty acid as a weight percent of TFAs (% TFAs) and the EPA % DCW of strains from Z6103 to Z6113.

TABLE 6

Total Lipid Content and Composition in Strain Z6109 and Its Siblings by Flask Assay

| Strain | DCW (g/L) | TFAs % DCW | % TFAs 16:0 | 16:1 | 18:0 | 18:1 | LA | ALA | EDA | DGLA | ARA | ETrA | ETA | EPA | EPA % DCW | EPA Rate (g/L/h) |
|---|---|---|---|---|---|---|---|---|---|---|---|---|---|---|---|---|
| Z6103 | 4.4 | 51.1 | 2.2 | 0.8 | 2.0 | 5.5 | 14.3 | 0.5 | 3.7 | 5.7 | 1.4 | 0.6 | 3.0 | 52.0 | 26.6 | 0.0084 |
| Z6104 | 4.7 | 55.3 | 2.1 | 0.7 | 2.8 | 5.9 | 15.9 | 0.6 | 3.6 | 5.8 | 1.3 | 0.7 | 3.2 | 49.7 | 27.5 | 0.0093 |
| Z6105 | 4.7 | 55.9 | 2.0 | 0.7 | 2.7 | 5.9 | 16.0 | 0.6 | 3.7 | 5.8 | 1.3 | 0.7 | 3.2 | 49.7 | 27.8 | 0.0093 |
| Z6106 | 4.6 | 53.8 | 2.0 | 0.7 | 2.6 | 5.5 | 15.2 | 0.6 | 3.4 | 5.8 | 1.2 | 0.6 | 3.3 | 51.4 | 27.6 | 0.0091 |
| Z6107 | 4.7 | 54.2 | 2.1 | 0.7 | 2.8 | 5.8 | 16.0 | 0.7 | 3.6 | 5.8 | 1.2 | 0.6 | 3.2 | 50.0 | 27.1 | 0.0091 |
| Z6108 | 4.9 | 55.1 | 2.0 | 0.7 | 2.7 | 6.2 | 16.9 | 0.7 | 3.7 | 5.8 | 1.1 | 0.6 | 3.0 | 49.5 | 27.2 | 0.0095 |
| Z6109 | 4.5 | 54.2 | 2.2 | 0.6 | 2.4 | 4.8 | 15.9 | 0.6 | 3.9 | 5.5 | 1.5 | 0.7 | 2.9 | 51.7 | 28.0 | 0.0090 |
| Z6110 | 4.3 | 50.4 | 1.7 | 0.6 | 2.1 | 5.0 | 12.9 | 0.5 | 3.4 | 6.1 | 1.1 | 0.7 | 3.9 | 54.0 | 27.2 | 0.0083 |
| Z6111 | 4.3 | 53.2 | 2.5 | 0.9 | 2.5 | 6.5 | 16.5 | 0.6 | 3.8 | 5.3 | 1.5 | 0.7 | 2.7 | 48.4 | 25.7 | 0.0079 |
| Z6112 | 4.5 | 55.2 | 2.1 | 0.8 | 2.2 | 5.7 | 15.0 | 0.6 | 3.5 | 5.7 | 1.3 | 0.7 | 3.2 | 51.1 | 28.2 | 0.0091 |
| Z6113 | 4.9 | 54.9 | 1.9 | 0.7 | 2.6 | 5.9 | 15.5 | 0.7 | 3.9 | 5.8 | 1.4 | 0.7 | 3.0 | 49.7 | 27.3 | 0.0095 |

The results in Table 6 generally indicate that heterologous expression of AtClo1S in strain Z5627 raised oil production (i.e., TFAs % DCW) and the percentage of EPA in the total fatty acids of oil (i.e., EPA % TFAs). Specifically, while strain Z5627 yielded 52 TFAs % DCW and 49.3 EPA %

TFAs (Table 4), strains Z6103 to Z6113 had average TFAs % DCW of 53.9 and EPA % TFAs of 50.7 (Table 6).

Specific strains analyzed in Table 6 had significantly higher oil and EPA levels compared to Z5627. For example, strain Z6109 had 54.2 TFAs % DCW and 51.7 EPA % TFAs. Z6109 altogether exhibited a 9.4% increase in the total amount of EPA produced (28 EPA % DCW) compared to that produced by Z5627 (25.6 EPA % DCW).

Example 2

Generation of Strain Z6903 Producing at Least about 51.4% EPA of Total Fatty Acids with at Least about 49.1% Total Lipid Content and Reduced Sugar Alcohol By-Products This Example describes the generation of *Y. lipolytica* strain Z6903 through genetic modification of strain Z5585. The genetic modification entailed knocking out the endogenous *Y. lipolytica* gene SOU2, which encodes Sou2 sorbitol utilization protein. The genetic modification further entailed introducing expression cassettes encoding phospholipid:diacylglycerol acyltransferase (PDAT), delta-12 desaturase, and a DGLA synthase multizyme (delta-9 elongase fused to delta-8 desaturase). The development of strain Z6903 was required in order to develop strain Z9276, which is described below in Example 4.

FIG. 3B shows the modification steps and intermediate strains (Z5585U21 and Z5585K2U) used for generating strain Z6903. Strains Z5585U21 and Z5585K2U were generated as follows.

Generation of Strain Z5585U21

Construct pZKUM (above) was used to disrupt the URA3 gene in strain Z5585 that was previously introduced by the plasmid pZKMP-ML9DCB, which carries sequences allowing for expression of MaLPAAT1S, YID9 and YICPT1 (see U.S. Pat. Appl. Publ. No. 2012-0052537). A total of eight 5-FOA-resistant transformants were grown and identified to possess a $Ura^-$ phenotype. These transformants were grown as described above for initial fatty acid screening.

GC analyses showed the presence of 37.7% EPA in the TFAs of pZKUM-transformant strain #6 cells picked from an FOA plate. This transformant was designated as strain Z5585U21.

Generation of Strain Z5585K2U ($Sou2^-$)

Strain Z5585K2U was generated by knocking out the endogenous *Y. lipolytica* SOU2 gene, which encodes Sou2 sorbitol utilization protein, in strain Z5585U21.

The identification of the SOU2 gene as a genetic target to modify lipid production in *Y. lipolytica* is described below in Example 5. Briefly, during the construction of strain Z3041 (FIG. 8), which involved the genetic modification of strain Z1978, it was observed that strain Z3041 produced more DCW, more oil, and less by-products compared to its parent strain, Z2636. Genome walking and sequencing analyses showed that the promoter region of the SOU2 gene (locus YALI0D18964g, GenBank Accession No. XM_503010, FIG. 5) was disrupted in strain Z3041 by an insertion occurring within the promoter region of SOU2 (FIG. 5). Sorbitol is a sugar alcohol; other sugar alcohols such as mannitol and arabitol are produced as by-products in the *Y. lipolytica* strains disclosed herein to be engineered for enhanced lipid production.

Plasmid pZKSOU2-New (FIG. 4B, SEQ ID NO:4) was used to knock-out a large portion of the SOU2 gene in strain Z5585U21. Table 7 describes the components contained in pZKSOU2-New. This vector contains 5'- and 3'-homology arms (denoted as ySOU2-5' and ySOU2-3', respectively) containing sequences derived from the endogenous *Y. lipolytica* SOU2 locus. Stuffer sequence (non-SOU2 sequence) is located between these homology arms.

TABLE 7

Description of Plasmid pZKSOU2-New (SEQ ID NO: 4)

| RE Sites and Nucleotide Positions | Description of Fragment and Chimeric Gene Components |
|---|---|
| SphI/BsiWI (5289-1) | 1102-bp 5' portion of *Yarrowia* SOU2 locus (GenBank Accession No. XM_503010, labeled as ySOU2-5' in FIG. 4B) |
| EcoRI/SwaI (203-1076) | 873-bp 3' portion of *Yarrowia* SOU2 locus (GenBank Accession No. XM_503010, labeled as ySOU2-3' in FIG. 4B) |
| BsiWI/EcoRI (1-203) | 202-bp stuffer DNA, derived from *Yarrowia* ALK2 gene (GenBank Accession No. CR382132) |
| SwaI/PacI (1076-2573) | *Yarrowia* URA3 gene (GenBank Accession No. AJ306421) |

The knock-out strategy entailed a "pop-in/pop-out" process as delineated in the diagram and legend of FIG. 6. Briefly, the pop-in event occurred as a result of homologous recombination between the 5'-homology arm of pZKSOU2-New and corresponding sequence at the endogenous *Y. lipolytica* SOU2 locus. This particular integration event resulted in the juxtaposition of a mutated SOU2 allele with the wild type SOU2 allele, and was selected on the basis that pZKSOU2-New integration rendered the cells of strain Z5585U21 ($Ura^-$) to be $Ura^+$.

The pop-out event occurred as a result of homologous recombination between the 3'-homology arm of the integrated mutant allele and corresponding sequence at the adjacent endogenous *Y. lipolytica* SOU2 locus (FIG. 6, left-hand pop-out event). Since this pop-out event resulted in removal of the URA3 gene that had been introduced during pop-in, cells in which the pop-out event occurred leaving behind the mutant SOU2 allele could be selected on FOA plates (i.e., cells are $Ura^-$).

Plasmid pZKSOU2-New was used to transform Z5585U21. A total of 60 $Ura^+$ transformants were grown on MM plates lacking uracil. Polymerase chain reaction (PCR) amplification analyses indicated that transformants #26 and #28 had undergone recombination between the 5'-arm homologous sequences of pZSOU2-New and the endogenous SOU2 gene.

Strain #26 was picked, grown in liquid YPD media, and then plated on FOA plates to select for cells that subsequently became $Ura^-$ due to a pop-out event (FIG. 6). A total of 96 $Ura^-$ strains were analyzed by PCR amplification to determine which ones had undergone pop-out events involving recombination at the 3'-arm homology sequences which removed the pZKOSOU2-New backbone sequences (AmpR and URA3) thereby leaving behind a mutated SOU2 allele. This PCR analysis was necessary, since certain $Ura^-$ cells could alternatively have a wild type SOU2 allele if the pop-out recombination event occurred at the 5'-arm homologous sequence (FIG. 6). In 9 of the 96 $Ura^-$ strains, PCR analyses detected recombination at the 3'-arm homologous sequences indicative of a mutant SOU2 allele. Two of these 9 strains were designated as Z5585K2U1 and Z5585K2U2.

The final genotype of both strains Z5585K2U1 and Z5585K2U2 with respect to wild type *Y. lipolytica* ATCC #20362 is: $Ura^-$, $Pex3^-$, unknown $1^-$, unknown 7, unknown $3^-$, unknown $4^-$, $YALI0E12947g^-$, unknown $6^-$, $YALI0B21890g^-$, unknown $8^-$, unknown $10^-$, unknown $11^-$, unknown 17, unknown 13⁻, unknown 14⁻, Sou2⁻, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M::Aco, FBAINm::EaD9eS/EaD8S::Lip2, DGAT2M::YID9::Lip1, GPDIN::YID9::Lip1, GPD::FmD12::Pex20, YAT1::FmD12::Oct, EXP1::FmD12S::Aco, GPDIN::FmD12::Pex16, EXP1::EgD5M::Pex16, FBAIN::EgD5SM::Pex20, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, EXP1::YICPT1::Oct, YAT1::MCS::Lip1, FBA::MCS::Lip1, EXP1::YIPCT::Pex16, YAT1::MaLPAAT1S::Pex16, ALK2LM1::MaLPAAT1S::Pex20, FBAINm::YILPAAT1::Lip1 (2 copies), YAT1::YIPDAT::Lip1 (2 copies).

Strain Z5585K2U1 is herein referred to as Z5585K2U.

Generation of Strain Z6903

Plasmid pZKADn-SyP298F (FIG. 7A, SEQ ID NO:5) was generated to integrate gene cassettes for expressing PDAT (SEQ ID NO:15, PDAT with an extra alanine at position 2 compared to wild type YIPDAT), delta-12 desaturase (SEQ ID NO:13), and a DGLA synthase multizyme (SEQ ID NO:17, delta-9 elongase fused to delta-8 desaturase) into the alcohol dehydrogenase 3 (ADH3) locus (GenBank Accession No. AF175273) of strain Z5585K2U. Table 8 describes the components contained in pZKADn-SyP298F.

TABLE 8

Description of Plasmid pZKADn-SyP298F (SEQ ID NO: 5)

| RE Sites and Nucleotide Positions | Description of Fragment and Chimeric Gene Components |
|---|---|
| AscI/BsiWI (6032-5255) | 777-bp 5' portion of *Yarrowia* ADH3 gene (GenBank Accession No. AF175273, labeled as yADH-5' in FIG. 7A) |
| PacI/SphI (9510-8740) | 756-bp 3' portion of *Yarrowia* ADH3 gene (GenBank Accession No. AF175273, labeled as yADH-3' in FIG. 7A) |
| SwaI/BsiWI (2697-5255) | ALK2LM1::FmD12S::Erp, comprising:<br>ALK2LM1: *Y. lipolytica* ALK2 promoter plus N-terminal 66-bp coding region of *Y. lipolytica* ALK2 gene (U.S. Pat. Appl. Publ. No. 2012-0052537);<br>FmD12S: codon-optimized delta-12 desaturase (SEQ ID NO: 12) derived from *Fusarium moniliforme* (U.S. Pat. No. 7,504,259);<br>Erp: terminator sequence (SEQ ID NO: 6) from *Yarrowia* ERP gene (GenBank Accession No. XP_501960) |
| PmeI/SwaI (1-2697) | SPS19-P3::YIPDAT::Lip1, comprising:<br>SPS19-P3: SPS19 promoter (409-bp) of *Y. lipolytica* SPS19 gene (U.S. Appl. Publ. No. 2013-0089911);<br>YIPDAT: *Y. lipolytica* PDAT (SEQ ID NO: 14) (U.S. Pat. Appl. Publ. No. 2012-0052537);<br>Lip1: terminator sequence from *Yarrowia* LIP1 gene (GenBank Accession No. Z50020) |
| ClaI/PmeI (11611-1) | SPS19LM::E389D9eS/EgD8M::Glo, comprising:<br>SPS19LM: SPS19 promoter (900-bp) of *Y. lipolytica* SPS19 gene (U.S. Appl. Publ. No. 2013-0089911);<br>E389D9eS/EgD8M (SEQ ID NO: 16): gene fusion comprising a codon-optimized delta-9 elongase derived from *Eutreptiella* sp. CCMP389 (E389D9eS), a linker, and a codon-optimized mutant delta-8 desaturase derived from *Euglena gracilis* (EgD8M) (U.S. Pat. Appl. Publ. No. 2008-0254191);<br>Glo: terminator sequence (SEQ ID NO: 7) from *Yarrowia* glyoxalase (GLO) gene (GenBank Accession No. CR382130) |
| SalI/PacI (11161-9510) | *Yarrowia* URA3 gene (GenBank Accession No. AJ306421) |

The pZKADn-SyP298F plasmid was digested with AscI, and then used to transform strain Z5585K2U. The transformed cells were plated onto uracil-minus MM plates and maintained at 30° C. for 5 to 6 days. Single colonies were grown as described above for initial fatty acid screening.

GC analyses showed that 9 strains of Z5585K2U transformed with pZKADn-SyP298F produced more than 51.1% EPA of TFAs. These strains (#10, #14, #15, #61, #76, #80, #82, #83, #96) produced about 52.4%, 51.9%, 51.6%, 53.2%, 52.3%, 52.4%, 51.9%, 51.3% and 51.1% EPA of TFAs and were designated as Z6897, Z6898, Z6899, Z6900, Z6901, Z6902, Z6903, Z6904 and Z6905, respectively.

Knockout of ADH3 locus in above strains Z6897 to Z6905 was not confirmed. The genotype of strains Z6903 and its eight siblings with respect to wild type *Y. lipolytica* ATCC #20362 was: Ura⁺, Pex3⁻, unknown 1⁻, unknown 7, unknown 3⁻, unknown 4⁻, YALI0E12947g⁻, unknown 6⁻, YALI0B21890g⁻, unknown 8⁻, unknown 10⁻, unknown 11⁻, unknown 17, unknown 13⁻, unknown 14⁻, Sou2⁻, unknown 15⁻, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, SPS19LM::E389D9eS/EgD8M::Glo YAT1::EgD9eS/EgD8M::Aco, FBAINm::EaD9eS/EaD8S::Lip2, DGAT2M::YID9::Lip1, GPDIN::YID9::Lip1, GPD::FmD12::Pex20, YAT1::FmD12::Oct, EXP1::FmD12S::Aco, ALK2LM1::FmD12S::Erp, GPDIN::FmD12::Pex16, EXP1::EgD5M::Pex16, FBAIN::EgD5SM::Pex20, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, EXP1::YICPT1::Oct, YAT1::MCS::Lip1, FBA::MCS::Lip1, EXP1::YIPCT::Pex16, YAT1::MaLPAAT1S::Pex16, ALK2LM1::MaLPAAT1S::Pex20, FBAINm::YILPAAT1::Lip1 (2 copies), YAT1::YIPDAT::Lip1 (2 copies), SPS19-P3::YIPDAT::Lip1.

Analysis of Total Lipid Content and Composition by Flask Assay

Cells of strains Z6903 and its siblings were grown and analyzed for total lipid content and fatty acid composition by the flask assay described above. Table 9 summarizes the DCW, the TFAs % DCW, the amount of each fatty acid as a weight percent of TFAs (% TFAs) and the EPA % DCW of strains from Z6103 to Z6113.

TABLE 9

Total Lipid Content and Composition in Strain Z6903 and Its Siblings by Flask Assay

| Strain | DCW (g/L) | TFAs % DCW | % TFAs 16:0 | 16:1 | 18:0 | 18:1 | LA | ALA | EDA | DGLA | ARA | ETrA | ETA | EPA | EPA % DCW | EPA Rate (g/L/h) |
|---|---|---|---|---|---|---|---|---|---|---|---|---|---|---|---|---|
| Z6897 | 4.4 | 47.6 | 2.0 | 0.7 | 2.2 | 5.5 | 15.9 | 0.8 | 3.7 | 5.1 | 0.8 | 0.5 | 3.6 | 52.1 | 24.8 | 0.0077 |
| Z6898 | 4.1 | 41.0 | 1.9 | 0.6 | 2.5 | 5.5 | 16.4 | 0.8 | 4.0 | 5.0 | 0.8 | 0.6 | 3.4 | 50.9 | 20.9 | 0.0061 |
| Z6899 | 4.7 | 46.1 | 1.9 | 0.8 | 1.9 | 6.0 | 15.6 | 0.8 | 3.6 | 5.1 | 0.7 | 0.5 | 3.5 | 52.5 | 24.2 | 0.0081 |
| Z6900 | 4.8 | 46.0 | 1.7 | 0.7 | 2.0 | 5.4 | 15.2 | 0.7 | 3.9 | 5.6 | 0.8 | 0.6 | 4.0 | 52.3 | 24.0 | 0.0083 |
| Z6901 | 4.9 | 48.7 | 2.0 | 0.7 | 2.3 | 5.9 | 16.3 | 0.8 | 3.9 | 5.0 | 0.9 | 0.5 | 3.6 | 51.2 | 24.9 | 0.0087 |
| Z6902 | 4.6 | 50.9 | 2.1 | 0.7 | 2.5 | 6.0 | 16.8 | 0.9 | 3.8 | 4.9 | 0.8 | 0.5 | 3.5 | 50.6 | 25.7 | 0.0084 |
| Z6903 | 4.9 | 49.1 | 2.0 | 0.7 | 2.2 | 5.7 | 16.4 | 0.8 | 3.8 | 5.0 | 0.8 | 0.5 | 3.6 | 51.4 | 25.2 | 0.0089 |
| Z6904 | 4.5 | 48.2 | 2.1 | 0.7 | 2.3 | 5.9 | 16.2 | 0.8 | 3.8 | 5.0 | 0.8 | 0.6 | 3.5 | 51.1 | 24.6 | 0.0079 |
| Z6905 | 4.8 | 52.8 | 2.0 | 0.7 | 2.7 | 6.3 | 17.6 | 0.9 | 3.7 | 4.7 | 0.7 | 0.4 | 3.2 | 50.0 | 26.4 | 0.0091 |

Table 9 shows that in strain Z6903, DCW was 4.9 g/L, TFAs % DCW was 49.1, EPA % TFAs was 51.4, and EPA % DCW was 25.2, which was the third highest EPA % DCW measurement among the analyzed strains. In strain Z6905, DCW was 4.8 g/L, TFAs % DCW was 52.8, EPA % TFAs was 50.0, and EPA % DCW was 26.4, which was the highest EPA % DCW measurement among the analyzed strains.

Strain Z6903 was further analyzed to determine the levels of the sugar alcohol by-products arabitol, mannitol and erythritol (Table 10). This analysis was also made with strain Z6109 (Example 1).

TABLE 10

Sugar Alcohols Produced by Strains Z6109 and Z6903

| | Z6109 | Z6903 |
|---|---|---|
| SOU2 gene | + | − |
| Arabitol (g/L) | 4.9 | 0.0 |
| Mannitol (g/L) | 3.5 | 0.0 |
| Erythritol (g/L) | 0.8 | 2.9 |
| Total sugar alcohols (g/L) | 9.2 | 2.9 |

The results in Table 10 indicate that strain Z6903 produced no mannitol or arabitol by-products, suggesting that the Sou2 protein is essential for mannitol and arabitol biosynthesis in *Y. lipolytica*. Also, compared to strain Z6109, strain Z6903 produced about 68% less total sugar alcohol by-products. These results indicate that down-regulation of SOU2 expression in *Y. lipolytica* significantly decreases the level of sugar alcohol by-product production.

Example 3

Generation of Strain Z7418 Producing at Least about 49.8% EPA of Total Fatty Acids with at Least about 49.3% Total Lipid Content This Example describes the generation of *Y. lipolytica* strain Z7418 through genetic modification of strain Z6903. The genetic modification entailed introducing expression cassettes encoding delta-8 desaturase, malonyl-CoA synthetase (MCS), and acyl-CoA:lysophosphatidic acid acyltransferase (LPAAT). The development of strain Z7418 was required in order to develop strain Z9276, which is described below in Example 4.

FIG. 3B shows the modification steps and intermediate strain (Z6903U) used for generating strain Z7418. Strain Z6903U was generated as follows.

Generation of Strain Z6903U

Construct pZKUM (above) was used to disrupt the URA3 gene in strain Z6903 that was introduced by the plasmid pZKADn-SyP298F (above). A total of eight 5-FOA-resistant transformants were grown and identified to possess a $Ura^-$ phenotype. Individual transformants were grown as described above for initial fatty acid screening.

GC analyses showed the presence of 35.0%, 32.7% and 37.7% EPA in the TFAs of pZKUM-transformant strains #5, #6 and #7 picked from an FOA plate, which were designated as Z6903U5, Z6903U6 and Z6903U7, respectively. These three transformants were collectively designated as strain Z6903U.

Generation of Strain Z7418

Plasmid pZK16-MyL8N was used to integrate gene cassettes for expressing a synthetic mutant delta-8 desaturase derived from *E. gracilis* (YAT1::EgD8M::Pex20; EgD8M is SEQ ID NO:19), a codon-optimized malonyl-CoA synthetase derived from *Rhizobium leguminosarum* bv. viciae 3841 (FBA::MCS::Lip1; MCS is SEQ ID NO:21), and a *Y. lipolytica* acyl-CoA:lysophosphatidic acid acyltransferase (YAT1::YlLPAAT1::Lip1; YlLPAAT1 is SEQ ID NO:23) into the YALI0B14795p locus (GenBank Accession No. XM_500900) of strain Z6903U. The construction of plasmid pZK16-MyL8N has been described (U.S. Pat. Appl. Publ. No. 2012-0052537, see Table 11 therein, which is incorporated herein by reference).

The pZK16-MyL8N plasmid was digested with AscI, and then used to transform strain Z6903U5. The transformed cells were plated onto uracil-minus MM plates and maintained at 30° C. for 5 to 6 days. Single colonies were grown as described above for initial fatty acid screening.

GC analyses showed that almost all of the selected 96 strains of Z6903U5 transformed with pZK16-MyL8N produced more than 50.0% EPA of TFAs. Ten strains (#8, #9, #34, #40, #43, #58, #59, #70, #79, #80) produced about 52.1%, 50.3%, 51.5%, 51.1%, 53.5%, 51.4%, 50.8%, 52.2%, 51.2% and 51.6% EPA of TFAs and were designated as Z7416, Z7417, Z7418, Z7419, Z7420, Z7421, Z7422, Z7423, Z7424 and Z7425, respectively.

Knockout of the YALI0B14795p locus in above strains Z7416 to Z7425 was not confirmed. The genotype of strains Z7418 and its nine siblings with respect to wild type *Y. lipolytica* ATCC #20362 was: $Ura^+$, $Pex3^-$, unknown $1^-$, unknown 7, unknown $3^-$, unknown $4^-$, $YALI0E12947g^-$, unknown $6^-$, $YALI0B21890g^-$, unknown $8^-$, unknown $10^-$, unknown $11^-$, unknown 17, unknown $13^-$, unknown $14^-$, $Sou2^-$, unknown $15^-$, unknown $16^-$, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::EgD8M::Pex20, EXP1::EgD8M::Pex16, FBAIN::EgD8M::Lip1, YAT1::EgD8M::Pex20, GPD::EaD8S::Pex16 (2 copies), YAT1::E389D9eS/EgD8M::Lip1, SPS19LM::E389D9eS/EgD8M::Glo YAT1::EgD9eS/EgD8M::Aco, FBAINm::EaD9eS/EaD8S::Lip2, DGAT2M::YID9::Lip1, GPDIN::YID9::Lip1, GPD::FmD12::Pex20, YAT1::FmD12::Oct, EXP1::FmD12S::Aco, ALK2LM1::FmD12S::Erp, GPDIN::FmD12::Pex16, EXP1::EgD5M::Pex16, FBAIN::EgD5SM::Pex20, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, EXP1::YICPT1::Oct, YAT1::MCS::Lip1, FBA::MCS::Lip1 (2 copies), EXP1::YIPCT::Pex16, YAT1::MaLPAAT1S::Pex16, ALK2LM1::MaLPAAT1S::Pex20, FBAINm::YILPAAT1::Lip1 (2 copies), YAT1::YILPAAT1::Lip1, YAT1::YIPDAT::Lip1 (2 copies), SPS19-P3::YIPDAT::Lip1.

Analysis of Total Lipid Content and Composition by Flask Assay

Cells of strains Z7418 and its siblings were grown and analyzed for total lipid content and fatty acid composition by the flask assay described above. Table 11 summarizes the DCW, the TFAs % DCW, the amount of each fatty acid as a weight percent of TFAs (% TFAs) and the EPA % DCW of strains from Z7416 to Z7425.

TABLE 11

Total Lipid Content and Composition in Strain Z7418 and Its Siblings by Flask Assay

| | DCW | TFAs % | % TFAs | | | | | | | | | | | | EPA % | EPA Rate |
|---|---|---|---|---|---|---|---|---|---|---|---|---|---|---|---|---|
| Strain | (g/L) | DCW | 16:0 | 16:1 | 18:0 | 18:1 | LA | ALA | EDA | DGLA | ARA | ETrA | ETA | EPA | DCW | (g/L/h) |
| Z7416 | 5.7 | 48.7 | 1.9 | 0.7 | 2.4 | 5.8 | 16.5 | 0.9 | 3.7 | 4.6 | 1.1 | 0.8 | 3.8 | 50.0 | 24.3 | 0.0099 |
| Z7417 | 5.9 | 52.2 | 2.0 | 0.8 | 2.2 | 7.2 | 17.5 | 1.0 | 4.1 | 4.6 | 0.9 | 0.6 | 3.5 | 47.7 | 24.9 | 0.0106 |
| Z7418 | 5.9 | 49.3 | 1.9 | 0.7 | 2.2 | 6.0 | 16.4 | 0.9 | 3.8 | 4.7 | 1.0 | 0.8 | 3.8 | 49.8 | 24.6 | 0.0103 |
| Z7419 | 5.7 | 49.8 | 1.9 | 0.7 | 2.3 | 6.1 | 16.7 | 0.9 | 3.8 | 4.5 | 1.0 | 0.8 | 3.7 | 49.7 | 24.7 | 0.0100 |
| Z7420 | 5.2 | 51.1 | 2.0 | 0.8 | 2.4 | 6.9 | 17.4 | 1.0 | 4.1 | 4.3 | 0.9 | 0.7 | 3.4 | 48.5 | 24.8 | 0.0092 |
| Z7421 | 5.0 | 48.8 | 1.9 | 0.6 | 2.4 | 5.7 | 16.2 | 0.9 | 3.7 | 4.5 | 1.0 | 0.8 | 3.7 | 50.5 | 24.6 | 0.0088 |
| Z7422 | 5.2 | 52.5 | 2.1 | 0.8 | 2.3 | 6.9 | 17.2 | 0.9 | 4.0 | 4.4 | 0.9 | 0.7 | 3.3 | 48.4 | 25.4 | 0.0094 |
| Z7423 | 6.2 | 48.2 | 2.0 | 0.8 | 2.3 | 6.8 | 17.5 | 1.0 | 3.8 | 4.5 | 1.0 | 0.8 | 3.7 | 48.2 | 23.2 | 0.0102 |
| Z7424 | 5.9 | 49.3 | 1.9 | 0.7 | 2.3 | 5.9 | 16.6 | 0.9 | 3.7 | 4.6 | 1.0 | 0.7 | 3.8 | 49.9 | 24.6 | 0.0103 |
| Z7425 | 6.2 | 48.7 | 2.0 | 0.7 | 2.4 | 6.0 | 16.7 | 1.0 | 3.6 | 4.7 | 0.9 | 0.6 | 3.8 | 49.7 | 24.2 | 0.0107 |

Table 11 shows that in strain Z7418, DCW was 5.9 g/L, TFAs % DCW was 49.8, EPA % TFAs was 49.3, and EPA % DCW was 24.6.

Example 4

Generation of Strain Z9276 Producing at Least about 57.5% EPA of Total Fatty Acids with at Least about 56.9% Total Lipid Content This Example describes the generation of *Y. lipolytica* strain Z9276 through genetic modification of strain Z7418. The genetic modification entailed introducing an expression cassette encoding a mutant acyl CoA: lysophosphatidylcholine acyltransferase (LPCAT). The construction and analysis of this and other mutant LPCATs is described in Examples 6-9.

FIG. 3B shows the modification steps and intermediate strain (Z7418U) used for generating strain Z9276. Strain Z7418U was generated as follows.

Generation of Strain Z7418U

Construct pZKUM (above) was used to disrupt the URA3 gene in strain Z7418 that was introduced by the plasmid pZK16-MyL8N (above). A total of twenty-four 5-FOA-resistant transformants were grown and identified to possess a Ura⁻ phenotype. These transformants were grown as described above for initial fatty acid screening.

GC analyses showed the presence of 35.7%, 36.1%, 32.3% 35.4 and 33.6% EPA in the TFAs of B group pZKUM-transformant strains #2, #3, #6, #7 and #8 picked from an FOA-plate, which were designated as Z7418BU1, Z7418BU2, Z7418BU3, Z7418BU4 and Z7418BU5, respectively. GC analyses also showed the presence of 35.9% EPA in the TFAs of C group pZKUM-transformant strain #6 picked from an FOA-plate, which was designated as Z74180U1. GC analyses also showed the presence of 24.2%, 34.9% and 34.0% EPA in the TFAs of D group pZKUM-transformant strains #3, #4 and #7 picked from an FOA-plate, which were designated as Z7418DU1, Z7418DU2 and Z7418DU3, respectively.

Generation of Strain Z9276

Plasmid pZKMPn-YD58 (FIG. 7B, SEQ ID NO:24) was generated to integrate a gene cassette for expressing a double-mutant *Y. lipolytica* acyl CoA:lysophosphatidylcholine acyltransferase (YILPCAT [M136S/T389A], SEQ ID NO:26) into the D-arabinitol 2-dehydrogenase locus (GenBank Accession No. XP_504895) of strain Z7418U. Table 12 describes the components contained in pZKMPn-YD58.

TABLE 12

Description of Plasmid pZKMPn-YD58 (SEQ ID NO: 24)

| RE Sites and Nucleotide Positions | Description of Fragment and Chimeric Gene Components |
|---|---|
| AscI/BsiWI (696-1) | 695-bp 5' portion of D-arabinitol 2-dehydrogenase locus (GenBank Accession No. XP_504895, labeled as yM1DP-5' in FIG. 7B) |
| PacI/SphI (4021-3404) | 797-bp 3' portion of D-arabinitol 2-dehydrogenase locus (GenBank Accession No. XP_504895, labeled as yM1DP-3' in FIG. 7B) |
| ClaI/SwaI (6302-8930) | YAT1::YILPCAT (M136S/T389A)::Lip1, comprising: YAT1: *Y. lipolytica* YAT1 promoter (U.S. Pat. Appl. Publ. No. 2010-0068789); YILPCAT: double mutant (M136S/T389A) (SEQ ID NO: 25) of *Y. lipolytica* acyl-CoA: lysophosphatidylcholine acyltransferase (U.S. Appl. No. 61/661,623, which is incorporated herein by reference); Lip1: Lip1 terminator sequence from *Yarrowia* LIP1 gene (GenBank Accession No. Z50020) |
| SalI/PacI (5852-4201) | *Yarrowia* URA3 gene (GenBank Accession No. AJ306421) |

The pZKMPn-YD58 plasmid was digested with AscI, and then used to transform strain Z7418BU1. The transformed cells were plated onto uracil-minus MM plates and maintained at 30° C. for 5 to 6 days. Single colonies were grown as described above for initial fatty acid screening.

GC analyses showed that nine of the selected 48 strains of Z7418BU1 transformed with pZKMPn-YD58 produced more than 55.0% EPA of TFAs. These nine strains (#11, #13, #14, #15, #24, #25, #33, #37, #48) produced about 55.9%, 55.9%, 55.0%, 56.3%, 56.1%, 57.1%, 55.3%, 55.1% and 56.1% EPA of TFAs and were designated as Z9256, Z9257, Z9258, Z9259, Z9260, Z9261, Z9262, Z9263 and Z9264, respectively.

GC analyses showed that eleven of the selected 60 strains of Z7418BU2 transformed with pZKMPn-YD58 produced more than 54.7% EPA of TFAs. These eleven strains (#1, #5, #8, #10, #18, #26, #30, #35, #42, #45, #54) produced about 56.5%, 54.8%, 57.9%, 56.1%, 56.1%, 57.3%, 58.8%, 54.9%. 54.7%, 55.4% and 55.5% EPA of TFAs and were designated as Z9265, Z9266, Z9267, Z9268, Z9269, Z9270, Z9271, Z9272, Z9273, Z9274 and Z9275, respectively.

GC analyses showed that four of the selected 44 strains of Z7418DU3 transformed with pZKMPn-YD58 produced more than 55.8% EPA of TFAs. These four strains (#10, #12, #15, #16) produced about 56.5%, 55.8%, 55.9% and 56.2% EPA of TFAs and were designated as Z9276, Z9277, Z9278 and Z9279, respectively.

Knockout of the D-arabinitol 2-dehydrogenase locus in above strains Z9256 to Z9279 was not confirmed. The genotype of these strains, including Z9276, with respect to wild type *Y. lipolytica* ATCC #20362 was: $Ura^+$, $Pex3^-$, unknown $1^-$, unknown $2^-$, unknown $3^-$, unknown $4^-$, YALI0E12947g$^-$, unknown $6^-$, YALI0B21890g$^-$, unknown $8^-$, unknown $10^-$, unknown $11^-$, unknown $12^-$, unknown $13^-$, unknown $14^-$, $Sou2^-$, unknown $15^-$, unknown $16^-$, unknown $17^-$, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::EgD8M::Pex20, EXP1::EgD8M::Pex16, FBAIN::EgD8M::Lip1, YAT1::EgD8M::Pex20, GPD::EaD8S::Pex16 (2 copies), YAT1::E389D9eS/EgD8M::Lip1, SPS19LM::E389D9eS/EgD8M::Glo YAT1::EgD9eS/EgD8M::Aco, FBAINm::EaD9eS/EaD8S::Lip2, DGAT2M::YlD9::Lip1, GPDIN::YlD9::Lip1, GPD::FmD12::Pex20, YAT1::FmD12::Oct, EXP1::FmD12S::Aco, ALK2LM1::FmD12S::Erp, GPDIN::FmD12::Pex16, EXP1::EgD5M::Pex16, FBAIN::EgD5SM::Pex20, EXP1::EgD5SM::Lip1, YAT1::EaD5SM::Oct, FBAINm::PaD17::Aco, EXP1::PaD17::Pex16, YAT1::PaD17S::Lip1, YAT1::YlCPT1::Aco, EXP1::YlCPT1::Oct, YAT1::MCS::Lip1, FBA::MCS::Lip1 (2 copies), EXP1::YlPCT::Pex16, YAT1::MaLPAAT1S::Pex16, ALK2LM1::MaLPAAT1S::Pex20, FBAINm::YlLPAAT1::Lip1 (2 copies), YAT1::YlLPAAT1::Lip1, YAT1::YlPDAT::Lip1 (2 copies), SPS19-P3::YlPDAT::Lip1, YAT1::YlLPCAT(M136S/T389A)::Lip1.

Analysis of Total Lipid Content and Composition by One-Step Flask Assay

Cells of strains Z9256 to Z9279, including Z9276, were grown and analyzed for total lipid content and fatty acid composition by the "one-step" flask assay, which is described as follows:

One loop of freshly streaked cells was inoculated into 3 mL One-Step Flask medium (recipe described below) and grown overnight at 250 rpm and 30° C. The $OD_{600\ nm}$ of the culture was measured and an aliquot of cells from the culture was added to a final $OD_{600\ nm}$ of 0.25 in 15 mL of One-Step Flask medium in a 125-mL flask. After one day in a shaker incubator at 250 rpm and at 30° C., 10 mL of a high glucose medium (80 g/L glucose, 1.9 g/L $KH_2PO_4$, 6.3 g/L $K_2HPO_4$, 8.4 g/L $NaHCO_3$, pH 7.2) was added into the same flask. After 5 days in a shaker incubator at 250 rpm and at 30° C., a 1-mL aliquot was used for fatty acid analysis and 10 mL dried for dry cell weight determination. The fatty acid and DCW analyses were performed as described above.

One-Step Flask Assay Media:

0.5 g/L urea, 2.5 g/L Yeast extract, 3.0 g/L $KH_2PO_4$, 1.7 g/L $Na_2PO_4.12H_2O$, 20 g/L D-glucose, 0.2 ml/L trace metal solution (100×), 0.25 g/L $MgSO_4.7H_2O$, 0.15 mg/L thiamine HCl.

Trace Metals Solution (100×):

10 g/L citric acid, 1.5 g/L $CaCl_2.2H_2O$, 10 g/L $FeSO_4.7H_2O$, 0.39 g/L $ZnSO_4.7H_2O$, 0.38 g/L $CuSO_4.5H_2O$, 0.2 g/L $CoCl_2.6H_2O$, 0.3 g/L $MnCl_2$. $4H_2O$.

Table 13 summarizes the DCW, the TFAs % DCW, the amount of each fatty acid as a weight percent of TFAs (% TFAs) and the EPA % DCW of strains from Z9256 to Z9279.

TABLE 13

Total Lipid Content and Composition in Strains Z9256 to Z9279, Including Z9276, by Flask Assay

| Strain | DCW (g/L) | TFAs % DCW | % TFAs[a] 16:0 | 16:1 | 18:0 | 18:1 | LA | ALA | EDA | DGLA | ARA | ETrA | ETA | EPA | EPA % DCW | EPA Rate (g/L/h) |
|---|---|---|---|---|---|---|---|---|---|---|---|---|---|---|---|---|
| Z9256 | 7.1 | 61.3 | 2.1 | 0.7 | 2.0 | 7.3 | 14.3 | 0.3 | 4.9 | 5.3 | 1.4 | 0.5 | 2.4 | 52.9 | 32.4 | 0.0165 |
| Z9257 | 7.0 | 61.0 | 1.9 | 0.6 | 2.0 | 7.3 | 14.4 | 0.3 | 4.8 | 5.3 | 1.4 | 0.6 | 2.6 | 52.7 | 32.2 | 0.0162 |
| Z9258 | 7.1 | 61.0 | 1.9 | 0.6 | 2.0 | 7.5 | 15.8 | 0.4 | 4.9 | 5.0 | 1.3 | 0.6 | 2.6 | 51.2 | 31.2 | 0.0158 |
| Z9259 | 7.0 | 61.2 | 2.0 | 0.6 | 2.0 | 7.2 | 13.5 | 0.3 | 4.8 | 5.5 | 1.5 | 0.5 | 2.4 | 53.9 | 33.0 | 0.0164 |
| Z9260 | 7.1 | 61.5 | 2.1 | 0.7 | 2.1 | 7.6 | 14.9 | 0.3 | 5.0 | 5.2 | 1.4 | 0.5 | 2.4 | 51.9 | 31.9 | 0.0161 |
| Z9261 | 6.3 | 62.0 | 1.9 | 0.6 | 1.9 | 7.9 | 13.8 | 0.3 | 4.9 | 5.1 | 1.4 | 0.5 | 2.3 | 53.5 | 33.2 | 0.0150 |
| Z9262 | 7.1 | 61.2 | 2.0 | 0.6 | 2.0 | 7.7 | 15.0 | 0.4 | 5.0 | 5.3 | 1.3 | 0.5 | 2.5 | 51.9 | 31.8 | 0.0162 |
| Z9263 | 7.3 | 59.7 | 2.0 | 0.7 | 2.0 | 7.4 | 14.7 | 0.4 | 4.9 | 5.3 | 1.3 | 0.5 | 2.5 | 52.5 | 31.4 | 0.0163 |
| Z9264 | 5.8 | 49.5 | 2.3 | 0.8 | 1.7 | 6.8 | 13.8 | 0.5 | 4.2 | 5.3 | 0.9 | 0.7 | 4.3 | 51.7 | 25.6 | 0.0106 |
| Z9265 | 5.1 | 50.6 | 1.9 | 0.8 | 1.3 | 5.6 | 10.2 | 0.3 | 3.6 | 4.7 | 1.1 | 0.7 | 2.7 | 60.0 | 30.4 | 0.0109 |
| Z9266 | 6.7 | 62.1 | 2.2 | 0.8 | 2.0 | 7.5 | 14.9 | 0.5 | 4.7 | 4.7 | 0.9 | 0.5 | 2.8 | 52.2 | 32.4 | 0.0155 |
| Z9267 | 6.2 | 53.3 | 2.4 | 0.9 | 1.9 | 5.3 | 11.3 | 0.4 | 3.6 | 4.4 | 1.2 | 0.7 | 2.4 | 57.7 | 30.8 | 0.0135 |
| Z9268 | 6.2 | 58.5 | 1.7 | 0.7 | 1.8 | 6.9 | 13.2 | 0.4 | 4.3 | 4.8 | 0.9 | 0.7 | 3.4 | 54.4 | 31.8 | 0.0141 |
| Z9269 | 5.9 | 56.1 | 1.7 | 0.7 | 1.7 | 6.9 | 13.4 | 0.5 | 4.3 | 4.8 | 0.9 | 0.6 | 3.3 | 54.5 | 30.6 | 0.0130 |
| Z9270 | 5.7 | 52.7 | 2.0 | 0.7 | 1.7 | 5.9 | 12.2 | 0.4 | 4.1 | 4.0 | 1.0 | 0.7 | 2.4 | 57.6 | 30.3 | 0.0124 |
| Z9271 | 5.7 | 51.1 | 2.1 | 0.8 | 1.7 | 4.5 | 8.8 | 0.2 | 3.3 | 4.3 | 1.3 | 0.7 | 2.2 | 62.2 | 31.8 | 0.0129 |
| Z9272 | 6.1 | 56.8 | 1.7 | 0.7 | 1.7 | 7.0 | 12.9 | 0.4 | 4.3 | 4.8 | 0.9 | 0.7 | 3.4 | 54.5 | 31.0 | 0.0135 |
| Z9273 | 5.8 | 56.2 | 2.0 | 0.8 | 1.9 | 6.8 | 11.2 | 0.3 | 4.2 | 5.0 | 1.0 | 0.6 | 3.0 | 56.8 | 31.9 | 0.0133 |

TABLE 13-continued

Total Lipid Content and Composition in Strains Z9256 to Z9279, Including Z9276, by Flask Assay

| Strain | DCW (g/L) | TFAs % DCW | % TFAs[a] 16:0 | 16:1 | 18:0 | 18:1 | LA | ALA | EDA | DGLA | ARA | ETrA | ETA | EPA | EPA % DCW | EPA Rate (g/L/h) |
|---|---|---|---|---|---|---|---|---|---|---|---|---|---|---|---|---|
| Z9274 | 6.1 | 56.7 | 1.7 | 0.7 | 1.7 | 7.1 | 12.7 | 0.4 | 4.2 | 4.9 | 0.9 | 0.6 | 3.3 | 55.5 | 31.4 | 0.0137 |
| Z9275 | 6.2 | 57.0 | 1.7 | 0.7 | 1.7 | 6.9 | 12.8 | 0.4 | 4.3 | 4.9 | 1.0 | 0.7 | 3.4 | 54.5 | 31.1 | 0.0138 |
| Z9276 | 6.1 | 56.9 | 1.8 | 0.7 | 1.8 | 6.8 | 10.7 | 0.2 | 4.3 | 5.7 | 1.7 | 0.5 | 2.5 | 57.5 | 32.7 | 0.0143 |
| Z9277 | 6.3 | 57.6 | 1.7 | 0.6 | 1.7 | 7.0 | 13.6 | 0.3 | 5.0 | 5.2 | 1.6 | 0.7 | 2.6 | 53.9 | 31.0 | 0.0140 |
| Z9278 | 6.0 | 56.0 | 1.7 | 0.7 | 1.6 | 7.1 | 14.0 | 0.3 | 4.7 | 5.3 | 1.6 | 0.5 | 2.4 | 53.7 | 30.0 | 0.0129 |
| Z9279 | 5.7 | 60.9 | 2.0 | 0.8 | 1.7 | 7.3 | 13.7 | 0.4 | 4.9 | 4.7 | 1.8 | 0.5 | 1.8 | 53.7 | 32.7 | 0.0133 |
| avg | 6.3 | 57.5 | 1.9 | 0.7 | 1.8 | 6.9 | 13.2 | 0.4 | 4.5 | 5.0 | 1.2 | 0.6 | 2.7 | 54.6 | 31.4 | 0.0142 |

[a]GLA was not detected in the oil produced by any of strains Z9256-Z9279.

Table 13 shows that with the exception of Z9264, all of the strains tested produced more than 30.0% EPA as DCW. The EPA profiles in strains Z9256, Z9259 and Z9276 were notable and are summarized as follows. In strain Z9256, TFAs % DCW was 61.3%, EPA % TFAs was 52.9%, and EPA % DCW was 32.4% with an EPA productivity of 0.0165 g/L/h. In strain Z9259, TFAs % DCW was 61.2%, EPA % TFAs was 53.9%, and EPA % DCW was 33.0% with an EPA productivity of 0.0164 g/L/h. In strain Z9276, TFAs % DCW was 56.9%, EPA % TFAs was 57.5%, and EPA % DCW was 32.7% with an EPA productivity of 0.0143 g/L/h.

The average oil content on a dry cell weight basis in the strains listed in Table 13 was 57.5% (TFAs % DCW). This average oil content is higher than the oil content of strain Z5585 (56.6%, Table 4) from which the strains in Table 13 were derived. More notably, the average EPA content in the total fatty acids of the oil (EPA % TFAs) in the strains in Table 13 was 54.6%, which was about 10.5% greater than the same measurement for Z5585 (49.4%, Table 4). This increase in the EPA content in the total fatty acids of the oil, while maintaining the total amount of oil produced relative to Z5585, resulted in a higher average amount of EPA on a dry cell weight basis (31.4%) in the strains of Table 13 compared to Z5585 (28%, Table 4). This represented an increase of about 12.1%, which is consistent with the ~10.5% increase observed with oil content.

Several strains in Table 13 exhibited significant increases in oil and EPA content relative to strain Z5585. For example, the total oil content (TFAs % DCW) of strains Z9256 and Z9259 increased by about 8.3% and 8.1%, respectively, compared to the total oil content in strain Z5585 (Table 4). The EPA content in the total fatty acids of the oil (EPA % TFAs) in strains Z9256 and Z9259 was increased by about 7.1% and 9.1% compared to the same measurement in Z5585 (Table 4). These robust increases in the oil content and EPA content in the total fatty acids of the oil resulted in increases of about 15.7% and 17.9% in the total EPA content (EPA % DCW) of strains Z9256 and Z9259, respectively, compared to the total EPA content of Z5585 (Table 4).

Another strain in Table 13, Z9276, exhibited a marginal increase in oil content compared to Z5585, but had a 16.4% increase in EPA content in the total fatty acids of the oil (EPA % TFAs) compared to the same measurement in Z5585 (Table 4). This substantial increase in EPA % TFAs resulted in an increase of about 16.8% in the total EPA content (EPA % DCW) of strain Z9276 compared to the total EPA content of Z5585 (Table 4).

The genetic modifications used to produce the strains in Table 13 from strain Z5585 (Table 4) thus resulted in total oil contents (TFAs % DCW) that were mostly similar to or greater than the total oil content of Z5585. More significantly, this maintenance or increase in total oil content was not coupled to a decrease in the EPA content in the total fatty acids of the oil (EPA % TFAs), which has generally been a problem in previous efforts to increase total EPA production. This previous problem is reflected in the data in Table 4, for example, which shows that increases in oil content (TFAs % DCW) through other genetic modifications generally led to decreases in the EPA content in the total fatty acids of the oil (EPA % TFAs). Thus, previous increases in total EPA content (EPA % DCW) were driven largely in part by increasing total oil production. The strains in Table 13 on the other hand exhibited increased total EPA content (EPA % DCW) that was driven in large part by increasing EPA content in the total fatty acids of the oil while maintaining or increasing total oil content.

It was notable that almost all the strains in Table 13 had very low levels of stearic acid as a percentage of total fatty acids in the oil (18:0% TFAs). Specifically, with the exception of strain Z9261, all the strains had 2.0% or less stearic acid by weight of total fatty acids. The average level for all the strains was 1.8% stearic acid.

The average dry cell weight of the strains in Table 13 (6.3 g/L) was substantially increased compared to the dry cell weights of strain Z5585 (4.6 g/L) and the other strains listed in Table 4. This represents an average increase of about 37% compared to the dry cell weight of Z5585. Certain individual strains in Table 13, such as Z9256, Z9259 and Z9263, exhibited increases in dry cell weight of about 54.3%, 52.2% and 58.7%, respectively, compared to Z5585.

In flask assays, previous strain Z5567 (Table 4) was shown to produce about 0.45 g organic acids/g DCW, and about 0.50 g sugar alcohol/g DCW by-products. Strain Z9276 on the other hand produced 0.27 g organic acids/g DCW, and 0.18 g sugar alcohol/g DCW. Given the increased production of EPA in strain Z9276 (Table 13) versus that of Z5567 (Table 4), and the decreased production of by-products by Z9276, it is apparent that Z9276 has enhanced carbon flux toward EPA production.

In summary, the genetic modifications employed in Examples 2-4 to develop the strains of Table 13 from strain Z5585 were as follows. In Example 2, Z5585 was first modified to down-regulate expression of the Sou2 protein to yield strain Z5585K2U. Gene cassettes for over-expressing PDAT, delta-12 desaturase and a DGLA synthase multizyme were then introduced to yield strain Z6903. In Example 3, gene cassettes were introduced for over-expressing delta-8 desaturase, MCS and LPAAT, thereby yielding strain Z7418. Finally, in the present Example, a gene cassette for over-expressing a mutant LPCAT was introduced to yield the strains of Table 13. All except one of these strains can produce an oil containing at least 30 percent EPA measured as a weight percent of dry cell weight.

Example 5

Identification of the SOU2 Gene as a Genetic Target to Modify Lipid Production and Sugar Alcohol Production in *Y. lipolytica*

This Example describes that the *Y. lipolytica* SOU2 gene, which encodes Sou2 sorbitol utilization protein, can regulate the level of lipids and certain sugar alcohols in *Y. lipolytica*. Specifically, it was shown that disrupting the SOU2 gene in a *Y. lipolytica* strain increased the amount of oil, and decreased the amount of arabitol and mannitol, produced by the strain.

The SOU2 gene was identified as a genetic target to modify lipid production in *Y. lipolytica* during the development of strain Z3041 from strain Z1978. The steps involved in this process involved intermediate strains Z1978U, Z2636 and Z2636U (FIG. 8). The development of *Y. lipolytica* strain Z1978U is described in U.S. Pat. Appl. Publ. No. 2012-0052537, which is incorporated herein by reference.

Strain Z2636 was produced by transforming Z1978U with plasmid pZKT2-ML9DCB (SEQ ID NO:27, FIG. 9A), which contains cassettes for expressing *Y. lipolytica* diacylglycerol cholinephosphotransferase (YlCPT1; U.S. Pat. No. 7,932,077), *Y. lipolytica* delta-9 desaturase (YlD9; U.S. Pat. Appl. Publ. No. 2012-0052537), and an *M. alpina* acyl-CoA:lysophosphatidic acid acyltransferase nucleotide sequence that was codon-optimized for expression in *Y. lipolytica* (MaLPAAT1S; U.S. Pat. No. 7,879,591). Construct pZKUM (above) was then used to disrupt the URA3 gene in strain Z2636 that was introduced by plasmid pZKT2-ML9DCB, thereby producing the Ura$^-$ strain Z2636U.

Strain Z3041 was produced by transforming Z2636U with AscI/SphI-digested plasmid pZKLY-PP2YAP (SEQ ID NO:28, FIG. 9B), which contains cassettes for expressing *Y. lipolytica* Yap1 (YlYAP1, GenBank Accession No. XM_504945), *Y. lipolytica* 6-phosphogluconolactonase (Yl6PGL, U.S. Pat. Appl. Publ. No. 2011-0244512), and *Y. lipolytica* glucose-6-phosphate dehydrogenase (YlG6PDH, with 440-bp intron; U.S. Pat. Appl. Publ. No. 2011-0244512). Z3041 was produced along with sibling strains Z3030-Z3040 and Z3042-Z3050.

Analysis of Total Lipid Content and Composition by Flask Assay

Cells of strains Z3029 to Z3050, including Z3041, were grown and analyzed for total lipid content and fatty acid composition by the flask assay described above. Table 14 summarizes the DCW, the TFAs % DCW, the amount of each fatty acid as a weight percent of TFAs (% TFAs) and the EPA % DCW of strains from Z3029 to Z3050. Each value represents an average of two measurements.

TABLE 14

Total Lipid Content and Composition in Strains Z3029 to Z3050, Including Z3041, by Flask Assay

| Strain | DCW (g/L) | TFAs % DCW | % TFAs 16:0 | 16:1 | 18:0 | 18:1 | LA | ALA | EDA | DGLA | ARA | ETrA | ETA | EPA | EPA % DCW |
|---|---|---|---|---|---|---|---|---|---|---|---|---|---|---|---|
| Z3029 | 3.5 | 41.5 | 1.7 | 0.8 | 1.7 | 6.1 | 12.7 | 0.7 | 3.7 | 3.9 | 0.9 | 0.6 | 2.3 | 55.3 | 23.0 |
| Z3030 | 3.3 | 38.8 | 1.9 | 0.5 | 2.6 | 5.4 | 12.4 | 0.8 | 3.3 | 3.2 | 0.7 | 0.7 | 2.5 | 57.3 | 22.2 |
| Z3031 | 3.3 | 38.7 | 2.0 | 0.5 | 2.6 | 5.5 | 12.4 | 0.8 | 3.3 | 3.2 | 0.7 | 0.7 | 2.5 | 57.1 | 22.1 |
| Z3032 | 3.2 | 38.5 | 2.3 | 0.6 | 2.4 | 5.3 | 12.4 | 0.7 | 3.3 | 3.3 | 0.7 | 0.6 | 2.3 | 57.3 | 22.1 |
| Z3033 | 3.2 | 38.2 | 2.3 | 0.7 | 2.3 | 5.4 | 12.2 | 0.7 | 3.1 | 3.4 | 0.8 | 0.5 | 2.3 | 57.2 | 21.9 |
| Z3034 | 3.3 | 38.8 | 2.0 | 0.5 | 2.6 | 5.4 | 12.4 | 0.8 | 3.4 | 3.3 | 0.7 | 0.7 | 2.6 | 56.8 | 22.0 |
| Z3035 | 3.3 | 39.1 | 1.6 | 0.6 | 1.7 | 5.3 | 11.9 | 0.6 | 3.4 | 3.9 | 0.9 | 0.6 | 2.3 | 57.2 | 22.3 |
| Z3036 | 2.9 | 31.3 | 1.2 | 0.3 | 2.2 | 3.4 | 8.3 | 0.5 | 2.5 | 3.2 | 0.5 | 1.1 | 3.4 | 63.7 | 19.9 |
| Z3037 | 3.1 | 40.0 | 1.6 | 0.6 | 1.7 | 5.1 | 11.9 | 0.6 | 3.4 | 3.9 | 0.9 | 0.6 | 2.3 | 57.6 | 23.1 |
| Z3038 | 3.2 | 39.8 | 1.8 | 0.7 | 1.7 | 5.9 | 12.9 | 0.7 | 3.6 | 3.8 | 0.9 | 0.5 | 2.3 | 55.5 | 22.1 |
| Z3039 | 3.1 | 39.2 | 1.7 | 0.6 | 1.7 | 5.4 | 12.2 | 0.6 | 3.5 | 3.8 | 0.9 | 0.5 | 2.3 | 56.9 | 22.3 |
| Z3040 | 3.0 | 38.0 | 1.4 | 0.6 | 1.5 | 4.6 | 10.9 | 0.5 | 3.1 | 4.2 | 1.0 | 0.5 | 2.4 | 59.4 | 22.5 |
| Z3041 | 3.3 | 42.1 | 1.3 | 0.5 | 1.5 | 5.8 | 12.2 | 0.7 | 4.2 | 3.6 | 0.9 | 0.9 | 2.5 | 56.8 | 23.9 |
| Z3042 | 2.5 | 34.6 | 1.9 | 0.6 | 2.1 | 4.4 | 10.8 | 0.5 | 3.1 | 3.9 | 0.8 | 0.6 | 2.6 | 58.5 | 20.2 |
| Z3043 | 3.0 | 40.0 | 1.6 | 0.6 | 1.7 | 5.2 | 12.0 | 0.6 | 3.5 | 3.9 | 0.9 | 0.5 | 2.3 | 57.4 | 22.9 |
| Z3044 | 2.9 | 36.1 | 2.1 | 0.8 | 1.6 | 5.3 | 11.8 | 0.5 | 3.3 | 3.9 | 1.0 | 0.4 | 2.2 | 56.6 | 20.4 |
| Z3045 | 3.0 | 39.3 | 1.9 | 0.5 | 2.6 | 5.2 | 12.1 | 0.8 | 3.2 | 3.2 | 0.7 | 0.7 | 2.5 | 57.5 | 22.6 |
| Z3046 | 2.9 | 35.5 | 2.2 | 0.6 | 2.0 | 4.7 | 10.7 | 0.6 | 2.7 | 3.2 | 0.8 | 0.4 | 2.0 | 59.7 | 21.2 |
| Z3047 | 3.0 | 38.1 | 2.2 | 0.6 | 2.6 | 5.2 | 12.0 | 0.7 | 3.2 | 3.4 | 0.7 | 0.5 | 2.3 | 57.2 | 21.8 |
| Z3048 | 3.1 | 39.4 | 1.9 | 0.5 | 2.5 | 5.4 | 12.4 | 0.8 | 3.3 | 3.3 | 0.7 | 0.7 | 2.5 | 57.0 | 22.5 |
| Z3049 | 2.8 | 36.5 | 2.2 | 0.6 | 2.2 | 5.1 | 11.9 | 0.7 | 3.0 | 3.4 | 0.8 | 0.5 | 2.2 | 57.9 | 21.1 |
| Z3050 | 2.9 | 40.1 | 2.1 | 0.6 | 2.3 | 5.8 | 13.0 | 0.8 | 3.5 | 3.4 | 0.8 | 0.6 | 2.4 | 55.0 | 22.1 |
| avg | 3.1 | 38.3 | 1.9 | 0.6 | 2.1 | 5.2 | 11.9 | 0.7 | 3.3 | 3.6 | 0.8 | 0.6 | 2.4 | 57.5 | 22.0 |

Strain Z3041 had the highest oil content (about 42.1 TFAs % DCW) compared to all of its sibling strains (Table 14). The oil content of Z3041 was also notable since most of its siblings had less than 40% oil, and the average oil content was 38.3% (Table 14). The average increase in oil content in strain Z3041 with respect to its siblings was about 10.7%. These observations suggested that the integrated sequence from pZKLY-PP2YAP in strain Z3041 provided an additional effect beyond the effects provided to all of the other strains in Table 14.

One possibility was that the integration itself provided an additional trait to Z3041 that contributed to oil synthesis. This prospect led to genome walking and sequencing analyses to determine what genetic trait(s) may have been altered in strain Z3041 to endow enhanced oil levels. The additional analyses found that the ~10.5 kbp AscI/SphI fragment of pZKLY-PP2YAP, which contains the YlYAP1, Yl6PGL and Yl6PDH expression cassettes, had integrated into the promoter of the SOU2 gene (locus YALI0D18964g, GenBank Accession No. XM_503010, FIG. 5). Specifically, the AscI/SphI plasmid fragment was integrated at −70 with respect to the ATG start codon of the SOU2 gene; this location is immediately downstream the presumptive TATA promoter consensus sequence. Given the location of the integration in the SOU2 promoter, the integration was predicted to down-regulate SOU2 gene expression (reduced transcription).

Aside from having increased oil content, strain Z3041 also exhibited lower levels of certain fermentation by-products compared to Z2636. Specifically, production of the sugar alcohols arabitol and mannitol in Z3041 was eliminated.

Additional studies were conducted to understand the role of the SOU2 gene in regulating oil and sugar alcohol production in *Yarrowia* (refer to Example 2). Briefly, the SOU2 gene was knocked out in strain Z5585, thereby producing strain Z5585K2U (FIG. 3). The knock-out of SOU2 entailed targeting and deleting about 522 base pairs of sequence beginning about 235 base pairs upstream the ATG start site and ending about 287 base pairs downstream the ATG start site (FIG. 5, refer to sequence between opposing triangles). SOU2 gene transcription and Sou2 protein expression were thus completely down-regulated in strain Z5585K2U and its descendent strains.

Example 6

Synthesis of Plasmid pY306-N Comprising Variant YlLPCAT

This Example and Examples 7-9 are disclosed in U.S. Appl. No. 61/661,623, which is incorporated herein by reference.

The wild type *Y. lipolytica* LPCAT (YlLPCAT) polynucleotide sequence and amino acid sequence are represented by SEQ ID NOs:39 and 40, respectively.

The present example describes the construction of a *Yarrowia* autonomously replicating vector comprising a variant YlLPCAT sequence (plasmid pY306-N, FIG. 10, SEQ ID NO:42). The variant YlLPCAT polynucleotide sequence, designated herein as YlLPCAT* (SEQ ID NO:41), lacks two NcoI restriction enzyme sites that are present in the wild type YlLPCAT coding region. Removal of these internal NcoI sites facilitated subsequent cloning procedures. YlLPCAT* encodes wild type YlLPCAT protein (SEQ ID NO:40).

As a control, the wild type YlLPCAT polynucleotide sequence (SEQ ID NO:39) was cloned into a *Yarrowia* autonomously replicating vector to result in plasmid pY306 (SEQ ID NO:43), comprising a ColE1 plasmid origin of replication, an ampicillin-resistance gene, an f1 origin of replication and the *Y. lipolytica* URA3 gene (Gen Bank Accession No. AJ306421).

The variant YlLPCAT* sequence was synthesized by GenScript Corporation (Piscataway, N.J.). Two internal NcoI restriction sites were removed by creation of silent mutations, while NcoI and NotI sites were added, respectively, at the 5' and 3' ends of the YlLPCAT open reading frame to facilitate cloning. Specifically, an A12T mutation (i.e., a change from adenosine [A] in YlLPCAT (SEQ ID NO:39) at position 12 to thymine [T] in the YlLPCAT* variant) and a T918C mutation (i.e., a change from thymine [T] in YlLPCAT (SEQ ID NO:39) at position 918 to cytosine [C] in the YlLPCAT* variant) were introduced into the YlLPCAT coding sequence. These two nucleotide substitutions were silent with respect to the amino acids encoded by the variant sequence. The nucleotide sequence encoding the variant YlLPCAT lacking its internal NcoI sites (i.e., YlLPCAT*) is represented by SEQ ID NO:41, while the amino acid sequence encoded thereby is represented by SEQ ID NO:40, which is wild type YlLPCAT protein.

YlLPCAT* was subsequently cloned into plasmid pY306, thereby producing pY306-N (SEQ ID NO:42; FIG. 10). Construct pY306-N contained the following components:

TABLE 15

Components of Plasmid pY306-N (SEQ ID NO: 42)

| RE Sites and Nucleotide Positions | Description of Fragment and Chimeric Gene Components |
|---|---|
| BsiWI/BsiWI 1-2809 | YAT1::YlLPCAT*::Lip1 (complementary), comprising:<br>YAT1: *Y. lipolytica* YAT1 promoter (U.S. Pat. Appl. Publ. No. 2010/0068789);<br>YlLPCAT*: variant YlLPCAT lacking two internal NcoI sites (SEQ ID NO: 41), but encoding wild type YlLPCAT protein;<br>Lip1: Lip1 terminator sequence from *Yarrowia* LIP1 gene (GenBank Accession No. Z50020) |
| BsiWI/EcoRI 2809-5605 | ColE1 plasmid origin of replication<br>Ampicillin-resistance gene<br>f1 origin of replication |
| EcoRI/PacI 5605-7021 | *Y. lipolytica* URA3 gene (GenBank Accession No. AJ306421) |

Plasmid pY306-N was used to prepare single- and double-mutants of YlLPCAT protein, as described below in Examples 7 and 9, respectively.

Example 7

Designing and Synthesizing Mutant *Yarrowia* LPCAT Enzymes with Modified Motifs Based on the premise that conserved amino acid motifs within YlLPCAT are likely involved in catalysis, it was concluded that generation of mutants having variant motifs could result in the identification of an LPCAT enzyme having improved functional activity.

A series of single amino acid substitutions were designed within the conserved sequence spanning amino acid residues 132 to 148 of SEQ ID NO:40 (i.e., Motif I) and the conserved sequence spanning amino acid residues 376 to 390 of SEQ ID NO:40 (i.e., Motif II). Within Motif I, a total of 195 amino acid substitutions were designed, as shown in Table 16, by creating various substitutions at each of the 17 amino acid residues within the motif.

TABLE 16

Single Amino Acid Substitutions within Motif I of YlLPCAT Protein

| Wild type residue | Single Amino Acid Substitutions | SEQ ID NO |
|---|---|---|
| M132 | M132A, M132N, M132C, M132G, M132Q, M132H, M132I, M132L, M132F, M132P, M132S, M132T, M132W, M132Y or M132V | 44 |

TABLE 16-continued

Single Amino Acid Substitutions within Motif I of YlLPCAT Protein

| Wild type residue | Single Amino Acid Substitutions | SEQ ID NO |
|---|---|---|
| V133 | V133A, V133N, V133C, V133G, V133Q, V133H, V133L, V133M, V133F, V133P, V133S, V133T, V133W or V133Y | 45 |
| L134 | L134A, L134N, L134C, L134G, L134Q, L134H, L134M, L134F, L134P, L134S, L134T, L134W, L134Y or L134V | 46 |
| C135 | C135R, C135N, C135D, C135G, C135E, C135Q, C135H, C135I, C135L, C135K, C135M, C135F, C135P, C135S, C135W or C135Y | 47 |
| M136 | M136A, M136N, M136C, M136G, M136H, M136I, M136F, M136P, M1365, M136T, M136W, M136Y or M136V | 48 |
| K137 | K137A, K137R, K137N, K137G, K137H, K137P, K137S, K137T, or K137Y | 49 |
| L138 | L138A, L138N, L138C, L138G, L138Q, L138H, L138I, L138M, L138F, L138P, L138S, L138T, L138W, or L138Y | 50 |
| S139 | S139A, S139N, S139C, S139G, S139H, S139L, S139M, S139F, S139P, S139W, or S139V | 51 |
| S140 | S140N, S140C, S140H, S140I, S140L, S140F, S140P, S140W, S140Y or S140V | 52 |
| F141 | F141A, F141N, F141G, F141H, F141I, F141M, F141P, F141S, F141T, F141W, or F141V | 53 |
| G142 | G142N, G142H, G142I, G142L, G142M, G142F, G142P, G142T, G142W, G142Y or G142V | 54 |
| W143 | W143A, W143G, W143H, W143L, W143K, W143P, W143S, W143T, or W143V | 55 |
| N144 | N144A, N144R, N144G, N144H, N144K, N144F, N144P, N144T or N144V | 56 |
| V145 | V145A, V145C, V145G, V145E, V145H, V145M, V145F, V145P, V145S, V145T, or V145W | 57 |
| Y146 | Y146R, Y146N, Y146D, Y146G, Y146E, Y146Q, Y146I, Y146L, Y146M, Y146F, Y146P, Y146W or Y146V | 58 |
| D147 | D147A, D147N, D147G, D147E, D147Q, D147H, D147F, D147S, or D147T | 59 |
| G148 | G148A, G148N, G148H, G148L, G148M, G148F, G148S, G148T or G148V | 60 |

Similarly, a total of 134 amino acid substitutions were designed within Motif II, as shown in Table 17, by creating various substitutions within 12 of the 15 amino acid residues within the motif. No substitutions were made at W379, H380 and G381, since the histidine of other LPCATs corresponding to H380 of YlLPCAT has been reported to be a likely active site residue (Lee et al., 2008, *Mol. Biol. Cell* 19:1174-1184).

TABLE 17

Single Amino Acid Substitutions within Motif II of YlLPCAT Protein

| Wild type residue | Single Amino Acid Substitutions | SEQ ID NO |
|---|---|---|
| S376 | S376A, S376G, S376H, S376L, S376F, S376P, S376T or S376V | 61 |
| A377 | A377N, A377G, A377H, A377L, A377F, A377P, A377S, A377T or A377V | 62 |
| F378 | F378A, F378N, F378C, F378G, F378H, F378L, F378P, F378S, F378T, F378W, or F378Y | 63 |
| T382 | T382A, T382N, T382G, T382Q, T382H, T382I, T382M, T382P, T382S, T382W, or T382Y | 64 |
| R383 | R383A, R383N, R383D, R383G, R383E, R383Q, R383H, R383I, R383L, R383K, R383M, R383F, R383P, R383T, R383W or R383V | 65 |
| P384 | P384A, P384R, P384G, P384H, P384I, P384L, P384K, P384M, P384F, P384S, P384T, P384W, P384Y or P384V | 66 |
| G385 | G385A, G385N, G385C, G385G, G385H, G385I, G385L, G385K, G385M, G385F, G385S, G385T, G385W, G385Y or G385V | 67 |
| Y386 | Y386A, Y386G, Y386H, Y386L, Y386F, Y386P, Y386S, Y386T or Y386V | 68 |

TABLE 17-continued

Single Amino Acid Substitutions within Motif II of YlLPCAT Protein

| Wild type residue | Single Amino Acid Substitutions | SEQ ID NO |
|---|---|---|
| Y387 | Y387A, Y387G, Y387H, Y387L, Y387F, Y387P, Y387S, Y387T, Y387W or Y387V | 69 |
| L388 | L388A, L388G, L388H, L388P, L388S, L388T, L388W, L388Y or L388V | 70 |
| T389 | T389A, T389C, T389G, T389H, T389I, T389L, T389M, T389F, T389P, T389S, T389W, T389Y or T389V | 71 |
| F390 | F390A, F390N, F390C, F390G, F390H, F390L, F390M, F390P, F390S, F390T or F390V | 72 |

Each of the 329 YlLPCAT mutants set forth above in Tables 16 and 17 were individually synthesized and cloned into NcoI/NotI-cut pY306-N vector by GenScript Corporation (Piscataway, N.J.).

Example 8

Identifying Single Amino Acid Substitutions in YlLPCAT Having Improved LPCAT Activity The present example describes the transformation of each of the 329 pY306-N vectors comprising a YlLPCAT mutant polynucleotide sequence (Example 7) into *Y. lipolytica* strain Y8406U2, followed by analysis of the lipid profiles of the transformants.

Improved LPCAT activity was indirectly evaluated, based on the observations set forth in U.S. Pat. Appl. Publ. No. 2010-0317882-A1, which is incorporated herein by reference. Specifically, improved LPCAT activity within *Y. lipolytica* strain Y8406U2 transformants comprising a mutated YlLPCAT was concluded based on an increase in the concentration of EPA as a weight % of TFAs (EPA % TFAs) and/or an increase in the conversion efficiency of the delta-9 elongase, when either factor was compared to the EPA % TFAs or the conversion efficiency of the delta-9 elongase, respectively, in *Y. lipolytica* strain Y8406U2 expressing the parent wild type YlLPCAT protein.

Transformation of Y. *Lipolytica* Strain Y8406U2

Strain Y8406U2 was transformed to individually express one of each of the pY306-N vectors containing a mutant YlLPCAT prepared in Example 7. Y8406U2 is a $Ura^-$ strain of Y8406. Details regarding the development of strains Y8406 and Y8406U2 are provided in U.S. Pat. Appl. Publ. No. 2010-0317882-A1. Following transformation, individual transformants were subjected to an initial fatty acid screening process as described above. Briefly, single colonies that were grown on MM plates at 30° C. for 5 to 6 days were re-streaked and grown for two days at 30° C. on MM plates. Single colonies were then inoculated into 3 mL MM in a 24-well plate and shaken at 250 rpm at 30° C. for 2 days. The cells from each well were collected by centrifugation, resuspended in HGM, and then shaken at 200 rpm for 5 days. Cells were then processed for fatty acid analysis as described above.

Analysis of Lipid Profiles within *Yarrowia* Transformed for Expression of Single Mutants of YlLPCAT Tables 18 (Batch 1), 19 (Batch 2), 20 (Batch 3), 21 (Batch 4) and 22 (Batch 5) below show the fatty acid profiles and delta-9 elongase conversion efficiencies of individual Y8406U2 transformants comprising a plasmid for expressing a particular single-mutated YlLPCAT (single amino acid substitution in Motif I or Motif II). These measurements were also made for certain controls: transformants comprising an empty vector (EV) (i.e., a replicating plasmid with no LPCAT gene [Batch #1 only]) or pY306-N (wild type YlLPCAT protein expression [WT]).

More specifically, each table summarizes the number of replicates analyzed for each particular transformant (#), the average concentration of each fatty acid as a weight percent of TFAs (% TFAs), the standard deviation for EPA % TFAs (EPA SD), and the delta-9 elongase conversion efficiency (% Conv). The % Conv. was calculated for each transformant according to the following formula: (EDA+DGLA+ARA+ERA+ETA+EPA)/(C18:2+C18:3+EDA+DGLA+ARA+ERA+ETA+EPA)*100.

Comparison of each mutant's performance relative to the wild type YlLPCAT control should only be made within the particular batch in which each mutant was analyzed (i.e., comparisons should not be made between Batch #1 and Batch #2, for example). Mutants shown in bold-face font and followed by a "+" were selected for further studies, as discussed below.

TABLE 18

Lipid Composition and Delta-9 Elongase Conversion Efficiency in Batch #1 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| EV control | 6 | 2.8 | 0.5 | 2.6 | 4.6 | 19.2 | 1.8 | 2.8 | 2.6 | 0.6 | 1.4 | 2.6 | 48.7 | 0.2 | 74 |
| WT | 15 | 2.8 | 0.5 | 2.7 | 4.5 | 17.9 | 1.8 | 2.7 | 2.7 | 0.6 | 1.4 | 2.4 | 50.4 | 1.1 | 75 |
| M132A | 3 | 2.8 | 0.4 | 2.9 | 4.8 | 19.7 | 2.2 | 2.5 | 2.3 | 0.6 | 1.4 | 2.0 | 49.3 | 0.4 | 73 |
| M132I | 3 | 2.7 | 0.5 | 2.8 | 4.8 | 19.4 | 2.0 | 2.7 | 2.5 | 0.6 | 1.5 | 2.3 | 48.6 | 0.3 | 73 |
| V133M | 3 | 2.6 | 0.5 | 2.9 | 5.4 | 19.3 | 2.1 | 2.8 | 2.4 | 0.6 | 1.5 | 2.2 | 49.0 | 0.7 | 73 |
| C135I | 3 | 3.0 | 0.5 | 2.8 | 4.6 | 17.5 | 1.7 | 2.6 | 2.6 | 0.7 | 1.5 | 2.2 | 50.7 | 2.5 | 76 |
| C135M | 3 | 2.5 | 0.5 | 2.9 | 5.6 | 20.1 | 2.5 | 3.0 | 2.3 | 0.6 | 1.5 | 2.0 | 47.8 | 1.7 | 72 |
| M136A | 3 | 2.7 | 0.4 | 2.9 | 4.8 | 19.4 | 2.2 | 2.5 | 1.6 | 0.6 | 1.4 | 2.1 | 49.6 | 0.1 | 73 |
| L138A | 3 | 2.9 | 0.5 | 2.9 | 3.1 | 18.0 | 1.8 | 2.6 | 2.6 | 0.7 | 1.4 | 2.1 | 50.5 | 1.9 | 75 |
| L138C | 3 | 3.0 | 0.5 | 2.8 | 4.8 | 19.8 | 2.1 | 2.6 | 2.3 | 0.7 | 1.4 | 2.0 | 48.6 | 0.9 | 72 |
| L138M | 3 | 2.7 | 0.6 | 2.9 | 5.2 | 16.8 | 1.5 | 2.8 | 3.0 | 0.7 | 1.5 | 2.4 | 51.0 | 3.0 | 77 |
| S139A | 3 | 2.7 | 0.4 | 2.8 | 4.8 | 19.5 | 2.3 | 2.6 | 2.2 | 0.6 | 1.4 | 2.0 | 48.8 | 1.2 | 73 |
| S139C | 3 | 3.2 | 0.5 | 2.8 | 4.6 | 19.6 | 2.0 | 2.5 | 2.3 | 0.6 | 1.4 | 2.0 | 48.8 | 0.6 | 73 |
| S139L | 3 | 2.7 | 0.5 | 2.8 | 5.0 | 17.9 | 1.8 | 2.7 | 2.6 | 0.7 | 1.5 | 2.2 | 50.7 | 2.2 | 75 |
| S139M | 3 | 2.5 | 0.4 | 3.0 | 5.4 | 19.7 | 2.3 | 2.8 | 2.4 | 0.6 | 1.5 | 2.1 | 48.6 | 0.2 | 72 |
| S140I | 3 | 3.1 | 0.5 | 2.8 | 4.6 | 17.7 | 1.7 | 2.7 | 2.7 | 0.7 | 1.5 | 2.3 | 50.1 | 2.7 | 76 |
| F141M+ | 3 | 2.8 | 0.7 | 2.7 | 4.9 | 14.8 | 0.9 | 2.8 | 3.4 | 0.8 | 1.6 | 2.6 | 53.1 | 0.5 | 80 |
| G142I | 3 | 3.1 | 0.6 | 2.7 | 5.0 | 18.3 | 1.8 | 2.9 | 2.6 | 0.7 | 1.5 | 2.3 | 49.0 | 3.1 | 75 |
| G142L | 3 | 2.5 | 0.5 | 2.8 | 5.5 | 19.2 | 2.0 | 3.0 | 2.5 | 0.6 | 1.6 | 2.3 | 48.7 | 1.1 | 73 |
| W143L | 3 | 2.7 | 0.5 | 2.8 | 5.1 | 17.9 | 1.8 | 2.8 | 1.6 | 0.6 | 1.5 | 2.3 | 50.4 | 2.0 | 75 |
| N144H | 3 | 2.7 | 0.6 | 2.6 | 4.7 | 18.9 | 1.8 | 2.8 | 2.7 | 0.6 | 1.6 | 2.8 | 48.1 | 1.6 | 74 |
| N144K | 3 | 2.7 | 0.5 | 2.8 | 5.3 | 17.7 | 1.8 | 2.8 | 2.7 | 0.6 | 1.5 | 2.2 | 50.5 | 3.2 | 76 |
| V145C | 3 | 3.0 | 0.4 | 2.8 | 4.7 | 19.6 | 2.1 | 2.5 | 2.3 | 0.6 | 1.4 | 2.0 | 49.4 | 0.5 | 73 |
| V145M+ | 3 | 2.9 | 0.7 | 2.7 | 5.0 | 16.2 | 1.3 | 2.8 | 3.1 | 0.7 | 1.5 | 2.4 | 51.4 | 2.1 | 78 |
| Y146D | 3 | 3.0 | 0.5 | 2.8 | 3.3 | 19.6 | 2.0 | 2.5 | 2.4 | 0.7 | 1.4 | 2.1 | 49.0 | 0.6 | 73 |
| Y146E | 3 | 3.2 | 0.5 | 2.9 | 4.9 | 19.7 | 2.0 | 2.5 | 2.5 | 0.7 | 1.3 | 2.1 | 48.8 | 0.3 | 73 |
| Y146I | 3 | 3.0 | 0.5 | 2.8 | 5.4 | 20.0 | 2.3 | 2.8 | 2.3 | 0.6 | 1.5 | 2.1 | 47.6 | 2.3 | 72 |
| Y146L | 3 | 2.6 | 0.5 | 2.7 | 5.0 | 17.7 | 1.6 | 2.7 | 2.8 | 0.6 | 1.5 | 2.4 | 50.8 | 2.2 | 76 |
| Y146M | 3 | 2.6 | 0.5 | 2.7 | 5.2 | 18.1 | 1.9 | 2.7 | 2.7 | 0.7 | 1.5 | 2.1 | 50.7 | 1.8 | 75 |
| D147E | 3 | 3.2 | 0.5 | 2.8 | 4.7 | 18.3 | 1.7 | 2.7 | 2.7 | 0.7 | 1.5 | 2.2 | 49.5 | 0.2 | 75 |
| F378A | 3 | 2.6 | 0.4 | 2.9 | 4.8 | 19.5 | 2.3 | 2.5 | 2.2 | 0.6 | 1.4 | 2.0 | 49.9 | 0.3 | 73 |
| T382A | 3 | 2.7 | 0.5 | 2.8 | 5.1 | 19.8 | 2.2 | 2.8 | 2.4 | 0.6 | 1.4 | 2.2 | 48.3 | 1.7 | 72 |
| R383A | 3 | 2.9 | 0.6 | 2.8 | 3.6 | 17.8 | 1.5 | 2.9 | 2.8 | 0.7 | 1.4 | 2.3 | 50.2 | 1.5 | 76 |
| R383D | 3 | 3.3 | 0.5 | 2.9 | 5.0 | 19.6 | 2.0 | 2.5 | 2.4 | 0.7 | 1.4 | 2.1 | 48.7 | 0.8 | 73 |
| R383I | 3 | 3.1 | 0.5 | 2.8 | 4.6 | 18.6 | 1.7 | 2.6 | 2.6 | 0.7 | 1.5 | 2.3 | 49.2 | 0.5 | 74 |
| R383K | 3 | 2.5 | 0.5 | 2.7 | 5.4 | 20.1 | 2.4 | 3.1 | 2.3 | 0.6 | 1.5 | 2.1 | 47.7 | 2.6 | 72 |
| R383L | 3 | 2.5 | 0.4 | 2.8 | 5.0 | 19.6 | 2.1 | 2.7 | 2.4 | 0.6 | 1.5 | 2.1 | 49.4 | 0.4 | 73 |
| R383M+ | 3 | 3.0 | 0.6 | 2.8 | 5.0 | 16.5 | 1.5 | 2.7 | 3.0 | 0.7 | 1.5 | 2.2 | 52.2 | 2.8 | 78 |

TABLE 18-continued

Lipid Composition and Delta-9 Elongase Conversion Efficiency in Batch #1 Transformants Comprising a Vector Encoding YILPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| R383N | 3 | 3.0 | 0.5 | 2.8 | 4.8 | 19.3 | 2.0 | 2.5 | 2.4 | 0.6 | 1.4 | 2.1 | 49.2 | 0.5 | 73 |
| P384I | 3 | 2.8 | 0.5 | 2.9 | 4.8 | 19.3 | 2.1 | 2.6 | 2.3 | 0.6 | 1.4 | 2.1 | 49.3 | 0.4 | 73 |
| P384L | 3 | 2.5 | 0.5 | 2.8 | 5.2 | 18.8 | 1.9 | 2.8 | 2.6 | 0.6 | 1.5 | 2.3 | 49.6 | 0.6 | 74 |
| G385I | 3 | 2.4 | 0.4 | 2.9 | 5.2 | 19.4 | 2.1 | 2.7 | 2.4 | 0.6 | 1.5 | 2.1 | 49.2 | 0.3 | 73 |
| G385L | 3 | 2.5 | 0.5 | 3.0 | 5.5 | 19.7 | 2.3 | 2.9 | 2.3 | 0.6 | 1.5 | 2.1 | 48.4 | 0.1 | 72 |
| Y387A | 3 | 2.7 | 0.4 | 2.9 | 4.5 | 19.6 | 2.1 | 2.5 | 2.4 | 0.7 | 1.3 | 2.0 | 49.8 | 0.2 | 73 |
| L388A | 3 | 2.6 | 0.5 | 2.8 | 4.8 | 19.9 | 2.1 | 2.5 | 2.5 | 0.7 | 1.3 | 2.3 | 48.9 | 1.4 | 73 |
| T389I | 3 | 2.5 | 0.5 | 2.8 | 5.1 | 19.7 | 2.1 | 2.7 | 2.4 | 0.6 | 1.5 | 2.2 | 48.9 | 0.8 | 73 |
| T389L | 3 | 2.5 | 0.4 | 2.9 | 5.2 | 19.9 | 2.3 | 2.7 | 2.3 | 0.6 | 1.5 | 2.0 | 48.9 | 0.3 | 72 |
| F390L | 3 | 2.5 | 0.4 | 2.9 | 5.3 | 19.7 | 2.3 | 2.7 | 2.3 | 0.6 | 1.5 | 2.1 | 48.9 | 0.4 | 72 |
| Mutant AVG | | 2.8 | 0.5 | 2.8 | 4.9 | 18.9 | 2.0 | 2.7 | 2.5 | 0.6 | 1.5 | 2.2 | 49.5 | | 74 |
| Mutant SD | | 0.2 | 0.1 | 0.1 | 0.5 | 1.2 | 0.3 | 0.2 | 0.3 | 0.0 | 0.1 | 0.2 | 1.1 | | 56 |

TABLE 19

Lipid Composition and Delta-9 Elongase Conversion Efficiency in Batch #2 Transformants Comprising a Vector Encoding YILPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 5 | 3.0 | 0.6 | 2.9 | 4.9 | 15.0 | 1.2 | 2.8 | 3.2 | 0.7 | 1.5 | 2.5 | 52.9 | 1.1 | 79.7 |
| M132F | 3 | 2.6 | 0.6 | 2.8 | 5.6 | 19.2 | 1.9 | 2.8 | 2.7 | 0.6 | 1.5 | 2.5 | 48.7 | 1.3 | 73.6 |
| M132W | 3 | 2.6 | 0.6 | 2.7 | 5.5 | 18.5 | 1.7 | 2.9 | 2.7 | 0.5 | 1.6 | 2.7 | 48.6 | 0.4 | 74.4 |
| M132Y | 3 | 2.6 | 0.6 | 2.7 | 2.3 | 18.9 | 1.8 | 2.8 | 2.7 | 0.5 | 1.6 | 2.8 | 48.1 | 1.0 | 73.8 |
| V133F | 3 | 2.6 | 0.5 | 3.0 | 5.6 | 19.5 | 2.3 | 2.8 | 2.5 | 0.5 | 1.5 | 2.3 | 48.6 | 0.4 | 72.7 |
| V133W | 3 | 2.5 | 0.5 | 2.8 | 4.2 | 19.7 | 2.1 | 2.9 | 2.5 | 0.5 | 1.5 | 2.4 | 47.8 | 1.1 | 72.6 |
| L134F | 3 | 3.0 | 0.6 | 3.1 | 5.8 | 16.7 | 1.4 | 3.3 | 3.0 | 0.6 | 1.6 | 2.6 | 50.0 | 2.2 | 77.2 |
| L134V | 3 | 3.1 | 0.6 | 2.8 | 5.0 | 15.4 | 1.1 | 2.8 | 3.1 | 0.7 | 1.6 | 2.5 | 52.3 | 0.3 | 79.2 |
| L134W | 3 | 2.6 | 0.7 | 2.5 | 5.1 | 16.2 | 0.9 | 3.0 | 3.4 | 0.8 | 1.5 | 2.7 | 51.0 | 1.9 | 78.5 |
| L134Y | 3 | 2.9 | 0.6 | 2.8 | 2.1 | 16.8 | 1.3 | 2.7 | 1.9 | 0.6 | 1.7 | 2.6 | 50.8 | 0.2 | 76.9 |
| C135F | 3 | 3.0 | 0.7 | 2.7 | 5.2 | 15.1 | 1.0 | 2.8 | 3.3 | 0.7 | 1.5 | 2.6 | 52.5 | 0.5 | 79.7 |
| C135W | 3 | 2.5 | 0.5 | 2.8 | 5.1 | 18.1 | 1.5 | 2.8 | 2.7 | 0.6 | 1.5 | 2.6 | 49.9 | 0.2 | 75.4 |
| C135Y | 3 | 2.5 | 0.6 | 2.9 | 5.4 | 18.1 | 1.5 | 3.0 | 2.7 | 0.6 | 1.6 | 2.8 | 49.0 | 0.4 | 75.2 |
| M136F | 3 | 2.8 | 0.6 | 2.8 | 5.1 | 16.6 | 1.2 | 2.8 | 3.1 | 0.7 | 1.6 | 2.5 | 51.8 | 0.3 | 77.8 |
| M136S+ | 3 | 3.3 | 0.7 | 2.5 | 4.9 | 12.6 | 0.9 | 2.7 | 3.2 | 0.7 | 1.6 | 2.3 | 55.0 | 0.5 | 82.9 |
| M136T | 3 | 2.7 | 0.6 | 2.8 | 5.4 | 14.7 | 1.1 | 3.0 | 3.2 | 0.6 | 1.5 | 2.6 | 52.7 | 2.6 | 80.1 |
| M136V+ | 3 | 3.6 | 0.7 | 2.7 | 5.2 | 13.0 | 0.9 | 2.7 | 3.3 | 0.7 | 1.5 | 2.5 | 54.1 | 0.7 | 82.3 |
| M136W | 3 | 2.8 | 0.6 | 2.7 | 4.9 | 15.3 | 1.1 | 2.8 | 3.2 | 0.6 | 1.6 | 2.6 | 52.7 | 0.2 | 79.4 |
| L138F | 3 | 2.4 | 0.6 | 2.9 | 5.3 | 16.4 | 1.3 | 3.0 | 3.0 | 0.6 | 1.6 | 2.8 | 50.9 | 2.0 | 77.7 |
| L138W | 3 | 2.8 | 0.6 | 2.8 | 5.1 | 16.2 | 1.2 | 2.8 | 3.1 | 0.6 | 1.5 | 2.5 | 51.7 | 0.4 | 78.2 |
| L138Y | 3 | 2.6 | 0.6 | 2.6 | 3.5 | 16.9 | 1.5 | 2.7 | 1.8 | 0.6 | 1.5 | 2.6 | 51.2 | 1.9 | 76.7 |
| S139F | 3 | 3.1 | 0.7 | 2.7 | 3.8 | 16.0 | 1.3 | 2.8 | 3.1 | 0.7 | 1.6 | 2.6 | 50.9 | 2.7 | 78.1 |
| S139W | 3 | 2.9 | 0.6 | 2.8 | 4.9 | 14.8 | 1.1 | 2.8 | 3.2 | 0.7 | 1.5 | 2.5 | 53.2 | 0.3 | 80.1 |
| S140F | 3 | 2.8 | 0.6 | 2.7 | 5.1 | 15.6 | 1.3 | 2.8 | 3.1 | 0.6 | 1.5 | 2.5 | 52.2 | 2.3 | 78.7 |
| S140W+ | 3 | 3.2 | 0.6 | 2.7 | 5.3 | 12.8 | 0.9 | 2.7 | 3.3 | 0.7 | 1.6 | 2.4 | 54.6 | 0.4 | 82.7 |
| S140Y | 3 | 3.1 | 0.8 | 2.4 | 4.7 | 14.2 | 0.9 | 2.8 | 3.4 | 0.7 | 1.7 | 2.8 | 52.5 | 1.9 | 80.9 |
| F141V | 3 | 3.3 | 0.7 | 2.8 | 3.6 | 14.0 | 1.0 | 3.0 | 3.2 | 0.6 | 1.7 | 2.6 | 52.8 | 1.3 | 81.0 |
| F141W+ | 3 | 3.1 | 0.7 | 2.8 | 5.1 | 14.1 | 1.0 | 2.8 | 3.3 | 0.7 | 1.6 | 2.5 | 53.6 | 0.3 | 81.0 |
| G142F | 3 | 2.7 | 0.7 | 2.5 | 3.5 | 16.7 | 1.2 | 2.9 | 3.1 | 0.7 | 1.6 | 2.7 | 50.7 | 1.4 | 77.5 |
| G142V | 3 | 3.1 | 0.7 | 2.7 | 5.0 | 15.0 | 1.1 | 2.8 | 3.3 | 0.7 | 1.6 | 2.6 | 52.6 | 0.2 | 79.9 |
| G142W | 3 | 2.9 | 0.7 | 2.5 | 4.7 | 15.3 | 1.0 | 3.0 | 3.3 | 0.7 | 1.7 | 2.9 | 51.5 | 1.1 | 79.5 |
| G142Y | 3 | 2.9 | 0.6 | 2.6 | 4.9 | 17.5 | 1.5 | 2.8 | 2.9 | 0.6 | 1.6 | 2.6 | 50.1 | 1.6 | 76.1 |
| V145F | 3 | 2.9 | 0.6 | 2.6 | 5.0 | 14.9 | 1.0 | 2.8 | 3.3 | 0.7 | 1.5 | 2.6 | 52.9 | 0.1 | 80.0 |
| V145W+ | 3 | 3.0 | 1.0 | 3.0 | 5.0 | 15.0 | 1.0 | 3.0 | 3.0 | 1.0 | 2.0 | 3.0 | 53.1 | 0.1 | 80.1 |
| F378S | 3 | 2.8 | 0.6 | 2.6 | 4.9 | 16.2 | 1.2 | 2.8 | 3.0 | 0.6 | 1.5 | 2.5 | 52.2 | 0.2 | 78.3 |
| F378T | 3 | 2.7 | 0.7 | 2.6 | 4.9 | 15.8 | 1.2 | 3.0 | 3.0 | 0.6 | 1.6 | 2.8 | 51.6 | 0.1 | 78.7 |
| F378Y+ | 3 | 3.0 | 0.7 | 2.6 | 3.5 | 14.4 | 1.0 | 2.7 | 3.4 | 0.7 | 1.6 | 2.7 | 52.7 | 1.0 | 80.6 |
| T382P+ | 3 | 2.9 | 0.6 | 2.8 | 5.0 | 15.0 | 1.0 | 2.8 | 3.3 | 0.7 | 1.5 | 2.5 | 53.0 | 0.2 | 79.9 |
| T382S | 3 | 2.7 | 0.6 | 2.7 | 5.1 | 16.3 | 1.5 | 2.9 | 2.9 | 0.6 | 1.6 | 2.6 | 51.3 | 1.7 | 77.6 |
| T382W | 3 | 2.7 | 0.7 | 2.6 | 5.3 | 16.3 | 1.3 | 2.8 | 3.1 | 0.6 | 1.6 | 2.8 | 51.1 | 2.6 | 77.9 |
| T382Y+ | 2 | 3.1 | 0.7 | 2.7 | 5.0 | 14.6 | 1.0 | 2.7 | 3.3 | 0.7 | 1.6 | 2.7 | 52.8 | | 80.3 |
| R383F | 3 | 2.7 | 0.6 | 2.6 | 5.0 | 16.9 | 1.5 | 2.7 | 2.9 | 0.6 | 1.5 | 2.5 | 51.4 | 1.7 | 77.1 |
| R383P | 3 | 2.6 | 0.6 | 2.7 | 5.1 | 17.7 | 1.4 | 2.8 | 2.8 | 0.6 | 1.6 | 2.5 | 50.4 | 0.5 | 76.1 |
| R383T | 3 | 2.5 | 0.6 | 2.9 | 5.3 | 15.8 | 1.2 | 3.0 | 3.0 | 0.6 | 1.6 | 2.7 | 51.9 | 0.7 | 78.7 |
| R383V | 3 | 3.1 | 0.6 | 2.8 | 2.1 | 17.9 | 1.4 | 2.8 | 2.9 | 0.6 | 1.5 | 2.7 | 49.2 | 1.3 | 75.5 |
| R383W | 3 | 2.7 | 0.6 | 2.9 | 5.3 | 17.2 | 1.4 | 2.8 | 2.8 | 0.6 | 1.6 | 2.5 | 50.8 | 0.5 | 76.7 |
| P384F | 3 | 2.6 | 0.6 | 2.8 | 5.3 | 17.6 | 1.4 | 2.9 | 2.9 | 0.6 | 1.5 | 2.6 | 50.0 | 0.4 | 76.2 |
| P384M | 3 | 2.8 | 0.6 | 2.8 | 5.3 | 17.2 | 1.4 | 2.8 | 2.9 | 0.6 | 1.5 | 2.5 | 51.1 | 0.4 | 76.8 |

TABLE 19-continued

Lipid Composition and Delta-9 Elongase Conversion Efficiency in Batch #2 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| P384T | 3 | 2.7 | 0.6 | 2.8 | 3.5 | 16.6 | 1.3 | 2.8 | 2.9 | 0.6 | 1.5 | 2.6 | 51.6 | 0.1 | 77.6 |
| P384W | 3 | 2.8 | 0.6 | 2.7 | 2.1 | 17.0 | 1.5 | 2.7 | 2.8 | 0.6 | 1.6 | 2.5 | 50.9 | 1.6 | 76.8 |
| P384Y | 3 | 2.8 | 0.7 | 2.6 | 3.7 | 17.6 | 1.4 | 2.9 | 3.0 | 0.6 | 1.7 | 2.8 | 49.2 | 0.7 | 76.1 |
| G385F | 3 | 2.5 | 0.5 | 3.0 | 5.5 | 18.5 | 1.8 | 2.8 | 2.6 | 0.6 | 1.5 | 2.5 | 48.9 | 0.1 | 74.3 |
| G385M | 3 | 2.7 | 0.5 | 3.2 | 5.8 | 19.2 | 2.1 | 2.9 | 2.5 | 0.6 | 1.6 | 2.3 | 48.1 | 0.2 | 73.1 |
| G385W | 3 | 2.9 | 0.6 | 2.8 | 5.1 | 18.9 | 2.0 | 2.8 | 2.4 | 0.5 | 1.7 | 2.4 | 47.9 | 0.4 | 73.5 |
| G385Y | 3 | 2.8 | 0.5 | 2.9 | 3.9 | 19.0 | 2.0 | 2.8 | 2.6 | 0.5 | 1.6 | 2.5 | 48.4 | 0.2 | 73.6 |
| Y387V | 3 | 2.9 | 0.5 | 2.9 | 5.1 | 17.8 | 1.5 | 2.7 | 2.7 | 0.6 | 1.6 | 2.4 | 49.9 | 0.2 | 75.6 |
| Y387W | 3 | 2.8 | 0.6 | 2.8 | 3.5 | 17.0 | 1.5 | 2.6 | 2.7 | 0.6 | 1.5 | 2.4 | 51.3 | 1.7 | 76.8 |
| L388V | 3 | 3.0 | 0.6 | 3.0 | 3.7 | 18.4 | 1.7 | 2.8 | 2.7 | 0.6 | 1.7 | 2.5 | 48.8 | 0.1 | 74.5 |
| L388W | 3 | 3.0 | 0.6 | 2.8 | 2.0 | 16.6 | 1.3 | 2.7 | 2.8 | 0.6 | 1.6 | 2.5 | 51.2 | 0.5 | 77.5 |
| L388Y+ | 3 | 2.8 | 0.7 | 2.5 | 4.8 | 15.3 | 1.0 | 2.7 | 3.3 | 0.7 | 1.5 | 2.6 | 52.9 | 1.5 | 79.7 |
| T389M | 3 | 3.1 | 0.6 | 2.9 | 5.2 | 15.6 | 1.1 | 2.9 | 3.2 | 0.7 | 1.5 | 2.5 | 52.0 | 0.3 | 78.9 |
| T389W | 3 | 2.6 | 0.7 | 2.6 | 2.3 | 19.2 | 1.9 | 2.8 | 2.6 | 0.5 | 1.6 | 2.8 | 47.3 | 0.7 | 73.2 |
| T389Y | 3 | 2.7 | 0.5 | 2.8 | 3.9 | 18.7 | 1.8 | 2.9 | 2.6 | 0.5 | 1.6 | 2.6 | 48.5 | 0.2 | 74.2 |
| Mutant AVG | | 2.8 | 0.6 | 2.7 | 4.6 | 16.5 | 1.3 | 2.8 | 2.9 | 0.6 | 1.6 | 2.6 | 51.0 | | 77.5 |
| Mutant SD | | 0.2 | 0.1 | 0.2 | 1.0 | 1.7 | 0.3 | 0.1 | 0.3 | 0.1 | 0.1 | 0.1 | 1.8 | | |

TABLE 20

Lipid Composition and Delta-9 Elongase Conversion Efficiency in Batch #3 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 3 | 2.9 | 0.6 | 2.7 | 4.6 | 14.4 | 1.0 | 2.6 | 3.0 | 0.6 | 1.5 | 2.5 | 54.2 | 0.5 | 80.6 |
| M132C | 3 | 2.8 | 0.6 | 2.6 | 4.6 | 18.0 | 1.5 | 2.6 | 2.8 | 0.5 | 1.6 | 2.7 | 50.4 | 0.2 | 75.7 |
| M132L | 3 | 2.9 | 0.6 | 2.8 | 5.0 | 18.7 | 1.8 | 2.6 | 2.5 | 0.5 | 1.6 | 2.4 | 49.7 | 0.5 | 74.3 |
| M132Q | 3 | 2.9 | 0.4 | 2.8 | 4.7 | 19.4 | 2.2 | 2.4 | 2.4 | 0.5 | 1.3 | 2.1 | 50.1 | 0.0 | 73.1 |
| V133L | 3 | 2.9 | 0.5 | 2.7 | 5.3 | 20.4 | 2.8 | 2.8 | 2.0 | 0.4 | 1.5 | 2.1 | 48.1 | 2.2 | 71.1 |
| L134A+ | 3 | 3.1 | 0.7 | 2.5 | 4.6 | 14.2 | 1.0 | 2.6 | 3.2 | 0.6 | 1.5 | 2.5 | 54.4 | 0.7 | 81.1 |
| L134M | 3 | 3.2 | 0.6 | 2.7 | 4.6 | 15.9 | 1.5 | 2.4 | 2.8 | 0.6 | 1.4 | 2.3 | 53.3 | 2.9 | 78.3 |
| C135L | 3 | 3.3 | 0.6 | 3.0 | 4.9 | 15.9 | 1.5 | 2.4 | 2.7 | 0.6 | 1.5 | 2.2 | 52.6 | 4.4 | 78.0 |
| M136I | 3 | 3.1 | 0.6 | 2.7 | 4.7 | 16.2 | 1.7 | 2.5 | 2.6 | 0.5 | 1.5 | 2.2 | 52.4 | 3.2 | 77.5 |
| M136Y | 3 | 2.7 | 0.6 | 2.6 | 4.5 | 17.6 | 1.4 | 2.7 | 2.8 | 0.5 | 1.5 | 2.5 | 51.1 | 0.6 | 76.3 |
| K137N+ | 3 | 3.4 | 0.7 | 2.6 | 4.7 | 13.2 | 1.0 | 2.7 | 3.2 | 0.6 | 1.5 | 2.4 | 55.2 | 0.8 | 82.2 |
| K137R | 3 | 3.0 | 0.6 | 2.6 | 4.6 | 17.1 | 1.3 | 2.7 | 2.8 | 0.6 | 1.6 | 2.6 | 51.4 | 0.3 | 77.0 |
| L138Q | 3 | 3.0 | 0.5 | 2.8 | 4.6 | 18.2 | 1.8 | 2.4 | 2.6 | 0.6 | 1.4 | 2.3 | 51.0 | 1.6 | 75.0 |
| S139V | 3 | 3.1 | 0.7 | 2.6 | 4.7 | 15.8 | 1.1 | 2.6 | 3.0 | 0.6 | 1.5 | 2.4 | 53.1 | 0.5 | 78.9 |
| S140L | 3 | 3.3 | 0.6 | 2.7 | 4.8 | 15.1 | 1.5 | 2.4 | 2.8 | 0.5 | 1.5 | 2.3 | 53.8 | 3.8 | 79.2 |
| S140V | 3 | 3.2 | 0.6 | 2.8 | 4.8 | 15.8 | 1.4 | 2.5 | 2.8 | 0.6 | 1.4 | 2.3 | 53.2 | 2.9 | 78.4 |
| F141I | 3 | 3.1 | 0.6 | 2.7 | 4.8 | 16.0 | 1.6 | 2.5 | 2.7 | 0.6 | 1.5 | 2.2 | 53.0 | 3.3 | 78.0 |
| G142T | 3 | 3.2 | 0.6 | 2.7 | 5.0 | 15.9 | 1.4 | 2.5 | 2.7 | 0.6 | 1.5 | 2.3 | 52.7 | 2.3 | 78.3 |
| W143A | 3 | 3.0 | 0.5 | 2.7 | 5.3 | 19.3 | 2.4 | 2.7 | 2.1 | 0.5 | 1.5 | 2.2 | 48.8 | 3.8 | 72.7 |
| W143V | 3 | 3.2 | 0.6 | 2.7 | 4.4 | 16.4 | 1.5 | 2.5 | 2.8 | 0.6 | 1.5 | 2.4 | 52.5 | 2.2 | 77.6 |
| N144R | 3 | 3.0 | 0.6 | 2.6 | 4.6 | 15.2 | 1.2 | 2.8 | 2.9 | 0.6 | 1.5 | 2.4 | 53.5 | 0.1 | 79.5 |
| N144T+ | 3 | 3.3 | 0.7 | 2.6 | 4.7 | 13.6 | 0.9 | 2.6 | 3.2 | 0.6 | 1.5 | 2.4 | 55.2 | 0.1 | 81.9 |
| V145E | 3 | 3.1 | 0.7 | 2.6 | 4.6 | 14.3 | 1.0 | 2.5 | 3.2 | 0.6 | 1.5 | 2.5 | 54.2 | 0.7 | 80.8 |
| Y146F | 3 | 3.3 | 0.6 | 2.8 | 4.6 | 16.1 | 1.5 | 2.4 | 2.8 | 0.6 | 1.4 | 2.3 | 52.9 | 2.7 | 78.1 |
| Y146Q | 3 | 3.3 | 0.6 | 2.7 | 4.6 | 14.7 | 1.1 | 2.5 | 3.0 | 0.6 | 1.5 | 2.3 | 54.1 | 0.3 | 80.3 |
| Y146R | 3 | 3.2 | 0.5 | 2.7 | 4.6 | 16.4 | 1.6 | 2.4 | 2.6 | 0.5 | 1.5 | 2.2 | 53.0 | 3.2 | 77.6 |
| Y146V | 2 | 3.1 | 0.6 | 2.7 | 4.8 | 17.6 | 1.9 | 2.6 | 2.5 | 0.5 | 1.5 | 2.2 | 50.7 | | 75.5 |
| G148A+ | 3 | 3.2 | 0.7 | 2.6 | 4.6 | 13.4 | 0.9 | 2.5 | 3.2 | 0.6 | 1.6 | 2.5 | 54.9 | 0.3 | 82.0 |
| G148L | 3 | 3.0 | 0.6 | 2.7 | 4.8 | 16.8 | 1.7 | 2.5 | 2.6 | 0.5 | 1.5 | 2.3 | 52.2 | 2.5 | 77.0 |
| S376L | 3 | 2.7 | 0.5 | 2.8 | 4.9 | 19.2 | 2.1 | 2.6 | 2.4 | 0.5 | 1.6 | 2.3 | 49.2 | 0.3 | 73.4 |
| F378L | 3 | 3.0 | 0.5 | 2.8 | 4.5 | 16.9 | 1.3 | 2.5 | 2.7 | 0.6 | 1.5 | 2.3 | 52.3 | 0.1 | 77.2 |
| F378W | 3 | 3.0 | 0.7 | 2.5 | 4.9 | 14.9 | 1.0 | 3.0 | 3.4 | 0.6 | 1.5 | 2.7 | 53.0 | 1.0 | 80.2 |
| T382I+ | 3 | 3.3 | 0.7 | 2.6 | 4.7 | 12.9 | 0.9 | 2.4 | 3.2 | 0.6 | 1.4 | 2.4 | 55.8 | 0.5 | 82.6 |
| T382M | 3 | 2.9 | 0.5 | 2.7 | 4.5 | 16.9 | 1.7 | 2.6 | 2.6 | 0.5 | 1.5 | 2.3 | 51.9 | 2.8 | 76.8 |
| R383E | 3 | 3.1 | 0.4 | 2.9 | 4.7 | 19.7 | 2.4 | 2.3 | 2.2 | 0.5 | 1.3 | 2.1 | 49.5 | 0.5 | 72.4 |
| R383H | 3 | 2.9 | 0.6 | 2.6 | 4.8 | 16.5 | 1.2 | 2.7 | 2.9 | 0.6 | 1.6 | 2.5 | 52.1 | 0.4 | 77.8 |
| R383Q | 3 | 3.3 | 0.6 | 2.8 | 4.7 | 16.9 | 1.3 | 2.5 | 2.9 | 0.6 | 1.4 | 2.4 | 51.5 | 1.2 | 77.1 |
| P384A+ | 3 | 3.2 | 0.7 | 2.6 | 4.4 | 15.0 | 1.1 | 2.6 | 2.9 | 0.6 | 1.6 | 2.4 | 53.5 | 0.7 | 79.8 |
| P384S | 3 | 3.3 | 0.6 | 2.7 | 4.6 | 15.9 | 1.2 | 2.7 | 2.9 | 0.6 | 1.5 | 2.4 | 52.5 | 0.9 | 78.6 |
| P384T | 3 | 2.9 | 0.5 | 2.8 | 5.1 | 19.4 | 2.3 | 2.5 | 2.2 | 0.5 | 1.5 | 2.3 | 49.2 | 0.4 | 72.8 |
| P384V | 3 | 2.8 | 0.6 | 2.7 | 4.8 | 17.4 | 1.5 | 2.6 | 2.7 | 0.5 | 1.5 | 2.4 | 51.4 | 0.2 | 76.5 |
| G385A | 3 | 2.8 | 0.5 | 2.9 | 5.0 | 19.2 | 2.2 | 2.7 | 2.3 | 0.5 | 1.6 | 2.3 | 48.6 | 0.8 | 73.1 |
| G385C | 3 | 3.0 | 0.5 | 2.9 | 5.2 | 19.9 | 2.4 | 2.5 | 2.2 | 0.5 | 1.6 | 2.2 | 48.5 | 0.8 | 72.0 |

TABLE 20-continued

Lipid Composition and Delta-9 Elongase Conversion Efficiency in Batch #3 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| G385V | 3 | 3.0 | 0.5 | 2.9 | 5.3 | 19.7 | 2.3 | 2.6 | 2.2 | 0.5 | 1.5 | 2.2 | 48.4 | 0.7 | 72.3 |
| Y387F | 3 | 3.1 | 0.5 | 2.8 | 4.8 | 18.3 | 1.8 | 2.4 | 2.4 | 0.5 | 1.5 | 2.2 | 50.8 | 1.5 | 74.8 |
| Y387L | 3 | 3.2 | 0.6 | 2.7 | 4.4 | 17.3 | 1.4 | 2.6 | 2.6 | 0.5 | 1.6 | 2.3 | 51.0 | 1.2 | 76.5 |
| T389A+ | 3 | 3.2 | 0.5 | 2.9 | 4.8 | 13.6 | 1.0 | 2.4 | 2.9 | 0.6 | 1.5 | 2.2 | 55.4 | 0.1 | 81.6 |
| T389C+ | 3 | 3.2 | 0.6 | 2.7 | 4.4 | 13.6 | 1.0 | 2.5 | 3.1 | 0.6 | 1.5 | 2.4 | 55.3 | 0.3 | 81.8 |
| T389S+ | 3 | 3.2 | 0.6 | 2.8 | 5.0 | 13.3 | 1.0 | 2.4 | 3.1 | 0.6 | 1.5 | 2.3 | 55.2 | 0.3 | 82.0 |
| T389V | 3 | 2.9 | 0.6 | 2.8 | 4.6 | 16.0 | 1.2 | 2.7 | 2.9 | 0.6 | 1.5 | 2.4 | 52.8 | 0.4 | 78.6 |
| Mutant AVG | | 3.1 | 0.6 | 2.7 | 4.7 | 16.3 | 1.5 | 2.6 | 2.7 | 0.6 | 1.5 | 2.3 | 52.3 | 1.3 | 77.7 |
| Mutant SD | | 0.2 | 0.1 | 0.1 | 0.2 | 1.9 | 0.4 | 0.1 | 0.3 | 0.0 | 0.1 | 0.1 | 2.0 | | 3.0 |

TABLE 21

Lipid Composition and Delta-9 Elongase Conversion Efficiency in Batch #4 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 6 | 3.0 | 0.6 | 2.7 | 4.5 | 14.4 | 1.0 | 2.5 | 3.1 | 0.6 | 1.5 | 2.3 | 54.6 | 0.8 | 82.0 |
| M132G | 3 | 2.6 | 0.6 | 2.7 | 5.5 | 19.6 | 1.9 | 2.6 | 2.4 | 0.4 | 1.5 | 2.3 | 49.1 | 1.8 | 74.4 |
| M132H | 3 | 2.6 | 0.5 | 2.9 | 5.1 | 19.4 | 2.4 | 2.5 | 2.3 | 0.4 | 1.5 | 2.2 | 50.5 | 0.1 | 74.5 |
| M132N | 3 | 2.4 | 0.5 | 2.6 | 4.9 | 18.6 | 1.8 | 2.6 | 2.7 | 0.5 | 1.5 | 2.7 | 50.0 | 1.6 | 75.9 |
| V133A | 3 | 2.8 | 0.5 | 2.8 | 4.6 | 17.0 | 1.3 | 2.5 | 2.8 | 0.6 | 1.5 | 2.2 | 52.9 | 0.5 | 78.7 |
| V133C | 3 | 2.6 | 0.6 | 2.7 | 4.4 | 15.5 | 1.1 | 2.5 | 3.0 | 0.5 | 1.6 | 2.3 | 54.7 | 0.1 | 80.8 |
| V133G | 3 | 2.9 | 0.7 | 2.9 | 5.6 | 17.8 | 1.5 | 3.3 | 2.8 | 0.5 | 1.6 | 2.3 | 49.8 | 3.2 | 77.0 |
| V133H | 3 | 2.6 | 0.5 | 2.9 | 4.8 | 18.4 | 1.8 | 2.5 | 2.4 | 0.4 | 1.5 | 2.2 | 51.8 | 0.1 | 76.4 |
| V133N | 3 | 2.6 | 0.6 | 2.7 | 4.6 | 18.0 | 1.4 | 2.4 | 2.8 | 0.5 | 1.4 | 2.4 | 52.2 | 2.0 | 77.3 |
| V133Q | 3 | 2.7 | 0.5 | 2.9 | 4.9 | 19.2 | 2.1 | 2.4 | 2.3 | 0.4 | 1.5 | 2.0 | 51.0 | 7.9 | 75.0 |
| L134C | 3 | 2.7 | 0.7 | 2.5 | 4.6 | 13.7 | 0.9 | 2.6 | 3.4 | 0.6 | 1.6 | 2.6 | 55.0 | 1.5 | 83.2 |
| L134G+ | 3 | 3.0 | 0.7 | 2.7 | 4.4 | 14.1 | 1.0 | 2.5 | 3.0 | 0.5 | 1.7 | 2.1 | 55.3 | 0.6 | 82.6 |
| L134H | 3 | 2.5 | 0.6 | 2.6 | 4.5 | 16.7 | 1.3 | 2.5 | 2.8 | 0.5 | 1.6 | 2.6 | 53.6 | 0.3 | 79.2 |
| L134N | 3 | 2.8 | 0.5 | 2.7 | 4.6 | 16.6 | 1.4 | 2.4 | 2.7 | 0.5 | 1.5 | 2.2 | 53.5 | 2.8 | 79.0 |
| L134Q | 3 | 2.8 | 0.6 | 2.7 | 4.5 | 15.9 | 1.1 | 2.5 | 3.0 | 0.5 | 1.5 | 2.5 | 54.3 | 1.5 | 80.4 |
| C135D | 3 | 2.9 | 0.6 | 2.7 | 4.5 | 13.7 | 1.1 | 2.3 | 3.0 | 0.5 | 1.5 | 2.2 | 56.5 | 0.2 | 83.1 |
| C135E | 3 | 2.5 | 0.6 | 2.8 | 4.8 | 17.4 | 1.5 | 2.7 | 2.7 | 0.4 | 1.6 | 2.3 | 52.2 | 1.7 | 78.0 |
| C135G | 3 | 2.7 | 0.6 | 2.7 | 4.5 | 16.1 | 1.2 | 2.4 | 2.9 | 0.5 | 1.5 | 2.3 | 54.0 | 0.2 | 80.0 |
| C135H | 2 | 2.7 | 0.8 | 3.3 | 7.6 | 20.8 | 1.3 | 5.5 | 3.1 | 0.5 | 2.0 | 2.7 | 42.1 | 10.8 | 72.7 |
| C135K | 3 | 2.6 | 0.6 | 2.6 | 5.1 | 17.6 | 1.5 | 2.7 | 2.9 | 0.5 | 1.6 | 2.6 | 51.8 | 2.8 | 77.7 |
| C135N | 3 | 2.9 | 0.6 | 2.7 | 4.8 | 15.0 | 1.3 | 2.5 | 3.0 | 0.6 | 1.5 | 2.2 | 54.3 | 4.4 | 81.0 |
| C135Q | 3 | 2.8 | 0.6 | 2.8 | 4.5 | 16.2 | 1.2 | 2.5 | 2.8 | 0.5 | 1.6 | 2.3 | 54.2 | 0.5 | 79.9 |
| C135R | 3 | 2.5 | 0.5 | 2.7 | 5.1 | 19.2 | 2.0 | 2.6 | 2.6 | 0.5 | 1.5 | 2.3 | 49.9 | 0.2 | 75.0 |
| M136C | 3 | 3.0 | 0.7 | 2.6 | 4.8 | 14.6 | 1.0 | 2.9 | 3.3 | 0.6 | 1.5 | 2.3 | 54.2 | 1.3 | 81.9 |
| M136G | 2 | 3.1 | 0.6 | 2.7 | 4.5 | 12.5 | 0.9 | 2.4 | 3.1 | 0.6 | 1.5 | 2.3 | 57.0 | | 84.7 |
| M136H | 3 | 2.8 | 0.6 | 2.7 | 4.7 | 17.3 | 1.5 | 2.6 | 2.6 | 0.5 | 1.6 | 2.3 | 52.9 | 0.7 | 78.2 |
| M136N | 3 | 3.0 | 0.5 | 2.8 | 4.6 | 15.6 | 1.5 | 2.4 | 2.8 | 0.5 | 1.4 | 2.1 | 54.6 | 4.1 | 80.2 |
| K137A | 3 | 2.9 | 0.5 | 2.9 | 4.4 | 15.8 | 1.4 | 2.4 | 2.8 | 0.6 | 1.4 | 2.2 | 54.2 | 3.5 | 79.8 |
| K137G | 3 | 2.9 | 0.6 | 2.7 | 4.5 | 14.3 | 1.0 | 2.5 | 3.1 | 0.5 | 1.4 | 2.2 | 55.8 | 0.5 | 82.4 |
| K137H+ | 3 | 3.2 | 0.6 | 2.6 | 4.4 | 12.0 | 0.9 | 2.3 | 3.2 | 0.5 | 1.5 | 2.2 | 58.6 | 0.2 | 85.6 |
| L138G | 3 | 2.7 | 0.6 | 2.7 | 4.5 | 15.2 | 1.0 | 2.5 | 3.1 | 0.5 | 1.5 | 2.4 | 54.8 | 0.1 | 81.3 |
| L138H | 3 | 2.9 | 0.6 | 2.7 | 4.3 | 14.3 | 1.1 | 2.5 | 3.1 | 0.5 | 1.5 | 2.4 | 55.8 | 0.2 | 82.4 |
| L138I | 2 | 3.0 | 0.6 | 2.6 | 4.2 | 15.0 | 1.1 | 2.3 | 2.9 | 0.5 | 1.5 | 2.4 | 56.1 | | 81.7 |
| L138N | 3 | 2.9 | 0.6 | 2.6 | 4.4 | 15.3 | 1.1 | 2.4 | 3.0 | 0.6 | 1.5 | 2.3 | 54.6 | 0.9 | 81.1 |
| S139G | 3 | 2.7 | 0.6 | 2.7 | 4.5 | 15.0 | 1.0 | 2.6 | 3.1 | 0.5 | 1.5 | 2.4 | 54.8 | 1.6 | 81.4 |
| S139H | 3 | 2.8 | 0.6 | 2.6 | 4.7 | 15.5 | 1.4 | 2.5 | 2.9 | 0.5 | 1.5 | 2.4 | 54.4 | 3.9 | 80.5 |
| S139N | 3 | 2.9 | 0.6 | 2.7 | 4.4 | 15.4 | 1.1 | 2.4 | 3.0 | 0.6 | 1.5 | 2.3 | 54.7 | 0.1 | 81.0 |
| S140C | 3 | 2.9 | 0.6 | 2.8 | 4.9 | 14.9 | 1.3 | 2.6 | 3.0 | 0.5 | 1.5 | 2.1 | 54.4 | 4.3 | 81.1 |
| S140H+ | 3 | 3.1 | 0.6 | 2.6 | 4.3 | 12.1 | 0.9 | 2.4 | 3.2 | 0.5 | 1.5 | 2.3 | 58.6 | 0.5 | 85.5 |
| S140N | 3 | 3.0 | 0.6 | 2.7 | 4.3 | 13.5 | 0.9 | 2.3 | 3.1 | 0.6 | 1.5 | 2.2 | 56.6 | 0.1 | 83.5 |
| F141A | 3 | 3.0 | 0.6 | 2.8 | 4.2 | 14.3 | 1.0 | 2.4 | 3.1 | 0.6 | 1.4 | 2.2 | 55.9 | 0.2 | 82.5 |
| F141G | 3 | 2.7 | 0.5 | 2.6 | 4.7 | 16.9 | 1.3 | 2.6 | 2.8 | 0.5 | 1.5 | 2.2 | 53.3 | 0.9 | 78.8 |
| F141H | 3 | 2.4 | 0.5 | 2.6 | 4.8 | 18.0 | 1.7 | 2.6 | 2.6 | 0.4 | 1.5 | 2.5 | 52.3 | 2.2 | 77.2 |
| F141N | 3 | 2.8 | 0.6 | 2.6 | 4.8 | 16.7 | 1.4 | 2.6 | 2.7 | 0.5 | 1.6 | 2.2 | 53.2 | 0.9 | 78.9 |
| G142H | 2 | 2.8 | 0.7 | 2.6 | 4.2 | 14.3 | 0.9 | 2.4 | 3.2 | 0.5 | 1.5 | 2.7 | 55.9 | | 82.7 |
| G142N | 3 | 2.4 | 0.7 | 2.3 | 4.6 | 15.5 | 1.0 | 2.6 | 3.4 | 0.5 | 1.6 | 3.0 | 53.0 | 0.9 | 80.9 |
| W143G | 3 | 2.7 | 0.6 | 2.7 | 4.8 | 16.5 | 1.4 | 2.6 | 2.8 | 0.5 | 1.5 | 2.2 | 53.3 | 3.1 | 79.1 |
| W143H | 3 | 2.9 | 0.6 | 2.7 | 4.4 | 15.2 | 1.1 | 2.5 | 3.0 | 0.5 | 1.6 | 2.5 | 55.1 | 0.4 | 81.3 |
| W143K | 3 | 2.8 | 0.6 | 2.6 | 4.8 | 16.5 | 1.3 | 2.6 | 2.7 | 0.5 | 1.6 | 2.3 | 54.0 | 0.3 | 79.4 |
| N144A+ | 3 | 3.2 | 0.6 | 2.7 | 4.4 | 12.5 | 0.9 | 2.3 | 3.2 | 0.6 | 1.4 | 2.2 | 57.5 | 0.1 | 84.8 |
| N144G | 3 | 2.9 | 0.7 | 2.5 | 4.5 | 14.7 | 1.1 | 2.5 | 3.2 | 0.5 | 1.4 | 2.6 | 54.5 | 2.5 | 81.8 |

TABLE 21-continued

Lipid Composition and Delta-9 Elongase Conversion Efficiency in Batch #4 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| V145A | 3 | 2.8 | 0.7 | 2.5 | 4.4 | 13.1 | 0.8 | 2.3 | 3.4 | 0.6 | 1.5 | 2.6 | 56.0 | 0.3 | 84.1 |
| V145G | 2 | 2.9 | 0.6 | 2.6 | 4.5 | 14.1 | 1.0 | 2.5 | 3.1 | 0.5 | 1.6 | 2.4 | 55.5 | | 82.7 |
| V145H | 3 | 3.1 | 0.6 | 2.7 | 4.6 | 15.5 | 1.2 | 2.5 | 2.9 | 0.5 | 1.6 | 2.4 | 54.5 | 1.2 | 80.7 |
| Y146G | 2 | 2.8 | 0.6 | 2.7 | 4.6 | 14.4 | 1.0 | 2.6 | 3.2 | 0.6 | 1.5 | 2.5 | 54.9 | | 82.2 |
| D147A | 3 | 2.8 | 0.6 | 2.6 | 4.6 | 15.6 | 1.4 | 2.5 | 2.9 | 0.5 | 1.6 | 2.3 | 53.9 | 4.0 | 80.2 |
| D147G | 3 | 2.4 | 0.6 | 3.2 | 6.5 | 20.5 | 1.9 | 4.2 | 2.7 | 0.4 | 1.8 | 2.4 | 45.2 | 7.2 | 72.9 |
| D147H+ | 3 | 3.4 | 0.6 | 2.6 | 4.2 | 13.3 | 1.0 | 2.4 | 3.0 | 0.5 | 1.5 | 2.2 | 57.5 | 0.9 | 83.9 |
| D147N | 3 | 2.9 | 0.6 | 2.7 | 4.4 | 14.5 | 1.0 | 2.5 | 3.1 | 0.6 | 1.6 | 2.3 | 55.1 | 3.2 | 82.1 |
| D147Q+ | 3 | 3.2 | 0.6 | 2.7 | 4.3 | 14.0 | 1.0 | 2.5 | 3.0 | 0.5 | 1.6 | 2.3 | 56.6 | 0.2 | 83.0 |
| G148H | 3 | 3.2 | 0.6 | 2.7 | 4.6 | 15.4 | 1.5 | 2.5 | 2.8 | 0.5 | 1.6 | 2.4 | 54.3 | 4.3 | 80.5 |
| G148N+ | 3 | 3.0 | 0.7 | 2.7 | 4.7 | 13.4 | 1.0 | 2.5 | 3.2 | 0.6 | 1.6 | 2.3 | 55.8 | 0.8 | 83.5 |
| S376A | 3 | 2.9 | 0.6 | 2.8 | 4.6 | 16.9 | 1.3 | 2.5 | 2.8 | 0.6 | 1.5 | 2.3 | 52.8 | 1.9 | 78.8 |
| S376G | 3 | 2.6 | 0.5 | 2.7 | 5.1 | 17.8 | 1.5 | 2.8 | 2.7 | 0.5 | 1.4 | 2.3 | 51.7 | 1.9 | 77.4 |
| S376H | 3 | 2.8 | 0.6 | 2.7 | 4.9 | 19.0 | 2.2 | 2.5 | 2.4 | 0.4 | 1.6 | 2.5 | 50.3 | 0.5 | 75.1 |
| A377G | 3 | 2.6 | 0.7 | 2.7 | 5.0 | 17.3 | 1.3 | 2.8 | 2.9 | 0.5 | 1.6 | 2.5 | 51.4 | 1.8 | 78.1 |
| A377H | 3 | 3.0 | 0.5 | 2.8 | 5.0 | 19.5 | 2.4 | 2.5 | 2.2 | 0.4 | 1.6 | 2.3 | 49.9 | 0.1 | 74.2 |
| A377L | 3 | 2.6 | 0.5 | 2.8 | 5.7 | 19.6 | 2.4 | 2.7 | 2.2 | 0.4 | 1.5 | 2.2 | 49.7 | 1.0 | 74.1 |
| A377N | 3 | 2.7 | 0.6 | 2.7 | 5.3 | 19.1 | 2.1 | 2.7 | 2.3 | 0.4 | 1.7 | 2.2 | 49.1 | 0.2 | 74.7 |
| F378C | 3 | 2.8 | 0.6 | 2.8 | 4.8 | 16.4 | 1.3 | 2.7 | 2.8 | 0.5 | 1.6 | 2.2 | 53.0 | 1.0 | 79.4 |
| F378G | 3 | 2.8 | 0.6 | 2.8 | 4.6 | 15.6 | 1.1 | 2.5 | 2.9 | 0.5 | 1.5 | 2.3 | 54.2 | 0.1 | 80.5 |
| F378H | 3 | 2.8 | 0.5 | 2.8 | 4.7 | 17.3 | 1.7 | 2.6 | 2.5 | 0.4 | 1.5 | 2.2 | 53.0 | 3.1 | 78.0 |
| F378N | 3 | 2.6 | 0.6 | 2.8 | 4.7 | 17.0 | 1.3 | 2.5 | 2.8 | 0.5 | 1.6 | 2.3 | 52.9 | 0.4 | 78.7 |
| T382G | 3 | 2.5 | 0.5 | 2.9 | 4.8 | 18.2 | 1.7 | 2.5 | 2.5 | 0.4 | 1.4 | 2.3 | 51.9 | 1.5 | 76.6 |
| T382H | 3 | 2.8 | 0.6 | 2.8 | 4.6 | 17.3 | 1.5 | 2.5 | 2.6 | 0.4 | 1.5 | 2.4 | 53.4 | 0.5 | 78.3 |
| T382N | 3 | 2.6 | 0.5 | 2.9 | 5.2 | 19.4 | 2.2 | 2.6 | 2.3 | 0.4 | 1.5 | 2.0 | 50.2 | 0.5 | 74.4 |
| T382Q | 2 | 2.9 | 0.7 | 3.1 | 5.7 | 16.8 | 1.0 | 3.9 | 3.2 | 0.5 | 1.8 | 2.7 | 50.0 | | 78.8 |
| R383G | 3 | 2.3 | 0.7 | 3.4 | 7.6 | 21.1 | 1.3 | 5.7 | 3.3 | 0.5 | 2.1 | 3.1 | 41.2 | 7.4 | 72.3 |
| P384G+ | 3 | 2.5 | 0.6 | 2.6 | 4.5 | 15.5 | 1.1 | 2.5 | 3.1 | 0.5 | 1.5 | 2.5 | 54.2 | 0.2 | 80.8 |
| P384H | 3 | 2.7 | 0.6 | 2.7 | 4.5 | 16.3 | 1.2 | 2.5 | 2.8 | 0.5 | 1.5 | 2.4 | 54.0 | 0.5 | 79.8 |
| P384K | 3 | 2.7 | 0.6 | 2.5 | 4.9 | 17.7 | 1.7 | 2.5 | 2.5 | 0.4 | 1.6 | 2.3 | 52.6 | 2.3 | 77.4 |
| P384R | 3 | 2.7 | 0.6 | 2.7 | 4.5 | 16.1 | 1.1 | 2.4 | 3.0 | 0.6 | 1.4 | 2.4 | 54.1 | 0.9 | 80.1 |
| G385G | 3 | 2.8 | 0.6 | 2.7 | 4.5 | 14.1 | 1.0 | 2.6 | 3.1 | 0.5 | 1.6 | 2.4 | 55.2 | 0.1 | 82.5 |
| G385H | 3 | 2.6 | 0.5 | 2.8 | 5.3 | 19.1 | 2.2 | 2.6 | 2.4 | 0.4 | 1.6 | 2.4 | 49.8 | 0.6 | 74.8 |
| G385K | 3 | 2.6 | 0.5 | 2.8 | 5.4 | 19.3 | 2.1 | 2.6 | 2.4 | 0.4 | 1.6 | 2.4 | 50.1 | 0.4 | 74.7 |
| G385N | 3 | 2.5 | 0.5 | 2.7 | 5.3 | 19.5 | 2.0 | 2.7 | 2.6 | 0.4 | 1.5 | 2.4 | 49.7 | 1.2 | 74.6 |
| Y386A | 3 | 2.7 | 0.5 | 2.9 | 4.9 | 19.2 | 2.0 | 2.5 | 2.5 | 0.5 | 1.5 | 2.2 | 50.1 | 0.3 | 74.9 |
| Y386G | 3 | 2.5 | 0.5 | 3.0 | 5.2 | 19.3 | 2.2 | 2.6 | 2.3 | 0.4 | 1.6 | 2.0 | 50.0 | 0.4 | 74.6 |
| Y386H | 3 | 2.8 | 0.5 | 2.9 | 5.2 | 19.3 | 2.2 | 2.5 | 2.3 | 0.4 | 1.6 | 2.4 | 50.0 | 0.5 | 74.6 |
| Y386L | 3 | 2.6 | 0.5 | 2.9 | 5.4 | 19.1 | 2.2 | 2.7 | 2.3 | 0.4 | 1.6 | 2.2 | 50.1 | 0.2 | 74.8 |
| Y387G | 3 | 2.5 | 0.6 | 2.6 | 5.1 | 17.9 | 1.5 | 2.8 | 2.8 | 0.5 | 1.6 | 2.5 | 51.0 | 2.1 | 77.2 |
| Y387H | 3 | 2.9 | 0.6 | 2.6 | 4.5 | 16.5 | 1.2 | 2.5 | 2.8 | 0.5 | 1.5 | 2.5 | 53.7 | 2.1 | 79.5 |
| L388G+ | 3 | 2.8 | 0.6 | 2.7 | 4.4 | 14.6 | 1.0 | 2.6 | 3.1 | 0.5 | 1.6 | 2.5 | 55.5 | 0.8 | 82.2 |
| L388H | 3 | 2.9 | 0.6 | 2.7 | 4.5 | 15.9 | 1.2 | 2.5 | 2.8 | 0.5 | 1.5 | 2.4 | 54.7 | 0.9 | 80.3 |
| T389G | 3 | 2.5 | 0.5 | 2.9 | 5.2 | 17.9 | 1.9 | 2.8 | 2.6 | 0.4 | 1.6 | 2.3 | 51.2 | 0.7 | 76.8 |
| T389H | 3 | 2.7 | 0.5 | 2.7 | 5.0 | 18.7 | 1.9 | 2.6 | 2.4 | 0.4 | 1.6 | 2.4 | 51.3 | 0.6 | 75.8 |
| F390A | 3 | 2.5 | 0.5 | 3.1 | 6.0 | 14.8 | 1.3 | 2.2 | 2.6 | 0.5 | 1.5 | 2.0 | 54.4 | 4.1 | 81.3 |
| F390C | 3 | 2.9 | 0.6 | 2.9 | 5.2 | 13.8 | 0.9 | 2.5 | 3.0 | 0.5 | 1.6 | 2.1 | 55.5 | 0.4 | 83.0 |
| F390G+ | 3 | 2.6 | 0.4 | 3.3 | 5.7 | 14.6 | 1.2 | 2.2 | 2.5 | 0.4 | 1.4 | 1.8 | 55.9 | 0.3 | 81.8 |
| F390H | 3 | 2.7 | 0.5 | 2.7 | 4.7 | 18.3 | 1.8 | 2.5 | 2.4 | 0.4 | 1.5 | 2.2 | 52.3 | 0.7 | 76.6 |
| F390N | 2 | 2.8 | 0.6 | 2.6 | 4.4 | 15.2 | 1.0 | 2.4 | 3.1 | 0.6 | 1.5 | 2.3 | 55.1 | 0.2 | 81.4 |
| Mutant AVG | | 2.8 | 0.6 | 2.7 | 4.8 | 16.4 | 1.4 | 2.6 | 2.8 | 0.5 | 1.5 | 2.3 | 53.1 | 1.5 | 79.3 |
| Mutant SD | | 0.2 | 0.1 | 0.2 | 0.6 | 2.1 | 0.4 | 0.5 | 0.3 | 0.1 | 0.1 | 0.2 | 2.9 | | 3.2 |

TABLE 22

Lipid Composition and Delta-9 Elongase Conversion Efficiency in Batch #5 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 6 | 2.9 | 0.6 | 2.4 | 4.0 | 13.6 | 1.0 | 2.0 | 2.9 | 0.5 | 1.6 | 2.3 | 58.3 | 1.5 | 82.2 |
| M132P | 3 | 2.7 | 0.5 | 2.3 | 4.8 | 19.5 | 2.7 | 2.2 | 2.0 | 0.4 | 1.5 | 1.9 | 52.1 | 1.1 | 73.0 |
| M132S | 3 | 2.7 | 0.5 | 2.7 | 5.2 | 19.3 | 2.4 | 2.5 | 2.1 | 0.2 | 1.6 | 2.2 | 51.0 | 0.1 | 73.3 |
| M132T | 3 | 2.6 | 0.7 | 2.4 | 5.5 | 19.6 | 2.4 | 2.7 | 2.3 | 0.4 | 1.6 | 2.4 | 50.1 | 1.4 | 73.0 |
| V133P | 3 | 2.7 | 0.5 | 2.5 | 5.0 | 19.4 | 2.2 | 2.3 | 2.2 | 0.5 | 1.5 | 1.9 | 51.3 | 0.4 | 73.4 |
| V133S | 3 | 2.8 | 0.6 | 2.7 | 5.0 | 17.7 | 1.7 | 1.7 | 2.6 | 0.3 | 1.6 | 2.4 | 52.4 | 0.1 | 75.9 |
| V133T | 3 | 2.9 | 0.6 | 2.5 | 5.0 | 18.7 | 2.3 | 2.5 | 2.2 | 0.4 | 1.5 | 2.1 | 52.0 | 2.6 | 74.3 |
| V133Y | 3 | 2.5 | 0.5 | 2.5 | 4.8 | 19.0 | 2.3 | 2.2 | 2.2 | 0.4 | 1.4 | 2.2 | 52.5 | 0.2 | 74.0 |

TABLE 22-continued

Lipid Composition and Delta-9 Elongase Conversion Efficiency in Batch #5 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| L134P | 3 | 2.5 | 0.5 | 2.3 | 4.4 | 18.9 | 2.4 | 2.0 | 2.1 | 0.4 | 1.5 | 2.1 | 53.2 | 0.4 | 74.2 |
| L134S | 3 | 2.8 | 0.6 | 2.7 | 5.6 | 19.9 | 2.6 | 2.6 | 2.2 | 0.2 | 1.6 | 2.1 | 49.6 | 6.0 | 72.1 |
| L134T | 3 | 2.8 | 0.5 | 2.6 | 5.3 | 20.0 | 2.8 | 2.5 | 1.9 | 0.3 | 1.5 | 1.9 | 50.6 | 0.5 | 72.0 |
| C135P | 3 | 2.5 | 0.5 | 2.3 | 4.2 | 18.2 | 2.0 | 1.9 | 2.3 | 0.4 | 1.5 | 2.3 | 54.1 | 0.6 | 75.5 |
| C135S | 3 | 3.0 | 0.6 | 2.6 | 4.6 | 15.4 | 1.3 | 2.5 | 2.8 | 0.5 | 1.6 | 2.4 | 55.0 | 0.7 | 79.5 |
| M136P | 3 | 3.0 | 0.6 | 2.2 | 3.7 | 12.6 | 0.9 | 1.8 | 2.8 | 0.5 | 1.5 | 2.3 | 60.2 | 0.7 | 83.6 |
| K137P | 3 | 2.6 | 0.5 | 2.4 | 4.3 | 17.8 | 2.1 | 2.1 | 2.3 | 0.4 | 1.4 | 2.1 | 54.5 | 3.5 | 76.0 |
| K137S | 3 | 3.0 | 0.7 | 2.5 | 4.4 | 14.0 | 1.1 | 2.5 | 3.1 | 0.5 | 1.7 | 2.5 | 56.6 | 0.5 | 81.6 |
| K137T | 3 | 2.9 | 0.6 | 2.4 | 4.7 | 18.0 | 2.3 | 2.3 | 2.2 | 0.4 | 1.6 | 2.1 | 53.1 | 4.4 | 75.3 |
| K137Y | 3 | 2.7 | 0.7 | 2.0 | 4.0 | 12.0 | 0.9 | 1.8 | 3.0 | 0.5 | 1.4 | 2.4 | 60.7 | 2.8 | 84.4 |
| L138P | 3 | 2.5 | 0.4 | 2.2 | 4.5 | 19.1 | 2.6 | 1.9 | 1.9 | 0.4 | 1.4 | 2.0 | 53.7 | 0.9 | 73.9 |
| L138S | 3 | 3.0 | 0.6 | 2.5 | 4.4 | 14.7 | 1.2 | 2.5 | 2.9 | 0.5 | 1.7 | 2.3 | 56.2 | 0.9 | 80.6 |
| L138T | 3 | 3.1 | 0.7 | 2.4 | 4.4 | 14.4 | 1.1 | 2.3 | 2.8 | 0.5 | 1.7 | 2.3 | 56.7 | 0.6 | 81.0 |
| S139P | 3 | 2.6 | 0.5 | 2.5 | 4.3 | 17.3 | 2.0 | 2.0 | 2.3 | 0.4 | 1.4 | 2.1 | 54.9 | 3.2 | 76.5 |
| S140P | 3 | 3.0 | 0.6 | 2.4 | 3.9 | 13.0 | 1.0 | 1.9 | 2.9 | 0.5 | 1.5 | 2.3 | 59.7 | 0.7 | 83.1 |
| F141P | 3 | 2.5 | 0.6 | 2.0 | 4.6 | 18.8 | 2.4 | 2.1 | 1.9 | 0.3 | 1.5 | 2.1 | 53.1 | 2.1 | 74.2 |
| F141S | 3 | 2.8 | 0.7 | 2.1 | 4.4 | 15.1 | 1.7 | 2.2 | 2.5 | 0.4 | 1.7 | 2.2 | 56.6 | 5.4 | 79.6 |
| F141T | 3 | 3.1 | 0.7 | 2.4 | 4.4 | 13.9 | 1.1 | 2.3 | 3.0 | 0.3 | 1.6 | 2.4 | 57.1 | 0.1 | 81.6 |
| G142M | 3 | 3.0 | 0.6 | 2.4 | 4.6 | 16.0 | 1.6 | 2.3 | 2.6 | 0.5 | 1.5 | 2.2 | 55.3 | 3.2 | 78.5 |
| G142P | 3 | 2.8 | 0.5 | 2.5 | 4.4 | 15.7 | 1.6 | 2.4 | 2.6 | 0.4 | 1.4 | 2.2 | 55.7 | 3.6 | 79.0 |
| W143P | 3 | 2.5 | 0.5 | 2.1 | 4.1 | 17.5 | 1.6 | 2.0 | 2.3 | 0.4 | 1.5 | 2.2 | 55.5 | 0.3 | 77.0 |
| W143S | 3 | 3.0 | 0.7 | 2.5 | 4.5 | 15.4 | 1.3 | 2.5 | 2.8 | 0.4 | 1.6 | 2.3 | 55.5 | 0.2 | 79.6 |
| W143T | 3 | 2.8 | 0.6 | 2.5 | 5.3 | 19.4 | 2.6 | 2.6 | 2.1 | 0.3 | 1.6 | 2.2 | 50.1 | 0.8 | 72.9 |
| N144F | 3 | 3.1 | 0.7 | 2.3 | 4.3 | 12.2 | 0.9 | 2.1 | 3.0 | 0.5 | 1.6 | 2.3 | 59.4 | 0.6 | 84.0 |
| N144P | 3 | 2.7 | 0.5 | 2.4 | 4.2 | 16.3 | 1.3 | 2.3 | 2.7 | 0.5 | 1.5 | 2.3 | 55.7 | 0.3 | 78.7 |
| N144V | 3 | 2.8 | 0.6 | 2.0 | 3.8 | 11.6 | 0.9 | 1.7 | 2.7 | 0.5 | 1.5 | 2.2 | 61.9 | 1.0 | 85.0 |
| V145P | 3 | 2.7 | 0.5 | 2.3 | 4.3 | 17.6 | 1.5 | 2.1 | 2.4 | 0.4 | 1.4 | 2.2 | 54.7 | 1.0 | 76.8 |
| V145S | 3 | 3.0 | 0.7 | 2.2 | 4.5 | 15.4 | 1.7 | 2.3 | 2.6 | 0.5 | 1.6 | 2.3 | 55.9 | 4.0 | 79.3 |
| V145T | 3 | 3.2 | 0.7 | 2.6 | 4.5 | 14.1 | 1.2 | 2.6 | 3.0 | 0.5 | 1.6 | 2.4 | 56.0 | 0.6 | 81.3 |
| Y146N | 3 | 2.7 | 0.6 | 2.1 | 4.0 | 15.4 | 1.5 | 1.8 | 2.4 | 0.4 | 1.4 | 2.2 | 57.8 | 3.6 | 79.6 |
| Y146P | 3 | 2.6 | 0.7 | 2.3 | 4.9 | 16.4 | 1.5 | 2.5 | 2.9 | 0.5 | 1.6 | 2.6 | 53.7 | 4.5 | 78.0 |
| D147F | 3 | 3.2 | 0.6 | 2.4 | 4.5 | 15.0 | 1.6 | 2.1 | 2.6 | 0.5 | 1.6 | 2.1 | 56.2 | 4.3 | 79.8 |
| D147S | 3 | 2.9 | 0.6 | 2.2 | 4.6 | 16.1 | 1.8 | 2.4 | 2.6 | 0.5 | 1.6 | 2.2 | 55.1 | 3.3 | 78.2 |
| D147T | 3 | 2.7 | 0.5 | 2.2 | 5.0 | 20.0 | 2.9 | 2.2 | 1.8 | 0.3 | 1.5 | 1.9 | 51.5 | 0.4 | 72.1 |
| G148F | 3 | 2.9 | 0.6 | 2.4 | 4.6 | 15.3 | 1.6 | 2.3 | 2.6 | 0.4 | 1.7 | 2.3 | 55.6 | 4.4 | 79.4 |
| G148M | 3 | 2.9 | 0.6 | 2.4 | 4.5 | 16.0 | 1.6 | 2.2 | 2.6 | 0.4 | 1.6 | 2.2 | 55.2 | 1.8 | 78.5 |
| G148S | 3 | 2.8 | 0.5 | 2.5 | 5.2 | 19.9 | 2.8 | 2.4 | 1.9 | 0.3 | 1.5 | 1.9 | 51.0 | 0.6 | 72.2 |
| G148T | 3 | 2.6 | 0.5 | 2.2 | 4.8 | 19.6 | 2.7 | 2.0 | 1.8 | 0.3 | 1.4 | 1.9 | 52.7 | 0.2 | 73.0 |
| G148V | 3 | 2.7 | 0.5 | 2.2 | 3.9 | 14.7 | 1.5 | 1.7 | 2.4 | 0.4 | 1.5 | 2.1 | 58.8 | 3.9 | 80.5 |
| S376F | 3 | 2.6 | 0.5 | 2.4 | 4.9 | 18.8 | 2.3 | 2.3 | 2.3 | 0.4 | 1.6 | 2.2 | 51.8 | 0.4 | 74.1 |
| S376P | 3 | 2.6 | 0.5 | 2.5 | 5.1 | 19.2 | 2.5 | 2.4 | 2.1 | 0.4 | 1.6 | 2.0 | 51.7 | 1.5 | 73.5 |
| S376V | 3 | 2.5 | 0.5 | 2.3 | 4.1 | 17.6 | 1.9 | 2.0 | 2.3 | 0.4 | 1.4 | 2.1 | 55.4 | 1.8 | 76.5 |
| A377F | 3 | 2.6 | 0.5 | 2.6 | 5.0 | 19.2 | 2.4 | 2.4 | 2.2 | 0.4 | 1.6 | 2.2 | 51.2 | 0.9 | 73.5 |
| A377P | 3 | 2.9 | 0.6 | 2.6 | 4.9 | 17.2 | 1.6 | 2.5 | 2.4 | 0.4 | 1.7 | 2.1 | 52.7 | 0.8 | 76.8 |
| A377S | 3 | 2.8 | 0.6 | 2.4 | 4.3 | 16.2 | 1.4 | 2.3 | 2.6 | 0.4 | 1.6 | 2.3 | 55.5 | 1.4 | 78.6 |
| A377T | 3 | 2.7 | 0.5 | 2.3 | 4.6 | 18.9 | 2.4 | 2.2 | 2.0 | 0.3 | 1.6 | 2.1 | 52.6 | 1.8 | 74.0 |
| A377V | 3 | 2.4 | 0.4 | 2.4 | 4.4 | 19.0 | 2.5 | 1.9 | 1.9 | 0.4 | 1.3 | 1.9 | 54.0 | 0.9 | 74.1 |
| F378P | 3 | 2.6 | 0.5 | 2.7 | 5.2 | 18.8 | 2.2 | 2.6 | 2.3 | 0.4 | 1.6 | 2.2 | 50.9 | 0.3 | 74.0 |
| G385S | 3 | 2.5 | 0.5 | 2.5 | 5.0 | 18.7 | 2.2 | 2.4 | 2.3 | 0.4 | 1.6 | 2.4 | 51.8 | 0.8 | 74.4 |
| G385T | 3 | 2.6 | 0.6 | 2.4 | 4.8 | 18.8 | 2.4 | 1.7 | 2.1 | 0.2 | 1.6 | 2.3 | 52.2 | 1.9 | 74.0 |
| Y386F | 3 | 2.9 | 0.9 | 2.1 | 4.7 | 16.5 | 1.3 | 2.3 | 2.6 | 0.4 | 1.6 | 2.4 | 54.0 | 2.7 | 78.1 |
| Y386P | 3 | 2.3 | 0.6 | 2.4 | 5.0 | 17.9 | 1.8 | 2.6 | 2.7 | 0.4 | 1.7 | 2.9 | 51.3 | 1.0 | 75.8 |
| Y386S | 3 | 2.7 | 0.6 | 2.6 | 5.3 | 19.2 | 2.3 | 2.5 | 2.2 | 0.4 | 1.6 | 2.2 | 51.0 | 0.2 | 73.5 |
| Y386T | 3 | 2.6 | 0.6 | 2.6 | 5.5 | 19.5 | 2.2 | 2.7 | 2.3 | 0.4 | 1.7 | 2.4 | 49.7 | 1.6 | 73.1 |
| Y386V | 3 | 2.4 | 0.4 | 2.5 | 4.5 | 18.9 | 2.4 | 2.1 | 2.0 | 0.3 | 1.4 | 2.0 | 53.3 | 1.3 | 74.1 |
| Y387P | 3 | 2.8 | 0.6 | 2.7 | 4.7 | 17.1 | 1.6 | 2.5 | 2.5 | 0.4 | 1.7 | 2.3 | 53.4 | 0.1 | 77.0 |
| Y387S | 3 | 2.6 | 0.7 | 2.5 | 4.9 | 17.1 | 1.6 | 2.6 | 2.6 | 0.4 | 1.6 | 2.4 | 53.4 | 1.9 | 77.2 |
| Y387T | 3 | 2.7 | 0.6 | 2.4 | 4.7 | 17.0 | 1.5 | 2.4 | 2.6 | 0.4 | 1.5 | 2.3 | 54.0 | 0.4 | 77.3 |
| L388P | 3 | 2.5 | 0.6 | 2.5 | 5.0 | 18.3 | 1.9 | 2.5 | 2.5 | 0.3 | 1.7 | 2.5 | 51.7 | 0.8 | 75.2 |
| L388S | 3 | 2.8 | 0.6 | 2.5 | 4.8 | 17.9 | 1.9 | 2.4 | 2.3 | 0.4 | 1.5 | 2.2 | 53.0 | 1.5 | 75.7 |
| L388T+ | 3 | 2.5 | 0.6 | 2.2 | 3.8 | 14.8 | 1.1 | 1.9 | 2.7 | 0.4 | 1.4 | 2.4 | 58.6 | 0.4 | 80.8 |
| T389F | 3 | 3.0 | 0.6 | 2.7 | 4.5 | 15.9 | 1.3 | 2.5 | 2.7 | 0.4 | 1.6 | 2.4 | 54.9 | 0.1 | 79.0 |
| T389P | 3 | 2.8 | 0.6 | 2.7 | 5.1 | 17.9 | 2.1 | 2.6 | 2.4 | 0.1 | 1.6 | 2.2 | 52.4 | 1.6 | 75.4 |
| F390M | 3 | 2.5 | 0.7 | 2.2 | 4.6 | 16.1 | 1.5 | 2.3 | 2.8 | 0.4 | 1.6 | 2.7 | 54.3 | 2.1 | 78.5 |
| F390P | 3 | 2.7 | 0.5 | 2.5 | 5.1 | 19.8 | 2.8 | 1.6 | 1.9 | 0.2 | 1.5 | 2.0 | 51.3 | 0.6 | 72.2 |
| F390S+ | 3 | 2.8 | 0.5 | 2.9 | 5.9 | 12.9 | 1.1 | 2.1 | 2.4 | 0.4 | 1.5 | 1.8 | 58.0 | 0.5 | 82.6 |
| F390T+ | 3 | 2.6 | 0.5 | 2.5 | 4.4 | 14.1 | 1.1 | 1.8 | 2.4 | 0.4 | 1.4 | 2.1 | 59.2 | 0.3 | 81.6 |
| F390V | 3 | 2.4 | 0.5 | 2.2 | 4.2 | 17.2 | 1.6 | 2.0 | 2.3 | 0.4 | 1.5 | 2.3 | 55.6 | 1.5 | 77.3 |
| Mutant AVG | | 2.7 | 0.6 | 2.4 | 4.6 | 17.0 | 1.8 | 2.2 | 2.4 | 0.4 | 1.5 | 2.2 | 54.3 | 1.5 | 77.0 |
| Mutant SD | | 0.2 | 0.1 | 0.2 | 0.5 | 2.3 | 0.6 | 0.3 | 0.3 | 0.1 | 0.1 | 0.2 | 2.8 | | 3.4 |

Based on the above data, it was clear that several of the YlLPCAT single-amino acid mutants functioned with approximately equal or improved activity when compared to the parent wild type YlLPCAT enzyme (SEQ ID NO:40). This conclusion was made based on measuring LPCAT activity as a function of EPA % TFAs and/or % Conv. In fact, all of the mutant YlLPCAT transformants had an EPA % TFAs of at least 75% of the EPA % TFAs measured in the control (transformants with wild type YlLPCAT). Also, all of the mutant YlLPCAT transformants had a % Conv. that was at least 87.6% of the % Conv. measured in the control.

Fifty-six (56) YlLPCAT mutants (comprising one of the following mutations with respect to SEQ ID NO:40: L134A, L134C, L134G, C135D, C135I, M136G, M136P, M136S, M136V, K137N, K137G, K137H, K137Y, L138A, L138H, L138M, 5139L, S139W, 5140N, 5140H, 5140P, 5140W, F141A, F141M, F141W, G142H, W143L, N144A, N144K, N144F, N144T, N144V, V145A, V145G, V145E, V145M, V145F, V145W, Y146G, Y146L, Y146M, D147N, D147Q, D147H, G148A, G148N, T382I, T382P, R383M, L388G, L388Y, T389A, T389C, T389S and F390C) were found to exhibit equivalent or improved EPA % TFAs and equivalent or improved % Conv. An additional 14 YlLPCAT mutants were determined to have equivalent or improved EPA % TFAs when compared to the control (but did not have an equivalent or improved % Conv.), including mutants V133C, M136N, L138G, L138I, L138N, S139G, S139N, W143H, G148V, L388H, L388T, F390G, F390N and F390T. An additional 12 YlLPCAT mutants were determined to have equivalent or improved % Conv. when compared to the control (but did not have an equivalent or improved EPA % TFAs), including mutants C135F, M136T, 5140Y, 51401, F141V, G142I, G142V, D147E, F378Y, T382Y, R383A and F390S.

A total of 26 YlLPCAT mutants, each comprising a single mutation within either Motif I or Motif II and having equivalent or improved EPA % TFAs and/or equivalent or improved % Conv. were selected for further evaluation (below, Example 9): L134A (100.4%, 100.6%), L134G (101.3%, 100.7%), M136S (104.0%, 104.0%), M136V (102.2%, 103.3%), K137H (107.3%, 104.4%), K137N (101.8%, 102.0%), S140H (107.3%, 104.3%), S140W (103.2%, 103.8%), F141 M (105.4%, 106.7%), F141W (101.2%, 101.6%), N144A (105.3%, 103.4%), N144T (101.8%, 101.6%), V145M (102.0%, 104.0%), V145W (100.4%, 100.5%), D147H (105.3%, 102.3%), D147Q (103.6%, 101.2%), G148A (101.3%, 101.8%), G148N (102.2%, 101.8%), T382I (102.9%, 102.5%), T382P (100.2%, 100.2%), R383M (103.6%, 104.0%), L388G (101.6%, 100.2%), L388Y (100.0%, 99.9%), T389A (102.2%, 101.2%), T389C (102.1%, 101.5%), T389S (101.9%, 101.7%), where the first and second percentages in each parenthetical set correspond to the percentage ratio of EPA % TFAs and % Conv., respectively, in the mutant YlLPCAT transformants relative to the EPA TFAs and % Conv. in the wild type YlLPCAT control transformants. An additional 8 YlLPCAT mutants, each comprising a single mutation within either Motif I or Motif II, also were selected for further evaluation (below, Example 9): F378Y (99.6%, 101.1%), T382Y (99.8%, 100.8%), P384A (98.7%, 99.0%), P384G (99.2%, 98.6%), L388T (100.5%, 98.3%), F390G (102.4%, 99.8%), F390S (99.4%, 100.5%) and F390T (101.6%, 99.3%), where the parenthetical sets are as above.

Example 9

Identifying Double Amino Acid Substitutions in YlLPCAT Having Improved LPCAT Activity The present example describes the synthesis of double YlLPCAT mutants, wherein the double mutants comprise both a single mutation within Motif I and a single mutation within Motif II. These double mutants were transformed into *Y. lipolytica* strain Y8406U2, followed by analysis of the lipid profiles of the transformants. As in Example 8, improved LPCAT activity was indirectly evaluated based on EPA % TFAs and % Conv.

Generation of Double YlLPCAT Mutants

Preferred single mutations within Motif I (L134A, L134G, M136S, M136V, K137H, K137N, 5140H, S140W, F141M, F141W, N144A, N144T, V145W, V145M, D147H, D147Q, G148A and G148N) were combined with preferred single mutations within Motif II (F378Y, T382I, T382P, T382Y, R383M, P384A, P384G, L388G, L388T, L388Y, T389A, T389C, T389S, F390G, F390S, F390T) to generate various combinations of double-mutant YlLPCAT sequences. Thus, for example, a YlLPCAT mutant comprising an S140W mutation within Motif I and a T382I mutation within Motif II is referred to herein as a YlLPCAT mutant S140W_T382. These double mutants were individually synthesized and cloned into Ncol-Notl cut pY306-N vector by GenScript Corporation (Piscataway, N.J.); SEQ ID NO:74 represents the mutant YlLPCAT proteins encoded by the cloned sequences.

Transformation of *Y. lipolytica* Strain Y8406U2 and Analysis of Lipid Profiles within pY306-N Transformants The plasmids were transformed into *Y. lipolytica* strain Y8406U2 and transformants were subsequently grown and subjected to lipid analysis, as described in Example 8. Tables 23 (Batch 6), 24 (Batch 7), 25 (Batch 8) and 26 (Batch 10) show the fatty acid profiles and delta-9 elongase conversion efficiencies of individual transformants of Y8406U2. These measurements were also made for control transformants comprising pY306-N (wild type YlLPCAT protein expression [WT]). The Tables are formatted as described in Example 8.

Comparison of each mutant's performance relative to the wild type YlLPCAT control should only be made within the particular batch in which each mutant was analyzed (i.e., comparisons should not be made between Batch #6 and Batch #7, for example). Mutants shown in bold-face font and followed by a "+" were selected for further studies including flask assays, as discussed below.

TABLE 23

Lipid Composition and Delta-9 Elongase Conversion Efficiency in Batch #6 Transformants Comprising a Vector Encoding YlLPCAT Having Double Amino Acid Substitutions

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 6 | 2.7 | 0.7 | 2.3 | 5.6 | 14.4 | 0.9 | 3.0 | 3.1 | 0.7 | 1.5 | 2.7 | 52.9 | 0.2 | 80.6 |
| S140W_T382I | 3 | 2.9 | 0.8 | 2.2 | 5.8 | 13.0 | 0.8 | 2.9 | 3.2 | 0.7 | 1.5 | 2.7 | 53.7 | 1.2 | 82.4 |
| S140W_T382P+ | 3 | 2.9 | 0.8 | 2.2 | 5.7 | 12.6 | 0.8 | 2.9 | 3.3 | 0.7 | 1.5 | 2.8 | 54.3 | 0.6 | 83.0 |

TABLE 23-continued

Lipid Composition and Delta-9 Elongase Conversion Efficiency in Batch #6 Transformants Comprising a Vector Encoding YlLPCAT Having Double Amino Acid Substitutions

| Mutant | # | % TFAs 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| S140W_T382Y | 3 | 2.7 | 0.7 | 2.2 | 5.6 | 13.6 | 0.9 | 2.8 | 3.2 | 0.7 | 1.5 | 2.8 | 53.8 | 0.6 | 81.8 |
| S140W_R383M | 3 | 2.9 | 0.7 | 2.3 | 5.8 | 12.6 | 0.8 | 2.9 | 3.3 | 0.8 | 1.5 | 2.6 | 54.8 | 0.6 | 83.1 |
| S140W_P384A | 3 | 2.8 | 0.7 | 2.3 | 5.7 | 13.9 | 0.9 | 2.9 | 3.1 | 0.7 | 1.5 | 2.7 | 53.1 | 1.3 | 81.2 |
| S140W_L388Y | 3 | 2.5 | 0.9 | 2.1 | 6.5 | 12.7 | 0.8 | 3.0 | 3.2 | 0.6 | 1.6 | 3.2 | 52.9 | 1.9 | 82.7 |
| S140W_T389A+ | 3 | 2.4 | 0.7 | 2.2 | 6.5 | 11.6 | 0.7 | 2.5 | 3.1 | 0.7 | 1.5 | 2.6 | 55.8 | 0.4 | 84.3 |
| S140W_T389C | 3 | 2.7 | 0.7 | 2.3 | 6.0 | 12.6 | 0.8 | 2.8 | 3.4 | 0.8 | 1.5 | 2.7 | 54.1 | 0.4 | 83.0 |
| S140W_T389S | 3 | 2.6 | 0.6 | 2.5 | 6.3 | 14.6 | 1.3 | 2.7 | 2.7 | 0.7 | 1.5 | 2.2 | 53.3 | 4.1 | 79.9 |
| M136V_F378Y+ | 3 | 2.5 | 0.7 | 2.2 | 4.0 | 14.7 | 1.3 | 2.8 | 2.9 | 0.7 | 1.5 | 2.6 | 52.8 | 4.3 | 79.8 |
| M136V_T382I | 3 | 2.5 | 0.7 | 2.3 | 6.1 | 14.5 | 1.2 | 2.9 | 2.9 | 0.7 | 1.6 | 2.8 | 52.1 | 4.5 | 80.0 |
| M136V_T382P | 3 | 2.7 | 0.8 | 2.2 | 5.6 | 12.8 | 0.8 | 2.9 | 3.3 | 0.8 | 1.6 | 2.8 | 54.3 | 0.4 | 82.8 |
| M136V_T382Y | 3 | 2.6 | 0.8 | 2.2 | 5.5 | 13.1 | 0.8 | 2.8 | 3.3 | 0.7 | 1.5 | 3.0 | 54.3 | 0.3 | 82.5 |
| M136V_R383M | 3 | 2.6 | 0.8 | 2.1 | 5.9 | 13.8 | 1.0 | 2.8 | 3.2 | 0.7 | 1.6 | 3.1 | 52.3 | 2.3 | 81.2 |
| M136V_P384A | 3 | 2.8 | 0.8 | 2.2 | 5.7 | 13.3 | 0.8 | 3.1 | 3.3 | 0.7 | 1.4 | 2.8 | 53.2 | 1.1 | 82.0 |
| M136V_L388Y | 3 | 2.7 | 0.8 | 2.3 | 5.5 | 14.0 | 0.9 | 3.0 | 3.3 | 0.7 | 1.6 | 2.9 | 53.0 | 1.5 | 81.3 |
| M136V_T389A+ | 3 | 2.7 | 0.7 | 2.4 | 6.1 | 11.8 | 0.8 | 2.6 | 3.0 | 0.7 | 1.4 | 2.3 | 56.2 | 0.4 | 84.0 |
| M136V_T389S+ | 3 | 2.7 | 0.7 | 2.4 | 6.1 | 11.7 | 0.8 | 2.6 | 3.0 | 0.7 | 1.4 | 2.3 | 56.5 | 0.8 | 84.2 |
| K137N_F378Y | 3 | 2.8 | 0.8 | 2.2 | 5.5 | 13.6 | 0.9 | 2.9 | 3.3 | 0.7 | 1.5 | 2.8 | 53.4 | 1.1 | 81.7 |
| K137N_T382I | 3 | 2.4 | 0.8 | 2.2 | 6.0 | 15.0 | 1.3 | 2.8 | 3.0 | 0.6 | 1.6 | 2.9 | 51.6 | 4.7 | 79.3 |
| K137N_T382P | 3 | 2.4 | 0.9 | 2.0 | 3.6 | 13.1 | 0.8 | 2.8 | 3.4 | 0.7 | 1.5 | 3.4 | 53.5 | 1.7 | 82.5 |
| K137N_T382Y | 3 | 2.3 | 0.7 | 2.2 | 2.2 | 15.6 | 1.3 | 2.7 | 2.9 | 0.6 | 1.5 | 2.8 | 51.5 | 2.6 | 78.6 |
| K137N_L388Y | 3 | 2.2 | 0.8 | 2.1 | 3.7 | 14.9 | 1.1 | 2.9 | 3.0 | 0.6 | 1.6 | 3.1 | 51.4 | 3.0 | 79.6 |
| K137N_T389C+ | 3 | 2.6 | 0.8 | 2.1 | 5.4 | 12.5 | 0.8 | 2.7 | 3.5 | 0.8 | 1.5 | 2.8 | 55.1 | 0.9 | 83.4 |
| K137N_T389S+ | 3 | 2.5 | 0.7 | 2.3 | 6.0 | 11.8 | 0.7 | 2.6 | 3.2 | 0.7 | 1.5 | 2.5 | 56.0 | 0.2 | 84.2 |
| N144T_F378Y | 3 | 2.8 | 0.8 | 2.3 | 5.5 | 12.8 | 0.8 | 2.9 | 3.3 | 0.8 | 1.5 | 2.6 | 54.4 | 0.3 | 82.8 |
| N144T_T382I | 3 | 2.4 | 0.8 | 2.1 | 4.1 | 13.7 | 1.0 | 2.9 | 3.0 | 0.7 | 1.7 | 3.2 | 52.4 | 4.3 | 81.3 |
| N144T_T382Y | 3 | 2.5 | 0.8 | 2.3 | 3.7 | 13.8 | 0.9 | 2.9 | 3.2 | 0.7 | 1.5 | 2.8 | 53.7 | 0.2 | 81.6 |
| N144T_R383M | 3 | 2.5 | 0.8 | 2.1 | 5.2 | 12.7 | 0.8 | 2.7 | 3.3 | 0.7 | 1.5 | 2.8 | 54.2 | 0.1 | 82.9 |
| N144T_T389A | 2 | 2.4 | 0.7 | 2.4 | 5.8 | 12.5 | 0.8 | 2.7 | 3.3 | 0.7 | 1.6 | 2.7 | 54.5 | | 83.2 |
| N144T_T389C | 2 | 2.2 | 0.8 | 1.7 | 4.8 | 11.9 | 0.8 | 2.3 | 3.1 | 0.7 | 1.6 | 2.8 | 56.1 | | 84.0 |
| N144T_T389S | 3 | 2.5 | 0.6 | 2.3 | 5.9 | 12.0 | 0.7 | 2.7 | 3.2 | 0.7 | 1.7 | 2.5 | 54.7 | 0.7 | 83.7 |
| V145W_F378Y | 3 | 2.5 | 0.8 | 2.2 | 5.6 | 13.5 | 0.9 | 2.9 | 3.3 | 0.7 | 1.5 | 2.9 | 52.6 | 1.4 | 81.7 |
| V145W_T382P | 3 | 2.5 | 0.8 | 2.2 | 2.2 | 14.4 | 0.9 | 3.2 | 3.2 | 0.7 | 1.6 | 2.8 | 52.5 | 1.0 | 80.6 |
| V145W_L388Y | 2 | 2.7 | 0.8 | 2.3 | 3.3 | 16.1 | 1.3 | 3.0 | 2.7 | 0.6 | 1.6 | 2.6 | 49.6 | | 77.5 |
| V145W_T389A | 3 | 2.5 | 0.7 | 2.4 | 6.1 | 13.5 | 1.0 | 2.9 | 3.1 | 0.7 | 1.5 | 2.7 | 53.4 | 1.3 | 81.6 |
| V145W_T389C | 3 | 2.6 | 0.7 | 2.4 | 3.9 | 15.3 | 1.3 | 2.9 | 2.9 | 0.7 | 1.5 | 2.6 | 51.7 | 3.5 | 79.0 |
| V145W_T389S | 3 | 2.7 | 0.6 | 2.5 | 4.2 | 14.1 | 1.0 | 2.8 | 3.1 | 0.7 | 1.5 | 2.5 | 53.2 | 0.7 | 80.9 |
| Mutant AVG | | 2.6 | 0.7 | 2.2 | 5.2 | 13.4 | 0.9 | 2.8 | 3.2 | 0.7 | 1.5 | 2.8 | 53.6 | 1.6 | 81.8 |
| Mutant SD | | 0.2 | 0.1 | 0.1 | 1.1 | 1.1 | 0.2 | 0.2 | 0.2 | 0.0 | 0.1 | 0.2 | 1.5 | 1.4 | 1.7 |

TABLE 24

Lipid Composition and Delta-9 Elongase Conversion Efficiency in Batch #7 Transformants Comprising a Vector Encoding YlLPCAT Having Double Amino Acid Substitutions

| Mutant | # | % TFAs 16:0 | 16:1 | 18:0 | 18:1 | LA | ALA | EDA | DGLA | ARA | ETrA | ETA | EPA | EPA SD | % Conv. |
|---|---|---|---|---|---|---|---|---|---|---|---|---|---|---|---|
| WT | 12 | 3.2 | 0.7 | 2.6 | 4.2 | 14.2 | 0.9 | 2.3 | 3.0 | 0.7 | 1.6 | 2.7 | 54.1 | 0.7 | 81.0 |
| M136S_F378Y | 3 | 3.4 | 0.7 | 2.6 | 4.7 | 12.0 | 0.8 | 2.1 | 3.0 | 0.7 | 1.6 | 2.5 | 56.4 | 1.3 | 84.0 |
| M136S_T382I | 3 | 3.4 | 0.8 | 2.6 | 5.2 | 11.2 | 0.8 | 2.2 | 2.9 | 0.6 | 1.6 | 2.6 | 56.3 | 1.2 | 85.0 |
| M136S_T382P | 3 | 2.9 | 0.8 | 2.3 | 4.5 | 11.5 | 0.7 | 2.1 | 3.3 | 0.6 | 1.5 | 3.1 | 56.2 | 1.6 | 85.0 |
| M136S_T382Y | 3 | 3.3 | 0.7 | 2.5 | 4.3 | 12.1 | 0.8 | 2.1 | 3.2 | 0.6 | 1.6 | 2.8 | 55.8 | 0.5 | 84.0 |
| M136S_R383M | 3 | 3.4 | 0.7 | 2.6 | 4.8 | 11.9 | 0.8 | 2.2 | 3.1 | 0.6 | 1.6 | 2.5 | 56.1 | 0.2 | 84.0 |
| M136S_P384A | 3 | 3.5 | 0.7 | 2.6 | 4.6 | 12.2 | 0.8 | 2.2 | 3.1 | 0.7 | 1.6 | 2.6 | 56.1 | 0.8 | 84.0 |
| M136S_L388Y | 3 | 3.3 | 0.7 | 2.5 | 4.3 | 12.2 | 0.8 | 2.3 | 3.2 | 0.6 | 1.6 | 2.6 | 56.1 | 1.5 | 84.0 |
| M136S_T389A+ | 3 | 3.2 | 0.6 | 2.6 | 4.6 | 11.0 | 0.8 | 2.0 | 2.7 | 0.6 | 1.6 | 2.1 | 57.9 | 0.6 | 85.0 |
| M136S_T389C+ | 3 | 3.3 | 0.6 | 2.7 | 4.8 | 11.2 | 0.8 | 2.1 | 3.0 | 0.7 | 1.6 | 2.3 | 57.3 | 0.2 | 85.0 |
| M136S_T389S+ | 3 | 2.8 | 0.6 | 2.7 | 5.3 | 11.2 | 0.7 | 2.0 | 2.9 | 0.6 | 1.6 | 2.2 | 57.7 | 0.8 | 85.0 |
| F141M_F378Y | 3 | 3.0 | 0.7 | 2.5 | 3.9 | 13.5 | 0.9 | 2.4 | 3.1 | 0.6 | 1.6 | 2.6 | 55.3 | 0.4 | 82.0 |
| F141M_T382I | 3 | 3.1 | 0.7 | 2.7 | 4.4 | 16.2 | 2.2 | 2.2 | 2.3 | 0.5 | 1.7 | 2.8 | 51.0 | 4.6 | 77.0 |
| F141M_T382P | 3 | 2.9 | 0.7 | 2.6 | 4.2 | 14.5 | 1.1 | 2.3 | 3.0 | 0.6 | 1.6 | 2.6 | 54.0 | 0.7 | 81.0 |
| F141M_T382Y | 3 | 3.0 | 0.7 | 2.5 | 4.1 | 14.1 | 0.9 | 2.3 | 3.0 | 0.7 | 1.6 | 2.7 | 54.2 | 0.3 | 81.0 |
| F141M_R383M | 3 | 3.1 | 0.7 | 2.5 | 3.9 | 13.4 | 0.9 | 2.3 | 3.1 | 0.7 | 1.5 | 2.6 | 55.3 | 0.1 | 82.0 |
| F141M_P384A | 3 | 3.1 | 0.7 | 2.5 | 3.8 | 14.3 | 0.9 | 2.3 | 3.2 | 0.6 | 1.6 | 2.8 | 54.5 | 1.0 | 81.0 |
| F141M_L388Y | 3 | 3.0 | 0.6 | 2.5 | 4.2 | 17.3 | 1.6 | 2.4 | 2.5 | 0.6 | 1.6 | 2.5 | 50.8 | 3.7 | 76.0 |
| F141M_T389A | 3 | 3.2 | 0.6 | 2.8 | 4.3 | 14.5 | 1.3 | 2.3 | 2.7 | 0.6 | 1.6 | 2.2 | 54.1 | 2.1 | 80.0 |
| F141M_T389C | 3 | 2.9 | 0.7 | 2.5 | 4.0 | 13.3 | 0.9 | 2.3 | 3.1 | 0.7 | 1.5 | 2.7 | 55.3 | 0.1 | 82.0 |
| F141M_T389S | 3 | 2.8 | 0.6 | 2.7 | 4.8 | 15.8 | 1.4 | 2.5 | 2.8 | 0.6 | 1.6 | 2.4 | 52.1 | 4.4 | 78.0 |
| F141W_F378Y | 3 | 3.2 | 0.7 | 2.6 | 4.7 | 12.8 | 0.9 | 2.3 | 3.1 | 0.6 | 1.6 | 2.5 | 55.5 | 1.2 | 83.0 |

TABLE 24-continued

Lipid Composition and Delta-9 Elongase Conversion Efficiency in Batch #7 Transformants Comprising a Vector Encoding YlLPCAT Having Double Amino Acid Substitutions

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| F141W_T382I+ | 3 | 3.0 | 0.7 | 2.5 | 4.6 | 11.7 | 0.8 | 2.1 | 3.2 | 0.7 | 1.5 | 2.5 | 57.1 | 0.5 | 84.0 |
| F141W_T382P | 3 | 3.3 | 0.8 | 2.6 | 4.2 | 13.5 | 0.9 | 2.3 | 3.2 | 0.7 | 1.5 | 2.7 | 54.8 | 1.6 | 82.0 |
| F141W_T382Y | 3 | 2.9 | 0.7 | 2.5 | 4.1 | 12.7 | 0.8 | 2.3 | 3.3 | 0.6 | 1.5 | 2.7 | 56.0 | 0.5 | 83.0 |
| F141W_R383M | 3 | 3.5 | 0.7 | 2.5 | 4.0 | 12.3 | 0.9 | 2.3 | 3.1 | 0.6 | 1.6 | 2.5 | 56.1 | 0.2 | 83.0 |
| F141W_P384A | 3 | 3.5 | 0.7 | 2.6 | 4.0 | 13.9 | 1.0 | 2.4 | 3.0 | 0.6 | 1.6 | 2.6 | 54.3 | 0.4 | 81.0 |
| F141W_L388Y | 3 | 3.2 | 0.7 | 2.7 | 4.3 | 14.2 | 1.0 | 2.4 | 3.0 | 0.6 | 1.5 | 2.6 | 53.9 | 0.8 | 81.0 |
| F141W_T389A | 3 | 3.3 | 0.6 | 2.8 | 4.6 | 12.3 | 0.9 | 2.1 | 2.9 | 0.6 | 1.6 | 2.2 | 56.3 | 0.4 | 83.0 |
| F141W_T389C | 3 | 3.3 | 0.7 | 2.8 | 4.4 | 12.5 | 1.0 | 2.4 | 3.0 | 0.6 | 1.4 | 2.4 | 55.7 | 0.8 | 83.0 |
| F141W_T389S | 3 | 3.1 | 0.6 | 2.7 | 4.4 | 12.5 | 0.9 | 2.2 | 3.0 | 0.6 | 1.5 | 2.4 | 56.0 | 1.2 | 83.0 |
| V145M_F378Y | 3 | 3.3 | 0.7 | 2.6 | 4.3 | 13.7 | 1.0 | 2.4 | 3.0 | 0.6 | 1.6 | 2.6 | 54.0 | 0.4 | 81.0 |
| V145M_T382I | 3 | 3.4 | 0.8 | 2.5 | 4.1 | 13.0 | 0.9 | 2.3 | 3.2 | 0.7 | 1.5 | 2.7 | 54.9 | 1.6 | 82.0 |
| V145M_T382P | 3 | 3.1 | 0.7 | 2.7 | 4.2 | 14.7 | 1.0 | 2.4 | 3.0 | 0.7 | 1.5 | 2.6 | 53.5 | 1.0 | 80.0 |
| V145M_T382Y | 3 | 3.6 | 0.7 | 2.7 | 4.3 | 14.4 | 1.0 | 2.3 | 3.0 | 0.6 | 1.6 | 2.6 | 53.6 | 2.7 | 81.0 |
| V145M_R383M | 3 | 3.4 | 0.7 | 2.5 | 4.0 | 13.3 | 0.9 | 2.3 | 2.9 | 0.6 | 1.6 | 2.4 | 54.9 | 0.6 | 82.0 |
| V145M_P384A | 3 | 3.2 | 0.8 | 2.4 | 3.9 | 15.4 | 1.0 | 2.4 | 2.8 | 0.6 | 1.7 | 2.8 | 51.4 | 3.6 | 79.0 |
| V145M_L388Y | 3 | 3.3 | 0.7 | 2.7 | 4.3 | 15.4 | 1.1 | 2.4 | 2.7 | 0.6 | 1.5 | 2.5 | 52.2 | 0.6 | 79.0 |
| V145M_T389A | 3 | 3.6 | 0.6 | 2.8 | 4.5 | 13.6 | 1.0 | 2.3 | 2.7 | 0.6 | 1.6 | 2.3 | 54.1 | 0.0 | 81.0 |
| V145M_T389C | 3 | 3.0 | 0.7 | 2.6 | 4.1 | 13.3 | 0.9 | 2.4 | 3.1 | 0.6 | 1.5 | 2.5 | 55.4 | 0.2 | 82.0 |
| V145M_T389S | 3 | 4.1 | 1.0 | 2.2 | 3.9 | 14.5 | 1.3 | 2.1 | 2.4 | 0.6 | 1.7 | 2.1 | 51.5 | 5.3 | 79.0 |
| G148A_F378Y | 3 | 3.3 | 0.7 | 2.6 | 4.3 | 12.5 | 0.9 | 2.3 | 3.1 | 0.6 | 1.5 | 2.5 | 55.9 | 0.3 | 83.0 |
| G148A_T382I | 3 | 3.3 | 0.7 | 2.6 | 4.7 | 11.8 | 0.8 | 2.3 | 3.1 | 0.6 | 1.6 | 2.5 | 56.4 | 0.5 | 84.0 |
| G148A_T382P | 3 | 2.9 | 0.6 | 2.6 | 4.4 | 15.1 | 1.2 | 2.4 | 2.9 | 0.6 | 1.6 | 2.7 | 53.0 | 3.7 | 79.0 |
| G148A_T382Y | 3 | 2.9 | 0.7 | 2.5 | 3.9 | 12.9 | 0.8 | 2.0 | 3.0 | 0.7 | 1.5 | 2.6 | 56.1 | 1.2 | 83.0 |
| G148A_R383M | 3 | 3.4 | 0.7 | 2.6 | 4.2 | 12.5 | 0.8 | 2.3 | 3.1 | 0.6 | 1.6 | 2.6 | 55.5 | 0.9 | 83.0 |
| G148A_P384A | 3 | 2.9 | 0.8 | 2.4 | 4.3 | 13.7 | 0.8 | 2.3 | 3.2 | 0.6 | 1.7 | 3.1 | 53.7 | 0.5 | 82.0 |
| G148A_L388Y | 3 | 2.7 | 0.8 | 2.3 | 4.0 | 13.8 | 0.9 | 2.4 | 3.2 | 0.6 | 1.6 | 3.0 | 54.2 | 0.5 | 82.0 |
| G148A_T389A | 3 | 3.0 | 0.6 | 2.7 | 4.8 | 12.5 | 0.8 | 2.2 | 3.0 | 0.6 | 1.5 | 2.4 | 56.1 | 0.2 | 83.0 |
| G148A_T389C | 3 | 3.5 | 0.7 | 2.6 | 4.2 | 12.6 | 0.9 | 2.3 | 3.0 | 0.6 | 1.5 | 2.4 | 55.8 | 0.1 | 83.0 |
| G148A_T389S | 3 | 3.3 | 0.6 | 2.8 | 4.7 | 14.8 | 1.3 | 2.4 | 2.7 | 0.6 | 1.6 | 2.3 | 52.9 | 5.0 | 80.0 |
| Mutant AVG | | 3.1 | 0.7 | 2.6 | 4.4 | 13.2 | 1.0 | 2.3 | 3.0 | 0.6 | 1.6 | 2.6 | 54.9 | 1.4 | 80.0 |
| Mutant SD | | 0.3 | 0.1 | 0.1 | 0.3 | 1.3 | 0.2 | 0.1 | 0.2 | 0.0 | 0.1 | 0.2 | 1.6 | | 2.0 |

TABLE 25

Lipid Composition and Delta-9 Elongase Conversion Efficiency in Batch #8 Transformants Comprising a Vector Encoding YlLPCAT Having Double Amino Acid Substitutions

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 3 | 2.6 | 0.7 | 2.6 | 4.3 | 14.4 | 1.0 | 2.6 | 3.2 | 0.6 | 1.7 | 2.8 | 53.8 | 0.8 | 81.0 |
| M136V_T389C+ | 3 | 2.8 | 0.6 | 2.6 | 4.8 | 12.1 | 0.9 | 2.3 | 3.3 | 0.6 | 1.5 | 2.6 | 56.6 | 0.5 | 84.0 |
| K137N_R383M | 3 | 2.8 | 0.7 | 2.5 | 4.4 | 12.9 | 0.9 | 2.4 | 3.3 | 0.6 | 1.5 | 2.8 | 55.8 | 0.4 | 83.0 |
| K137N_P384A | 3 | 2.6 | 0.6 | 2.7 | 4.9 | 17.7 | 1.9 | 2.8 | 2.6 | 0.6 | 1.6 | 2.5 | 49.8 | 4.2 | 75.0 |
| K137N_T389A+ | 3 | 2.6 | 0.5 | 2.7 | 4.9 | 12.4 | 0.9 | 2.2 | 3.1 | 0.7 | 1.6 | 2.3 | 56.8 | 0.6 | 83.0 |
| N144T_T382P | 3 | 2.7 | 0.6 | 2.6 | 4.3 | 14.1 | 1.0 | 2.6 | 3.3 | 0.7 | 1.6 | 2.7 | 54.4 | 0.6 | 81.0 |
| N144T_P384A | 3 | 2.6 | 0.6 | 2.5 | 4.2 | 14.4 | 1.0 | 2.5 | 3.2 | 0.7 | 1.6 | 2.7 | 54.3 | 0.6 | 81.0 |
| N144T_L388Y | 3 | 2.5 | 0.7 | 2.4 | 3.9 | 14.0 | 0.9 | 2.4 | 3.4 | 0.7 | 1.5 | 3.0 | 54.7 | 0.7 | 82.0 |
| V145W_T382I | 3 | 2.9 | 0.6 | 2.6 | 4.7 | 13.0 | 0.9 | 2.5 | 3.3 | 0.7 | 1.5 | 2.6 | 55.5 | 0.3 | 83.0 |
| V145W_T382Y | 3 | 2.6 | 0.6 | 2.6 | 4.4 | 16.5 | 1.6 | 2.5 | 2.8 | 0.6 | 1.5 | 2.6 | 52.1 | 3.3 | 77.0 |
| V145W_R383M | 3 | 2.8 | 0.6 | 2.6 | 4.7 | 16.1 | 1.5 | 2.6 | 2.8 | 0.6 | 1.6 | 2.4 | 52.3 | 3.9 | 78.0 |
| V145W_P384A | 3 | 2.6 | 0.6 | 2.6 | 4.2 | 15.6 | 1.1 | 2.7 | 3.1 | 0.7 | 1.6 | 2.7 | 52.7 | 0.3 | 79.0 |
| Mutant AVG | | 2.7 | 0.6 | 2.6 | 4.5 | 14.4 | 1.1 | 2.5 | 3.1 | 0.7 | 1.6 | 2.6 | 54.1 | 1.3 | 79.0 |
| Mutant SD | | 0.1 | 0.1 | 0.1 | 0.3 | 1.7 | 0.3 | 0.2 | 0.3 | 0.1 | 0.1 | 0.2 | 2.1 | | 2.8 |

TABLE 26

Lipid Composition and Delta-9 Elonciase Conversion Efficiency in Batch #10 Transformants Comprising a Vector Encoding YlLPCAT Having Double Amino Acid Substitutions

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | | 2.9 | 0.7 | 2.7 | 4.2 | 14.6 | 1.1 | 2.6 | 3.0 | 0.6 | 1.5 | 2.6 | 53.1 | 1.7 | 80.1 |
| L134A_T382I+ | | 3.0 | 0.7 | 2.6 | 4.6 | 12.5 | 0.9 | 2.2 | 3.1 | 0.6 | 1.5 | 2.5 | 55.9 | 0.6 | 83.0 |
| L134A_P384G | | 2.7 | 0.6 | 2.8 | 4.2 | 15.9 | 1.2 | 2.4 | 2.8 | 0.6 | 1.5 | 2.4 | 52.7 | 0.2 | 78.5 |

TABLE 26-continued

Lipid Composition and Delta-9 Elonciase Conversion Efficiency in Batch #10 Transformants Comprising a Vector Encoding YILPCAT Having Double Amino Acid Substitutions

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| L134A_L388G | | 2.8 | 0.6 | 2.7 | 4.4 | 14.6 | 1.1 | 2.4 | 2.9 | 0.6 | 1.5 | 2.5 | 53.9 | 0.3 | 80.3 |
| L134A_L388T | | 2.7 | 0.6 | 2.8 | 4.5 | 17.3 | 1.7 | 2.4 | 2.5 | 0.5 | 1.6 | 2.3 | 51.0 | 2.7 | 76.0 |
| L134A_F390G | | 2.7 | 0.4 | 3.4 | 5.4 | 14.7 | 1.2 | 2.1 | 2.4 | 0.5 | 1.5 | 2.0 | 53.6 | 0.3 | 79.6 |
| L134A_F390S | | 2.7 | 0.5 | 3.2 | 5.6 | 15.6 | 1.7 | 2.2 | 2.3 | 0.5 | 1.5 | 1.9 | 52.5 | 4.4 | 77.9 |
| L134A_F390T | | 2.7 | 0.5 | 3.0 | 4.7 | 14.4 | 1.1 | 2.3 | 2.8 | 0.5 | 1.5 | 2.4 | 54.2 | 0.5 | 80.5 |
| L134G_T382I | | 2.6 | 0.6 | 2.8 | 4.7 | 18.2 | 2.0 | 2.5 | 2.5 | 0.5 | 1.5 | 2.4 | 49.6 | 3.1 | 74.5 |
| L134G_P384G | | 2.6 | 0.6 | 2.7 | 4.2 | 16.3 | 1.3 | 2.4 | 2.7 | 0.6 | 1.5 | 2.5 | 52.4 | 0.7 | 78.0 |
| L134G_L388G | | 2.7 | 0.6 | 2.8 | 4.1 | 15.0 | 1.1 | 2.5 | 2.9 | 0.6 | 1.6 | 2.6 | 53.4 | 0.2 | 79.8 |
| L134G_L388T | | 2.7 | 0.7 | 2.6 | 4.1 | 15.5 | 1.2 | 2.5 | 2.8 | 0.6 | 1.6 | 2.6 | 52.4 | 0.5 | 78.9 |
| L134G_F390G | | 2.7 | 0.4 | 3.2 | 5.3 | 15.1 | 1.3 | 2.1 | 2.4 | 0.5 | 1.5 | 2.1 | 53.3 | 0.0 | 79.1 |
| L134G_F390S | | 2.8 | 0.5 | 3.1 | 5.4 | 15.7 | 1.7 | 2.4 | 2.3 | 0.5 | 1.6 | 2.2 | 52.0 | 3.6 | 77.8 |
| L134G_F390T | | 2.6 | 0.5 | 2.8 | 4.5 | 14.7 | 1.1 | 2.4 | 2.8 | 0.6 | 1.6 | 2.6 | 53.5 | 1.0 | 80.0 |
| K137N_P384G | | 2.9 | 0.6 | 2.7 | 4.1 | 14.4 | 1.0 | 2.4 | 3.0 | 0.6 | 1.5 | 2.6 | 54.2 | 0.3 | 80.7 |
| K137N_L388G | | 3.1 | 0.7 | 2.6 | 4.4 | 13.5 | 1.0 | 2.6 | 3.2 | 0.6 | 1.5 | 2.6 | 54.5 | 1.0 | 81.7 |
| K137N_L388T | | 3.1 | 0.6 | 2.7 | 4.2 | 13.9 | 1.0 | 2.3 | 3.0 | 0.6 | 1.5 | 2.5 | 54.8 | 0.4 | 81.3 |
| K137N_F390G+ | | 2.4 | 0.5 | 3.0 | 5.5 | 13.1 | 0.9 | 1.9 | 2.7 | 0.5 | 1.5 | 2.4 | 55.2 | 0.9 | 82.1 |
| K137N_F390S | | 2.8 | 0.5 | 3.2 | 5.5 | 13.9 | 1.1 | 2.1 | 2.6 | 0.5 | 1.5 | 2.1 | 54.5 | 1.2 | 80.9 |
| K137N_F390T | | 2.8 | 0.6 | 2.9 | 4.6 | 14.1 | 1.0 | 2.2 | 2.7 | 0.6 | 1.6 | 2.3 | 54.2 | 0.4 | 80.9 |
| K137H_T382I | | 3.1 | 0.6 | 2.8 | 4.7 | 14.8 | 1.5 | 2.2 | 2.7 | 0.5 | 1.5 | 2.3 | 53.7 | 4.7 | 79.4 |
| K137H_P384G | | 2.7 | 0.8 | 2.4 | 4.1 | 13.3 | 0.9 | 2.3 | 3.3 | 0.6 | 1.6 | 3.0 | 54.7 | 0.3 | 82.2 |
| K137H_L388G+ | | 3.2 | 0.7 | 2.5 | 4.3 | 12.5 | 0.9 | 2.2 | 3.1 | 0.6 | 1.5 | 2.5 | 56.2 | 0.6 | 83.1 |
| K137H_L388T+ | | 3.1 | 0.7 | 2.7 | 4.3 | 13.0 | 0.9 | 2.2 | 3.0 | 0.6 | 1.5 | 2.5 | 55.6 | 0.1 | 82.5 |
| K137H_F390G | | 2.8 | 0.5 | 3.3 | 5.7 | 14.6 | 1.2 | 2.0 | 2.5 | 0.5 | 1.5 | 2.1 | 53.6 | 1.2 | 79.7 |
| K137H_F390S | | 2.6 | 0.6 | 3.1 | 6.0 | 12.9 | 1.0 | 2.1 | 2.6 | 0.5 | 1.6 | 2.4 | 54.5 | 0.8 | 82.1 |
| K137H_F390T | | 2.8 | 0.5 | 2.9 | 4.9 | 14.0 | 1.0 | 2.2 | 2.8 | 0.5 | 1.5 | 2.5 | 54.4 | 0.6 | 81.0 |
| S140H_T382I+ | | 3.3 | 0.7 | 2.7 | 4.9 | 11.9 | 0.9 | 2.4 | 3.0 | 0.6 | 1.6 | 2.6 | 55.4 | 1.9 | 83.6 |
| S140H_P384G | | 3.0 | 0.7 | 2.7 | 3.8 | 14.1 | 1.0 | 2.2 | 3.0 | 0.6 | 1.6 | 2.7 | 54.5 | 0.7 | 81.1 |
| S140H_L388G+ | | 3.0 | 0.7 | 2.5 | 4.2 | 12.7 | 0.8 | 2.3 | 3.2 | 0.6 | 1.5 | 2.7 | 55.7 | 0.1 | 83.0 |
| S140H_L388T | | 3.2 | 0.7 | 2.5 | 4.1 | 13.2 | 0.9 | 2.4 | 3.0 | 0.6 | 1.7 | 2.6 | 54.7 | 0.4 | 82.1 |
| S140H_F390G | | 2.6 | 0.5 | 2.8 | 5.5 | 13.9 | 1.0 | 2.0 | 2.7 | 0.5 | 1.6 | 2.6 | 54.1 | 1.2 | 81.0 |
| S140H_F390S | | 2.8 | 0.5 | 3.1 | 5.2 | 14.1 | 1.1 | 2.2 | 2.6 | 0.5 | 1.5 | 2.2 | 54.1 | 0.4 | 80.6 |
| S140H_F390T | | 3.0 | 0.6 | 2.9 | 4.7 | 16.0 | 1.3 | 2.5 | 2.7 | 0.5 | 1.6 | 2.5 | 51.8 | 1.4 | 78.1 |
| N144A_T382I | | 3.1 | 0.6 | 2.7 | 4.8 | 14.5 | 1.5 | 2.2 | 2.7 | 0.5 | 1.6 | 2.4 | 53.8 | 5.3 | 79.8 |
| N144A_P384G | | 3.0 | 0.7 | 2.7 | 4.0 | 14.2 | 1.0 | 2.4 | 3.1 | 0.6 | 1.6 | 2.6 | 54.1 | 0.2 | 80.9 |
| N144A_L388G | | 3.4 | 0.8 | 2.7 | 4.2 | 13.2 | 1.0 | 2.2 | 3.1 | 0.6 | 1.6 | 2.5 | 54.7 | 0.2 | 82.1 |
| N144A_L388T | | 3.2 | 0.7 | 2.8 | 4.2 | 13.6 | 1.0 | 2.3 | 3.0 | 0.6 | 1.6 | 2.5 | 54.6 | 0.4 | 81.5 |
| N144A_F390G | | 2.8 | 0.5 | 3.4 | 5.9 | 13.5 | 1.1 | 1.9 | 2.4 | 0.5 | 1.5 | 1.9 | 54.6 | 0.4 | 81.2 |
| N144A_F390S+ | | 2.7 | 0.5 | 3.2 | 6.0 | 12.8 | 1.0 | 1.9 | 2.5 | 0.6 | 1.5 | 2.0 | 55.6 | 1.2 | 82.3 |
| N144A_F390T | | 2.8 | 0.6 | 2.9 | 4.7 | 13.9 | 1.0 | 2.2 | 2.8 | 0.6 | 1.5 | 2.5 | 54.5 | 1.1 | 81.1 |
| D147Q_T382I | | 3.2 | 0.7 | 2.6 | 4.4 | 12.7 | 0.9 | 2.2 | 3.1 | 0.6 | 1.6 | 2.5 | 55.6 | 0.4 | 82.7 |
| D147Q_P384G | | 2.9 | 0.6 | 2.7 | 4.1 | 16.4 | 1.3 | 2.5 | 2.7 | 0.6 | 1.7 | 2.5 | 52.0 | 0.2 | 77.8 |
| D147Q_L388G | | 3.1 | 0.7 | 2.6 | 4.0 | 15.0 | 1.1 | 2.5 | 2.9 | 0.6 | 1.7 | 2.5 | 53.4 | 0.4 | 79.8 |
| D147Q_L388T | | 2.7 | 0.7 | 2.6 | 4.0 | 15.1 | 1.1 | 2.3 | 2.9 | 0.6 | 1.6 | 2.7 | 53.1 | 0.1 | 79.7 |
| D147Q_F390G | | 2.8 | 0.5 | 3.1 | 5.2 | 16.1 | 1.5 | 2.3 | 2.4 | 0.5 | 1.7 | 2.2 | 51.7 | 1.6 | 77.7 |
| D147Q_F390S | | 2.7 | 0.5 | 3.1 | 5.1 | 14.0 | 1.1 | 2.2 | 2.5 | 0.6 | 1.5 | 2.1 | 54.7 | 0.7 | 80.9 |
| D147Q_F390T | | 2.8 | 0.5 | 2.9 | 4.5 | 15.5 | 1.2 | 2.4 | 2.7 | 0.6 | 1.6 | 2.4 | 52.8 | 0.5 | 79.0 |
| D147H_T382I+ | | 3.2 | 0.7 | 2.6 | 4.6 | 12.4 | 0.9 | 2.3 | 3.1 | 0.6 | 1.6 | 2.4 | 55.8 | 0.1 | 83.2 |
| D147H_P384G | | 2.7 | 0.7 | 2.5 | 3.9 | 15.0 | 1.0 | 2.4 | 3.1 | 0.6 | 1.8 | 2.8 | 52.9 | 0.5 | 79.9 |
| D147H_L388G | | 2.9 | 0.7 | 2.6 | 4.3 | 14.1 | 1.0 | 2.4 | 3.0 | 0.6 | 1.6 | 2.6 | 54.3 | 0.3 | 81.1 |
| D147H_L388T | | 2.8 | 0.6 | 2.6 | 4.2 | 14.4 | 1.0 | 2.4 | 3.0 | 0.6 | 1.6 | 2.6 | 54.0 | 0.2 | 80.7 |
| D147H_F390G | | 2.8 | 0.5 | 3.1 | 5.4 | 15.4 | 1.3 | 2.2 | 2.5 | 0.5 | 1.5 | 2.2 | 52.4 | 2.2 | 78.6 |
| D147H_F390S | | 2.8 | 0.5 | 3.1 | 5.6 | 13.7 | 1.1 | 2.1 | 2.6 | 0.5 | 1.5 | 2.1 | 54.5 | 0.5 | 81.1 |
| D147H_F390T | | 2.8 | 0.5 | 2.9 | 4.6 | 14.8 | 1.1 | 2.4 | 2.8 | 0.5 | 1.6 | 2.5 | 53.5 | 0.4 | 79.9 |
| G148A_P384G | | 2.7 | 0.8 | 2.5 | 4.1 | 14.6 | 0.9 | 2.4 | 3.3 | 0.6 | 1.7 | 3.1 | 53.1 | 0.4 | 80.6 |
| G148A_L388G | | 3.1 | 0.7 | 2.7 | 4.1 | 14.1 | 1.1 | 2.5 | 3.0 | 0.6 | 1.6 | 2.6 | 54.3 | 0.4 | 81.0 |
| G148A_L388T+ | | 3.2 | 0.7 | 2.9 | 4.7 | 16.7 | 1.9 | 2.8 | 2.4 | 0.5 | 1.7 | 2.5 | 50.2 | 3.4 | 76.3 |
| G148A_F390G | | 2.9 | 0.5 | 3.2 | 5.3 | 16.4 | 1.8 | 2.2 | 2.2 | 0.4 | 1.5 | 2.0 | 51.7 | 4.4 | 76.8 |
| G148A_F390S+ | | 2.6 | 0.5 | 3.3 | 5.8 | 12.3 | 1.0 | 2.1 | 2.6 | 0.5 | 1.5 | 2.0 | 56.1 | 0.3 | 82.9 |
| G148A_F390T | | 3.0 | 0.5 | 3.0 | 4.6 | 14.0 | 1.1 | 2.2 | 2.6 | 0.5 | 1.6 | 2.3 | 54.7 | 0.2 | 80.9 |
| G148N_T382I+ | | 3.6 | 0.7 | 2.7 | 4.3 | 10.6 | 0.7 | 2.2 | 3.2 | 0.6 | 1.4 | 2.5 | 58.5 | 3.2 | 85.8 |
| G148N_P384G | | 2.7 | 0.6 | 2.7 | 4.0 | 15.0 | 1.1 | 2.5 | 2.9 | 0.6 | 1.5 | 2.6 | 53.5 | 0.3 | 79.8 |
| G148N_L388G | | 2.9 | 0.7 | 2.6 | 4.5 | 15.0 | 1.1 | 2.7 | 3.2 | 0.6 | 1.6 | 2.9 | 52.2 | 3.3 | 79.7 |
| G148N_L388T | | 2.8 | 0.6 | 2.7 | 4.1 | 14.4 | 1.1 | 2.5 | 3.0 | 0.6 | 1.6 | 2.7 | 54.0 | 0.7 | 80.6 |
| G148N_F390G | | 2.5 | 0.4 | 3.2 | 5.7 | 13.6 | 1.1 | 2.0 | 2.5 | 0.5 | 1.4 | 2.0 | 55.3 | 0.3 | 81.3 |
| G148N_F390S+ | | 2.5 | 0.4 | 3.2 | 6.0 | 12.4 | 1.0 | 2.0 | 2.6 | 0.5 | 1.4 | 2.0 | 56.2 | 0.2 | 82.8 |
| G148N_F390T | | 2.7 | 0.5 | 3.0 | 4.8 | 16.2 | 1.7 | 2.4 | 2.6 | 0.5 | 1.5 | 2.5 | 52.0 | 3.8 | 77.4 |
| Mutant AVG | | 2.9 | 0.6 | 2.8 | 4.7 | 14.3 | 1.1 | 2.3 | 2.8 | 0.6 | 1.6 | 2.4 | 53.9 | 1.1 | 80.4 |

Based on the data set forth above, it is clear that most of the 167 YILPCAT double mutants analyzed above functioned with approximately equal or improved activity when compared to the parent wild type enzyme (SEQ ID NO:40). This conclusion was made based on measuring LPCAT activity as a function of EPA % TFAs and/or % Conv.

More specifically, 106 YILPCAT mutants comprising a single amino acid mutation within Motif I and a single amino acid mutation within Motif II were found to exhibit equivalent or improved EPA % TFAs and equivalent or improved % Conv. These mutants were L134A_T382I, L134A_L388G, L134A_F390T_M136S_F378Y, M136S_T382I, M136S_T382P, M136S_T382Y, M136S_R383M, M136S_P384A, M136S_L388Y, M136S_T389A, M136S_T389C, M136S_T389S, M136V_T382P, M136V_T382Y, M136V_P384A, M136V_L388Y, M136V_T389A, M136V_T389C, M136V_T389S, K137H_P384G, K137H_L388G, K137H_L388T, K137H_F390S, K137H_F390T, K137N_T382P, K137N_R383M, K137N_P384G, K137N_F378Y, K137N_L388G, K137N_L388T, K137N_T389A, K137N_T389C, K137N_T389S, K137N_F390G, K137N_F390S, K137N_F390T, S140H_T382I, S140H_P384G, S140H_L388G, S140H_L388T, S140H_F390G, S140H_F390S, S140W_T382I, S140W_T382P, S140W_T382Y, S140W_R383M, S140W_P384A, S140W_L388Y, S140W_T389A, S140W_T389C, F141M_F378Y, F141M_T382Y, F141M_R383M, F141M_P384A, F141M_T389C, F141W_F378Y, F141W_T382I, F141W_T382P, F141W_T382Y, F141W_R383M, F141W_P384A, F141W_T389A, F141W_T389C, F141W_T389S, N144A_P384G, N144A_L388G, N144A_L388T, N144A_F390G, N144A_F390S, N144A_F390T, N144T_F378Y, N144T_T382P, N144T_T382Y, N144T_R383M, N144T_P384A, N144T_L388Y, N144T_T389A, N144T_T389C, N144T_T389S, V145M_T382I, V145M_R383M, V145M_T389A, V145M_T389C, V145W_T382I, D147H_T382I, D147H_L388G, D147H_L388T, D147H_F390S, D147Q_T382I, D147Q_F390S, G148A_F378Y, G148A_T382I, G148A_T382Y, G148A_R383M, G148A_P384G, G148A_L388G, G148A_L388Y, G148A_T389A, G148A_T389C, G148A_F390S, G148A_F390T, G148N_T382I, G148N_L388T, G148N_F390G and G148N_F390S).

An additional 15 YILPCAT double mutants (of the 167 analyzed) had equivalent or improved EPA % TFAs when compared to the control, while an additional 6 YILPCAT double mutants (of the 167 analyzed) were determined to have equivalent or improved % Conv. when compared to the control.

Confirmation of Improved LPCAT Activity by Flask Assay

A total of 23 YILPCAT double mutants, each comprising a single amino acid mutation within Motif I and a single amino acid mutation within Motif II, and having equivalent or improved EPA % TFAs and/or equivalent or improved % Conv., were selected for further evaluation (these mutants are noted in bold and with a "+" in Tables 23-26). These mutants were: S140W_T382P, S140W_T389A, M136V_T389A, M136V_T389C, M136V_T389S, K137N_T389A, K137N_T389C, K137N_T389S, M136S_T389A, M136S_T389C, M136S_T389S, F141W_T382I, L134A_T382I, K137N_F390G, K137H_L388G, K137H_L388T, S140H_T382I, S140H_L388G, N144A_F390S, D147H_T382I, G148A_F390S, G148N_T382I and G148N_F390S. Additionally, mutants M136V_F378Y and G148A_L388T, each having slightly diminished EPA % TFAs and slightly diminished % Conv. in comparison to the control, were selected for further evaluation.

Transformants expressing these double mutant YILPCAT proteins were subjected to flask assays for a detailed analysis of the total lipid content and composition. Specifically, the double mutant strains were individually inoculated into 3 mL FM in 15-mL Falcon™ tubes and grown overnight at 30° C. and 250 rpm. The $OD_{600\ nm}$ was measured and an aliquot of the cells was added to a final $OD_{600\ nm}$ of 0.3 in 25 mL FM medium in a 125-mL flask. After 2 days in a Multitron shaking incubator at 250 rpm and at 30° C., 6 mL of the culture was harvested by centrifugation and resuspended in 25 mL HGM in the original 125-mL flask. After 5 days (120 hours) in a shaking incubator at 250 rpm and at 30° C., water was added to flasks to bring the total volume back to 25 mL (thereby accounting for evaporation). An aliquot was used for fatty acid analysis (above) and 10 mL of the culture was dried for dry cell weight determination (above).

The flask assay results are shown below in Tables 27 (Group I) and 28 (Group II). The Tables summarize the number of replicates analyzed for each particular transformant (#), the average total dry cell weight of the cells (DCW), the average total lipid content of the cells (TFAs % DCW), the average concentration of each fatty acid as a weight percent of TFAs ("% TFAs), the delta-9 elongase conversion efficiency (% Conv.) and the average EPA content as a percent of the dry cell weight (EPA % DCW).

TABLE 27

Total Lipid Content, Composition and Delta-9 Elongase Conversion Efficiency in Selected Transformants Comprising a Vector Encoding YILPCAT Having Double Amino Acid Substitutions, by Flask Assay (Group I)

| | | DCW | TFAs % | % TFAs | | | | | | | | | | | | % | EPA % |
|---|---|---|---|---|---|---|---|---|---|---|---|---|---|---|---|---|---|
| Mutant | # | (g/L) | DCW | 16:0 | 16:1 | 18:0 | 18:1 | LA | ALA | EDA | DGLA | ARA | ETrA | ETA | EPA | Conv. | DCW |
| WT | 2 | 3.7 | 26.0 | 2.7 | 0.7 | 2.6 | 4.8 | 13.7 | 1.1 | 2.5 | 3.5 | 1.0 | 0.7 | 2.9 | 53.9 | 81.3 | 14.0 |
| S140W_T382P | 2 | 3.9 | 28.6 | 2.7 | 0.7 | 2.5 | 5.2 | 11.8 | 0.9 | 2.6 | 4.0 | 1.1 | 0.9 | 3.3 | 54.2 | 83.8 | 15.5 |
| S140W_T389A | 2 | 4.0 | 28.2 | 2.7 | 0.6 | 2.8 | 6.1 | 11.7 | 0.9 | 2.4 | 3.4 | 0.9 | 0.6 | 2.5 | 55.5 | 83.7 | 15.7 |
| M136V_F378Y | 2 | 4.0 | 27.7 | 2.9 | 0.7 | 2.5 | 5.4 | 12.0 | 0.9 | 2.7 | 3.7 | 1.0 | 0.7 | 3.0 | 54.2 | 83.4 | 15.0 |
| M136V_T389A | 2 | 4.1 | 27.1 | 2.8 | 0.6 | 2.8 | 5.9 | 12.0 | 1.0 | 2.5 | 3.3 | 1.0 | 0.7 | 2.6 | 54.6 | 83.3 | 14.8 |
| M136V_T389C+ | 2 | 4.0 | 27.3 | 3.0 | 0.5 | 2.7 | 5.0 | 11.6 | 1.0 | 2.6 | 3.3 | 1.0 | 0.6 | 2.6 | 56.2 | 84.0 | 15.4 |
| M136V_T389S | 2 | 4.0 | 28.2 | 2.8 | 0.6 | 2.8 | 5.8 | 11.7 | 1.0 | 2.5 | 3.3 | 1.0 | 0.7 | 2.6 | 54.8 | 83.7 | 15.5 |
| K137N_T389A | 2 | 3.8 | 25.8 | 3.0 | 0.5 | 3.0 | 5.6 | 12.1 | 1.1 | 2.4 | 3.1 | 0.9 | 0.6 | 2.3 | 55.8 | 83.2 | 14.4 |
| K137N_T389C | 2 | 4.0 | 27.4 | 2.8 | 0.8 | 2.5 | 5.4 | 13.2 | 1.0 | 2.8 | 3.8 | 1.0 | 0.6 | 3.1 | 53.2 | 81.9 | 14.6 |
| K137N_T389S | 2 | 3.9 | 27.2 | 2.7 | 0.7 | 2.7 | 6.0 | 12.3 | 1.0 | 2.6 | 3.5 | 0.9 | 0.6 | 2.6 | 54.8 | 83.9 | 14.9 |
| M136S_T389A+ | 2 | 3.9 | 27.7 | 2.7 | 0.6 | 2.8 | 5.9 | 11.7 | 1.0 | 2.5 | 3.3 | 0.9 | 0.6 | 2.5 | 55.8 | 83.3 | 15.5 |

TABLE 27-continued

Total Lipid Content, Composition and Delta-9 Elongase Conversion Efficiency in Selected Transformants Comprising a Vector Encoding YlLPCAT Having Double Amino Acid Substitutions, by Flask Assay (Group I)

| Mutant | # | DCW (g/L) | TFAs % DCW | % TFAs 16:0 | 16:1 | 18:0 | 18:1 | LA | ALA | EDA | DGLA | ARA | ETrA | ETA | EPA | % Conv. | EPA % DCW |
|---|---|---|---|---|---|---|---|---|---|---|---|---|---|---|---|---|---|
| M136S_T389C+ | 2 | 3.9 | 26.9 | 3.0 | 0.5 | 2.8 | 5.3 | 11.7 | 1.0 | 2.5 | 3.3 | 0.9 | 0.7 | 2.6 | 56.0 | 83.9 | 15.1 |
| M136S_T389S+ | 2 | 3.7 | 27.7 | 2.8 | 0.6 | 2.9 | 5.8 | 11.4 | 1.0 | 2.3 | 3.1 | 1.0 | 0.7 | 2.4 | 55.8 | 84.1 | 15.5 |
| F141W_T382I | 2 | 3.8 | 28.7 | 2.5 | 0.8 | 2.5 | 5.7 | 11.9 | 0.8 | 2.6 | 4.2 | 1.0 | 0.7 | 3.4 | 53.4 | 83.7 | 15.3 |

TABLE 28

Total Lipid Content, Composition and Delta-9 Elongase Conversion Efficiency in Selected Transformants Comprising a Vector Encoding YlLPCAT Having Double Amino Acid Substitutions, by Flask Assay (Group II)

| Mutant | # | DCW (g/L) | TFAs % DCW | % TFAs 16:0 | 16:1 | 18:0 | 18:1 | LA | ALA | EDA | DGLA | ARA | ETrA | ETA | EPA | % Conv. | EPA % DCW |
|---|---|---|---|---|---|---|---|---|---|---|---|---|---|---|---|---|---|
| WT | | 2.0 | 26.0 | 3.0 | 0.7 | 2.5 | 4.2 | 13.7 | 0.9 | 2.4 | 3.4 | 0.7 | 0.5 | 3.5 | 54.7 | 82 | 14.2 |
| L134A_T382I | | 2.0 | 24.0 | 3.3 | 0.7 | 2.6 | 4.4 | 12.6 | 0.9 | 2.2 | 3.5 | 0.8 | 0.6 | 3.5 | 53.3 | 83 | 12.9 |
| K137N_F390G | | 2.1 | 27.3 | 2.1 | 0.4 | 2.5 | 6.2 | 12.4 | 0.9 | 1.9 | 3.7 | 0.8 | 0.8 | 3.8 | 54.1 | 83 | 14.8 |
| K137H_L388G | | 2.0 | 28.1 | 3.2 | 0.7 | 2.4 | 4.3 | 12.6 | 0.9 | 2.4 | 3.5 | 0.8 | 0.6 | 3.5 | 54.6 | 83 | 15.4 |
| K137H_L388T | | 2.0 | 27.4 | 2.9 | 0.7 | 2.4 | 4.4 | 13.2 | 0.9 | 2.4 | 3.6 | 0.7 | 0.6 | 3.5 | 54.8 | 82 | 15.0 |
| S140H_T382I | | 2.1 | 21.3 | 3.4 | 0.9 | 2.6 | 4.8 | 12.6 | 0.9 | 2.4 | 3.7 | 0.7 | 0.5 | 3.6 | 52.7 | 82 | 11.3 |
| S140H_L388G | | 2.0 | 26.1 | 2.7 | 0.8 | 2.2 | 4.4 | 13.0 | 0.9 | 2.5 | 3.9 | 0.7 | 0.6 | 4.0 | 54.3 | 83 | 14.2 |
| N144A_F390S+ | | 2.1 | 26.2 | 2.6 | 0.4 | 2.8 | 6.7 | 12.0 | 0.8 | 1.9 | 3.2 | 0.7 | 0.5 | 3.1 | 55.9 | 84 | 14.7 |
| D147H_T382I | | 2.1 | 26.6 | 3.0 | 0.7 | 2.3 | 4.6 | 12.4 | 0.9 | 2.4 | 3.6 | 0.8 | 0.5 | 3.7 | 54.3 | 83 | 14.4 |
| G148A_F390S+ | | 2.1 | 27.0 | 2.8 | 0.4 | 3.0 | 6.5 | 12.0 | 0.8 | 2.1 | 2.9 | 0.8 | 0.7 | 3.0 | 55.1 | 83 | 14.9 |
| G148N_T382I+ | | 1.9 | 26.5 | 3.3 | 0.7 | 2.3 | 4.7 | 12.2 | 0.8 | 2.3 | 3.5 | 0.8 | 0.6 | 3.5 | 56.7 | 84 | 15.0 |
| G148N_F390S+ | | 2.1 | 26.7 | 2.8 | 0.4 | 2.9 | 6.5 | 12.0 | 0.8 | 2.0 | 3.0 | 0.7 | 0.6 | 2.9 | 55.9 | 84 | 14.9 |
| G148A_L388T | | 2.0 | 24.7 | 2.5 | 0.6 | 2.2 | 5.4 | 11.7 | 0.9 | 2.2 | 3.6 | 0.8 | 0.5 | 3.7 | 55.1 | 84 | 13.6 |

Of the 25 YlLPCAT double mutants analyzed, each comprising a single amino acid mutation within Motif I and a single amino acid mutation within Motif II, 17 were observed to have both equivalent or improved EPA % TFAs and equivalent or improved % Conv., while the remaining 8 had equivalent or improved % Conv.

Based on the data set forth above, 22 of the 25 YlLPCAT double mutants analyzed above functioned with improved activity when compared to the parent wild type enzyme (SEQ ID NO:40).

Also, the over-expression of certain double-mutant LPCAT polypeptides resulted in increased total lipid content (TFAs % DCW) in the recombinant *Yarrowia*. For example, over-expression of mutant LPCAT polypeptides comprising the S140W_T382P, S140W_T389A, M136V_T389S and F141W_T382I, or K137H_L388G mutation pairs resulted in total lipid contents that were 8% or more increased relative to the total lipid content of the control (Tables 27 and 28). Interestingly, certain transformants had both increased total lipid content and EPA % TFAs. For example, transformants that over-expressed LPCATs with S140W_T389A, M136V_T389C, M136S_T389A, or M136S_T389S mutation pairs had at least a 5% increase in total lipid content and at least a ~3% increase in EPA % TFAs with respect to control (Tables 27 and 28). This is a significant observation since it had previously been difficult to induce a simultaneous increase in both total lipid content and EPA % TFAs. Usually, an increase in total lipid content had corresponded with a decrease in EPA % TFAs, and vice versa.

The double mutant YlLPCAT polypeptides listed in bold and with a "+" in Tables 27 and 28, i.e., M136S_T389A, M136S_T389C, M136S_T389S, M136V_T389C, N144A_F390S, G148A_F390S, G148N_T382I and G148N_F390S, are disclosed herein as SEQ ID NOs:26, 75, 76, 77, 78, 79, 80 and 81, respectively.

What is claimed is:

1. A recombinant *Yarrowia* cell that produces an oil comprising at least 28 percent eicosapentaenoic acid (EPA) measured as a weight percent of dry cell weight, wherein the cell comprises:

(a) at least one polynucleotide sequence encoding an acyl-CoA:lysophosphatidylcholine acyltransferase (LPCAT) having an amino acid sequence that is at least 90% identical to the sequence set forth in SEQ ID NO: 40 (YlLPCAT), and (b) the LPCAT comprises mutations at (i) amino acid position 136 changing methionine to a different amino acid, and (ii) amino acid position 389 changing threonine to a different amino acid, wherein said LPCAT has LPCAT activity, and wherein the polynucleotide encoding LPCAT is operably linked to at least one regulatory sequence.

2. The recombinant *Yarrowia* cell of claim 1, wherein the LPCAT is a *Yarrowia lipolytica* LPCAT corresponding to the sequence set forth in SEQ ID NO:40 and the LPCAT comprises mutations at (i) amino acid position 136 changing methionine to a different amino acid, and (ii) amino acid position 389 changing threonine to a different amino acid.

3. The recombinant microbial *Yarrowia* cell of claim 1 or claim 2, wherein the cell further comprises a down-regulation of an endogenous polynucleotide sequence encoding Sou2 sorbitol utilization protein.

4. The recombinant *Yarrowia* cell of claim 3, wherein said down-regulation is due to a mutation of said endogenous polynucleotide sequence, and wherein the mutation is selected from the group consisting of a substitution, deletion and insertion.

5. The recombinant *Yarrowia* cell of claim 4, wherein the Sou2 sorbitol utilization protein comprises an amino acid sequence that is at least 95% identical to SEQ ID NO:10.

6. The recombinant *Yarrowia* cell of claim 3, wherein said down-regulation decreases the total amount of sugar alcohols produced by said cell.

7. The recombinant *Yarrowia* cell of claim 1 or claim 2, wherein the cell further comprises:

(a) at least one polynucleotide sequence encoding phospholipid:diacylglycerol acyltransferase (PDAT), (b) at least one polynucleotide sequence encoding delta-12 desaturase, and (c) at least one polynucleotide sequence encoding a dihomo-gamma-linolenic acid (DGLA) synthase multizyme;

wherein each of the polynucleotide sequences of (a)-(c) is operably linked to at least one regulatory sequence.

8. The recombinant *Yarrowia* cell of claim 7, wherein the DGLA synthase multizyme comprises a delta-9 elongase linked to a delta-8 desaturase.

9. The recombinant *Yarrowia* cell of claim 1 or claim 2, wherein the cell further comprises:

(a) at least one polynucleotide sequence encoding delta-8 desaturase, (b) at least one polynucleotide sequence encoding malonyl-CoA synthetase (MCS), and (c) at least one polynucleotide sequence encoding acyl-CoA:lysophosphatidic acid acyltransferase (LPAAT)

wherein each of the polynucleotide sequences of (a)-(c) is operably linked to at least one regulatory sequence.

10. The recombinant *Yarrowia* cell of claim 1 or claim 2, wherein the oil comprises at least 30 percent EPA measured as a weight percent of the dry cell weight of the cell.

11. A method of producing a microbial oil comprising eicosapentaenoic acid, said method comprising:

a) culturing the recombinant *Yarrowia* cell of claim 1, wherein a microbial oil comprising eicosapentaenoic acid is produced; and b) optionally recovering the microbial oil of step (a).

* * * * *